United States Patent
Namiki et al.

(10) Patent No.: US 12,240,855 B2
(45) Date of Patent: Mar. 4, 2025

(54) PYRROLOPYRAZOLE DERIVATIVE

(71) Applicant: DAIICHI SANKYO COMPANY, LIMITED, Tokyo (JP)

(72) Inventors: Hidenori Namiki, Tokyo (JP); Masanori Saitou, Tokyo (JP); Satoshi Matsui, Tokyo (JP); Yoshihiro Shibata, Tokyo (JP); Yoshito Kawamoto, Tokyo (JP); Rie Ichikawa, Tokyo (JP); Yohei Yoshihama, Tokyo (JP); Akiko Otsuka, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 712 days.

(21) Appl. No.: 17/436,500

(22) PCT Filed: Mar. 5, 2020

(86) PCT No.: PCT/JP2020/009357
§ 371 (c)(1),
(2) Date: Sep. 3, 2021

(87) PCT Pub. No.: WO2020/179859
PCT Pub. Date: Sep. 10, 2020

(65) Prior Publication Data
US 2022/0185815 A1    Jun. 16, 2022

(30) Foreign Application Priority Data
Mar. 6, 2019   (JP) ................................ 2019-040649

(51) Int. Cl.
| | | |
|---|---|---|
| *C07D 487/04* | (2006.01) | |
| *A61K 31/4162* | (2006.01) | |
| *A61K 31/423* | (2006.01) | |
| *A61K 31/427* | (2006.01) | |
| *A61P 35/00* | (2006.01) | |
| *A61P 43/00* | (2006.01) | |

(52) U.S. Cl.
CPC ........ *C07D 487/04* (2013.01); *C07B 2200/13* (2013.01)

(58) Field of Classification Search
CPC ............... C07D 487/04; C07B 2200/13; A61P 35/00; A61P 43/00; A61K 31/4162; A61K 31/423; A61K 31/427
See application file for complete search history.

(56) References Cited

U.S. PATENT DOCUMENTS

| | | |
|---|---|---|
| 2010/0210632 A1 | 8/2010 | Kai et al. |
| 2011/0183939 A1 | 7/2011 | Kai et al. |
| 2018/0073084 A1 | 3/2018 | Yoshihama et al. |

FOREIGN PATENT DOCUMENTS

| | | |
|---|---|---|
| CN | 104520300 A | 4/2015 |
| CN | 104876936 A | 9/2015 |
| WO | WO-2008/120725 A1 | 10/2008 |
| WO | WO-2010/035727 A1 | 4/2010 |
| WO | WO-2012/046030 A2 | 4/2012 |
| WO | WO-2016/148115 A1 | 9/2016 |

OTHER PUBLICATIONS

Office Action issued in corresponding Chinese Patent Application No. 202080018933.7, dated Jul. 27, 2023.
Vance et al., "Formation and function of phosphatidylserine and phosphatidylethanolamine in mammalian cells," Biochimica et Biophysica Acta (BBA)—Molecular and Cell Biology of Lipids, vol. 1831, Issue 3, Mar. 2013, pp. 543-554.
Tomohiro et al., "Purification and characterization of human phosphatidylserine synthases 1 and 2," Biochemical Journal, vol. 418, Issue 2, 2009, pp. 421-429.
Saito et al., "Genetic Evidence That Phosphatidylserine Synthase II Catalyzes the Conversion of Phosphatidylethanolamine to Phosphatidylserine in Chinese Hamster Ovary Cells*," The Journal of Biological Chemistry, vol. 273, No. 27, Jul. 3, 1998, pp. 17199-17205.
Stone et al., "Cloning and expression of murine liver phosphatidylserine synthase (PSS)-2: differential regulation of phospholipid metabolism by PSS1 and PSS2," Biochemical Journal, vol. 342, No. 1, 1999, pp. 57-64.
Arikketh et al., "Defining the Importance of Phosphatidylserine Synthase-1 (PSS1): Unexpected Viability of PSS1-Deficient Mice*," Journal of Biological Chemistry, vol. 283, Issue 19, May 9, 2008, pp. 12888-12897.
Zhou et al., "Small molecules inhibitex vivotumor growth in bone," Bioorganic & Medicinal Chemistry Elsevier, vol. 26, No. 23, pp. 6128-6134.
Mangiatordi et al., "Novel chemotypes targeting tubulin at the colchicine binding site and unbiasing P-glycoprotein," European Journal of Medicinal Chemistry, vol. 139, 2017, pp. 792-803.

(Continued)

*Primary Examiner* — Sun Jae Yoo
(74) *Attorney, Agent, or Firm* — Foley & Lardner LLP

(57) ABSTRACT

The present invention provides a low molecular compound that inhibits phosphatidylserine synthase 1 or a pharmaceutically acceptable salt thereof, a pharmaceutical containing thereof, and a therapeutic agent for cancer having a suppressed function of phosphatidylserine synthase 2. The compound represented by formula (1) or a pharmaceutically acceptable salt thereof, wherein $R^1$, ring $Q^1$, ring $Q^2$, and W are as defined in the specification.

[Chemical Formula 1]

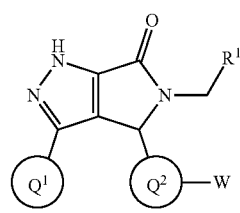

(1)

20 Claims, 4 Drawing Sheets

(56) References Cited

OTHER PUBLICATIONS

International Searching Authority, "International Search Report," in connection with International Patent Application No. PCT/JP2020/009357, dated May 26, 2020.
International Searching Authority, "Written Opinion," in connection with International Patent Application No. PCT/JP2020/009357, dated May 26, 2020.
Office Action issued in corresponding Taiwanese Patent Application No. 109107195, dated Jul. 12, 2023.

PYRROLOPYRAZOLE DERIVATIVE

CROSS-REFERENCE TO RELATED APPLICATIONS

The present application claims priority under 37 U.S.C. § 371 to International Patent Application No. PCT/JP2020/009357, filed Mar. 5, 2020, which claims priority to and the benefit of Japanese Patent Application No. 2019-040649, filed on Mar. 6, 2019. The contents of these applications are hereby incorporated by reference in their entireties.

TECHNICAL FIELD

The present invention relates to a low molecular compound that inhibits phosphatidylserine synthase 1 (hereinafter, sometimes referred to as "PSS1") or a pharmaceutically acceptable salt thereof, a pharmaceutical containing thereof, and a therapeutic agent for cancer having a suppressed phosphatidylserine synthase 2 (hereinafter, sometimes referred to as "PSS2") function.

BACKGROUND ART

Phosphatidylserine is an acidic phospholipid having a negative charge on its polar head under physiological conditions and occupies about 5 to 15% of cell membrane phospholipids. It is known that phosphatidylserine is generated in mammalian cells by two enzymes, phosphatidylserine synthase 1 (PSS1) and phosphatidylserine synthase 2 (PSS2) (Non Patent Literatures 1 and 2).

PSS1 is an enzyme that generates phosphatidylserine by exchanging the choline moiety of phosphatidylcholine into L-serine, and PSS2 is an enzyme that generates phosphatidylserine by a parallel base exchange reaction of phosphatidylethanolamine (Non Patent Literatures 1 and 2). PSS1 and PSS2 share about 28% in amino acid sequence (Non Patent Literature 3, 4).

It has been reported that no obvious phenotype has been found in the knock-out mouse of the PTDSS1 gene encoding PSS1, whereas a tendency of male sub-fertility has been observed in the knock-out mouse of PTDSS2 which is a gene encoding PSS2. PTDSS1 and PTDSS2 double knock-out mice are embryonic lethal, so that phosphatidylserine is considered to be a molecule essential for survival (Non Patent Literature 5).

It has been revealed that PSS1 and PSS2 have a synthetic lethal relationship (Patent Literature 1). Therefore, treatment that inhibits PSS1 is a promising approach for treatment of a cancer having a suppressed PSS2 function (hereinafter, sometimes referred to as "PSS2 function-suppressed cancer"). Examples of specific means to achieve the inhibition of PSS1 include providing a low molecular compound that inhibits PSS1.

A plurality of compounds having a pyrrolopyrazole skeleton are known, and examples thereof include P2X$_3$ and/or P2X$_{2/3}$ receptor antagonists directed to pain drugs (Patent Literatures 2 and 3), and PDE inhibitors directed to therapeutic drugs for viral infections or cancers (Patent Literature 4). However, each of them has a structure different from that of the compound disclosed in the present invention.

CITATION LIST

Patent Literature

PTL 1: International Publication No. WO 2016/148115
PTL 2: International Publication No. WO 2008/120725
PTL 3: International Publication No. WO 2010/035727
PTL 4: International Publication No. WO 2012/046030

Non Patent Literature

NPL 1: Vance, J. E. et al. Biochim. Biophys. Acta, 1831, 543-554 (2013)
NPL 2: Tomohiro, S. et al. Biochem. J., 418, 421-429 (2009)
NPL 3: Saito, K. et al. Biochemistry, 273, 17199-17205 (1998)
NPL 4: Stone, S. J. et al. Biochem. J., 342, 57-64 (1999)
NPL 5: Arikketh et al. J. Biol. Chem., 283, 12888-12897 (2008)

SUMMARY OF INVENTION

Technical Problem

The present invention provides a new low molecular compound having a PSS1 inhibitory effect. The present invention also provides a pharmaceutical containing the new low molecular compound having the PSS1 inhibitory effect for treatment of diseases sensitive to PSS1 inhibitors, in particular, a pharmaceutical exhibiting an anticancer effect on PSS2 function-suppressed cancers.

Solution to Problem

The present inventors have conducted studies of new low molecular compounds for developing a PSS1 inhibitor. Then, the present inventors have found that a compound having a specific structure disclosed in the present invention or a pharmaceutically acceptable salt thereof has a PSS1 inhibitory effect and is useful as a medicament for treatment of PSS2 function-suppressed cancers, thereby completing the present invention. The compound disclosed in the present invention or a pharmaceutically acceptable salt thereof has not been known before, and their pharmacological activities have also not been known before.

The present invention relates to the following [1] to [35].

[1] A compound represented by general formula (1) or a pharmaceutically acceptable salt thereof.

[Chemical Formula 1]

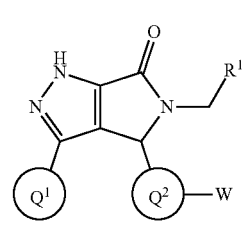

(1)

wherein
R$^1$ represents a halogeno C$_{1-6}$ alkyl group, a C$_{3-8}$ cycloalkyl group, or a 5- or 6-membered aromatic heterocyclic group, ring $Q^1$ represents any one of formulas (2A) to (2C):

[Chemical Formula 2]

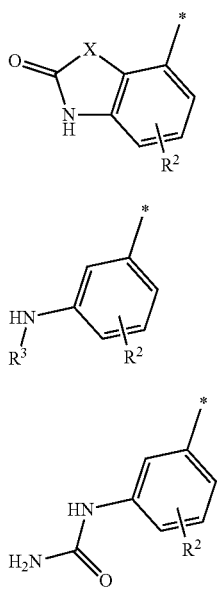

(2A)

(2B)

(2C)

wherein
* represents a bond,
X represents an oxygen atom, a sulfur atom, or —NH—,
$R^2$ represents a hydrogen atom, a halogen atom, or a phenoxy group, and
$R^3$ represents a $C_{1-6}$ alkanoyl group,
ring $Q^2$ represents a phenylene group which may have 1 or 2 substituents independently selected from substituent group 1, a 6-membered aromatic heterocyclic group which may have 1 or 2 substituents independently selected from substituent group 1, a 5-membered aromatic heterocyclic group which may have a substituent selected from substituent group 1, or a 9-membered bicyclic aromatic heterocyclic group which may have a substituent selected from substituent group 1,
W is any one substituent selected from substituent group 1, or represents formula (3A):

[Chemical Formula 3]

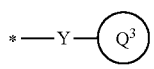

(3A)

wherein
* represents a bond,
Y represents an oxygen atom, a single bond, a sulfur atom, —NH—, *—O—$R^4$—** (wherein * is bonded to ring $Q^2$ and ** is bonded to ring $Q^3$), a $C_{1-6}$ alkylene group, a $C_{1-6}$ alkoxy $C_{1-6}$ alkylene group, or a halogeno $C_{1-6}$ alkylene group,
$R^4$ represents a $C_{1-6}$ alkylene group, and
ring $Q^3$ represents a phenyl group which may have 1 to 3 substituents independently selected from substituent group 2, a 6-membered aromatic heterocyclic group which may have 1 or 2 substituents independently selected from substituent group 2, a 5-membered aromatic heterocyclic group which may have 1 or 2 substituents independently selected from substituent group 2, a 3- to 8-membered saturated hydrocarbon ring group which may have 1 or 2 substituents independently selected from substituent group 2, a 6-membered saturated heterocyclic group which may have 1 or 2 substituents independently selected from substituent group 2, a 9-membered bicyclic aromatic heterocyclic group which may have a substituent selected from substituent group 2, or a 10-membered bicyclic partially unsaturated heterocyclic group which may have 1 to 4 substituents independently selected from substituent group 2;
substituent group 1 represents a group consisting of a halogen atom, a $C_{1-6}$ alkyl group, a halogeno $C_{1-6}$ alkyl group, a halogeno $C_{1-6}$ alkoxy group, and a $C_{3-8}$ cycloalkyl group; and
substituent group 2 represents a group consisting of a halogen atom, a $C_{1-6}$ alkyl group, a halogeno $C_{1-6}$ alkyl group, a halogeno $C_{1-6}$ alkoxy group, a halogeno $C_{1-6}$ alkylsulfanyl group, and a halogeno $C_{1-6}$ alkylsulfonyl group.

[2] The compound according to [1] or a pharmaceutically acceptable salt thereof, wherein $R^1$ is a trifluoromethyl group, a 1,1-difluoroethyl group, a 1,1-difluoropropyl group, a cyclopropyl group, a 2-pyridinyl group, or an oxazol-2-yl group.

[3] The compound according to [1] or a pharmaceutically acceptable salt thereof, wherein $R^1$ is a 1,1-difluoroethyl group.

[4] The compound according to any one of [1] to [3] or a pharmaceutically acceptable salt thereof, wherein ring $Q^1$ represents either formula (4A) or (4B):

[Chemical Formula 4]

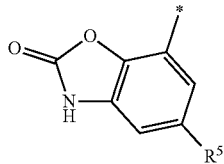

(4A)

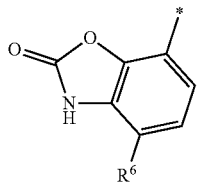

(4B)

wherein
* represents a bond,
$R^5$ represents a hydrogen atom or a halogen atom, and
$R^6$ represents a halogen atom.

[5] The compound according to any one of [1] to [3] or a pharmaceutically acceptable salt thereof, wherein ring Q represents either formula (5A) or (5B):

[Chemical Formula 5]

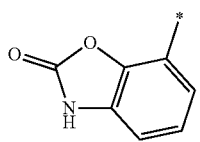

(5A)

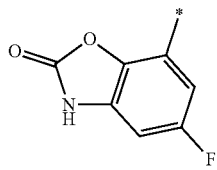

wherein * represents a bond.

[6] The compound according to any one of [1] to [5] or a pharmaceutically acceptable salt thereof, wherein ring $Q^2$ represents any one of formulas (6A) to (6G):

[Chemical Formula 6]

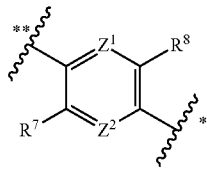
(6A)

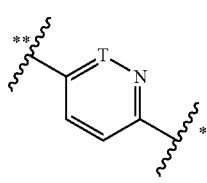
(6B)

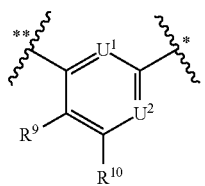
(6C)

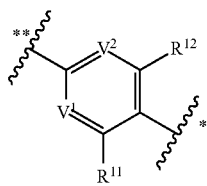
(6D)

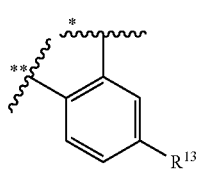
(6E)

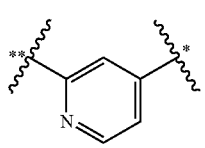
(6F)

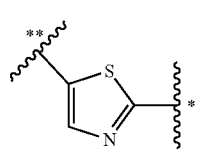
(6G)

wherein
* is bonded to W,
in formula (1), ** is bonded to a carbon atom represented by a in a moiety represented by formula (1A) (hereinafter, referred to as "the carbon atom represented by a"):

[Chemical Formula 7]

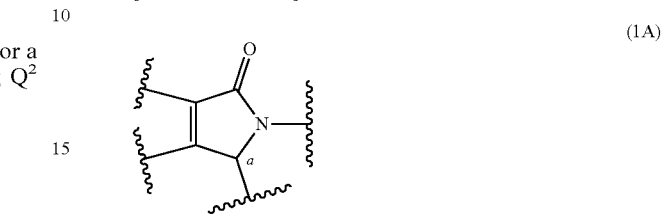
(1A)

$R^7$ represents a hydrogen atom, a halogen atom, or a $C_{1-6}$ alkyl group, $R^8$ represents a hydrogen atom, a halogen atom, a $C_{1-6}$ alkyl group, a halogeno $C_{1-6}$ alkyl group, a halogeno $C_{1-6}$ alkoxy group, or a $C_{3-8}$ cycloalkyl group, $R^9$ represents a hydrogen atom or a halogen atom, $R^{10}$ represents a hydrogen atom or a halogeno $C_{1-6}$ alkyl group, $R^{11}$ and $R^{12}$ each independently represent a $C_{1-6}$ alkyl group, $R^{13}$ represents a halogen atom, $Z^1$ and $Z^2$ each independently represent CH or a nitrogen atom, T represents CH or a nitrogen atom, $U^1$ and $U^2$ each independently represent a CH or a nitrogen atom, and $V^1$ and $V^2$ each independently represent a CH or a nitrogen atom.

[7] The compound according to any one of [1] to [5] or a pharmaceutically acceptable salt thereof, wherein ring $Q^2$ represents any one of formulas (7A) to (7C):

[Chemical Formula 8]

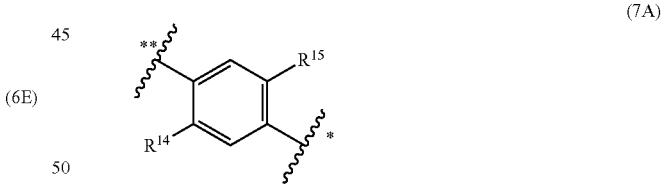
(7A)

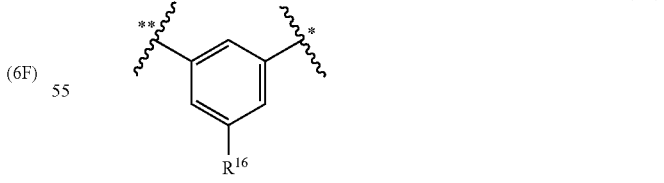
(7B)

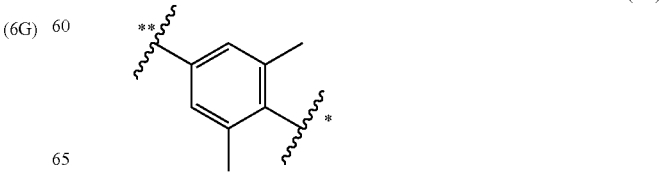
(7C)

wherein
* is bonded to W
** is bonded to the carbon atom represented by a,
R$^{14}$ represents a hydrogen atom, a fluorine atom, a chlorine atom, or a methyl group,
R$^{15}$ represents a hydrogen atom, a chlorine atom, a methyl group, an ethyl group, a trifluoromethyl group, a trifluoromethoxy group, a 4,4,4-trifluorobutoxy group, or a cyclopropyl group, and
R$^{16}$ represents a hydrogen atom or a trifluoromethyl group.

[8] The compound according to any one of [1] to [5] or a pharmaceutically acceptable salt thereof, wherein ring Q$^2$ represents any one of formulas (8A) to (8E):

[Chemical Formula 9]

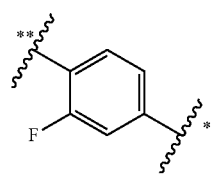
(8A)

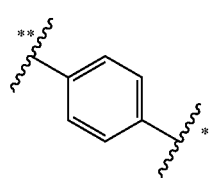
(8B)

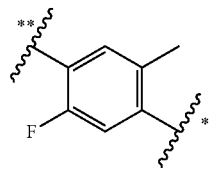
(8C)

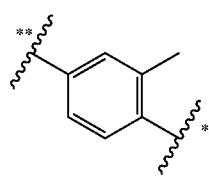
(8D)

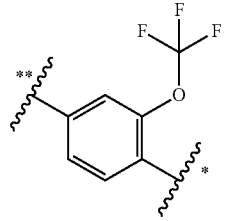
(8E)

wherein
* is bonded to W, and
** is bonded to the carbon atom represented by a.

[9] The compound according to any one of [1] to [8] or a pharmaceutically acceptable salt thereof, wherein W is a fluorine atom, a chlorine atom, an n-butyl group, an n-hexyl group, a trifluoromethyl group, a trifluoromethoxy group, or a 4,4,4-trifluorobutoxy group.

[10] The compound according to any one of [1] to [8] or a pharmaceutically acceptable salt thereof, wherein W represents formula (3A);
in formula (3A), Y is as defined above;
ring Q$^3$ represents any one of formulas (9A) to (9J):

[Chemical Formula 10]

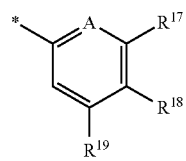
(9A)

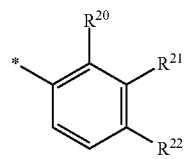
(9B)

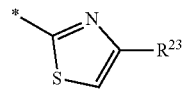
(9C)

(9D)

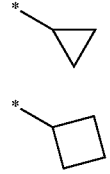
(9E)

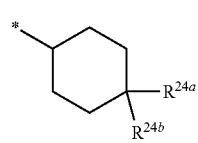
(9F)

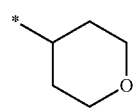
(9G)

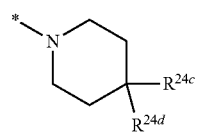
(9H)

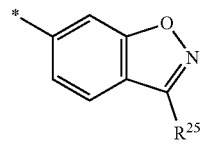
(9I)

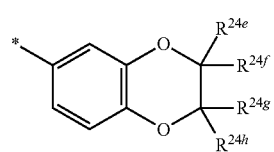
(9J)

wherein
* represents a bond,
R$^{17}$ and R$^{19}$ each independently represent a hydrogen atom, a halogen atom, a C$_{1-6}$ alkyl group, a halogeno C$_{1-6}$ alkyl group, or a halogeno C$_{1-6}$ alkoxy group, $R^{18}$ represents a hydrogen atom, a halogen atom, a halogeno $C_{1-6}$ alkyl group, a halogeno $C_{1-6}$ alkoxy group, a halogeno $C_{1-6}$ alkylsulfanyl group, or a halogeno $C_{1-6}$ alkylsulfonyl group, A represents CH or a nitrogen atom, $R^{20}$ represents a halogen atom, a $C_{1-6}$ alkyl group, a halogeno $C_{1-6}$ alkyl group, or a halogeno $C_{1-6}$ alkoxy group, $R^{21}$ represents a hydrogen atom or a halogen atom, $R^{22}$ represents a hydrogen atom, a halogeno $C_{1-6}$ alkyl group, or a halogeno $C_{1-6}$ alkoxy group, $R^{23}$ represents a halogeno $C_{1-6}$ alkyl group, $R^{24a}$ and $R^{24b}$ are identical and represent a halogen atom, $R^{24c}$ and $R^{24d}$ are identical and represent a halogen atom, $R^{24e}$, $R^{24f}$, $R^{24g}$, and $R^{24h}$ are identical and represent a halogen atom, and $R^{25}$ represents a halogeno $C_{1-6}$ alkyl group.

[11] The compound according to any one of [1] to [8] or a pharmaceutically acceptable salt thereof, wherein W represents formula (3A);

in formula (3A), Y is as defined above; and ring $Q^3$ represents any one of formulas (10A) to (1°C.):

[Chemical Formula 11]

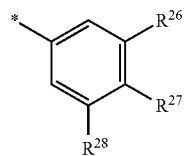
(10A)

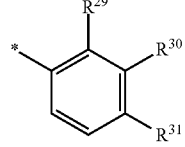
(10B)

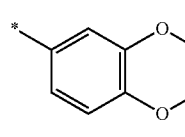
(10C)

wherein

\* represents a bond, $R^{26}$ and $R^{28}$ each independently represent a hydrogen atom, a chlorine atom, a methyl group, a trifluoromethyl group, or a trifluoromethoxy group, $R^{27}$ represents a hydrogen atom, a fluorine atom, a chlorine atom, a trifluoromethyl group, a trifluoromethoxy group, a trifluoromethylsulfanyl group, or a trifluoromethylsulfonyl group, $R^{29}$ represents a fluorine atom, a chlorine atom, a methyl group, a trifluoromethyl group, or a trifluoromethoxy group, $R^{30}$ represents a hydrogen atom or a chlorine atom, and $R^{31}$ represents a hydrogen atom, a trifluoromethyl group, or a trifluoromethoxy group.

[12] The compound according to any one of [1] to [8] or a pharmaceutically acceptable salt thereof, wherein W represents formula (3A);

in formula (3A), Y is as defined above; and ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group.

[13] The compound according to any one of [1] to [8] and [10] to [12] or a pharmaceutically acceptable salt thereof, wherein Y represents an oxygen atom, a single bond, a sulfur atom, —NH—, a methylene group, or any one of formulas (11A) to (11C):

[Chemical Formula 12]

(11A)

(11B)

(11C)

wherein

\* is bonded to ring $Q^3$,

\*\* is bonded to ring $Q^2$, and $R^{32}$ represents a hydrogen atom or a methyl group.

[14] The compound according to any one of [1] to [8] and [10] to [12] or a pharmaceutically acceptable salt thereof, wherein Y represents an oxygen atom or formula (12A):

[Chemical Formula 13]

(12A)

wherein \* is bonded to ring $Q^3$, and \*\* is bonded to ring $Q^2$.

[15] The compound according to any one of [1] to [8] and [10] to [12] or a pharmaceutically acceptable salt thereof, wherein Y is an oxygen atom.

[16] The compound according to [1] or a pharmaceutically acceptable salt thereof, wherein $R^1$ is a trifluoromethyl group, a 1,1-difluoroethyl group, a 1,1-difluoropropyl group, a cyclopropyl group, a 2-pyridyl group, or an oxazol-2-yl group;

ring Q represents either formula (4A) or (4B):

[Chemical Formula 14]

(4A)

(4B)

wherein
* represents a bond,
$R^5$ represents a hydrogen atom or a halogen atom, and
$R^6$ represents a halogen atom;
ring $Q^2$ represents any one of formulas (7A) to (7C):

[Chemical Formula 15]

(7A)

(7B)

(7C)

wherein
* is bonded to W,
** is bonded to the carbon atom represented by a,
$R^{14}$ represents a hydrogen atom, a fluorine atom, a chlorine atom, or a methyl group,
$R^{15}$ represents a hydrogen atom, a chlorine atom, a methyl group, an ethyl group, a trifluoromethyl group, a trifluoromethoxy group, a 4,4,4-trifluorobutoxy group, or a cyclopropyl group, and
$R^{16}$ represents a hydrogen atom or a trifluoromethyl group;
W is a fluorine atom, a chlorine atom, an n-butyl group, an n-hexyl group, a trifluoromethyl group, a trifluoromethoxy group, or a 4,4,4-trifluorobutoxy group, or W represents formula (3A);
ring $Q^3$ represents any one of formulas (10A) to (1° C.):

[Chemical Formula 16]

(10A)

(10B)

(10C)

wherein
* represents a bond,
$R^{26}$ and $R^{28}$ each independently represent a hydrogen atom, a chlorine atom, a methyl group, a trifluoromethyl group, or a trifluoromethoxy group,
$R^{27}$ represents a hydrogen atom, a fluorine atom, a chlorine atom, a trifluoromethyl group, a trifluoromethoxy group, a trifluoromethylsulfanyl group, or a trifluoromethylsulfonyl group,
$R^{29}$ represents a fluorine atom, a chlorine atom, a methyl group, a trifluoromethyl group, or a trifluoromethoxy group,
$R^{30}$ represents a hydrogen atom or a chlorine atom, and
$R^{31}$ represents a hydrogen atom, a trifluoromethyl group, or a trifluoromethoxy group; and
Y represents an oxygen atom, a single bond, a sulfur atom, —NH—, a methylene group, or any one of formulas (11A) to (11C):

[Chemical Formula 17]

(11A)

(11B)

(11C)

wherein

* is bonded to ring Q³,

** is bonded to ring Q², and

R³² represents a hydrogen atom or a methyl group.

[17] The compound according to [1] or a pharmaceutically acceptable salt thereof, wherein R¹ is a 1,1-difluoroethyl group;

ring Q represents formula (5A) or (5B):

[Chemical Formula 18]

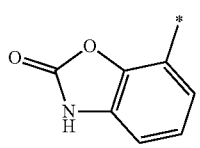
(5A)

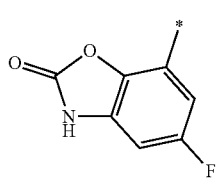
(5B)

wherein * represents a bond;

ring Q² represents any one of formulas (8A) to (8E):

[Chemical Formula 19]

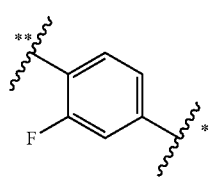
(8A)

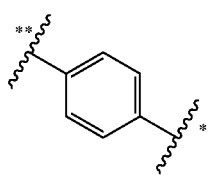
(8B)

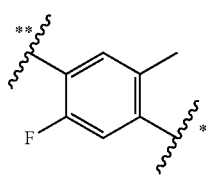
(8C)

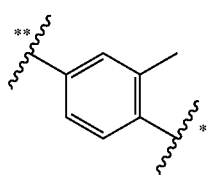
(8D)

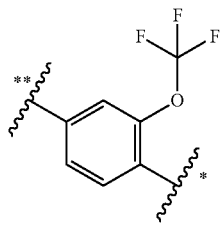
(8E)

wherein

* is bonded to W, and

** is bonded to the carbon atom represented by a;

W represents formula (3A);

ring Q³ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group; and Y is an oxygen atom.

[18] The compound or a pharmaceutically acceptable salt thereof, wherein the compound is any one selected from the group consisting of:

(−)-7-[5-(2,2-difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one, (−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one, (−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one, (−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one, (−)-7-[4-{4-[3-chloro-5-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one, (−)-7-{5-(2,2-difluoropropyl)-4-[3-(4-fluorophenoxy)phenyl]-6-oxo-1,4,5,6-tetrahydropyrrolo[3,4-c]pyrazol-3-yl}-1,3-benzoxazol-2(3H)-one, (−)-7-{4-[4-(4-chlorophenoxy)phenyl]-5-(2,2-difluoropropyl)-6-oxo-1,4,5,6-tetrahydropyrrolo[3,4-c]pyrazol-3-yl}-1,3-benzoxazol-2(3H)-one, and (−)-7-{4-[4-(4-chlorophenoxy)-2-fluorophenyl]-5-(2,2-difluoropropyl)-6-oxo-1,4,5,6-tetrahydropyrrolo[3,4-c]pyrazol-3-yl}-1,3-benzoxazol-2(3H)-one.

[19] An inhibitor of phosphatidylserine synthase 1 comprising the compound according to any one of [1] to [18] or a pharmaceutically acceptable salt thereof as an active substance.-

[20] A pharmaceutical composition comprising the compound according to any one of [1] to [18] or a pharmaceutically acceptable salt thereof, and a pharmaceutically acceptable carrier.

[21] The pharmaceutical composition according to [20], wherein the pharmaceutical composition is for treatment of cancer.

[22] The pharmaceutical composition according to [21], wherein the cancer is testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer.

[23] The pharmaceutical composition according to [21], wherein the cancer is testicular germ cell tumor, ovarian cancer, bladder cancer, lung cancer, breast cancer, or esophageal cancer.

[24] The pharmaceutical composition according to any one of [21] to [23], wherein the cancer is a cancer having a suppressed function of phosphatidylserine synthase 2.

[25] The pharmaceutical composition according to [24], wherein the suppressed function of phosphatidylserine synthase 2 is a homozygous deletion or heterozygous deletion of a gene encoding phosphatidylserine synthase 2, or a decreased expression of phosphatidylserine synthase 2.

[26] The pharmaceutical composition according to any one of [21] to [25], wherein the cancer is a cancer having LOH (loss of heterozygosity) of chromosome 11p15.5.

[27] A method for treating cancer, comprising administering the compound according to any one of [1] to [18] or a pharmaceutically acceptable salt thereof.

[28] The compound according to any one of [1] to [18] or a pharmaceutically acceptable salt thereof used as a medicament for treatment of cancer.

[29] Use of the compound according to any one of [1] to [18] or a pharmaceutically acceptable salt thereof for manufacturing a medicament for treatment of cancer.

[30] A method for predicting responsiveness to treatment of cancer with the compound according to any one of [1] to [18] or a pharmaceutically acceptable salt thereof, comprising using a biological sample derived from a test subject to detect the presence or absence of suppressed function of phosphatidylserine synthase 2 in the biological sample, and determining the test subject in which the suppressed function of phosphatidylserine synthase 2 is detected, as being responsive to treatment of cancer with the compound according to any one of [1] to [18] or a pharmaceutically acceptable salt thereof.

[31] A method for predicting responsiveness to treatment of cancer with the compound according to any one of [1] to [18] or a pharmaceutically acceptable salt thereof, comprising using a biological sample derived from a test subject to determine the test subject in which the suppressed function of phosphatidylserine synthase 2 is detected, as being responsive to treatment of cancer with the compound according to any one of [1] to [18] or a pharmaceutically acceptable salt thereof.

[32] A method for screening for a subject for treatment of cancer with the compound according to any one of [1] to [18] or a pharmaceutically acceptable salt thereof, comprising using a biological sample derived from a test subject to detect the presence or absence of suppressed function of phosphatidylserine synthase 2 in the biological sample, and screening for the test subject in which the suppressed function of phosphatidylserine synthase 2 is detected, as the subject for treatment of cancer with the compound according to any one of [1] to [18] or a pharmaceutically acceptable salt thereof.

[33] A method for screening for a subject for treatment of cancer with the compound according to any one of [1] to [18] or a pharmaceutically acceptable salt thereof, comprising using a biological sample derived from a test subject to screen for the test subject in which the suppressed function of phosphatidylserine synthase 2 is detected, as the subject for treatment of cancer with the compound according to any one of [1] to [18] or a pharmaceutically acceptable salt thereof.

[34] A method for treating cancer having a suppressed function of phosphatidylserine synthase 2, comprising using a biological sample derived from a test subject to detect the presence or absence of suppressed function of phosphatidylserine synthase 2 in the biological sample, and administering the compound according to any one of [1] to [18] or a pharmaceutically acceptable salt thereof to the test subject in which the suppressed function of phosphatidylserine synthase 2 is detected.

[35] A method for treating cancer having a suppressed function of phosphatidylserine synthase 2, comprising using a biological sample derived from a test subject to administer the compound according to any one of [1] to [18] or a pharmaceutically acceptable salt thereof to the test subject in which the suppressed function of phosphatidylserine synthase 2 is detected.

The present invention also relates to the following [A1] to [A64].

[A1] A compound represented by general formula (1) or a pharmaceutically acceptable salt thereof:

[Chemical Formula 20]

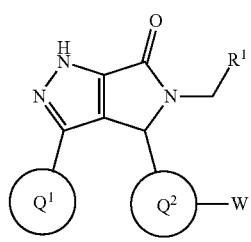

(1)

wherein $R^1$ represents a halogeno $C_{1-6}$ alkyl group, a $C_{3-8}$ cycloalkyl group, or a 5- or 6-membered aromatic heterocyclic group, ring Q represents any one of formulas (2A) to (2C):

[Chemical Formula 21]

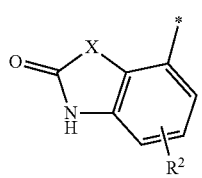

(2A)

-continued (2B)

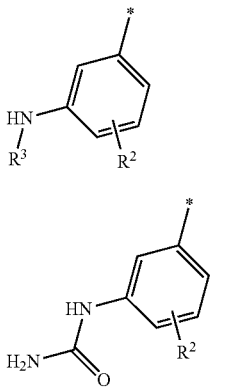

(2C)

wherein
* represents a bond,
X represents an oxygen atom, a sulfur atom, or —NH—,
R² represents a hydrogen atom, a halogen atom, or a phenoxy group, and
R³ represents a $C_{1-6}$ alkanoyl group,
ring Q² represents a phenylene group which may have 1 or 2 substituents independently selected from substituent group 1, a 6-membered aromatic heterocyclic group which may have 1 or 2 substituents independently selected from substituent group 1, a 5-membered aromatic heterocyclic group which may have a substituent selected from substituent group 1, or a 9-membered bicyclic aromatic heterocyclic group which may have a substituent selected from substituent group 1,
W is any one substituent selected from substituent group 1, or represents formula (3A):

[Chemical Formula 22]

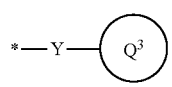
(3A)

wherein
* represents a bond,
Y represents an oxygen atom, a single bond, a sulfur atom, —NH—, *—O—R⁴—** (wherein * is bonded to ring Q² and ** is bonded to ring Q³), a $C_{1-6}$ alkylene group, a $C_{1-6}$ alkoxy $C_{1-6}$ alkylene group, or a halogeno $C_{1-6}$ alkylene group,
R⁴ represents a $C_{1-6}$ alkylene group, and
ring Q³ represents a phenyl group which may have 1 to 3 substituents independently selected from substituent group 2, a 6-membered aromatic heterocyclic group which may have 1 or 2 substituents independently selected from substituent group 2, a 5-membered aromatic heterocyclic group which may have 1 or 2 substituents independently selected from substituent group 2, a 3- to 8-membered saturated hydrocarbon ring group which may have 1 or 2 substituents independently selected from substituent group 2, a 6-membered saturated heterocyclic group which may have 1 or 2 substituents independently selected from substituent group 2, a 9-membered bicyclic aromatic heterocyclic group which may have a substituent selected from substituent group 2, or a 10-membered bicyclic partially unsaturated heterocyclic group which may have 1 to 4 substituents independently selected from substituent group 2;

substituent group 1 represents a group consisting of a halogen atom, a $C_{1-6}$ alkyl group, a halogeno $C_{1-6}$ alkyl group, a halogeno $C_{1-6}$ alkoxy group, and a $C_{3-8}$ cycloalkyl group; and substituent group 2 represents a group consisting of a halogen atom, a $C_{1-6}$ alkyl group, a halogeno $C_{1-6}$ alkyl group, a halogeno $C_{1-6}$ alkoxy group, a halogeno $C_{1-6}$ alkylsulfanyl group, and a halogeno $C_{1-6}$ alkylsulfonyl group;

wherein the compound represented by formula (1):

[Chemical Formula 23]

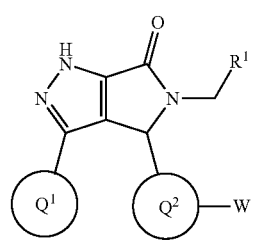
(1)

wherein R¹, Q¹, Q², and W are as defined above,
may include its tautomer, a compound represented by formula (1'):

[Chemical Formula 24]

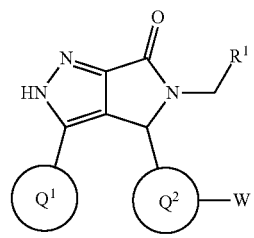
(1')

wherein R¹, Q¹, Q², and W are as defined above,
in any ratio, and
the ratio of the compound represented by formula (1) may be 100%, or the ratio of the compound represented by formula (1') may be 100%.

[A2] The compound according to [A1] or a pharmaceutically acceptable salt thereof, wherein R¹ is a trifluoromethyl group, a 1,1-difluoroethyl group, a 1,1-difluoropropyl group, a cyclopropyl group, a 2-pyridinyl group, or an oxazol-2-yl group.

[A3] The compound according to [A1] or a pharmaceutically acceptable salt thereof, wherein R¹ is a 1,1-difluoroethyl group.

[A4] The compound according to any one of [A1] to [A3] or a pharmaceutically acceptable salt thereof, wherein ring Q¹ represents either formula (4A) or (4B):

[Chemical Formula 25]

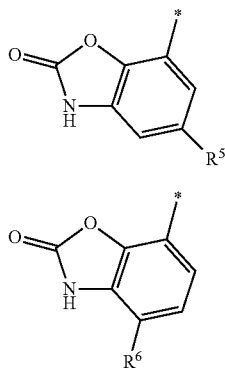

(4A)

(4B)

wherein
* represents a bond,
R⁵ represents a hydrogen atom or a halogen atom, and
R⁶ represents a halogen atom.

[A5] The compound according to any one of [A1] to [A3] or a pharmaceutically acceptable salt thereof, wherein ring $Q^1$ represents either formula (5A) or (5B):

[Chemical Formula 26]

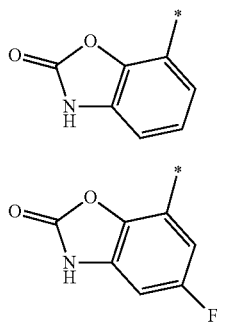

(5A)

(5B)

wherein * represents a bond.

[A6] The compound according to any one of [A1] to [A5] or a pharmaceutically acceptable salt thereof, wherein ring $Q^2$ represents any one of formulas (6A) to (6G):

[Chemical Formula 27]

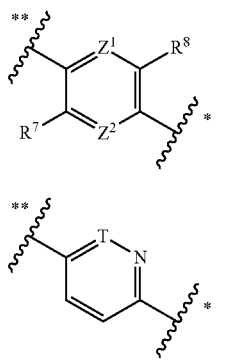

(6A)

(6B)

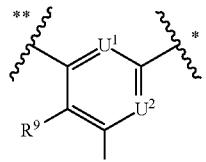

(6C)

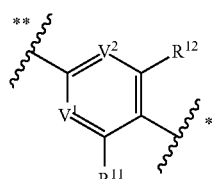

(6D)

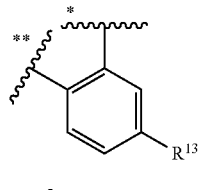

(6E)

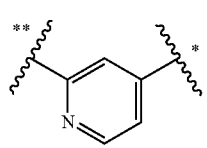

(6F)

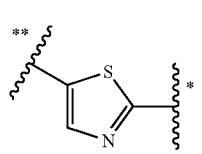

(6G)

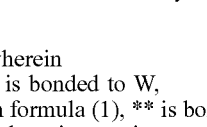

wherein
* is bonded to W,
in formula (1), ** is bonded to a carbon atom represented by a in a moiety represented by formula (1A) (hereinafter, referred to as "the carbon atom represented by a"):

[Chemical Formula 28]

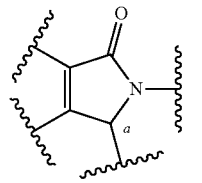

(1A)

$R^7$ represents a hydrogen atom, a halogen atom, or a $C_{1-6}$ alkyl group,
$R^1$ represents a hydrogen atom, a halogen atom, a $C_{1-6}$ alkyl group, a halogeno $C_{1-6}$ alkyl group, a halogeno $C_{1-6}$ alkoxy group, or a $C_{3-8}$ cycloalkyl group,
$R^9$ represents a hydrogen atom or a halogen atom,
$R^{10}$ represents a hydrogen atom or a halogeno $C_{1-6}$ alkyl group,
$R^{11}$ and $R^{12}$ each independently represent a $C_{1-6}$ alkyl group,
$R^{13}$ represents a halogen atom,
$Z^1$ and $Z^2$ each independently represent CH or a nitrogen atom, T represents CH or a nitrogen atom, U¹ and U² each independently represent a CH or a nitrogen atom, and V¹ and V² each independently represent a CH or a nitrogen atom.

[A7] The compound according to any one of [A1] to [A5] or a pharmaceutically acceptable salt thereof, wherein ring $Q^2$ represents any one of formulas (7A) to (7C):

[Chemical Formula 29]

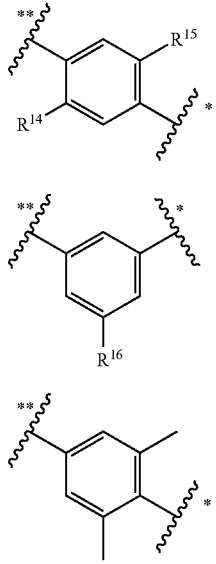

(7A)

(7B)

(7C)

wherein

* is bonded to W

** is bonded to the carbon atom represented by a, $R^{14}$ represents a hydrogen atom, a fluorine atom, a chlorine atom, or a methyl group, $R^{15}$ represents a hydrogen atom, a chlorine atom, a methyl group, an ethyl group, a trifluoromethyl group, a trifluoromethoxy group, a 4,4,4-trifluorobutoxy group, or a cyclopropyl group, and $R^{16}$ represents a hydrogen atom or a trifluoromethyl group.

[A8] The compound according to any one of [A1] to [A5] or a pharmaceutically acceptable salt thereof, wherein ring $Q^2$ represents any one of formulas (8A) to (8E):

[Chemical Formula 30]

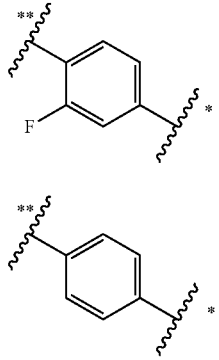

(8A)

(8B)

(8C)

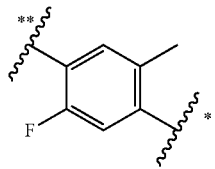

(8D)

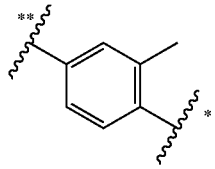

(8E)

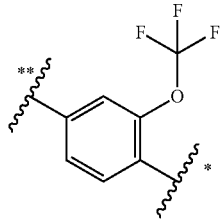

wherein

* is bonded to W, and

** is bonded to the carbon atom represented by a.

[A9] The compound according to any one of [A1] to [A8] or a pharmaceutically acceptable salt thereof, wherein W is a fluorine atom, a chlorine atom, an n-butyl group, an n-hexyl group, a trifluoromethyl group, a trifluoromethoxy group, or a 4,4,4-trifluorobutoxy group.

[A10] The compound according to any one of [A1] to [A8] or a pharmaceutically acceptable salt thereof, wherein W represents formula (3A);

in formula (3A), Y is as defined above;

ring $Q^3$ represents any one of formulas (9A) to (9J):

[Chemical Formula 31]

(9A)

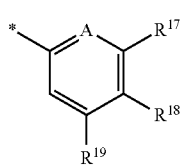

(9B)

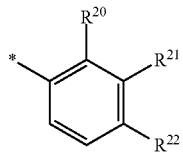

(9C)

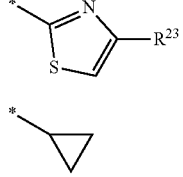

(9D)

-continued

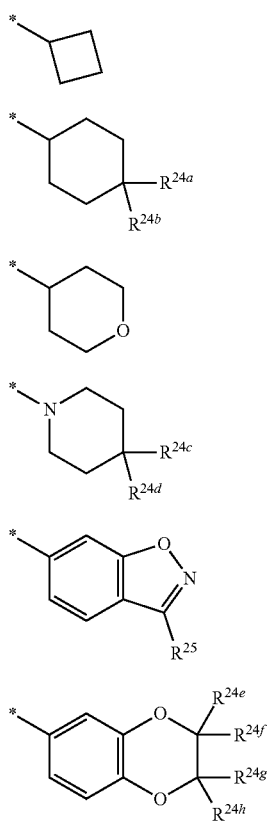

wherein

* represents a bond, $R^{17}$ and $R^{19}$ each independently represent a hydrogen atom, a halogen atom, a $C_{1-6}$ alkyl group, a halogeno $C_{1-6}$ alkyl group, or a halogeno $C_{1-6}$ alkoxy group, $R^{18}$ represents a hydrogen atom, a halogen atom, a halogeno $C_{1-6}$ alkyl group, a halogeno $C_{1-6}$ alkoxy group, a halogeno $C_{1-6}$ alkylsulfanyl group, or a halogeno $C_{1-6}$ alkylsulfonyl group, A represents CH or a nitrogen atom, $R^{20}$ represents a halogen atom, a $C_{1-6}$ alkyl group, a halogeno $C_{1-6}$ alkyl group, or a halogeno $C_{1-6}$ alkoxy group, $R^{21}$ represents a hydrogen atom or a halogen atom, $R^{22}$ represents a hydrogen atom, a halogeno $C_{1-6}$ alkyl group, or a halogeno $C_{1-6}$ alkoxy group, $R^{23}$ represents a halogeno $C_{1-6}$ alkyl group, $R^{24a}$ and $R^{24b}$ are identical and represent a halogen atom, $R^{24c}$ and $R^{24d}$ are identical and represent a halogen atom, $R^{24e}$, $R^{24f}$, $R^{24g}$, and $R^{24h}$ are identical and represent a halogen atom, and $R^{25}$ represents a halogeno $C_{1-6}$ alkyl group.

[A11] The compound according to any one of [A1] to [A8] or a pharmaceutically acceptable salt thereof, wherein W represents formula (3A);

in formula (3A), Y is as defined above; and ring $Q^3$ represents any one of formulas (10A) to (1° C.):

[Chemical Formula 32]

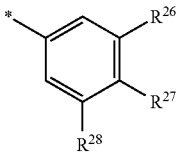

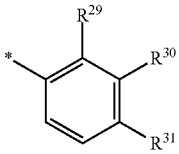

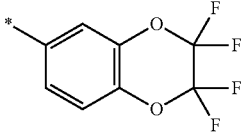

wherein

* represents a bond, $R^{26}$ and $R^{28}$ each independently represent a hydrogen atom, a chlorine atom, a methyl group, a trifluoromethyl group, or a trifluoromethoxy group, $R^{27}$ represents a hydrogen atom, a fluorine atom, a chlorine atom, a trifluoromethyl group, a trifluoromethoxy group, a trifluoromethylsulfanyl group, or a trifluoromethylsulfonyl group, $R^{29}$ represents a fluorine atom, a chlorine atom, a methyl group, a trifluoromethyl group, or a trifluoromethoxy group, $R^{30}$ represents a hydrogen atom or a chlorine atom, and $R^{31}$ represents a hydrogen atom, a trifluoromethyl group, or a trifluoromethoxy group.

[A12] The compound according to any one of [A1] to [A8] or a pharmaceutically acceptable salt thereof, wherein W represents formula (3A);

in formula (3A), Y is as defined above; and ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group.

[A13] The compound according to any one of [A1] to [A8] and [A10] to [A12] or a pharmaceutically acceptable salt thereof, wherein Y represents an oxygen atom, a single bond, a sulfur atom, —NH—, a methylene group, or any one of formulas (11A) to (11C):

[Chemical Formula 33]

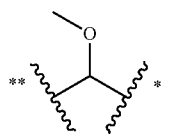
(11A)

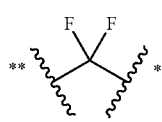
(11B)

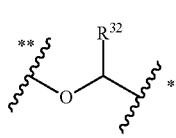
(11C)

wherein

* is bonded to ring $Q^3$,

** is bonded to ring $Q^2$, and $R^{32}$ represents a hydrogen atom or a methyl group.

[A14] The compound according to any one of [A1] to [A8] and [A10] to [A12] or a pharmaceutically acceptable salt thereof, wherein Y represents an oxygen atom or formula (12A):

[Chemical Formula 34]

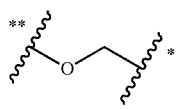
(12A)

wherein * is bonded to ring $Q^3$, and ** is bonded to ring $Q^2$.

[A15] The compound according to any one of [A1] to [A8] and [A10] to [A12] or a pharmaceutically acceptable salt thereof, wherein Y is an oxygen atom.

[A16] The compound according to [A1] or a pharmaceutically acceptable salt thereof, wherein $R^1$ is a trifluoromethyl group, a 1,1-difluoroethyl group, a 1,1-difluoropropyl group, a cyclopropyl group, a 2-pyridyl group, or an oxazol-2-yl group;

ring Q represents either formula (4A) or (4B):

[Chemical Formula 35]

(4A)

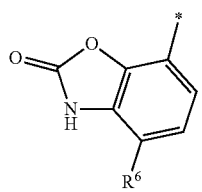
(4B)

wherein

* represents a bond, $R^5$ represents a hydrogen atom or a halogen atom, and $R^6$ represents a halogen atom;

ring $Q^2$ represents any one of formulas (7A) to (7C):

[Chemical Formula 36]

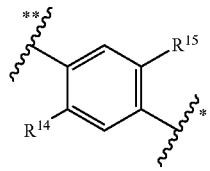
(7A)

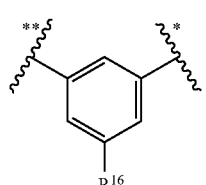
(7B)

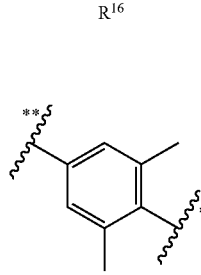
(7C)

wherein

* is bonded to W,

** is bonded to the carbon atom represented by a, $R^{14}$ represents a hydrogen atom, a fluorine atom, a chlorine atom, or a methyl group, $R^{15}$ represents a hydrogen atom, a chlorine atom, a methyl group, an ethyl group, a trifluoromethyl group, a trifluoromethoxy group, a 4,4,4-trifluorobutoxy group, or a cyclopropyl group, and $R^{16}$ represents a hydrogen atom or a trifluoromethyl group;

W is a fluorine atom, a chlorine atom, an n-butyl group, an n-hexyl group, a trifluoromethyl group, a trifluoromethoxy group, or a 4,4,4-trifluorobutoxy group, or W represents formula (3A);

ring Q³ represents any one of formulas (10A) to (1°C.):

[Chemical Formula 37]

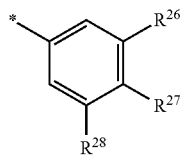
(10A)

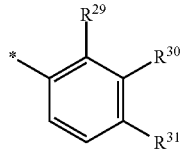
(10B)

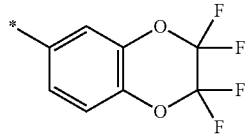
(10C)

wherein
* represents a bond,
R²⁶ and R²⁸ each independently represent a hydrogen atom, a chlorine atom, a methyl group, a trifluoromethyl group, or a trifluoromethoxy group,
R²⁷ represents a hydrogen atom, a fluorine atom, a chlorine atom, a trifluoromethyl group, a trifluoromethoxy group, a trifluoromethylsulfanyl group, or a trifluoromethylsulfonyl group,
R²⁹ represents a fluorine atom, a chlorine atom, a methyl group, a trifluoromethyl group, or a trifluoromethoxy group,
R³⁰ represents a hydrogen atom or a chlorine atom, and
R³¹ represents a hydrogen atom, a trifluoromethyl group, or a trifluoromethoxy group; and
Y represents an oxygen atom, a single bond, a sulfur atom, —NH—, a methylene group, or any one of formulas (11A) to (11C):

[Chemical Formula 38]

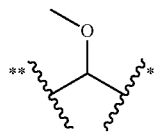
(11A)

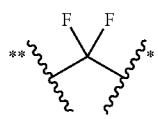
(11B)

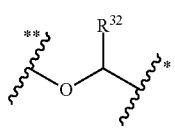
(11C)

wherein
* is bonded to ring Q³,
** is bonded to ring Q², and
R³² represents a hydrogen atom or a methyl group.

[A17] The compound according to [A1] or a pharmaceutically acceptable salt thereof, wherein
R¹ is a 1,1-difluoroethyl group;
ring Q represents formula (5A) or (5B):

[Chemical Formula 39]

(5A)

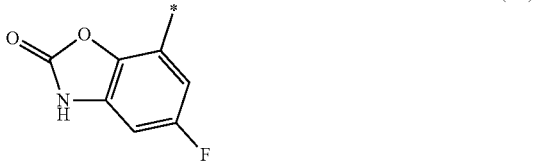
(5B)

wherein * represents a bond;
ring Q² represents any one of formulas (8A) to (8E):

[Chemical Formula 40]

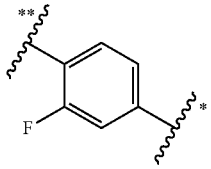
(8A)

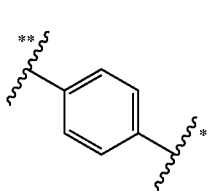
(8B)

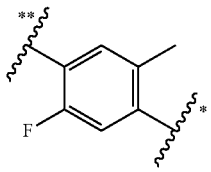
(8C)

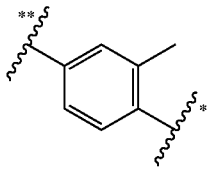
(8D)

-continued (8E)

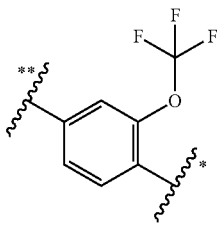

wherein
* is bonded to W, and
** is bonded to the carbon atom represented by a;
W represents formula (3A);
ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group; and Y is an oxygen atom.

[A18] The compound according to [A1] or a pharmaceutically acceptable salt thereof, wherein the compound is any one selected from the group consisting of:
(−)-7-[5-(2,2-difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one,
(−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
(−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one,
(−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one,
(−)-7-[4-{4-[3-chloro-5-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one,
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
(−)-7-{5-(2,2-difluoropropyl)-4-[3-(4-fluorophenoxy)phenyl]-6-oxo-1,4,5,6-tetrahydropyrrolo[3,4-c]pyrazol-3-yl}-1,3-benzoxazol-2(3H)-one,
(−)-7-{4-[4-(4-chlorophenoxy)phenyl]-5-(2,2-difluoropropyl)-6-oxo-1,4,5,6-tetrahydropyrrolo[3,4-c]pyrazol-3-yl}-1,3-benzoxazol-2(3H)-one, and
(−)-7-{4-[4-(4-chlorophenoxy)-2-fluorophenyl]-5-(2,2-difluoropropyl)-6-oxo-1,4,5,6-tetrahydropyrrolo[3,4-c]pyrazol-3-yl}-1,3-benzoxazol-2(3H)-one.

[A19]
(−)-7-[4-{4-[3,5-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1] or a pharmaceutically acceptable salt thereof,
wherein
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 41]

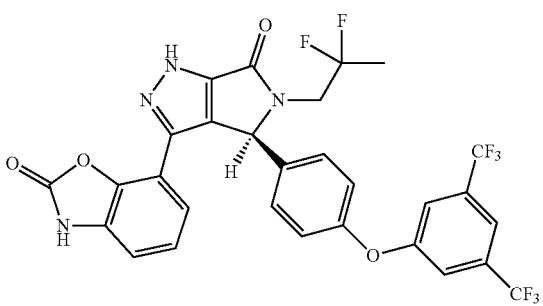

(13A)

may include its tautomer,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 42]

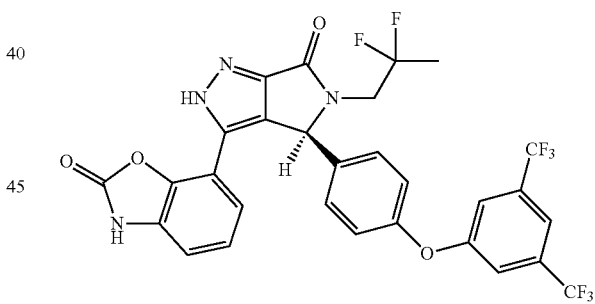

(13B)

in any ratio, and
the ratio of the compound represented by formula (13A) may be 100%, or the ratio of the compound represented by formula (13B) may be 100%.

[A20]
(−)-7-[4-{4-[3,5-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1] or a pharmaceutically acceptable salt thereof,
wherein
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 43]

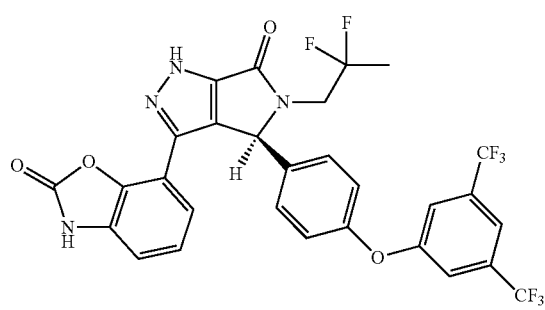

(13A)

does not include its tautomer,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 44]

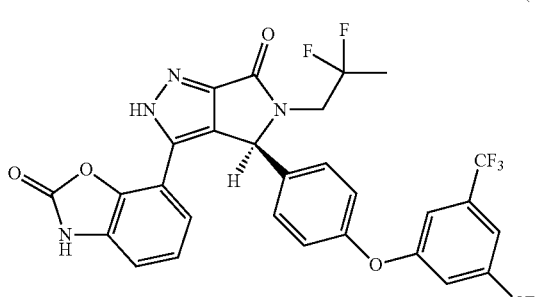

(13B)

[A21]
7-[(4S)-4-{4-[3,5-Bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to [A1] or a pharmaceutically acceptable salt thereof, wherein
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 45]

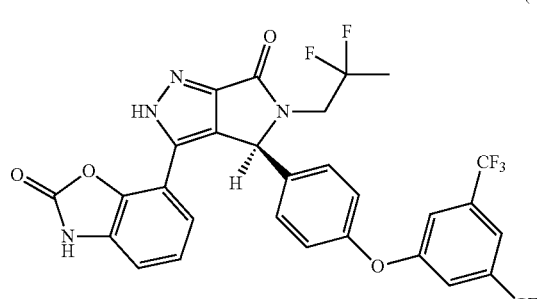

(13B)

may include its tautomer,
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 46]

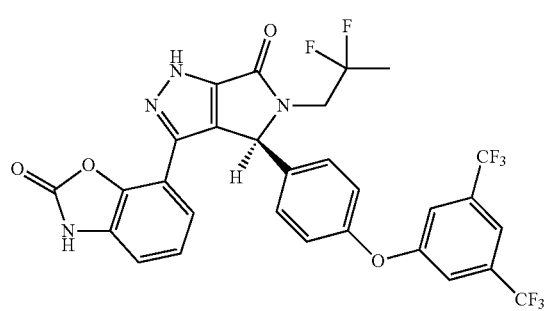

(13A)

in any ratio, and
the ratio of the compound represented by formula (13A) may be 100%, or the ratio of the compound represented by formula (13B) may be 100%.

[A22]
7-[(4S)-4-{4-[3,5-Bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to [A1] or a pharmaceutically acceptable salt thereof, wherein
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 47]

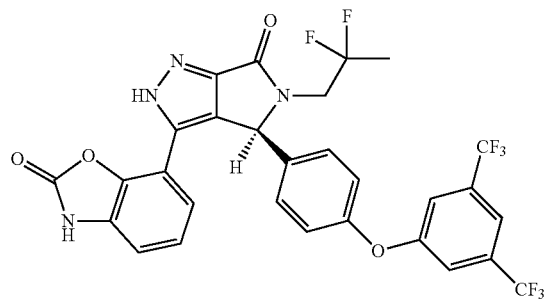

(13B)

does not include its tautomer,
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 48]

(13A)

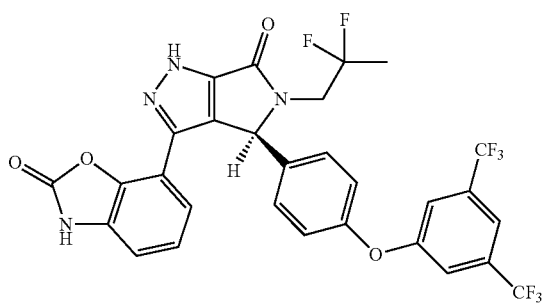

[A23] A 2-methylpropane-2-amine salt of (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1],
wherein
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 49]

(13A)

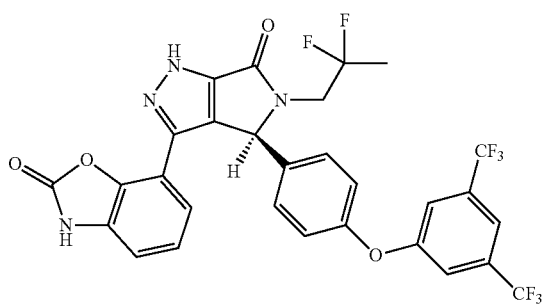

may include its tautomer,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 50]

(13B)

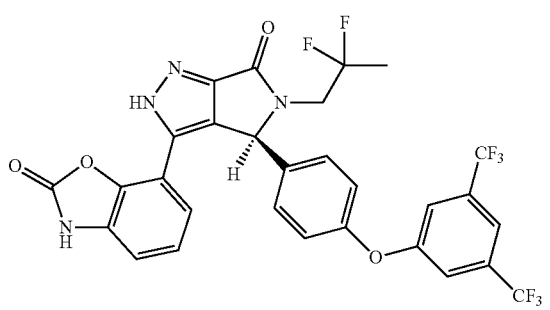

in any ratio, and
the ratio of the compound represented by formula (13A) may be 100%, or the ratio of the compound represented by formula (13B) may be 100%.

[A24] A 2-methylpropane-2-amine salt of (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1],
wherein
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 51]

(13A)

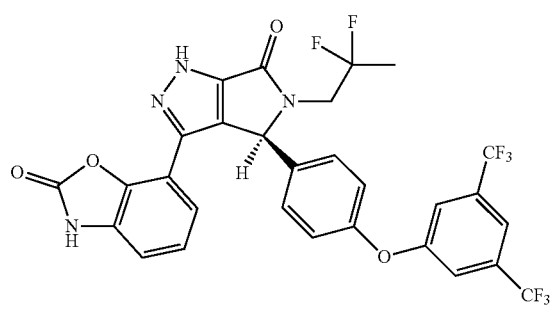

does not include its tautomer,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 52]

(13B)

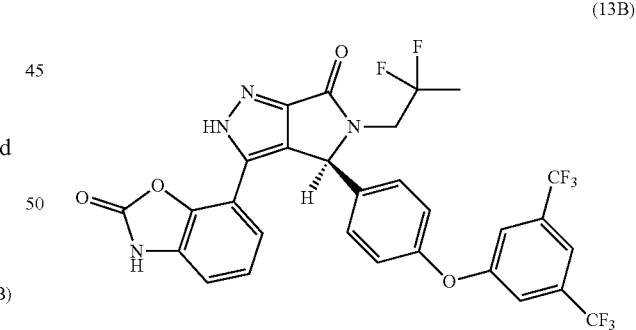

[A25] A 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to [A1],
wherein
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 53]

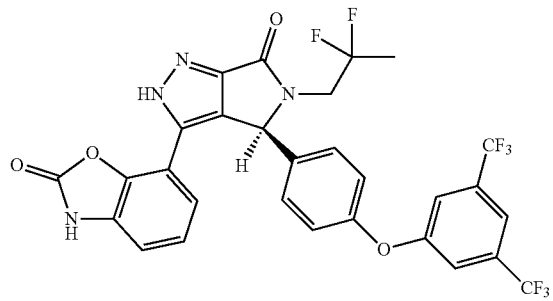

(13B)

may include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 54]

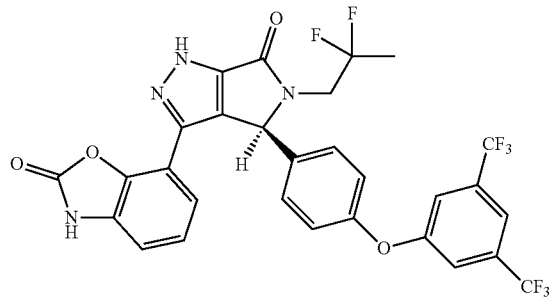

(13A)

in any ratio, and the ratio of the compound represented by formula (13A) may be 100%, or the ratio of the compound represented by formula (13B) may be 100%.

[A26] A 2-methylpropane-2-amine salt of
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to [A1],
wherein
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 55]

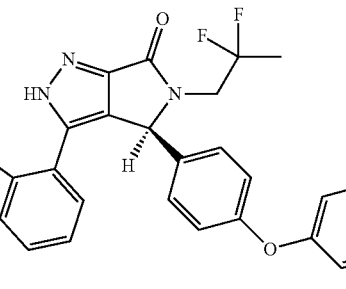

(13B)

does not include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 56]

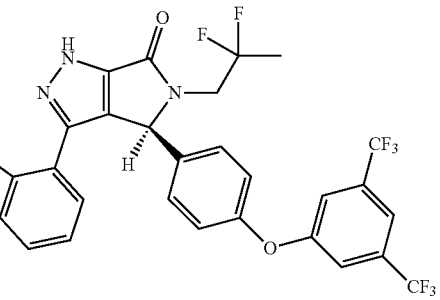

(13A)

[A27] An isonicotinamide adduct of
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1].

[A28]
(−)-7-[5-(2,2-Difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one according to [A1] or a pharmaceutically acceptable salt thereof.

[A29] A 2-methylpropane-2-amine salt of
(−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one according to [A1].

[A30] An isonicotinamide adduct of
(−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one according to [A1].

[A31]
(−)-7-[5-(2,2-Difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one according to [A1] or a pharmaceutically acceptable salt thereof.

[A32] A 2-methylpropane-2-amine salt of (−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one according to [A1].

[A33]
(−)-7-[4-{4-[3-Chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1] or a pharmaceutically acceptable salt thereof.

[A34] A 2-methylpropane-2-amine salt of (−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1].

[A35] An isonicotinamide adduct of (−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1].

[A36]
(−)-7-[5-(2,2-Difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one according to [A1] or a pharmaceutically acceptable salt thereof.

[A37] A 2-methylpropane-2-amine salt of (−)-7-[5-(2,2-difluoropropyl)-6-oxo-4-{4-[4-(trifluoromethoxy)phenoxy]phenyl}-1,4,5,6-tetra hydropyrrolo[3,4-c]pyrazol-3-yl]-1,3-benzoxazol-2(3H)-one according to [A1].

[A38] A crystal of a 2-methylpropane-2-amine salt of (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2 in a powder X-ray diffraction diagram obtained by irradiation with copper Kα, radiation (λ=1.54 angstrom), wherein
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 57]

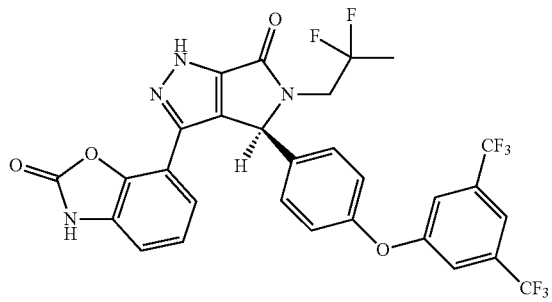

(13A)

does not include its tautomer,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 58]

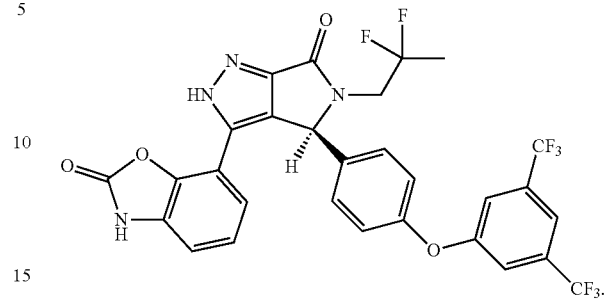

(13B)

[A39] A crystal of a 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2 in a powder X-ray diffraction diagram obtained by irradiation with copper Kα, radiation (κ=1.54 angstrom), wherein
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

[Chemical Formula 59]

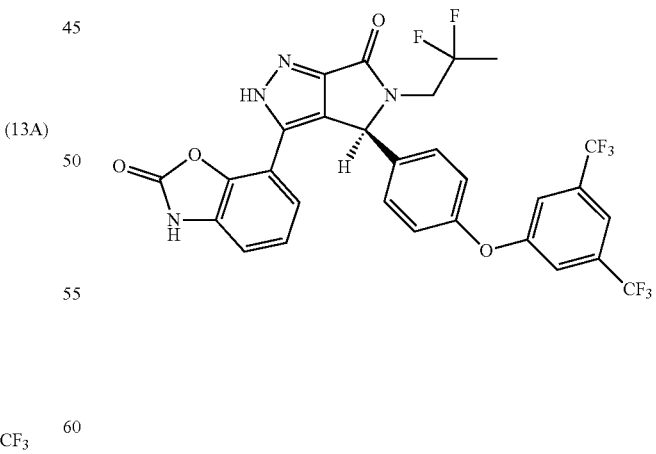

(13B)

does not include its tautomer,
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

[Chemical Formula 60]

(13A)

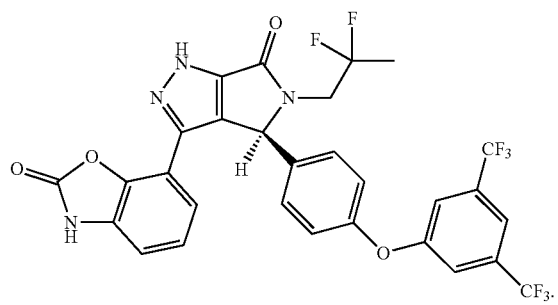

[A40] A crystal of an isonicotinamide adduct of (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 3.46±0.2, 4.54±0.2, 6.96±0.2, 10.54±0.2, 11.74±0.2, 13.96±0.2, 17.98±0.2, 20.86±0.2, 24.70±0.2, and 26.64±0.2 in a powder X-ray diffraction diagram obtained by irradiation with copper Kα, radiation (λ=1.54 angstrom).

[A41] A crystal of a 2-methylpropane-2-amine salt of (−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 6.92±0.2, 10.42±0.2, 12.96±0.2, 15.60±0.2, 17.58±0.2, 18.12±0.2, 19.22±0.2, 19.80±0.2, 21.72±0.2, and 22.26±0.2 in a powder X-ray diffraction diagram obtained by irradiation with copper Kα, radiation (λ=1.54 angstrom).

[A42] A crystal of an isonicotinamide adduct of (−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 6.58±0.2, 8.80±0.2, 11.62±0.2, 15.34±0.2, 17.14±0.2, 19.02±0.2, 20.06±0.2, 22.36±0.2, 23.82±0.2, and 24.58±0.2 in a powder X-ray diffraction diagram obtained by irradiation with copper Kα, radiation (λ=1.54 angstrom).

[A43] A crystal of a 2-methylpropane-2-amine salt of (−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one of [A1], wherein the crystal has at least five peaks at diffraction angles (2θ) selected from 8.42±0.2, 9.92±0.2, 12.62±0.2, 15.40±0.2, 15.96±0.2, 18.36±0.2, 19.90±0.2, 21.64±0.2, 22.96±0.2, and 23.74±0.2 in a powder X-ray diffraction diagram obtained by irradiation with copper Kα, radiation (λ=1.54 angstrom).

[A44] A crystal of a 2-methylpropane-2-amine salt of (−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 10.12±0.2, 12.80±0.2, 15.66±0.2, 17.94±0.2, 18.70±0.2, 19.64±0.2, 21.36±0.2, 22.42±0.2, 22.98±0.2, and 23.46±0.2 in a powder X-ray diffraction diagram obtained by irradiation with copper Kα, radiation (λ=1.54 angstrom).

[A45] A crystal of an isonicotinamide adduct of (−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to [A1], wherein the crystal has at least five peaks at diffraction angles (2θ) selected from 6.60±0.2, 9.18±0.2, 15.08±0.2, 17.88±0.2, 18.80±0.2, 20.02±0.2, 21.26±0.2, 22.36±0.2, 23.78±0.2, and 25.20±0.2 in a powder X-ray diffraction diagram obtained by irradiation with copper Kα, radiation (λ=1.54 angstrom).

[A46] A crystal of a 2-methylpropane-2-amine salt of (−)-7-[5-(2,2-difluoropropyl)-6-oxo-4-{4-[4-(trifluoromethoxy)phenoxy]phenyl}-1,4,5,6-tetra hydropyrrolo[3,4-c]pyrazol-3-yl]-1,3-benzoxazol-2(3H)-one according to [A1], wherein the crystal has at least five peaks at diffraction angles (2θ) selected from 10.52±0.2, 15.88±0.2, 16.52±0.2, 18.00±0.2, 19.96±0.2, and 22.52±0.2 in a powder X-ray diffraction diagram obtained by irradiation with copper Kα, radiation (λ=1.54 angstrom).

[A47] An inhibitor of phosphatidylserine synthase 1 comprising the compound according to any one of [A1] to [A37] or a pharmaceutically acceptable salt thereof or the crystal according to any one of [A38] to [A46] as an active substance.

[A48] A pharmaceutical composition comprising the compound according to any one of [A1] to [A37] or a pharmaceutically acceptable salt thereof or the crystal according to any one of [A38] to [A46], and a pharmaceutically acceptable carrier.

[A49] The pharmaceutical composition according to [A48], wherein the pharmaceutical composition is for treatment of cancer.

[A50] The pharmaceutical composition according to [A49], wherein the cancer is testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer.

[A51] The pharmaceutical composition according to [A49], wherein the cancer is ovarian cancer, lung cancer, breast cancer, prostate cancer, stomach cancer, melanoma, bowel cancer, blood cancer, or pancreatic cancer.

[A52] The pharmaceutical composition according to [A49], wherein the cancer is breast cancer, stomach cancer, melanoma, bowel cancer, or blood cancer.

[A53] The pharmaceutical composition according to any one of [A49] to [A52], wherein the cancer is a cancer having a suppressed function of phosphatidylserine synthase 2.

[A54] The pharmaceutical composition according to [A53], wherein the suppressed function of phosphatidylserine synthase 2 is a homozygous deletion or heterozygous deletion of a gene encoding phosphatidylserine synthase 2, or a decreased expression of phosphatidylserine synthase 2.

[A55] The pharmaceutical composition according to any one of [A49] to [A54], wherein the cancer is a cancer having LOH (loss of heterozygosity) of chromosome 11p15.5.

[A56] A method for treating cancer, comprising administering the compound according to any one of [A1] to [A37] or a pharmaceutically acceptable salt thereof or the crystal according to any one of [A38] to [A46].

[A57] The compound according to any one of [A1] to [A37] or a pharmaceutically acceptable salt thereof or the crystal according to any one of [A38] to [A46], used as a medicament for treatment of cancer.

[A58] Use of the compound according to any one of [A1] to [A37] or a pharmaceutically acceptable salt thereof or the crystal according to any one of [A38] to [A46] for manufacturing a medicament for treatment of cancer.

[A59] A method for predicting responsiveness to treatment of cancer with the compound according to any one of [A1] to [A37] or a pharmaceutically acceptable salt thereof or the crystal according to any one of [A38] to [A46], comprising using a biological sample derived from a test subject to detect the presence or absence of suppressed function of phosphatidylserine synthase 2 in the biological sample, and determining the test subject in which the suppressed function of phosphatidylserine synthase 2 is detected, as being responsive to treatment of cancer with the compound according to any one of [A1] to [A37] or a pharmaceutically acceptable salt thereof or the crystal according to any one of [A38] to [A46].

[A60] A method for predicting responsiveness to treatment of cancer with the compound according to any one of [A1] to [A37] or a pharmaceutically acceptable salt thereof or the crystal according to any one of [A38] to [A46], comprising using a biological sample derived from a test subject to determine the test subject in which the suppressed function of phosphatidylserine synthase 2 is detected, as being responsive to treatment of cancer with the compound according to any one of [A1] to [A37] or a pharmaceutically acceptable salt thereof or the crystal according to any one of [A38] to [A46].

[A61] A method for screening a subject for treatment of cancer with the compound according to any one of [A1] to [A37] or a pharmaceutically acceptable salt thereof or the crystal according to any one of [A38] to [A46], comprising using a biological sample derived from a test subject to detect the presence or absence of suppressed function of phosphatidylserine synthase 2 in the biological sample, and screening the test subject in which the suppressed function of phosphatidylserine synthase 2 is detected, as the subject for treatment of cancer with the compound according to any one of [A1] to [A37] or a pharmaceutically acceptable salt thereof or the crystal according to any one of [A38] to [A46].

[A62] A method for screening a subject for treatment of cancer with the compound according to any one of [A1] to [A37] or a pharmaceutically acceptable salt thereof or the crystal according to any one of [A38] to [A46], comprising using a biological sample derived from a test subject to screen the test subject in which the suppressed function of phosphatidylserine synthase 2 is detected, as the subject for treatment of cancer with the compound according to any one of [A1] to [A37] or a pharmaceutically acceptable salt thereof or the crystal according to any one of [A38] to [A46].

[A63] A method for treating cancer having a suppressed function of phosphatidylserine synthase 2, comprising using a biological sample derived from a test subject to detect the presence or absence of suppressed function of phosphatidylserine synthase 2 in the biological sample, and administering the compound according to any one of [A1] to [A37] or a pharmaceutically acceptable salt thereof or the crystal according to any one of [A38] to [A46] to the test subject in which the suppressed function of phosphatidylserine synthase 2 is detected.

[A64] A method for treating cancer having a suppressed function of phosphatidylserine synthase 2, comprising using a biological sample derived from a test subject to administer the compound according to any one of [A1] to [A37] or a pharmaceutically acceptable salt thereof or the crystal according to any one of [A38] to [A46] to the test subject in which the suppressed function of phosphatidylserine synthase 2 is detected.

Advantageous Effects of Invention

The compound of the present invention or a pharmaceutically acceptable salt thereof has an inhibitory effect on PSS1. That is, the compound of the present invention or a pharmaceutically acceptable salt thereof can be used as a PSS1 inhibitor, and can be particularly preferably used for treatment of PSS2 function-suppressed cancers by administering to mammals (e.g., human, cattle, horses, or pigs) or birds (e.g., chicken) as a pharmaceutical composition further containing a pharmaceutically acceptable carrier. Examples of PSS2 function-suppressed cancers include testicular germ cell tumor, ovarian cancer, bladder cancer, lung cancer, breast cancer, prostate cancer, stomach cancer, melanoma, bowel cancer, blood cancer, pancreatic cancer, and esophageal cancer.

DESCRIPTION OF EMBODIMENTS

Figure 1:
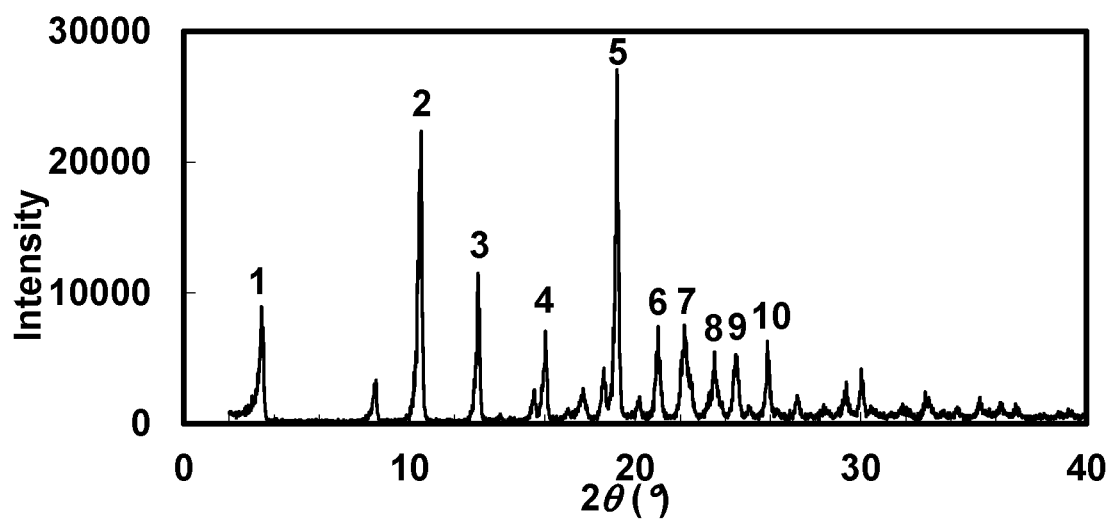
FIG. 1 is a powder X-ray diffraction diagram of the crystal obtained in Example 96. The ordinate indicates the diffraction intensity (Intensity) in units of counts/second (cps), and the abscissa indicates the value of diffraction angle 2θ.

Unless otherwise defined, all technical and scientific terms used herein have the same meaning as is generally understood by those skilled in the art to which the present invention pertains.

In the present invention, the "halogen atom" is a fluorine atom, a chlorine atom, a bromine atom, or an iodine atom.

In the present invention, the "$C_{1-6}$ alkyl group" refers to a linear or branched alkyl group having 1 to 6 carbon atoms. Examples thereof include a methyl group, an ethyl group, an n-propyl group, an isopropyl group, an n-butyl group, a sec-butyl group, a tert-butyl group, an n-pentyl group, an isopentyl group, a 2-methylbutyl group, a neopentyl group, a 1-ethylpropyl group, an n-hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group.

In the present invention, the "$C_{1-6}$ alkoxy group" refers to a group in which the above "$C_{1-6}$ alkyl group" is bonded to an oxygen atom. Examples thereof include a methoxy group, an ethoxy group, an n-propoxy group, an isopropoxy group, an n-butoxy group, a sec-butoxy group, a tert-butoxy group, an n-pentoxy group, an isopentoxy group, a 2-methylbutoxy group, and an n-hexyloxy group.

In the present invention, the "halogeno $C_{1-6}$ alkyl group" refers to a group in which one to three hydrogen atoms of the above "$C_{1-6}$ alkyl group" are substituted with the above "halogen atom". Examples thereof include a fluoromethyl group, a difluoromethyl group, a trifluoromethyl group, a chloromethyl group, a dichloromethyl group, a trichloromethyl group, a 1-fluoroethyl group, a 1-chloroethyl group, a 2-fluoroethyl group, a 1,1-difluoroethyl group, a 1,1-difluoropropyl group, a 1,2-difluoropropyl group, and a 2,2,2-trifluoroethyl group.

In the present invention, the "halogeno $C_{1-6}$ alkylsulfonyl group" refers to a group in which the above "halogeno $C_{1-6}$ alkyl group" is bonded to a sulfur atom of a sulfonyl group. Examples thereof include a trifluoromethylsulfonyl group, a 1,1-difluoroethylsulfonyl group, a 2,2,2-trifluoroethylsulfonyl group, and a 3,3,3-trifluoropropylsulfonyl group.

In the present invention, the "$C_{1-6}$ alkylene group" refers to a linear or branched alkylene group having 1 to 6 carbon atoms. Examples thereof include a methylene group, an ethylene group [—$(CH_2)_2$—], a trimethylene group [—$(CH_2)_3$—], a tetramethylene group, a pentamethylene group, a hexamethylene group, a methylmethylene group [—$CH(CH_3)$—], a methylethylene group [—$CH(CH_3)CH_2$— or —$CH_2CH(CH_3)$—], an ethylethylene group [—$CH(CH_2CH_3)CH_2$— or —$CH_2CH(CH_2CH_3)$—], a 1,2-dimethylethylene group [—$CH(CH_3)CH(CH_3)$—], and a 1,1,2,2-tetramethylethylene group [—$C(CH_3)_2C(CH_3)_2$—].

In the present invention, the "halogeno $C_{1-6}$ alkoxy group" refers to a group in which one to three hydrogen atoms of the above "$C_{1-6}$ alkoxy group" are substituted with the above "halogen atom". Examples thereof include a fluoromethoxy group, a difluoromethoxy group, a trifluoromethoxy group, a chloromethoxy group, a dichloromethoxy group, a 1-fluoroethoxy group, a 1-chloroethoxy group, a 2-fluoroethoxy group, a 1,2-difluoropropoxy group, and a 4,4,4-trifluorobutoxy group.

In the present invention, the "$C_{1-6}$ alkanoyl group" refers to a group in which the following "$C_{1-5}$ alkyl group" is bonded to a carbon atom of a carbonyl group. Examples thereof include an acetyl group, a propionyl group, a butyryl group, an isobutyryl group, a pivaloyl group, a valeryl group, an isovaleryl group, and a hexanoyl group.

In the present invention, the "$C_{1-5}$ alkyl group" refers to a linear or branched alkyl group having 1 to 5 carbon atoms. Examples thereof include a methyl group, an ethyl group, an n-propyl group, an isopropyl group, an n-butyl group, a sec-butyl group, a tert-butyl group, an n-pentyl group, an isopentyl group, a 2-methylbutyl group, a neopentyl group, and a 1-ethylpropyl group.

In the present invention, a "$C_{1-6}$ alkoxy $C_{1-6}$ alkylene group" refers to a group in which a hydrogen atom of the above "$C_{1-6}$ alkylene group" is substituted with the above "$C_{1-6}$ alkoxy group". Examples thereof include substituents shown in the following formula:

[Chemical Formula 61]

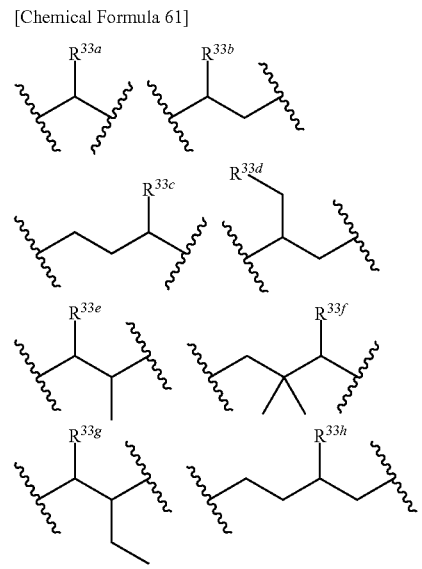

wherein $R^{33a}$, $R^{33b}$, $R^{33c}$, $R^{33d}$, $R^{33e}$, $R^{33f}$, $R^{33g}$ and $R^{33h}$ each independently represent a $C_{1-6}$ alkoxy group.

In the present invention, the "halogeno $C_{1-6}$ alkylene group" refers to a group in which one or two hydrogen atoms of the above "$C_{1-6}$ alkylene group" are substituted with the above "halogen atom". Examples thereof include substituents shown in the following formula:

[Chemical Formula 62]

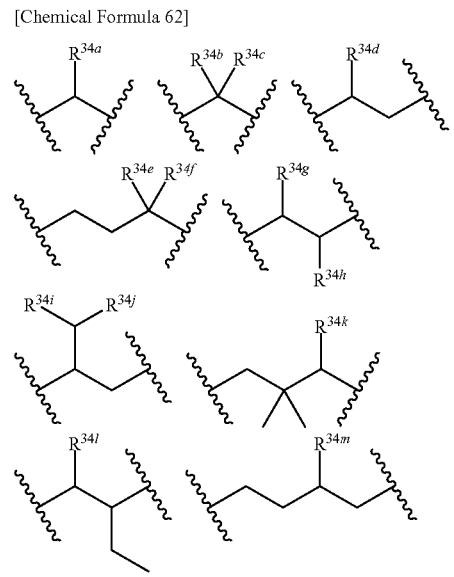

wherein $R^{34a}$, $R^{34b}$, $R^{34c}$, $R^{34d}$, $R^{34e}$, $R^{34f}$, $R^{34g}$, $R^{34h}$, $R^{34i}$, $R^{34j}$, $R^{34k}$, $R^{34l}$, and $R^{34m}$ each independently represent a halogen atom.

In the present invention, the "halogeno $C_{1-6}$ alkylsulfanyl group" refers to a group in which a hydrogen atom of a sulfanyl group (mercapto group) is substituted with the above "halogeno $C_{1-6}$ alkyl group". Examples thereof include a trifluoromethylsulfanyl group, a 2,2,2-trifluoroethylsulfanyl group, and a 3-chloropropylsulfanyl group.

In the present invention, the "phenyl $C_{1-6}$ alkyl group" refers to a group in which a hydrogen atom of the above "$C_{1-6}$ alkyl group" is substituted with a phenyl group. Examples thereof include a benzyl group, a 1-phenylethyl group, and a 3-phenylpropyl group.

In the present invention, the "5- or 6-membered aromatic heterocyclic group" refers to a monovalent group derived from a 5- or 6-membered monocyclic aromatic compound containing one or two heteroatoms independently selected from the group consisting of a nitrogen atom, an oxygen atom, and a sulfur atom, as ring-constituting atoms, in addition to carbon atoms. Examples thereof include an oxazolyl group, an isoxazolyl group, a thiazolyl group, an imidazolyl group, a pyrazolyl group, a pyridinyl group, a pyrazinyl group, a pyridazinyl group, and a pyrimidinyl group. The "5- or 6-membered aromatic heterocyclic group" in $R^1$ is preferably a 5- or 6-membered aromatic heterocyclic group (the aromatic heterocyclic group has one or two heteroatoms independently selected from the group consisting of a nitrogen atom and an oxygen atom, in the ring), more preferably a pyridinyl group or an oxazolyl group, and even more preferably a 2-pyridinyl group or an oxazol-2-yl group.

In the present invention, the "6-membered aromatic heterocyclic group" in ring $Q^2$ refers to a divalent group derived from a 6-membered monocyclic aromatic compound containing 1 to 4 nitrogen atoms, as ring-constituting atoms, in addition to carbon atoms. Examples thereof include a pyridinediyl group, a pyrazinediyl group, a pyridazinediyl group, a pyrimidinediyl group, a triazinediyl group, and a tetrazinediyl group. The "6-membered aromatic heterocyclic group" in ring $Q^2$ is preferably a 6-membered aromatic heterocyclic group (the aromatic heterocyclic group has one or two nitrogen atoms in the ring), and more preferably a pyridinediyl group, a pyrazinediyl group, a pyridazinediyl group, or a pyrimidinediyl group.

In the present invention, the "6-membered aromatic heterocyclic group" in ring $Q^3$ refers to a monovalent group derived from a 6-membered monocyclic aromatic compound containing 1 to 4 nitrogen atoms, as ring-constituting atoms, in addition to carbon atoms. Examples thereof include a pyridinyl group, a pyrazinyl group, a pyridazinyl group, a pyrimidinyl group, a triazinyl group, and a tetrazinyl group. The "6-membered aromatic heterocyclic group" in ring $Q^3$ is preferably a pyridinyl group, and more preferably a 2-pyridinyl group.

In the present invention, the "5-membered aromatic heterocyclic group" in ring $Q^2$ refers to a divalent group derived from a 5-membered monocyclic aromatic compound containing one or two heteroatoms independently selected from the group consisting of a nitrogen atom, an oxygen atom, and a sulfur atom, as ring-constituting atoms, in addition to carbon atoms. Examples thereof include a pyrrolediyl group, a furandiyl group, a thiophenediyl group, an oxazolediyl group, an isoxazolediyl group, an imidazolediyl group, a thiazolediyl group, and an isothiazolediyl group. The "5-membered aromatic heterocyclic group" in ring $Q^2$ is preferably a 5-membered aromatic heterocyclic group (the aromatic heterocyclic group has one or two heteroatoms independently selected from the group consisting of a nitrogen atom and a sulfur atom in the ring), and more preferably a thiazolediyl group.

In the present invention, the "5-membered aromatic heterocyclic group" in ring $Q^3$ refers to a monovalent group derived from a 5-membered monocyclic aromatic compound containing one or two heteroatoms independently selected from the group consisting of a nitrogen atom, an oxygen atom, and a sulfur atom, as ring-constituting atoms, in addition to carbon atoms. Examples thereof include a pyrrolyl group, a furanyl group, a thiophenyl group, an oxazolyl group, an isoxazolyl group, a pyrazolyl group, an imidazolyl group, a thiazolyl group, and an isothiazolyl group. The "5-membered aromatic heterocyclic group" in ring $Q^3$ is preferably a 5-membered aromatic heterocyclic group (the aromatic heterocyclic group has one or two heteroatoms independently selected from the group consisting of a nitrogen atom and a sulfur atom in the ring), and more preferably a thiazolyl group.

In the present invention, the "9-membered bicyclic aromatic heterocyclic group" in ring $Q^2$ refers to a divalent group derived from a 9-membered bicyclic condensed aromatic compound containing two heteroatoms independently selected from the group consisting of a nitrogen atom and an oxygen atom, as ring-constituting atoms, in addition to carbon atoms. Examples thereof include a 1,2-benzoxazolediyl group, a 1H-indazolediyl group, and a 1H-pyrrolo[2,3-b]pyridinediyl group. The "9-membered bicyclic aromatic heterocyclic group" in ring $Q^2$ is preferably a 1H-indazolediyl group.

In the present invention, the "9-membered bicyclic aromatic heterocyclic group" in ring $Q^3$ refers to a monovalent group derived from a 9-membered bicyclic condensed aromatic compound containing two heteroatoms independently selected from the group consisting of a nitrogen atom and an oxygen atom, as ring-constituting atoms, in addition to carbon atoms. Examples thereof include a 1,2-benzoxazolyl group, a 1H-indazolyl group, and 1H-pyrrolo[2,3-b]pyridinyl group. The "9-membered bicyclic aromatic heterocyclic group" in ring $Q^3$ is preferably a 1,2-benzoxazolyl group, and more preferably a 1,2-benzoxazol-5-yl group.

In the present invention, the "3- to 8-membered saturated hydrocarbon ring group" and the "$C_{3-8}$ cycloalkyl group" refer to a monovalent group derived from a 3- to 8-membered monocyclic saturated compound in which ring-constituting atoms are only carbon atoms. Examples thereof include a cyclopropyl group, a cyclobutyl group, a cyclopentyl group, a cyclohexyl group, cycloheptyl group, or a cyclooctyl group. The "$C_{3-8}$ cycloalkyl group" in $R^1$ is preferably a cyclopropyl group. The "3- to 8-membered saturated hydrocarbon ring group" in ring $Q^3$ is preferably a cyclobutyl group or a cyclohexyl group.

In the present invention, the "6-membered saturated heterocyclic group" refers to a monovalent group derived from a 6-membered monocyclic saturated compound containing a heteroatom selected from the group consisting of a nitrogen atom, an oxygen atom, and a sulfur atom, as ring-constituting atoms, in addition to carbon atoms. Examples thereof include a piperidyl group, an oxanyl group (tetrahydropyranyl group), and tetrahydrothiopyranyl group. The "6-membered saturated heterocyclic group" in ring $Q^3$ is preferably a 6-membered saturated heterocyclic group (the saturated heterocyclic group has a nitrogen atom or an oxygen atom in the ring), more preferably a piperidyl group or an oxanyl group (tetrahydropyranyl group), and even more preferably a 1-piperidyl group or an oxan-4-yl group (tetrahydropyran-4-yl group).

In the present invention, the "10-membered bicyclic partially unsaturated heterocyclic group" refers to a monovalent group derived from a 10-membered bicyclic condensed ring compound (the condensed ring compound has an unsaturated bond in a part of the ring) containing two oxygen atoms, as ring-constituting atoms, in addition to carbon atoms. The "10-membered bicyclic partially unsaturated heterocyclic group" in ring Q³ is preferably a 2,3-dihydro-1,4-benzodioxinyl group, and more preferably a 2,3-dihydro-4-benzodioxin-6-yl group.

In the present invention, phosphatidylserine synthase 1 (PSS1) is a protein encoded by the PTDSS1 gene. PTDSS1 is registered in NCBI as Gene ID: 9791, RefSEQ: accession NM_014754.2 (protein: RefSeq NP_055569.1).

In the present invention, phosphatidylserine synthase 2 (PSS2) is a protein encoded by the PTDSS2 gene. PTDSS2 is registered in NCBI as Gene ID: 81490, RefSEQ: accession NM_030783.1_(protein: RefSeq NP_110410.1).

In the present invention, the terms "tumor" and "cancer" are used interchangeably. Also, in the present invention, tumors, malignant tumors, cancers, malignant neoplasms, carcinomas, sarcomas, and the like may be collectively represented by "tumor" or "cancer".

The "suppression of the phosphatidylserine synthase 2 (PSS2) function" in the present invention includes deletion of PTDSS2, decreased expression of PSS2, and inactivation of PSS2. The deletion of PTDSS2 includes homozygous deletion and heterozygous deletion. The decreased expression of PSS2 includes both decreased expression at a transcriptional level and decreased expression at a translational level. The inactivation of PSS2 typically includes an inactivating mutation of PTDSS2.

In the present invention, the "test subject" means a human and a non-human mammal to be tested by a method for predicting responsiveness to a PSS1 inhibitor. For example, the test subject means a human and a non-human mammal suffering from a disease for which the PSS1 inhibitor is expected to have a therapeutic effect. Preferred examples of the disease for which the PSS1 inhibitor is expected to have a therapeutic effect include cancer. The non-human mammal may be any organism as long as the organism is categorized as a mammal, including, monkeys, dogs, cats, cattle, and horses. Preferred examples of the "test subject" in the present invention include a human and a non-human mammal suspected of having cancer, and a human and a non-human mammal diagnosed with cancer.

In the present invention, the "biological sample" refers to tissue, fluid, cells, and mixtures thereof isolated from an individual, and examples thereof include, but are not limited to, tumor biopsy, spinal fluid, pleural fluid, intraperitoneal fluid, lymph fluid, skin sections, blood, urine, feces, sputum, respiratory tract, intestinal tract, genitourinary tract, saliva, milk, digestive organ, and cells collected therefrom. Preferred examples of the "biological sample" include a portion of excised tissue obtained from an operation performed for treatment of cancer, a portion of tissue collected from a subject suspected of having cancer by biopsy and the like, and cells derived from blood or pleural fluid or intraperitoneal fluid.

The biological sample may be a protein extract or a nucleic acid extract prepared from, for example, tissue, fluid, cell isolated from an individual, and mixtures thereof. Preparation of the protein extract or the nucleic acid extract can be conducted using a known method for preparing protein or a known method for preparing nucleic acid.

The biological sample is preferably a biological sample collected before the treatment by the PSS1 inhibitor. Use of such a biological sample allows predicting the sensitivity to the PSS1 inhibitor before conducting the treatment by the PSS1 inhibitor, and as a result, the determination of whether or not to apply the treatment including the PSS1 inhibitor to the test subject, that is, the screening for the test subject to which the treatment including the PSS1 inhibitor is applied can be conducted.

Preferred substituents in the compound of the present invention and preferred aspects of the present invention will be described below.

Preferably, $R^1$ is a trifluoromethyl group, a 1,1-difluoroethyl group, a 1,1-difluoropropyl group, a cyclopropyl group, a 2-pyridyl group, or an oxazol-2-yl group. More preferably, $R^1$ is a 1,1-difluoroethyl group.

Ring $Q^1$ preferably represents any one of formulas (4A) to (4G):

[Chemical Formula 63]

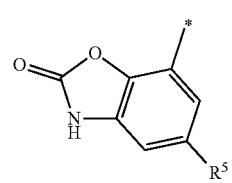
(4A)

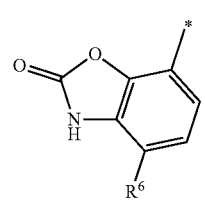
(4B)

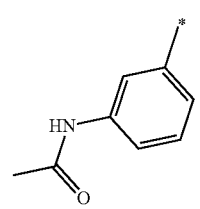
(4C)

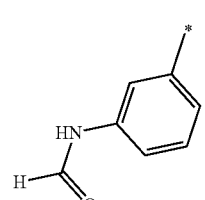
(4D)

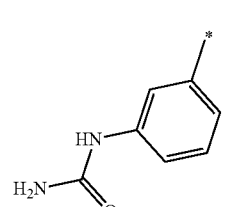
(4E)

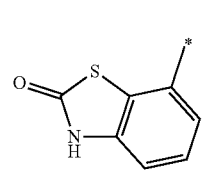
(4F)

(4G)

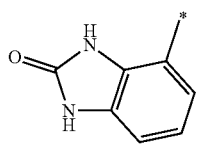

wherein * represents a bond, $R^5$ represents a hydrogen atom or a halogen atom, and $R^6$ represents a halogen atom. More preferably, ring $Q^1$ represents either formula (4A) or (4B).

Even more preferably, ring $Q^1$ represents either formula (5A) or (5B):

[Chemical Formula 64]

(5A)

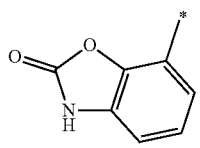

(5B)

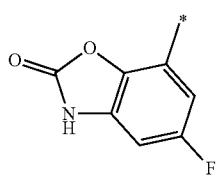

wherein * represents a bond.

Ring $Q^2$ preferably represents any one of formulas (6A) to (6G):

[Chemical Formula 65]

(6A)

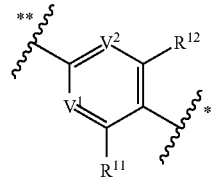

(6B)

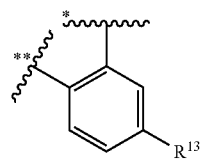

(6C)

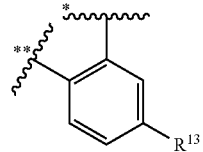

(6D)

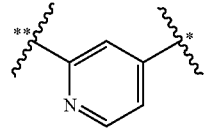

(6E)

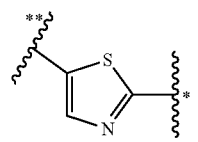

(6F)

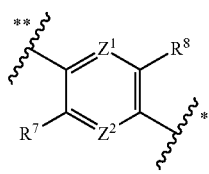

(6G)

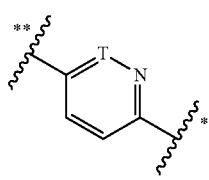

wherein * is bonded to W, ** is bonded to the carbon atom represented by a, $R^7$ represents a hydrogen atom, a halogen atom, or a $C_{1-6}$ alkyl group, $R^8$ represents a hydrogen atom, a halogen atom, a $C_{1-6}$ alkyl group, a halogeno $C_{1-6}$ alkyl group, a halogeno $C_{1-6}$ alkoxy group, or a $C_{3-8}$ cycloalkyl group, $R^9$ represents a hydrogen atom or a halogen atom, $R^{10}$ represents a hydrogen atom or a halogeno $C_{1-6}$ alkyl group, $R^{11}$ and $R^{12}$ each independently represent a $C_{1-6}$ alkyl group, $R^{13}$ represents a halogen atom, $Z^1$ and $Z^2$ each independently represent CH or a nitrogen atom, T represents CH or a nitrogen atom, $U^1$ and $U^2$ each independently represent CH or a nitrogen atom, and $V^1$ and $V^2$ each independently represent CH or a nitrogen atom.

More preferably, ring $Q^2$ represents any one of formulas (7A) to (7C):

[Chemical Formula 66]

(7A)

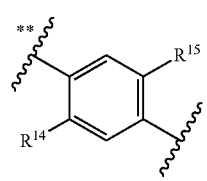

(7B)

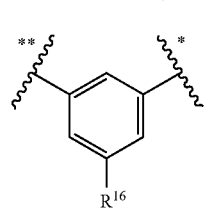

-continued (7C)
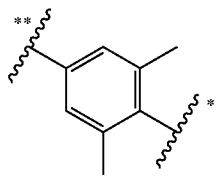

wherein * is bonded to W, ** is bonded to the carbon atom represented by a, $R^{14}$ represents a hydrogen atom, a fluorine atom, a chlorine atom, or a methyl group, $R^{15}$ represents a hydrogen atom, a chlorine atom, a methyl group, an ethyl group, a trifluoromethyl group, a trifluoromethoxy group, a 4,4,4-trifluorobutoxy group, or a cyclopropyl group, and $R^{16}$ represents a hydrogen atom or a trifluoromethyl group.

Even more preferably, ring $Q^2$ represents any one of formulas (8A) to (8E):

[Chemical Formula 67]

(8A)
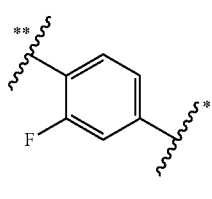

(8B)
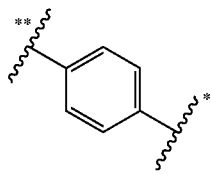

(8C)
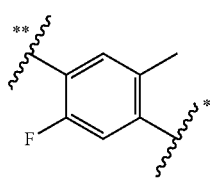

(8D)
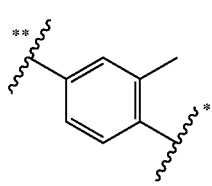

(8E)
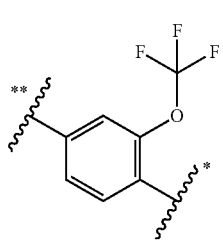

wherein * is bonded to W, and ** is bonded to the carbon atom represented by a.

W is preferably a halogen atom, a $C_{1-6}$ alkyl group, a halogeno $C_{1-6}$ alkyl group, or a halogeno $C_{1-6}$ alkoxy group.

More preferably, W is a fluorine atom, a chlorine atom, an n-butyl group, an n-hexyl group, a trifluoromethyl group, a trifluoromethoxy group, or a 4,4,4-trifluorobutoxy group.

Ring $Q^3$ preferably represents any one of formulas (9A) to (9J):

[Chemical Formula 68]

(9A)
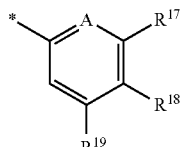

(9B)
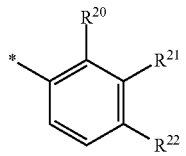

(9C)
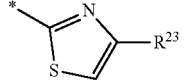

(9D)

(9E)

(9F)
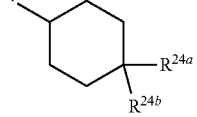

(9G)
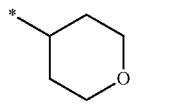

(9H)
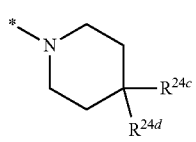

(9I)
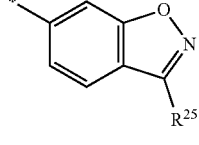

(9J)
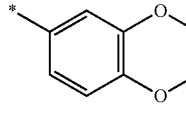

wherein * represents a bond, $R^{17}$ and $R^{19}$ each independently represent a hydrogen atom, a halogen atom, a $C_{1-6}$ alkyl group, a halogeno $C_{1-6}$ alkyl group, or a halogeno $C_{1-6}$ alkoxy group, $R^{18}$ represents a hydrogen atom, a halogen atom, a halogeno $C_{1-6}$ alkyl group, a halogeno $C_{1-6}$ alkoxy group, a halogeno $C_{1-6}$ alkylsulfanyl group, or a halogeno $C_{1-6}$ alkylsulfonyl group, A represents CH or a nitrogen atom, $R^{20}$ represents a halogen atom, a $C_{1-6}$ alkyl group, a halogeno $C_{1-6}$ alkyl group, or a halogeno $C_{1-6}$ alkoxy group, $R^{21}$ represents a hydrogen atom or a halogen atom, $R^{22}$ represents a hydrogen atom, a halogeno $C_{1-6}$ alkyl group, or a halogeno $C_{1-6}$ alkoxy group, $R^{23}$ represents a halogeno $C_{1-6}$ alkyl group, $R^{24a}$ and $R^{24b}$ are identical and represent a halogen atom, $R^{24c}$ and $R^{24d}$ are identical and represent a halogen atom, $R^{24e}$, $R^{24f}$, $R^{24g}$, and $R^{24h}$ are identical and represent a halogen atom, and $R^{25}$ represents a halogeno $C_{1-6}$ alkyl group.

More preferably, ring $Q^3$ represents any one of formulas (10A) to (10C):

[Chemical Formula 69]

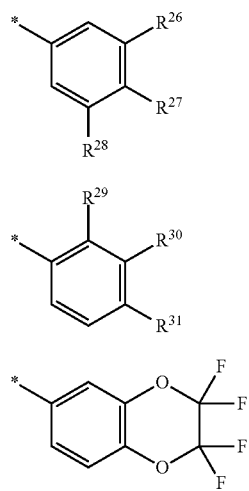

(10A)

(10B)

(10C)

wherein * represents a bond, $R^{26}$ and $R^{28}$ each independently represent a hydrogen atom, a chlorine atom, a methyl group, a trifluoromethyl group, or a trifluoromethoxy group, $R^{27}$ represents a hydrogen atom, a fluorine atom, a chlorine atom, a trifluoromethyl group, a trifluoromethoxy group, a trifluoromethylsulfanyl group, or a trifluoromethylsulfonyl group, $R^{29}$ represents a fluorine atom, a chlorine atom, a methyl group, a trifluoromethyl group, or a trifluoromethoxy group, $R^{30}$ represents a hydrogen atom or a chlorine atom, and $R^{31}$ represents a hydrogen atom, a trifluoromethyl group, or a trifluoromethoxy group.

Even more preferably, ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl) phenyl group, a 4-(trifluoromethoxy)-3-(trifluoromethyl) phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group.

Y preferably represents an oxygen atom, a single bond, a sulfur atom, —NH—, a methylene group, or any one of formulas (11A) to (11C):

[Chemical Formula 70]

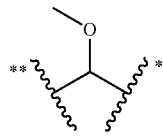

(11A)

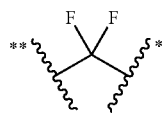

(11B)

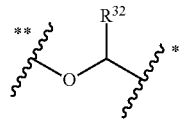

(11C)

wherein * is bonded to ring $Q^3$, ** is bonded to ring $Q^2$, and $R^{32}$ represents a hydrogen atom or a methyl group.

More preferably, Y represents an oxygen atom or formula (12A):

[Chemical Formula 71]

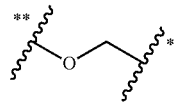

(12A)

wherein * is bonded to ring $Q^3$, and ** is bonded to ring $Q^2$.

Even more preferably, Y is an oxygen atom.

Preferably, the compound of the present invention is a compound or a pharmaceutically acceptable salt thereof, wherein in general formula (1), $R^1$ is a trifluoromethyl group, a 1,1-difluoroethyl group, a 1,1-difluoropropyl group, a cyclopropyl group, a 2-pyridyl group, or an oxazol-2-yl group;

ring Q represents any one of formula (4A) or (4B):

[Chemical Formula 72]

(4A)

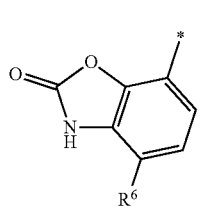

(4B)

wherein * represents a bond, $R^5$ represents a hydrogen atom or a halogen atom, and $R^6$ represents a halogen atom;

ring $Q^2$ represents any one of formulas (7A) to (7C):

[Chemical Formula 73]

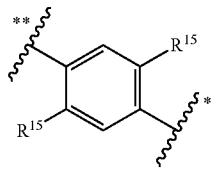
(7A)

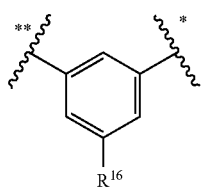
(7B)

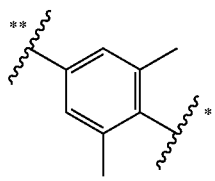
(7C)

wherein * is bonded to W, ** is bonded to the carbon atom represented by a, $R^{14}$ represents a hydrogen atom, a fluorine atom, a chlorine atom, or a methyl group, $R^{15}$ represents a hydrogen atom, a chlorine atom, a methyl group, an ethyl group, a trifluoromethyl group, a trifluoromethoxy group, a 4,4,4-trifluorobutoxy group, or a cyclopropyl group, and $R^{16}$ represents a hydrogen atom or a trifluoromethyl group;

W is a fluorine atom, a chlorine atom, an n-butyl group, an n-hexyl group, a trifluoromethyl group, a trifluoromethoxy group, or a 4,4,4-trifluorobutoxy group, or W represents formula (3A);

ring $Q^3$ represents any one of formulas (10A) to (1° C.):

[Chemical Formula 74]

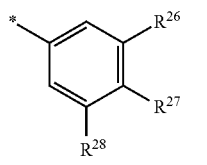
(10A)

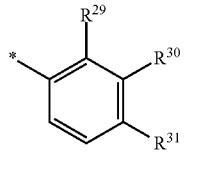
(10B)

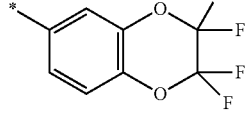
(10C)

wherein * represents a bond, $R^{26}$ and $R^{28}$ each independently represent a hydrogen atom, a chlorine atom, a methyl group, a trifluoromethyl group, or a trifluoromethoxy group, $R^{27}$ represents a hydrogen atom, a fluorine atom, a chlorine atom, a trifluoromethyl group, a trifluoromethoxy group, a trifluoromethylsulfanyl group, or a trifluoromethylsulfonyl group, $R^{29}$ represents a fluorine atom, a chlorine atom, a methyl group, a trifluoromethyl group, or a trifluoromethoxy group, $R^{30}$ represents a hydrogen atom or a chlorine atom, and $R^{31}$ represents a hydrogen atom, a trifluoromethyl group, or a trifluoromethoxy group; and Y represents an oxygen atom, a single bond, a sulfur atom, —NH—, a methylene group, or any one of formulas (11A) to (11C):

[Chemical Formula 75]

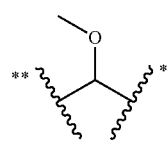
(11A)

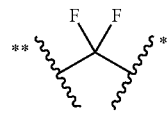
(11B)

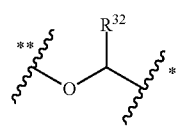
(11C)

wherein * is bonded to ring $Q^3$, ** is bonded to ring $Q^2$, and $R^{32}$ represents a hydrogen atom or a methyl group.

More preferably, the compound of the present invention is a compound or a pharmaceutically acceptable salt thereof, wherein in general formula (1), $R^1$ is a 1,1-difluoroethyl group;

ring Q represents either formula (5A) or (5B):

[Chemical Formula 76]

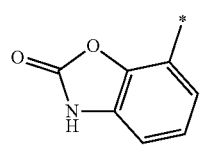
(5A)

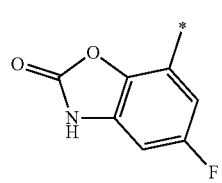
(5B)

wherein * represents a bond;
ring $Q^2$ represents any one of formulas (8A) to (8E):

[Chemical Formula 77]

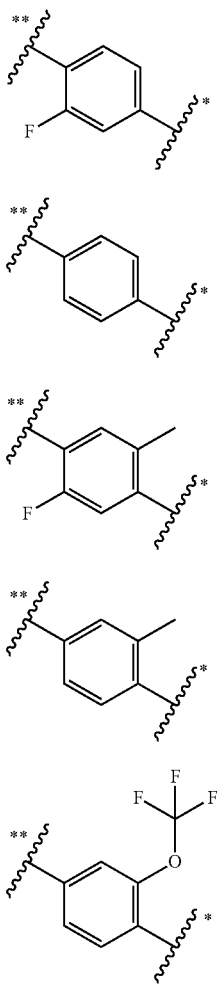

wherein * is bonded to W, ** is bonded to the carbon atom to which ring $Q^2$ is bonded;
W represents formula (3A);
ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group; and
Y is an oxygen atom.
Preferably, the compound of the present invention is any compound selected from the group consisting of:
(−)-7-[5-(2,2-difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one,
(−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
(−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one,
(−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one,
(−)-7-[4-{4-[3-chloro-5-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
(−)-7-{5-(2,2-difluoropropyl)-4-[3-(4-fluorophenoxy)phenyl]-6-oxo-1,4,5,6-tetrahydropyrrolo[3,4-c]pyrazol-3-yl}-1,3-benzoxazol-2(3H)-one,
(−)-7-{4-[4-(4-chlorophenoxy)phenyl]-5-(2,2-difluoropropyl)-6-oxo-1,4,5,6-tetrahydropyrrolo[3,4-c]pyrazol-3-yl}-1,3-benzoxazol-2(3H)-one, and
(−)-7-{4-[4-(4-chlorophenoxy)-2-fluorophenyl]-5-(2,2-difluoropropyl)-6-oxo-1,4,5,6-tetrahydropyrrolo[3,4-c]pyrazol-3-yl}-1,3-benzoxazol-2(3H)-one,
or a pharmaceutically acceptable salt thereof.

More preferably, the compound of the present invention is any one selected from the following compounds:
(−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one,
7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one,
(−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one,
(−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one,
(−)-7-[4-{4-[3-chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one, and
(−)-7-[5-(2,2-difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one, or pharmaceutically acceptable salts thereof (preferably, a 2-methylpropane-2-amine salt or an isonicotinamide adduct).

The compound of the present invention or a pharmaceutically acceptable salt thereof has excellent properties in terms of PSS1 inhibitory effect, solubility, cell membrane permeability, oral absorbability, blood concentration, metabolic stability, tissue penetration, bioavailability, in vitro activity, in vivo activity, rapid onset of drug efficacy, persistence of drug efficacy, physical stability, drug interaction, toxicity, and the like, and is useful as a pharmaceutical.

One aspect of the present invention relates to an inhibitor of phosphatidylserine synthase 1 containing a compound represented by general formula (1) or a pharmaceutically acceptable salt thereof as an active substance.

Another aspect of the present invention relates to a pharmaceutical composition containing a compound represented by general formula (1) or a pharmaceutically acceptable salt thereof, and a pharmaceutically acceptable carrier.

Another aspect of the present invention relates to a pharmaceutical composition for treatment of cancer containing a compound represented by general formula (1) or a pharmaceutically acceptable salt thereof, and a pharmaceutically acceptable carrier.

Another aspect of the present invention relates to a method for treating cancer, comprising administering a compound represented by general formula (1) or a pharmaceutically acceptable salt thereof.

Another aspect of the present invention relates to a compound represented by general formula (1) or a pharmaceutically acceptable salt thereof used as a medicament for treatment of cancer.

Another aspect of the present invention relates to use of a compound represented by general formula (1) or a pharmaceutically acceptable salt thereof for manufacturing a medicament for treatment of cancer.

The disease to be treated is not particularly limited, as long as it is a disease that is confirmed to be sensitive to the inhibitor of PSS1, and is preferably cancer, more preferably testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer, and even more preferably, testicular germ cell tumor, ovarian cancer, bladder cancer, lung cancer, breast cancer, or esophageal cancer. The disease is even more preferably ovarian cancer, lung cancer, breast cancer, prostate cancer, stomach cancer, melanoma, bowel cancer, blood cancer, or pancreatic cancer, and most preferably breast cancer, stomach cancer, melanoma, bowel cancer, or blood cancer (preferably, mantle cell lymphoma).

Preferably, the cancer to be treated is a cancer having a suppressed function of phosphatidylserine synthase 2. More preferably, the cancer to be treated is testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer (testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer described above has a suppressed function of phosphatidylserine synthase 2). Even more preferably, the cancer to be treated is testicular germ cell tumor, ovarian cancer, bladder cancer, lung cancer, breast cancer, or esophageal cancer (testicular germ cell tumor, ovarian cancer, bladder cancer, lung cancer, breast cancer, or esophageal cancer described above has a suppressed function of phosphatidylserine synthase 2). Most preferably, the cancer to be treated is testicular germ cell tumor, ovarian cancer, bladder cancer, lung cancer, breast cancer, or esophageal cancer (testicular germ cell tumor, ovarian cancer, bladder cancer, lung cancer, breast cancer, or esophageal cancer described above has a homozygous deletion or heterozygous deletion of a gene encoding phosphatidylserine synthase 2, or a decreased expression of phosphatidylserine synthase 2). Even more preferably, the cancer to be treated is ovarian cancer, lung cancer, breast cancer, prostate cancer, stomach cancer, melanoma, bowel cancer, blood cancer, or pancreatic cancer (ovarian cancer, lung cancer, breast cancer, prostate cancer, stomach cancer, melanoma, bowel cancer, blood cancer, or pancreatic cancer described above has a suppressed function of phosphatidylserine synthase 2), and most preferably, the cancer to be treated is breast cancer, stomach cancer, melanoma, bowel cancer, or blood cancer (breast cancer, stomach cancer, melanoma, bowel cancer, or blood cancer described above has a suppressed function of phosphatidylserine synthase 2).

The suppression of the phosphatidylserine synthase 2 function is preferably a homozygous deletion or heterozygous deletion of a gene encoding phosphatidylserine synthase 2, or a decreased expression of phosphatidylserine synthase 2.

Preferably, the cancer to be treated is a cancer having LOH (loss of heterozygosity) of chromosome 11p15.5. More preferably, the cancer to be treated is testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer (testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer described above has LOH of chromosome 11p15.5). Even more preferably, the cancer to be treated is testicular germ cell tumor, ovarian cancer, bladder cancer, lung cancer, breast cancer, or esophageal cancer (testicular germ cell tumor, ovarian cancer, bladder cancer, lung cancer, breast cancer, or esophageal cancer described above has LOH of chromosome 11p15.5). Even more preferably, the cancer to be treated is ovarian cancer, lung cancer, breast cancer, prostate cancer, stomach cancer, melanoma, bowel cancer, blood cancer, or pancreatic cancer (ovarian cancer, lung cancer, breast cancer, prostate cancer, stomach cancer, melanoma, bowel cancer, blood cancer, or pancreatic cancer described above has LOH of chromosome 11p15.5), and most preferably, breast cancer, stomach cancer, melanoma, bowel cancer, or blood cancer (breast cancer, stomach cancer, melanoma, bowel cancer, or blood cancer described above has LOH of chromosome 11p15.5).

Preferably, the cancer to be treated is:
(i) the cancer having a suppressed function of phosphatidylserine synthase 2; and
(ii) the cancer having LOH (loss of heterozygosity) of chromosome 11p15.5.

More preferably, the cancer to be treated is testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer, in which:
(i) testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer described above is the cancer having a suppressed function of phosphatidylserine synthase 2; and (ii) testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer described above is the cancer having LOH (loss of heterozygosity) of chromosome 11p15.5.

Even more preferably, the cancer to be treated is testicular germ cell tumor, ovarian cancer, bladder cancer, lung cancer, breast cancer, or esophageal cancer, in which:

(i) testicular germ cell tumor, ovarian cancer, bladder cancer, lung cancer, breast cancer, or esophageal cancer described above is a cancer having a suppressed function of phosphatidylserine synthase 2; and (ii) testicular germ cell tumor, ovarian cancer, bladder cancer, lung cancer, breast cancer, or esophageal cancer described above is the cancer having LOH (loss of heterozygosity) of chromosome 11p15.5.

Most preferably, the cancer to be treated is testicular germ cell tumor, ovarian cancer, bladder cancer, lung cancer, breast cancer, or esophageal cancer, in which:

(i) testicular germ cell tumor, ovarian cancer, bladder cancer, lung cancer, breast cancer, or esophageal cancer described above is the cancer having a homozygous deletion or heterozygous deletion of a gene encoding phosphatidylserine synthase 2, or a decreased expression of phosphatidylserine synthase 2; and (ii) testicular germ cell tumor, ovarian cancer, bladder cancer, lung cancer, breast cancer, or esophageal cancer described above is the cancer having LOH (loss of heterozygosity) of chromosome 11p15.5.

Even more preferably, the cancer to be treated is ovarian cancer, lung cancer, breast cancer, prostate cancer, stomach cancer, melanoma, bowel cancer, blood cancer, or pancreatic cancer, in which:

(i) ovarian cancer, lung cancer, breast cancer, prostate cancer, stomach cancer, melanoma, bowel cancer, blood cancer, or pancreatic cancer described above is the cancer having a suppressed function of phosphatidylserine synthase 2; and (ii) ovarian cancer, lung cancer, breast cancer, prostate cancer, stomach cancer, melanoma, bowel cancer, blood cancer, or pancreatic cancer described above is the cancer having LOH (loss of heterozygosity) of chromosome 11p15.5.

Most preferably, the cancer to be treated is breast cancer, stomach cancer, melanoma, bowel cancer, or blood cancer, in which:

(i) breast cancer, stomach cancer, melanoma, bowel cancer, or blood cancer described above is the cancer having a homozygous deletion or heterozygous deletion of a gene encoding phosphatidylserine synthase 2, or a decreased expression of phosphatidylserine synthase 2; and (ii) breast cancer, stomach cancer, melanoma, bowel cancer, or blood cancer described above is the cancer having LOH (loss of heterozygosity) of chromosome 11p15.5.

Since PSS1 and PSS2 have a synthetic lethal relationship, the inhibitor of PSS1 is useful as a medicament for treatment of a cancer having a suppressed PSS2 function. Suppression of the PSS2 function is found in various cancers such as testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, and pancreatic cancer (see International Publication No. WO 2016/148115, Test Examples, FIG. 1 for the PTDSS2 gene status in various cancer tissues). It has been known from studies using the RNA interference against PTDSS1 that the production of phosphatidylserine is more strongly inhibited in the PTDSS2 heterozygous deletion strain as compared in the PTDSS2 wild type cell line (International Publication No. WO 2016/148115, Test Examples, FIG. 5). Further, according to the same studies, it has been reported that a significant cell growth inhibition caused by the RNA interference against PTDSS1 is observed in ZR-75-1 (derived from human breast cancer), TE-1 (derived from human esophageal cancer), MDA-MB-435S (derived from human breast cancer), and PTDSS2 gene-disrupted HCT116 cells (derived from human bowel cancer), which are PTDSS2 heterozygous deletion strains (International Publication No. WO 2016/148115, Test Examples, FIGS. 4 and 7). The compound of the present invention or a pharmaceutically acceptable salt thereof has an inhibitory effect on PSS1, so that it is useful to treat a cancer having a suppressed PSS2 function (preferably, testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer, and more preferably, testicular germ cell tumor, ovarian cancer, bladder cancer, lung cancer, breast cancer, or esophageal cancer).

Since a correlation between the LOH (loss of heterozygosity) of chromosome 11p15.5 where the PTDSS2 gene is present and a poor prognosis of non-small cell lung cancer has been reported (Journal of Clinical Oncology, Vol 20, No 5 (March 1), 2002: pp 1353-1360), non-small cell lung cancer having LOH of chromosome 11p15.5 may be a target of treatment. In addition, there was a trend observed that the PTDSS2 deletion did not occur together with an EGFR mutation and ALK fusion gene mutation in lung adenocarcinoma, and thus, the present invention provides a new therapeutic drug for lung adenocarcinoma patients not recognized to have the EGFR mutation or ALK mutation which have only chemotherapeutic agents as a drug treatment option at present.

Since PSS1 and PSS2 are in a synthetic lethal relationship, the compound of the present invention having an inhibitory effect on PSS1 or a pharmaceutically acceptable salt thereof is useful to a medicament for treatment of a cancer having a suppressed PSS2 function. That is, to evaluate and determine the responsiveness to treatment of cancer with the compound of the present invention or a pharmaceutically acceptable salt thereof, suppression of PSS2 function can be used as an index. Therefore, another aspect of the present invention provides a method for predicting responsiveness to treatment of cancer with a compound represented by general formula (1) or a pharmaceutically acceptable salt thereof, comprising using a biological sample derived from a test subject to detect the presence or absence of suppressed function of phosphatidylserine synthase 2 (preferably, a homozygous deletion or heterozygous deletion of a gene encoding phosphatidylserine synthase 2, or a decreased expression of phosphatidylserine synthase 2) in the biological sample, and determining the test subject in which the suppressed function of phosphatidylserine synthase 2 (preferably, a homozygous deletion or heterozygous deletion of a gene encoding phosphatidylserine synthase 2, or a decreased expression of phosphatidylserine synthase 2) is detected, as being responsive to treatment of cancer with the compound represented by general formula (1) or a pharmaceutically acceptable salt thereof. Further, another aspect of the present invention also provides a method for predicting responsiveness to treatment of cancer with a compound represented by general formula (1) or a pharmaceutically acceptable salt thereof, comprising using a biological sample derived from a test subject to determine the test subject in which the suppressed function of phosphatidylserine synthase 2 (preferably, a homozygous deletion or heterozygous deletion of a gene encoding phosphatidylserine synthase 2, or a decreased expression of phosphatidylserine synthase 2) is detected, as being responsive to treatment of cancer with the compound represented by general formula (1) or a pharmaceutically acceptable salt thereof.

The test subject in which the suppression of PSS2 function is thus detected is suitable for treatment of cancer with the compound of the present invention or a pharmaceutically acceptable salt thereof, and effective treatment can be performed by screening for patients who should or should not receive treatment of cancer with the compound of the present invention or a pharmaceutically acceptable salt thereof using suppression of PSS2 function as an index. Therefore, another aspect of the present invention also provides a method for screening for a subject for treatment of cancer with a compound represented by general formula (1) or a pharmaceutically acceptable salt thereof, comprising using a biological sample derived from a test subject to detect the presence or absence of suppressed function of phosphatidylserine synthase 2 (preferably, a homozygous deletion or heterozygous deletion of a gene encoding phosphatidylserine synthase 2, or a decreased expression of phosphatidylserine synthase 2) in the biological sample, and screening for the test subject in which the suppressed function of phosphatidylserine synthase 2 (preferably, a homozygous deletion or heterozygous deletion of a gene encoding phosphatidylserine synthase 2, or a decreased expression of phosphatidylserine synthase 2) is detected, as the subject for treatment of cancer with the compound represented by general formula (1) or a pharmaceutically acceptable salt thereof. Further, another aspect of the present invention also provides a method for screening for a subject for treatment of cancer with a compound represented by general formula (1) or a pharmaceutically acceptable salt thereof, comprising using a biological sample derived from a test subject to screen for the test subject in which the suppressed function of phosphatidylserine synthase 2 (preferably, a homozygous deletion or heterozygous deletion of a gene encoding phosphatidylserine synthase 2, or a decreased expression of phosphatidylserine synthase 2) is detected, as the subject for treatment of cancer with the compound represented by general formula (1) or a pharmaceutically acceptable salt thereof.

Another aspect of the present invention provides a method for treating cancer having a suppressed function of phosphatidylserine synthase 2 (preferably, a homozygous deletion or heterozygous deletion of a gene encoding phosphatidylserine synthase 2, or a decreased expression of phosphatidylserine synthase 2), comprising using a biological sample derived from a test subject to detect the presence or absence of suppressed function of phosphatidylserine synthase 2 in the biological sample (preferably, a homozygous deletion or heterozygous deletion of a gene encoding phosphatidylserine synthase 2, or a decreased expression of phosphatidylserine synthase 2), and administering the compound represented by general formula (1) or a pharmaceutically acceptable salt thereof to the test subject in which the suppressed function of phosphatidylserine synthase 2 (preferably, a homozygous deletion or heterozygous deletion of a gene encoding phosphatidylserine synthase 2, or a decreased expression of phosphatidylserine synthase 2) is detected. Another aspect of the present invention also provides a method for treating cancer having a suppressed function of phosphatidylserine synthase 2 (preferably, a homozygous deletion or heterozygous deletion of a gene encoding phosphatidylserine synthase 2, or a decreased expression of phosphatidylserine synthase 2), comprising using a biological sample derived from a test subject to administer a compound represented by general formula (1) or a pharmaceutically acceptable salt thereof to the test subject in which the suppressed function of phosphatidylserine synthase 2 (preferably, a homozygous deletion or heterozygous deletion of a gene encoding phosphatidylserine synthase 2, or a decreased expression of phosphatidylserine synthase 2) is detected.

The compound of the present invention may have geometrical isomers such as cis isomers and trans isomers and tautomers according to the type and combination of substituents, or when the compound of the present invention has asymmetric carbon atoms, optical isomers such as d isomers and l isomers (e.g., enantiomers or diastereomers) may be present. Unless defined otherwise, the compound of the present invention includes all such isomers and mixtures of such isomers in any ratio.

In the present invention, the compound represented by formula (1):

[Chemical Formula 78]

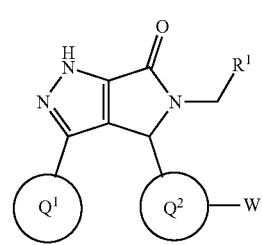

(1)

wherein R¹, Q¹, Q², and W are as defined above,
may include its tautomer, a compound represented by formula (1'):

[Chemical Formula 79]

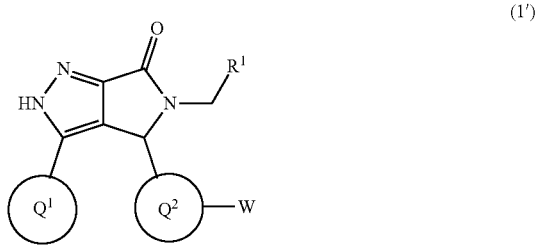

(1')

wherein R¹, Q¹, Q², and W are as defined above,
in any ratio. The ratio of the compound represented by formula (1) may be 100%, or the ratio of the compound represented by formula (1') may be 100%.

In the present application, unless otherwise specified, any tautomers and mixtures of both tautomers in any ratio will be represented by the structural formula of formula (1) and the chemical name corresponding to formula (1), for convenience.

The salt of the compound represented by general formula (1) of the present invention includes both
(i) the salt formed from the compound represented by general formula (1) in which a proton is dissociated from its acidic group, and a protonated base; and
(ii) the adduct formed from the compound represented by general formula (1) in which a proton is not dissociated from its acidic group, and an unprotonated base, and the "salt" of the present invention may mean either the above (i) or (ii).

The salt in the compound of the present invention includes salts that may be formed by combining a base, an acid, or the like to be added to the compound of the present invention with the compound of the present invention in any proportion. For example, the 2-methylpropane-2-amine salt includes salts that may be formed when the equivalent of 2-methylpropane-2-amine to the compound of the present invention takes any numerical value such as 1, ½, and ⅔, and the isonicotinamide adduct includes adducts that may be formed when the equivalent of isonicotinamide to the compound of the present invention takes any numerical value such as 1, ½, and ⅔.

In the present invention, a pharmaceutically acceptable salt includes both a pharmaceutically acceptable acid addition salt and a pharmaceutically acceptable base addition salt.

When the compound of the present invention has a basic group such as an amino group, a pharmaceutically acceptable acid addition salt can be formed, in general. Examples of such an acid addition salt include hydrohalide salts such as hydrofluoride, hydrochloride, hydrobromide, and hydroiodide; inorganic acid salts such as nitrate, perchlorate, sulfate, and phosphate; lower alkanesulfonic acid salts such as methanesulfonate, trifluoromethanesulfonate, and ethanesulfonate; aryl sulfonic acid salts such as benzenesulfonate and p-toluenesulfonate; organic acid salts such as acetate, malate, fumarate, succinate, citrate, tartrate, oxalate, and maleate; or amino acid salts such as ornithinate, glutamate, and aspartate.

When the compound of the present invention has an acidic group such as a carboxy group, a pharmaceutically acceptable base addition salt can be formed, in general. Examples of such a base addition salt include alkaline metal salts such as sodium salt, potassium salt, and lithium salt; alkaline earth metal salts such as calcium salt and magnesium salt; inorganic salts such as ammonium salt; or organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'-dibenzylethylenediamine salt, diethanol amine salt, N-benzyl-N-(2-phenylethoxy)amine salt, piperazine salt, tetramethylammonium salt, tris(hydroxymethyl)aminomethane salt, and 2-methylpropane-2-amine.

The compound of the present invention may be present as a non-solvate or a solvate. The solvate is not particularly limited as long as it is pharmaceutically acceptable one, and specifically, a hydrate, an ethanolate, and the like are preferred.

The compound of the present invention may contain unnatural proportions of isotopes at one or more of the atoms that constitute such a compound. Examples of the isotope include deuterium ($^2$H;D), tritium ($^3$H;T), iodine-125 ($^{125}$I) or carbon-14 (14C). The compound of the present invention may be radiolabeled with a radioisotope such as tritium (3H), iodine-125 ($^{125}$I), or carbon-14 (14C). The radiolabeled compound is useful as a therapeutic or prophylactic agent, a research reagent (e.g., assay reagent), and a diagnostic agent (e.g., in vivo image diagnostic agent). The compound of the present invention containing radioactive or non-radioactive isotopes in all proportions is included within the scope of the present invention.

It is known that a low molecular compound containing a deuterium atom ($^2$H;D) at one or more of the hydrogen atoms that constitute the compound may exhibit a useful profile (e.g., drug efficacy and safety) as a pharmaceutical (Sanderson, Nature, 2009, DOI: 10.1038/458269a, Maltais et al, J. Med. Chem., 2009, 52, 7993-8001). Also in the compound of the present invention, the same effect as the above may be expected by introducing a deuterium atom into one or more of the hydrogen atoms that constitute the compound.

In the present invention, the crystal refers to a solid whose internal structure is constituted by three-dimensional regular repeats of constituent atoms and molecules, and is distinguished from an amorphous solid or a non-crystalline form free from such a regular internal structure. The crystalline state of the compound of the present invention or a salt thereof can be confirmed by using powder X ray crystal analysis. In general, because of the variations inherent in peak values due to the differences between measurement apparatuses, samples, and sample preparations in powder X-ray diffraction, diffraction angles (2θ) may vary within the range of about ±0.2 (degree), and thus, the value of the diffraction angle in the present invention is recognized to include numerical values in the range of about ±0.2. Therefore, the range of the present invention includes not only crystals whose diffraction angles (2θ) in powder X-ray diffraction perfectly match, but also crystals whose diffraction angles match within the range of ±0.2. As used herein, the unit of the diffraction angle (2θ) is the degree (also referred to as "°"), and when the numerical values of diffraction angles (2θ) are described, the unit may be omitted.

In the present invention, the crystal includes the crystal of the compound represented by general formula (1), the hydrate crystal of the compound represented by general formula (1), the solvate crystal of the compound represented by general formula (1), the crystal of pharmaceutically acceptable salt of the compound represented by general formula (1), the hydrate crystal of pharmaceutically acceptable salt of the compound represented by general formula (1), and the solvate crystal of pharmaceutically acceptable salt of the compound represented by general formula (1). The hydrate crystal of the present invention may take the form of, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 hydrate, and some increase or decrease in the water of hydration may be caused by humidity.

The crystal of the present invention (hereinafter sometimes referred to as "the crystal of Inventive Example 96", "the crystal of Inventive Example 97", "the crystal of Inventive Example 98", "the crystal of Inventive Example 99", "the crystal of Inventive Example 100", "the crystal of Inventive Example 101", "the crystal of Inventive Example 102", and "the crystal of Inventive Example 103") can be stably supplied as a crystal of a drug substance used for preparing pharmaceuticals and is excellent in hygroscopicity or stability. In particular, the difference between these crystalline forms is distinguished by powder X-ray diffraction.

The crystal of Inventive Example 96 has peaks at diffraction angles (2θ) of 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2, in the powder X-ray diffraction diagram obtained by irradiation with copper Kα, radiation (λ=1.54 angstrom).

The crystal of Inventive Example 96 is preferably a 1(2-methylpropane-2-amine) salt. Here, the "1(2-methylpropane-2-amine) salt" refers to a salt that may be formed when the equivalent of 2-methylpropane-2-amine to the compound of the present invention has the numerical value of one.

The crystal of Inventive Example 96 is preferably an anhydride (sometimes referred to as "anhydrate").

The crystal of Inventive Example 97 has peaks at diffraction angles (2θ) of 3.46±0.2, 4.54±0.2, 6.96±0.2, 10.54±0.2, 11.74±0.2, 13.96±0.2, 17.98±0.2, 20.86±0.2, 24.70±0.2, and 26.64±0.2, in the powder X-ray diffraction diagram obtained by irradiation with copper Kα, radiation (λ=1.54 angstrom).

The crystal of Inventive Example 97 is preferably a 0.5 isonicotinamide adduct (sometimes referred to as "½ isonicotinamide adduct"). Here, the "0.5 isonicotinamide adduct" refers to an adduct that may be formed when the equivalent of isonicotinamide to the compound of the present invention has the numerical value of 0.5.

The crystal of Inventive Example 97 is preferably a 0.5 hydrate.

The crystal of Inventive Example 98 has peaks at diffraction angles (2θ) of 6.92±0.2, 10.42±0.2, 12.96±0.2, 15.60±0.2, 17.58±0.2, 18.12±0.2, 19.22±0.2, 19.80±0.2, 21.72±0.2, and 22.26±0.2, in the powder X-ray diffraction diagram obtained by irradiation with copper Kα, radiation (λ=1.54 angstrom).

The crystal of Inventive Example 99 has peaks at diffraction angles (2θ) of 6.58±0.2, 8.80±0.2, 11.62±0.2, 15.34±0.2, 17.14±0.2, 19.02±0.2, 20.06±0.2, 22.36±0.2, 23.82±0.2, and 24.58±0.2, in the powder X-ray diffraction diagram obtained by irradiation with copper Kα, radiation (λ=1.54 angstrom).

The crystal of Inventive Example 100 has peaks at diffraction angles (2θ) of 8.42±0.2, 9.92±0.2, 12.62±0.2, 15.40±0.2, 15.96±0.2, 18.36±0.2, 19.90±0.2, 21.64±0.2, 22.96±0.2, and 23.74±0.2, in the powder X-ray diffraction diagram obtained by irradiation with copper Kα, radiation (λ=1.54 angstrom).

The crystal of Inventive Example 101 has peaks at diffraction angles (2θ) of 10.12±0.2, 12.80±0.2, 15.66±0.2, 17.94±0.2, 18.70±0.2, 19.64±0.2, 21.36±0.2, 22.42±0.2, 22.98±0.2, and 23.46±0.2, in the powder X-ray diffraction diagram obtained by irradiation with copper Kα, radiation (λ=1.54 angstrom).

The crystal of Inventive Example 102 has peaks at diffraction angles (2θ) of 6.60±0.2, 9.18±0.2, 15.08±0.2, 17.88±0.2, 18.80±0.2, 20.02±0.2, 21.26±0.2, 22.36±0.2, 23.78±0.2, and 25.20±0.2, in the powder X-ray diffraction diagram obtained by irradiation with copper Kα, radiation (λ=1.54 angstrom).

The crystal of Inventive Example 103 has peaks at diffraction angles (2θ) of 10.52±0.2, 15.88±0.2, 16.52±0.2, 18.00±0.2, 19.96±0.2, and 22.52±0.2, in the powder X-ray diffraction diagram obtained by irradiation with copper Kα, radiation (λ=1.54 angstrom).

[Manufacturing Method]

Next, representative methods for manufacturing the compound represented by general formula (1) and an enantiomer thereof (ent-1) will be described. The compound of the present invention can be manufactured by various manufacturing methods, and the manufacturing methods shown below are an example and should not be construed as limiting the present invention.

The compound represented by general formula (1), the enantiomer thereof (ent-1), pharmaceutically acceptable salts thereof, and manufacture intermediates thereof can be manufactured by applying various known manufacturing methods using the characteristics based on their basic skeletons or the type of substituents. Examples of the known method include the methods described in "ORGANIC FUNCTIONAL GROUP PREPARATIONS", 2nd edition, ACADEMIC PRESS, INC., 1989, and "Comprehensive Organic Transformations", VCH Publishers Inc., 1989.

At that time, depending on the type of the functional group present in the compound, it is sometimes advantageous to protect the functional group with an appropriate protective group at the stage of raw material or intermediate, or to replace the functional group with a group that can be easily converted into the functional group, in terms of manufacturing technique.

Examples of such a functional group include an amino group, a hydroxyl group, and a carboxy group, and examples of their protective groups include protective groups described in "Protective Groups in Organic Synthesis (5th edition, 2014)" by P. G. Wuts.

The protective group or the group that can be easily converted into the functional group may be appropriately selected and used depending on the reaction conditions of each manufacturing method for manufacturing the compound.

According to such a method, the desired compound can be obtained by introducing the group to perform a reaction, followed by removing the protective group or converting to the desired group, as necessary.

The compound represented by general formula (1) and the enantiomer thereof (ent-1) can be manufactured by, for example, the following method A-1 or method A-2. The compounds 2a, 3a, 4a, and 5a, which are manufacture intermediates, can be manufactured by, for example, the following methods B to G.

When a compound serving as a reaction substrate in the reaction in each step of the following methods A to G has a functional group or a partial structure that inhibit the reaction of interest such as an amino group, a hydroxy group, a carboxy group, or a heteroatom on a cyclic compound, introduction of a protective group into them and removal of the introduced protective group may be appropriately performed, as necessary. Such a protective group is not particularly limited, as long as it is a protective group commonly used, and may be, for example, the protective group described in "Protective Groups in Organic Synthesis (5th edition, 2014)". The reaction for introducing and removing such a protective group can be performed according to the ordinary methods described in the above literature.

Respective compounds of the following methods A to G can be replaced with a group that can be easily converted into the desired functional group at the stage of raw material or intermediate, depending on the type of the functional group present in the compound. The conversion into the desired functional group can be performed at an appropriate stage according to a known method. Examples of the known method include the methods described in "ORGANIC FUNCTIONAL GROUP PREPARATIONS" and "Comprehensive Organic Transformations" described above.

Respective compounds of the following methods A to G may be isolated and purified as various solvates such as a non-solvate, a salt thereof, or a hydrate. The salt can be manufactured by common methods. Examples of the salt include hydrochloride or sulfate and sodium salt or potassium salt.

The solvent used in the reaction in each step of the following methods A to G is not particularly limited, as long as it does not inhibit the reaction and partially dissolve starting materials, and for example, is selected from the following solvent group. The solvent group consists of aliphatic hydrocarbons such as hexane, pentane, petroleum ether, and cyclohexane; aromatic hydrocarbons such as benzene, toluene, and xylene; halogenated hydrocarbons such as dichloromethane (methylene chloride), chloroform, carbon tetrachloride, dichloroethane, chlorobenzene, and dichlorobenzene; ethers such as diethyl ether, diisopropylether, tetrahydrofuran, dioxane, dimethoxyethane, and diethylene glycol dimethylether; ketones such as acetone, methylethylketone, methylisobutylketone, and cyclohexanone; esters such as ethyl acetate, propyl acetate, and butyl acetate; nitriles such as acetonitrile, propionitrile, butyronitrile, and isobutyronitrile; carboxylic acids such as acetic acid and propionic acid; alcohols such as methanol, ethanol, 1-propanol, 2-propanol, 1-butanol, 2-butanol, 2-methyl-1-propanol, and 2-methyl-2-propanol; amides such as formamide, N,N-dimethylformamide, N,N-dimethylacetamide, N-methyl-2-pyrrolidone, and hexamethylphosphorotriamide; sulfoxides such as dimethylsulfoxide and tetrahydrothiophene 1,1-dioxide; water; and mixtures thereof.

The acid used in the reaction in each step of the following methods A to G is not particularly limited, as long as it does not inhibit the reaction, and is selected from the following acid group. The acid group consists of inorganic acids such as hydrochloric acid, hydrobromic acid, hydroiodic acid, phosphoric acid, sulfuric acid, and nitric acid; organic acids such as acetic acid, propionic acid, trifluoroacetic acid, and pentafluoropropionic acid; organic sulfonic acids such as methanesulfonic acid, trifluoromethanesulfonic acid, p-toluenesulfonic acid, and camphorsulfonic acid; and Lewis acids such as boron tribromide, indium(III) bromide, boron trifluoride, aluminum(III) chloride, and trimethylsilyl trifluoromethanesulfonate.

The base used in the reaction in each step of the following methods A to G is not particularly limited, as long as it does not inhibit the reaction, and is selected from the following base group. The base group consists of alkali metal carbonate salts such as lithium carbonate, sodium carbonate, potassium carbonate, and cesium carbonate; alkali metal hydrogen carbonate salts such as lithium hydrogen carbonate, sodium hydrogen carbonate, and potassium hydrogen carbonate; alkali metal hydroxides such as lithium hydroxide, sodium hydroxide, and potassium hydrate; alkaline earth metal hydroxides such as calcium hydroxide and barium hydroxide; alkali metal hydrides such as lithium hydride, sodium hydride, and potassium hydride; alkali metal amides such as lithium amide, sodium amide, and potassium amide; alkali metal alkoxides such as lithium methoxide, sodium methoxide, sodium ethoxide, sodium tert-butoxide, and potassium tert-butoxide; lithium alkyl amides such as lithium diisopropylamide; silyl amides such as lithium bistrimethylsilylamide and sodium bistrimethylsilylamide; alkyl lithium such as n-butyllithium, sec-butyllithium, and tert-butyllithium; alkyl magnesium halides such as methyl magnesium chloride, methyl magnesium bromide, methyl magnesium iodide, ethyl magnesium chloride, ethyl magnesium bromide, isopropyl magnesium chloride, isopropyl magnesium bromide, and isobutyl magnesium chloride; and organic amines such as triethylamine, tributylamine, N,N-diisopropylethylamine, 1-methylpiperidine, 4-methylmorpholine, 4-ethylmorpholine, pyridine, picoline, 4-dimethylaminopyridine, 4-pyrrolidinopyridine, 2,6-di-tert-butyl-4-methylpyridine, quinoline, N,N-dimethylaniline, N,N-diethylaniline, 1,5-diazabicyclo[4,3,0]-5-nonene (DBN), 1,4-diazabicyclo[2,2,2]octane (DABCO), 1,8-diazabicyclo[5,4,0]-7-undecene (DBU), and imidazole.

In the reaction in each step of the following methods A to G, the reaction temperature varies depending on the solvent, the starting material, the reagent, and the like, and the reaction time varies depending on the solvent, the starting material, the reagent, the reaction temperature, and the like.

In the reaction in each step of the following methods A to G, after terminating the reaction, the compound of interest of each step is isolated from the reaction mixture according to an ordinary method. The compound of interest can be obtained by, for example, (i) filtering off insoluble materials such as a catalyst, as necessary, (ii) adding water and a water-immiscible solvent (e.g., dichloromethane, diethyl ether, ethyl acetate, and toluene) to the reaction mixture to extract the compound of interest, (iii) washing the organic layer with water and drying it using a drying agent such as anhydrous magnesium sulfate, and (iv) distilling off the solvent. The compound of interest obtained can be further purified by an ordinary method such as recrystallization, reprecipitation, distillation, or column chromatography using silica gel or alumina (including normal phase and reverse phase), if necessary. The compound of interest obtained is identified by standard analysis techniques such as elemental analysis, NMR, mass spectroscopy, and IR analysis, and its composition or purity can be analyzed. The compound of interest of each step can be used in the next reaction as it is, without purification.

In each step of the following methods A to G, optical isomers can be separated and purified by fractional recrystallization using optically active amines such as (R)-(+)- or (S)-(−)-1-phenethylamine or optically active carboxylic acids such as (+)- or (−)-10-camphorsulfonic acid, or separation using an optically active column.

The raw material and the reagent used to manufacture the compound of the present invention can be purchased from commercial suppliers or can be synthesized by a method described in the literature or a method similar thereto.

Method A

[Chemical Formula 80]

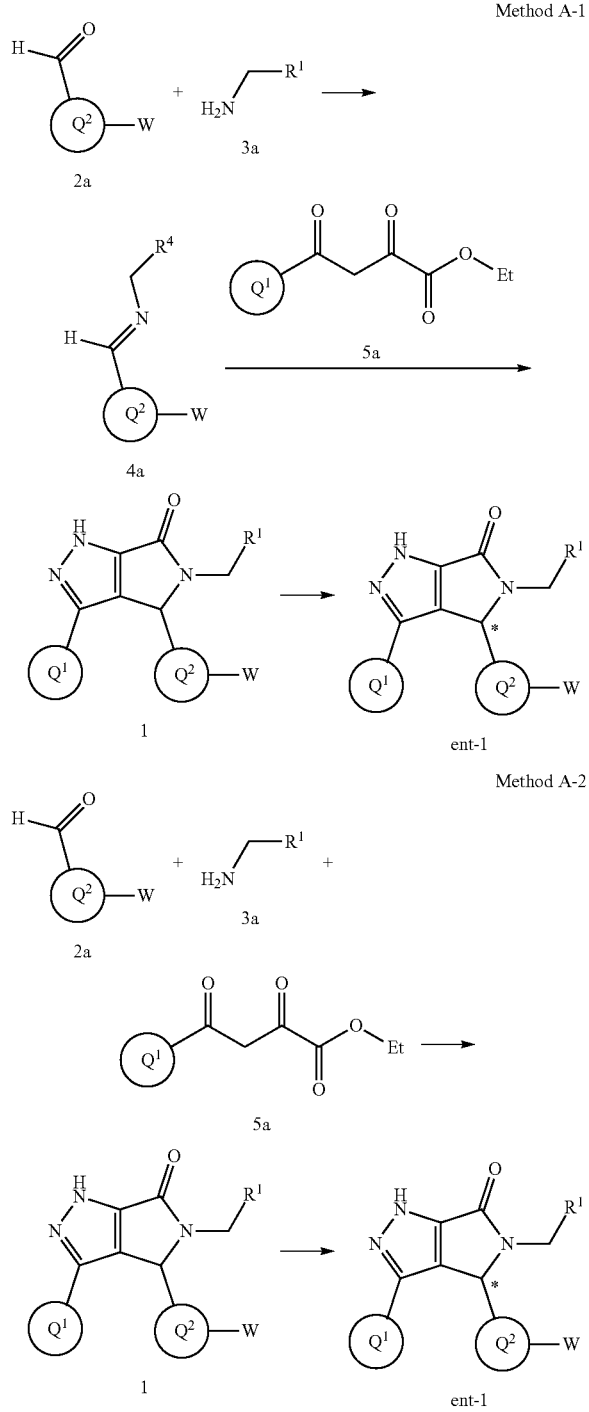

[In the formula, $R^1$, ring $Q^1$, ring $Q^2$, and W are as defined above. The ent attached before the number of the compound represents that the compound is an enantiomer. Et represents an ethyl group.]

Hereinafter, the reaction in each step of method A-1 and method A-2 will be described.

Method A-1

(A-1-1) Transformation of Compound 2a and Compound 3a into Compound 4a

It can be carried out by reacting compound 2a with compound 3a in a solvent inert to the reaction (e.g., tetrahydrofuran, dichloromethane, N,N-dimethylformamide, acetonitrile, and water). A drying agent (e.g., magnesium sulfate and sodium sulfate) may be used. When a salt of compound 3a (e.g., hydrochloride) is used as a raw material instead of compound 3a, it is preferably carried out by adding a base (e.g., triethylamine, N,N-diisopropylethylamine, pyridine, 4-dimethylaminopyridine, and sodium hydrogen carbonate). Preferably, the reaction temperature is −15° C. to room temperature and the reaction time is 2 hours to 6 days.

(A-1-2) Transformation of Compound 4a and Compound 5a into Compound 1

It can be carried out by reacting compound 4a with compound 5a in a solvent inert to the reaction (e.g., acetic acid, 1,4-dioxane, and acetonitrile), and then treating with hydrazine monohydrate. Preferably, the reaction temperature is room temperature to 100° C. and the reaction time is 30 minutes to 6 days.

(A-1-3) Manufacture of Compound Ent-1 from Compound 1

It can be carried out by optical resolution using an optically active column (e.g., CHIRALPAK (registered trademark, Daicel Corporation) IA, IB, IC, IG, IH, and AD-H, or CHIRALFLASH (registered trademark, Daicel Corporation) IA and IC) as a stationary phase, and various solvents (e.g., n-hexane, ethanol, tetrahydrofuran, 2-propanol, ethyl acetate, acetonitrile, and mixtures thereof) as a mobile phase.

Method A-2

(A-2-1) Transformation of Compound 2a, Compound 3a, and Compound 5a into Compound 1

It can be carried out by reacting compound 2a and compound 3a with compound 5a in a solvent inert to the reaction (e.g., acetic acid, 1,4-dioxane, and acetonitrile), and then treating with hydrazine monohydrate. When a salt of compound 3a (e.g., hydrochloride) is used as a raw material instead of compound 3a, it is preferably carried out by adding a base (e.g., triethylamine, N,N-diisopropylethylamine, pyridine, 4-dimethylaminopyridine, and sodium hydrogen carbonate). Preferably, the reaction temperature is room temperature to 100° C. and the reaction time is 30 minutes to 6 days.

(A-2-2) Manufacture of Compound Ent-1 from Compound 1

It can be carried out in the same manner as step A-1-3.

Next, the method for manufacturing compound 2a will be described.

Compound 2a is known or manufactured according to a known method or a method similar thereto using a known compound as a starting material. The known compound can be purchased from commercial suppliers or can be easily synthesized by a method described in the literature or a method similar thereto. Examples of the known literature include J. Med. Chem., 58, 3036-3059 (2015), WO 2009/125606 A1, Eur. J. Med. Chem., 115, 453-462 (2016), WO 2008/066131 A1, WO 2006/135826 A1, WO 2009/127949

A1, WO 2002/078693 A2, US 2007/0185058 A1, Bioorg. Med. Chem. Lett., 25, 5228-5231 (2015), WO 2015/118019 A1, Med. Chem. Res., 21, 2428-2442 (2012), US 2015/0291632 A1, WO 2009/105220 A1, WO 2011/022348 A1, WO 2016/115282 A1, and J. Am. Chem. Soc., 128, 10694-10695 (2006).

Hereinafter, methods B to E will be described as examples of methods for manufacturing compound 2a, but the method for synthesizing 2a is not limited thereto.

When the structure of compound 2a is represented by compound 2a-1, compound 2a-1 can be manufactured by, for example, method B or method C.

Method B

[Chemical Formula 81]

Method B-1

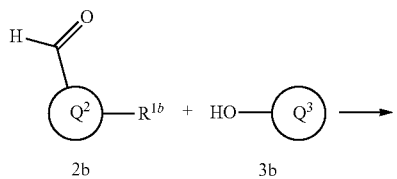

2b  3b

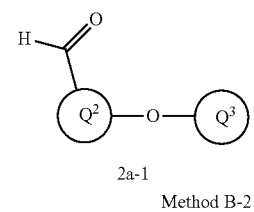

2a-1

Method B-2

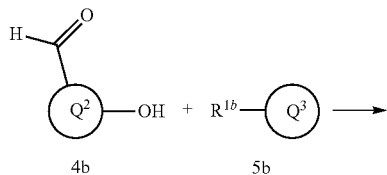

4b  5b

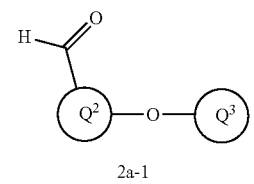

2a-1

[In the formula, ring $Q^2$ and ring $Q^3$ are as defined above. $R^{1b}$ represents a leaving group (e.g., a fluorine atom, a chlorine atom, a bromine atom, a methylsulfonyloxy group, and a trifluoromethylsulfonyloxy group).]

Method B-1

Method B-1 can be carried out by reacting compound 2b with compound 3b in a solvent inert to the reaction (e.g., dimethylsulfoxide, N,N-dimethylformamide, N-methyl-2-pyrrolidone, N,N-dimethylacetamide, acetonitrile, and tetrahydrofuran), in the presence of a base (e.g., potassium carbonate, cesium carbonate, triethylamine, N,N-diisopropylethylamine, and pyridine). Preferably, the reaction temperature is room temperature to 160° C. and the reaction time is 30 minutes to 2 days, and it can also be carried out under microwave irradiation.

Method B-2

Method B-2 can be carried out by reacting compound 4b with compound 5b in the same reaction conditions as method B-1.

With respect to method B-1 and method B-2, examples of the known literature include WO 2007/061670 A1, Synlett, 3, 431-434 (2002), US 2015/0274721 A1, J. Med. Chem., 60, 6451-6457 (2017), WO 2004/048320 A1, US 2009/0227560 A1, WO 2009/051956 A2, WO 2016/164201 A1, WO 2014/021281 A1, J. Org. Chem., 78, 5804-5809 (2013), and JP 2003/321406 A.

Method C

[Chemical Formula 82]

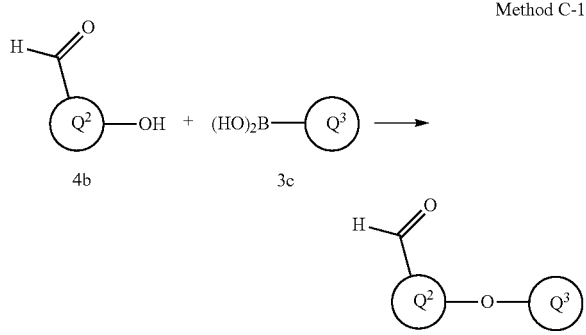

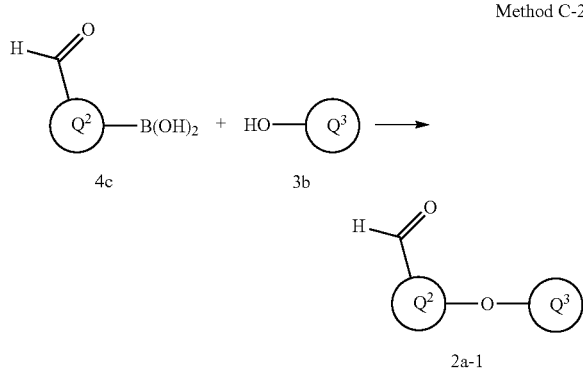

[In the formula, ring $Q^2$ and ring $Q^3$ are as defined above.]

Method C-1

Method C-1 can be carried out by reacting compound 4b with compound 3c in a solvent inert to the reaction (e.g., dichloromethane, N,N-dimethylformamide, N-methyl-2-pyrrolidone, N,N-dimethylacetamide, and tetrahydrofuran), in the presence of a copper catalyst (e.g., copper(II) acetate and copper(I) iodide), a base (e.g., pyridine, triethylamine, N,N-diisopropylethylamine, and potassium carbonate), and molecular sieves 4A. Preferably, the reaction temperature is room temperature to 100° C. and the reaction time is 1 hour to 6 days.

Method C-2

Method C-2 can be carried out by reacting compound 4c with compound 3b in the same reaction conditions as method C-1.

With respect to method C-1 and method C-2, examples of the known literature include WO 2008/050199 A2, US 2009/0312315 A1, WO 2007/085557 A2, WO 2009/111676 A2, WO 2009/068214 A2, WO 2013/021021 A1, WO 2013/061052 A1, J. Med. Chem., 57, 8984-8998 (2014), WO 2012/131277 A1, and Bioorg. Med. Chem., 9, 677-694 (2001).

When the structure of compound 2a is represented by 2a-2, compound 2a-2 can be manufactured by, for example, method D or method E.

Method D

Method D

[Chemical Formula 83]

[In the formula, $R^{1d}$ represents a $C_{1-6}$ alkyl group, a halogeno $C_{1-6}$ alkyl group, a $C_{3-8}$ cycloalkyl group, or a phenyl $C_{1-6}$ alkyl group (the phenyl group of the phenyl $C_{1-6}$ alkyl group may have a substituent).]

It can be carried out by reacting compound 4b with compound 3d in a solvent inert to the reaction (e.g., tetrahydrofuran, dichloromethane, toluene, and ethyl acetate), in the presence of an azodicarboxylic acid derivative (e.g., diethyl azodicarboxylate, diisopropyl azodicarboxylate, di-tert-butyl azodicarboxylate, and N,N,N',N'-tetramethylazodicarboxamide) and a phosphorus compound (e.g., triphenylphosphine and tri-n-butylphosphine). Instead of the azodicarboxylic acid derivative and the phosphorus compound, a phosphorus ylide compound (e.g., cyanomethylene tributylphosphorane and cyanomethylene trimethylphosphorane) may be used. Preferably, the reaction temperature is −10° C. to 100° C. and the reaction time is 5 minutes to 6 days. Depending on the chemical structure of compound 3d, inversion of the asymmetric center may occur.

With respect to method D, examples of the known literature include WO 2013/082345 A1, Org. Lett., 6, 397-400 (2004), WO 2009/004430 A1, WO 2010/093704 A1, and J. Med. Chem., 55, 3228-3241 (2012).

Method E

Method E

[Chemical Formula 84]

[In the formula, $R^{1e}$ represents a $C_{1-6}$ alkyl group, a halogeno $C_{1-6}$ alkyl group, a $C_{3-8}$ cycloalkyl group, a halogeno $C_{3-8}$ cycloalkyl group, or a saturated heterocyclic group, $R^{2b}$ represents a leaving group (e.g., a bromine atom, an iodine atom, a chlorine atom, a methanesulfonyloxy group, a p-toluene sulfonyloxy group, and a trifluoromethanesulfonyloxy group).]

It can be carried out by reacting compound 4b with compound 3e in a solvent inert to the reaction (e.g., N,N-dimethylformamide, N-methyl-2-pyrrolidone, N,N-dimethylacetamide, acetonitrile, dimethylsulfoxide, and tetrahydrofuran), in the presence of a base (e.g., potassium carbonate, cesium carbonate, sodium hydride, triethylamine, N,N-diisopropylethylamine, and pyridine). Preferably, the reaction temperature is −10° C. to 160° C. and the reaction time is 30 minutes to 3 days.

With respect to method E, examples of the known literature include WO 2002/068439 A1, Synthesis, 2671-2683 (2011), US 2009/0156610 A1, WO 2007/140005 A2, J. Med. Chem., 45, 3891-3904 (2002), and WO 2012/000945 A1.

Since compound 2a has a formyl group on ring Q, it can also be derived from a precursor having a group that can be easily transformed into this functional group (e.g., a hydroxymethyl group, a $C_{1-6}$ alkoxycarbonyl group, a carboxy group, and a halogeno group (e.g., an iodo group and a bromo group)). The precursor is known or manufactured according to a known method or a method similar thereto using a known compound as a starting material. The known compound can be purchased from commercial suppliers or can be easily synthesized by a method described in the literature or a method similar thereto. Examples of the known literature include WO 2012/141338 A1, US 2004/0132708 A1, Bioorg. Med. Chem., 18, 5208-5223 (2010), WO 2007/105637 A1, Bioorg. Med. Chem. Lett., 21, 6470-6475 (2011), WO 2009/058921 A1, WO 2007/018956 A2, US 2006/0276446 A1, WO 2008/136324 A1, J. Med. Chem., 50, 5589-5599 (2007), WO 2007/022371 A2, WO 2007/047397 A2, Bioorg. Med. Chem., 14, 8086-8093 (2006), WO 2006/051477 A2, Synthetic Commun., 31, 2885-2889 (2001), Synthetic Commun., 31, 1253-1256 (2001), Eur. J. Med. Chem., 80, 523-534 (2014), J. Org. Chem., 81, 3619-3628 (2016), WO 2014/068988 A1, WO 2013/161312 A1, WO 2013/038374 A1, WO 2012/093174 A1, WO 2009/144494 A1, JP 2009/155212 A, JP 2009/120553 A, WO 2008/072726 A1, J. Am. Chem. Soc., 129, 3408-3419 (2007), Tetrahedron Lett., 49, 5024-5027 (2008), Org. Lett., 18, 3630-3633 (2016), Bioorg. Med. Chem., 20, 1240-1250 (2012), WO 2017/069601 A1, WO 2012/150220 A1, WO 2011/088201 A1, WO 2012/150220 A1, JP 2006/241065 A, WO 2016/168059 A1, J. Med. Chem., 60, 9299-9319 (2017), WO 2012/101011 A2, J. Am. Chem. Soc., 135, 16705-16713 (2013), WO 2001/053274 A1, Angew. Chem. Int. Ed., 56, 13426-13430 (2017), Bioorg. Med. Chem., 11, 875-884 (2003), Bioorg. Med. Chem. Lett., 21, 3452-3456 (2011), WO 2017/147700, WO 2001072687 A1, WO 2002/018333 A1, WO 2009/144961 A1, WO 2010/003127 A2, WO 2002/018333 A1, WO 2002/083643 A1, WO 2001/032174 A1, WO 2018/087527 A1, and WO 2017/200825 A1.

When the structure of compound 2a is represented by compound 2a-3, compound 2a-3 is known or can be manufactured by appropriately combining known methods or methods similar thereto using a known compound as a starting material. Hereinafter, examples of the literature for the above known methods will be illustrated for each type of Y', but are not limited thereto.

[Chemical Formula 85]

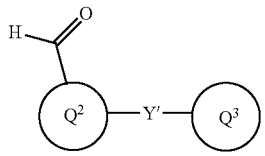

2a-3

[In the formula, ring $Q^2$ and ring $Q^3$ are as defined above, Y' represents a single bond, a sulfur atom, —NH—, a $C_{1-6}$ alkoxy $C_{1-6}$ alkylene group, or a halogeno $C_{1-6}$ alkylene group.]

When Y' is a single bond in the structure of compound 2a-3, examples of the literature include Eur. J. Med. Chem., 115, 453-462 (2016), WO 2009/129625 A1, and Tetrahedron, 70, 3471-3477 (2014).

When Y' is a sulfur atom in the structure of compound 2a-3, examples of the literature include WO 2016/019588 A1, WO 2010/115736 A2, Angew. Chem. Int. Ed., 56, 874-879 (2017), Synlett, 1143-1148 (2011), Tetrahedron Lett., 54, 1677-1680 (2013), and Synlett, 23, 2223-2226 (2012).

When Y' is —NH— in the structure of compound 2a-3, examples of the literature include J. Med. Chem., 61, 6379-6397 (2018), WO 2016/112637 A1, WO 2016/057770 A1, J. Am. Chem. Soc., 130, 6686-6687 (2008), Angew. Chem. Int. Ed., 55, 13219-13223 (2016), WO 2010/123599 A2, Org. Lett., 6, 2631-2634 (2004), and WO 2002/078693 A2.

When Y' is a $C_{1-6}$ alkoxy $C_{1-6}$ alkylene group in the structure of compound 2a-3, examples of the literature include WO 2013/075083 A1, Bioorg. Med. Chem., 20, 4279-4289 (2012), US 2012/0142934 A1, WO 2004/022526 A1, and WO 2003/101916 A1.

When Y' is a halogeno $C_{1-6}$ alkylene group in the structure of compound 2a-3, examples of the literature include Tetrahedron, 64, 9837-9842 (2008), WO 2016/019588 A1, WO 2012/054721 A1, WO 2010/124114 A1, and J. Am. Chem. Soc., 140, 9404-9408 (2018).

When the structure of compound 2a is represented by compound 2a-4, compound 2a-4 is known or can be manufactured by appropriately combining known methods or methods similar thereto using a known compound as a starting material. With respect to the known method, examples of the literature include Eur. J. Med. Chem., 102, 320-333 (2015), WO 2014/151761 A1, and Eur. J. Med. Chem., 43, 1706-1714 (2008), but are not limited thereto.

[Chemical Formula 86]

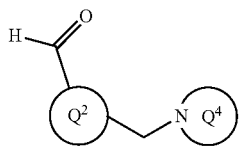

2a-4

[In the formula, ring $Q^4$ represents a heterocyclic ring having a nitrogen atom in the ring (the heterocyclic ring may have a substituent), and examples thereof include a piperidine ring.]

Compound 3a is known or manufactured according to a known method or a method similar thereto using a known compound as a starting material. The known compound can be purchased from commercial suppliers or can be easily synthesized by a method described in the literature or a method similar thereto.

Next, the method for manufacturing compound 5a will be described.

Compound 5a is known or manufactured according to a known method or a method similar thereto using a known compound as a starting material. The known compound can be purchased from commercial suppliers or can be easily synthesized by a method described in the literature or a method similar thereto. There are many reports on the known literatures such as Synthetic Commun., 43, 110-117 (2013), Synthesis, 15, 2325-2330 (2003), WO 2004/018428 A1, Tetrahedron, 71, 1940-1951 (2015), WO 2013/170115 A1, WO 2013/067302 A1, and Bioorg. Med. Chem, 23, 1082-1095 (2015).

Hereinafter, method F will be described as an example of the method for manufacturing compound 5a, but the synthesis method of 5a is not limited thereto.

Method F

Method F

[Chemical Formula 87]

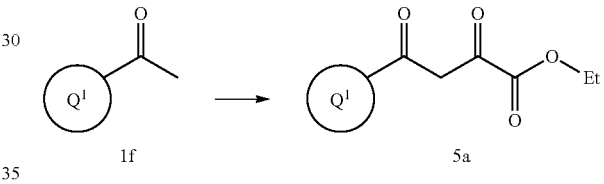

[In the formula, Q is as defined above. Et represents an ethyl group.]

It can be carried out by treating compound 1f with a base (e.g., potassium tert-butoxide, sodium ethoxide, sodium hydride, and sodium bis(trimethylsilyl)amide) in a solvent inert to the reaction (e.g., tetrahydrofuran, ethanol, methanol, N,N-dimethylformamide, and toluene), and then reacting it with diethyl oxalate. Preferably, the reaction temperature is −78° C. to 100° C. and the reaction time is 30 minutes to 3 days.

Next, the method for manufacturing compound 1f will be described.

Compound 1f is known or manufactured according to a known method or a method similar thereto using a known compound as a starting material. The known compound can be purchased from commercial suppliers or can be easily synthesized by a method described in the literature or a method similar thereto. Examples of the known literature include J. Med. Chem., 56, 3833-3851 (2013), Archives of Pharmacal Reseach, 37, 588-599 (2014), WO 2004/018468 A2, Comptes Rendus de I'Academie Bulgare des Sciences, 61, 41-48 (2008), Synlett, 1920-1922 (2011), J. Org. Chem., 71, 6652-6654 (2006), WO 2006/101860 A1, and Med. Chem. Res., 23, 4814-4824 (2014).

When the structure of compound 1f is represented by compound 1f-1, compound 1f-1 can be manufactured by, for example, method G.

Method G

Method G

[Chemical Formula 88]

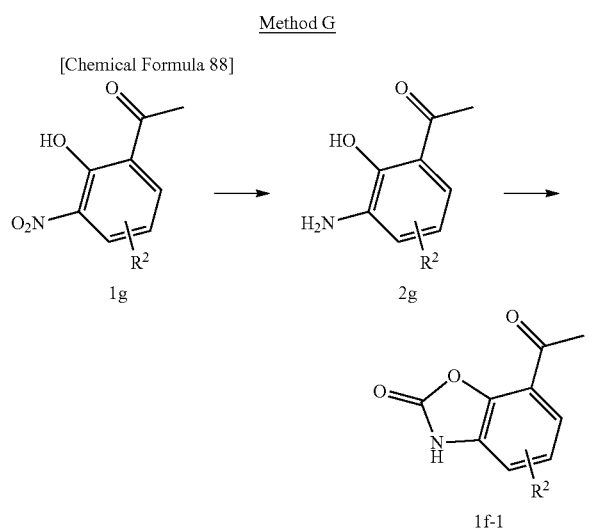

[In the formula, $R^2$ represents a hydrogen atom, a halogen atom, or a phenoxy group.]

Hereinafter, the reaction in each step of method G will be described.

(G-1) Transformation of Compound 1g into Compound 2g

It can be carried out by treating compound 1g with zinc (powder) in a solvent inert to the reaction (e.g., ethanol, methanol, tetrahydrofuran, 1,4-dioxane, water, or mixtures thereof), in the presence of an acid (e.g., acetic acid, ammonium chloride, and hydrochloric acid). Preferably, the reaction temperature is room temperature to 100° C. and the reaction time is 2 hours to 2 days.

(G-2) Transformation of Compound 2g into Compound 1f-1

It can be carried out by treating compound 2g with 1,1'-carbonyldiimidazole in a solvent inert to the reaction (e.g., tetrahydrofuran, N,N-dimethylformamide, acetonitrile, and dichloromethane). Preferably, the reaction temperature is 0° C. to 130° C. and the reaction time is 15 minutes to 6 days.

With respect to method G, examples of the known literature include Synthesis, 1789-1792 (2004), JP 11029540 A, JP 03095144 A, WO 2011/023753 A1, J. Med. Chem., 29, 538-549 (1986), WO 2015/005429 A1, WO 2008/147544 A1, Synthesis, 940-942 (1982), J. Med. Chem., 52, 7142-7156 (2009), and J. Med. Chem., 57, 878-902 (2014).

Since compound if has an acetyl group on ring $Q^1$, it can also be derived from a precursor having a group that can be easily transformed into this functional group (e.g., a $C_{1-6}$ alkoxycarbonyl group, a carboxy group, a halogeno group (e.g., an iodo group and a bromo group), and a formyl group). The precursor is known or manufactured according to a known method or a method similar thereto using a known compound as a starting material. The known compound can be purchased from commercial suppliers or can be easily synthesized by a method described in the literature or a method similar thereto. Examples of the known literature include J. Med. Chem., 54, 6761-6770 (2011), WO 2006/069063 A1, WO 2012/053186 A1, J. Am. Chem. Soc., 127, 751-760 (2005), Org. Lett., 3, 295-297 (2001), Synlett, 1440-1442 (2004), J. Org. Chem., 76, 2062-2071 (2011), WO 2010/006130 A2, WO 2011/137024 A1, WO 2014/092104 A1, J. Org. Chem., 18, 1092-1103 (1953), and WO 9948880 A1.

The PSS1 inhibitory activity of the compound of the present invention or the pharmaceutically acceptable salt can be measured using the assay described in the following Test Example 1 or 2. In the present invention, the "PSS1 inhibitory activity" refers to an enzyme inhibitory activity against the synthesis of phosphatidylserine mediated by PSS1.

The cell growth inhibitory activity of the compound of the present invention or a pharmaceutically acceptable salt thereof can be examined using a growth inhibition test method that is commonly used by those skilled in the art. The cell growth inhibitory activity can be examined by, for example, comparing the degree of cell growth in the presence or absence of a test compound, as described in the following Test Example 3. The degree of the growth can be examined using, for example, a test system for measuring living cells. Examples of the method for measuring living cells include the ATP measurement method, the [$^3$H]-thymidine uptake test, the BrdU method, and the MTT assay.

The in vivo antitumor activity can be examined using a method for testing antitumor activity that is commonly used by those skilled in the art. For example, as described in the following Test Example 4, the in vivo antitumor activity of the present invention can be confirmed by transplanting various tumor cells into mice, rats, or the like, confirming the engraftment of the transplanted cells, then orally or intravenously administering the compound of the present invention, and comparing the tumor growth in the drug non-administration group with the tumor growth in the compound administration group a few days or a few weeks later.

The approach for "detecting suppression of PSS2 function" in the present invention is not particularly limited, and examples thereof include the following methods. The method for extracting genomic DNA or RNA from a biological sample derived from a test subject is not particularly limited, and a known approach can be appropriately selected and used. For example, examples of the method for extracting genomic DNA include the SDS phenol method (a method in which proteins of a tissue stored in a solution containing urea or ethanol are denatured with a proteolytic enzyme (proteinase K), a surfactant (SDS), and phenol, and DNA is extracted from the tissue by precipitation with ethanol), and methods for extracting DNA using Clean Columns (registered trademark, manufactured by NexTec), AquaPure (registered trademark, manufactured by Bio-Rad), ZR Plant/Seed DNA Kit (manufactured by Zymo Research), AquaGenomicSolution (registered trademark, manufactured by Mo Bi Tec), prepGEM (registered trademark, manufactured by ZyGEM), BuccalQuick (registered trademark, manufactured by TrimGen), or the like. Examples of the method for extracting RNA include extraction methods using phenol and a chaotropic salt (more specifically, extraction methods using a commercially available kit such as Trizol (manufactured by Invitrogen) and ISOGEN (manufactured by Wako Pure Chemical Industries, Ltd.)), and methods using other commercially available kits (RNAPrep Total RNA Extraction Kit (manufactured by Beckman Coulter), RNeasy Mini (manufactured by QIAGEN), and RNA Extraction Kit (manufactured by Pharmacia Biotech). Further, the reverse transcriptase used to prepare cDNA from the extracted RNA is not particularly limited, and examples thereof include reverse transcriptases derived from retroviruses such as RAV (Rous associated virus) and AMV (Avian myeloblastosis virus), and reverse transcriptases derived from retroviruses of mice such as MMLV (Moloney murine leukemia virus.

—Detection of Deletion of PTDSS2—

The deletion of PTDSS2 can be confirmed by analyzing the genotype of PTDSS2. To analyze the genotype of PTDSS2, any known method can be used. For example, the analysis of genotype can be carried out by detecting the copy number variation (CNV) of PTDSS2 DNA. CNV refers to a phenomenon in which a genomic DNA extending over 1 kb or more on a chromosome is 1 copy or less or 3 copies or more, which is 2 copies in a normal human somatic cell, that is, in a diploid genome. It can be considered that when the gene copy number is 1 copy or less, the genomic DNA is deleted, and when the gene copy number is 3 copies or more, the genomic DNA is duplicated. Detection of CNV can be carried out using a known method, and specific examples of such a method include the array CGH method, the single nucleotide polymorphism (SNP) array method, the quantitative real-time PCR (Quantitative Real Time Polymerase Chain Reaction; qPCR) method, the multiplex ligation-dependent probe amplification method, the next-generation sequencing, and the digital PCR method.

—Detection of Decreased Expression of PSS2—

As used herein, "decreased expression" means that the expression level is lower as compared with that of the control (e.g., the average expression level of healthy individuals or the expression level in a non-cancer tissue of the same patient).

Specifically, the analysis of the expression of the PTDSS2 gene in a biological sample can be carried out by, for example, measuring the amount of mRNA which is a transcript of the gene to be measured, or measuring the amount of protein which is a gene product of the object to be measured.

As the method for measuring the amount of mRNA, a known method for detecting gene expression can be used. For example, the amount of mRNA can be measured using various molecular biology approaches such as Northern blotting, dot blotting, polymerase chain reaction (PCR), reverse transcription PCR (RT-PCR), quantitative RT-PCR, hybridization method, and DNA array method, next-generation sequencing, and digital PCR. Also, the amount of mRNA can be measured by a known method using a polynucleotide having a DNA sequence that hybridizes with the gene to be measured under stringent conditions as a probe. For example, in the preparation of the probe, a label such as a fluorescent label is appropriately bonded to the probe, which is hybridized with mRNA isolated and purified from a biological sample or with cDNA synthesized from the mRNA. Thereafter, the fluorescence intensity derived from the hybridized probe is measured, so that the amount of mRNA of the gene to be measured is detected. The probe can be used by being immobilized on a support such as glass beads or a glass substrate. That is, the probe can be used in the form of a DNA array or a DNA chip in which the probe prepared for the gene to be measured is immobilized on a support. The support is not particularly limited, as long as it can immobilize a polynucleotide, and it may have any shape and may be made of any material. In general, examples of the support include inorganic materials such as glass plate, silicon wafer, and resin; nitrocellulose as a natural polymer material; and nylon as a synthetic polymer material.

Commercially available DNA chips and DNA arrays can be used. The polynucleotide to be immobilized on the support may be a synthetic oligonucleotide. It is also possible to introduce a nucleic acid derivative capable of fluorescent labeling on the sequence of the synthetic oligonucleotide. Both the Affymetrix-type DNA chip technique capable of synthesizing the oligonucleotide of interest on a support and the Stanford-type DNA chip technique of immobilizing the synthesized DNA fragment by spotting as a DNA probe can be used. Further, the desired polynucleotide can be spotted and immobilized on a cylindrical surface of the 3D-Gene (manufactured by TORAY INDUSTRIES, INC.) having a support with a three-dimensional structure. Note that, "hybridize under stringent conditions" means that the hybridization is maintained, for example, even after washing treatment at 42° C. with a buffer solution containing 1×SSC (0.15 M NaCl, 0.015 M sodium citrate) and 0.1% sodium dodecyl sulfate (SDS) at 42° C. In addition to the above temperature conditions, there are various elements that affect the stringency of hybridization, and those skilled in the art could combine various elements to achieve a stringency equivalent to the stringency of hybridization illustrated above.

The probe and primer set for quantitatively detecting mRNA and cDNA derived from the PTDSS2 gene are not particularly limited, as long as they can specifically detect the mRNA and cDNA, but an oligonucleotide consisting of 12 to 26 bases are preferred. Such a probe and primer set can be appropriately designed based on the base sequence information of the gene to be measured, and an oligonucleotide having the determined sequence can be synthesized by, for example, an ordinary method using a DNA synthesizer. The desired one of commercially available primers and probes for gene detection can also be selected and used.

As a method for quantitatively measuring PSS2, a known protein measurement method can be used. For example, various methods using an antibody against PSS2 can be applied. Specific examples thereof include Western blot, Enzyme-Linked Immuno Sorbent Assay (ELISA), and Radio Immuno Assay (RIA).

The antibody against PSS2 has PSS2 as the antigen, and as long as it is specifically bonded to the antigen, a human type antibody, a mouse antibody, a rat antibody, a rabbit antibody, a sheep antibody, and the like can be appropriately used. The antibody may be a polyclonal antibody or a monoclonal antibody, but the monoclonal antibody is preferred because it can stably produce a homogeneous antibody. The polyclonal antibody and monoclonal antibody can be prepared by the methods well known to those skilled in the art. The desired antibody of commercially available antibodies can also be selected and used.

The hybridoma that generates the monoclonal antibody can be basically prepared using a known technique as follows. That is, it can be prepared by using an antigen of interest or cells expressing the antigen of interest as sensitizing antigens, immunizing these to the desired animal according to a conventional immunization method, fusing the resulting immune cells with known parental cells by a conventional cell fusion method, and thereafter, screening for the desired monoclonal antibody generating cells (hybridoma cells) by a conventional screening method. For example, the preparation of hybridomas can be carried out according to the method of Milstein et al. ("Methods of Enzymology", 1981, vol. 73, p. 3-46) and the like.

Here, in preparation of the monoclonal antibody, PSS2 and its fragment can be used as antigens. Those skilled in the art could easily obtain PSS2 and its fragment, for example, according to the method described in publications such as Sambrook et al. ed., "Molecular Cloning A Laboratory Manual", 2nd edition, Vol. 1-3, Cold Spring Harbor Laboratory Press, New York 1989.

To quantify PSS2, the PSS2 protein, its fragment, and the antibody against that can be used by being immobilized on a support. The support is not limited, as long as it can immobilize proteins, and examples thereof include inorganic materials such as glass plate, silicon wafer, and resin; nitrocellulose as a natural polymer material; and nylon and polystyrene as a synthetic polymer material, in general.

The detection of PSS2 can also be performed using mass spectrometry (MS). In particular, analysis by a mass spectrometer coupled with liquid chromatography (LC/MS) is sensitive and thus is advantageous. Measurement by mass spectrometry can be performed by, for example, preparing a protein from a biological sample, labeling the protein, fractionating the protein, subjecting the fractionated protein to mass spectrometry, and identifying PSS2 from the mass spectrometry value. An isotopically labeled reagent known in the art can be used as a label, and an appropriate labeling reagent can be obtained as a commercial product. Also, fractionation can be performed by a method known in the art, and for example, it can be performed using a commercially available strong cation column, and the like.

On the other hand, it is known in the art that hypermethylation of the promoter is one of the factors of the decreased expression of a gene. Therefore, in the detection of the presence or absence of suppression of PSS2 function, it is also considered to detect it using the methylation of the PSS2 gene promoter as an index. To detect the methylation of the promoter, for example, a known method such as a method for directly detecting the change in the base sequence after the treatment with bisulfite, which has an activity of transforming methylated cytosine to uracil, by sequencing, or a method for indirectly detecting the change by using a restriction endonuclease that can recognize (cleave) the base sequence before the bisulfite treatment, but cannot recognize (cleave) the base sequence after the bisulfite treatment can be used.

—Detection of Mutation of PTDSS2—

In the present invention, "to detect a mutation" means detecting a mutation on a genomic DNA in principle, but when the mutation on the genomic DNA is reflected in the base change in a transcript and the amino acid change in a translation product, it also means detecting the changes in the transcript and translation product (that is, indirect detection).

A preferred aspect of the method of the present invention is a method for detecting a mutation by directly determining the base sequence in the PTDSS2 gene region in a biological sample derived from a test subject. As used herein, the "PTDSS2 gene region" means a certain region on a genomic DNA containing the PTDSS2 gene. The region includes the expression control region of the PTDSS2 gene (e.g., a promoter region and an enhancer region), the 3'terminal untranslated region of the PTDSS2 gene, and the like. Mutations in these regions may, for example, influence the transcriptional activity of the PTDSS2 gene.

Determination of the base sequences can be performed by a method known to those skilled in the art, such as the Maxam-Gilbert method or the Sanger method.

The presence or absence of the mutation in the PTDSS2 gene region in a test tissue can be determined by comparing the determined base sequence of DNA or cDNA with that of the control (e.g., the base sequence of the DNA or cDNA derived from a non-cancer tissue of the same patient).

The method for detecting a mutation in the PTDSS2 gene region can be performed by various methods capable of detecting the mutation, in addition to the method for directly determining the base sequence of DNA and cDNA.

For example, the detection of the mutation in the present invention can be performed by the following methods. First, a DNA or cDNA sample is prepared from a biological sample. Then, an oligonucleotide probe that has a base sequence complementary to a base sequence containing a mutation in the PTDSS2 gene region and is labeled with a reporter fluorescent dye and a quencher fluorescent dye is prepared. Subsequently, the oligonucleotide probe is hybridized to the DNA sample, and the base sequence containing the mutation in the PTDSS2 gene region is amplified using the DNA sample to which the oligonucleotide probe is hybridized as a template. Thereafter, the fluorescence emitted by the reporter fluorescent dye is detected by the degradation of the oligonucleotide probe associated with the amplification, and then, the detected fluorescence is compared with that of the control. Examples of such a method include the double dye probe method, the so-called TaqMan® probe method.

In still another method, a DNA or cDNA sample is prepared from a biological sample. Then, in a reaction system containing an intercalator that emits fluorescence when inserted between DNA double strands, the base sequence containing the mutation in the PTDSS2 gene region is amplified using the DNA sample as a template. Subsequently, the temperature of the reaction system is changed, the change in the intensity of the fluorescence emitted by the intercalator is detected, and the change in the intensity of the fluorescence associated with the change in the detected temperature is compared with that of the control. Examples of such a method include the HRM (high resolution melting) method.

In still another method, first, a DNA or cDNA sample is prepared from a biological sample. Then, the DNA containing a mutation site of a PTDSS2 gene region is amplified. Further, the amplified DNA is cleaved by a restriction enzyme. Then, the DNA fragments are separated according to their size. Then, the size of the detected DNA fragment is compared with that of the control. Examples of such a method include methods using Restriction Fragment Length Polymorphism (RFLP) and the PCR-RFLP method.

In still another method, first, a DNA or cDNA sample is prepared from a biological sample. Then, the DNA containing a mutation site of a PTDSS2 gene region is amplified. Further, the amplified DNA is dissociated into single-stranded DNA. Then, the dissociated single-stranded DNA is separated on a non-modified gel. The mobility of the separated single-stranded DNA on the gel is compared with that of the control. Examples of such a method include the PCR-SSCP (single-strand conformation polymorphism) method.

In still another method, first, a DNA or cDNA sample is prepared from a biological sample. Then, the DNA containing a mutation site of a PTDSS2 gene region is amplified. Further, the amplified DNA is separated on a gel in which the concentration of a DNA denaturant gradually increases. Then, the mobility of the separated DNA on the gel is compared with that of the control. Examples of such a method include the denaturant gradient gel electrophoresis (DGGE) method.

As still another method, there is a method using a DNA containing a mutation site of a PTDSS2 gene region prepared from a biological sample and a substrate having an oligonucleotide probe immobilized thereon to be hybridized with the DNA. Examples of such a method include the DNA array method.

In still another method, first, a DNA or cDNA sample is prepared from a biological sample. In addition, "an oligonucleotide primer having a base sequence complementary to the base adjacent 3' to the base of a mutation site of a PTDSS2 gene region and the base sequence 3' to the base" is prepared. Then, a ddNTP primer extension reaction is performed using the DNA as a template and using the primer. Then, the primer extension reaction product is subjected to a mass spectrometer for the mass measurement.

Then, the genotype is determined from the mass measurement result. Then, the determined genotype is compared with that of the control. Examples of such a method include the MALDI-TOF/MS method.

In still another method, first, a DNA or cDNA sample is prepared from a biological sample. Then, an oligonucleotide probe consisting of 5'—"a base sequence complementary to the base of a mutation site of a PTDSS2 gene region and the base sequence 5' to the base"-"a base sequence not hybridized with the base adjacent 3' to the mutation site of the PTDSS2 gene region and the base sequence 3' to the base"—3' (flap) is prepared. In addition, "an oligonucleotide probe having a base sequence complementary to the base of a mutation site of a PTDSS2 gene region and the base sequence 3' to the base" is prepared. Then, the above two oligonucleotide probes are hybridized to the prepared DNA. Then, the hybridized DNA is cleaved with a single-stranded DNA cleaving enzyme to release the flap. In the present invention, the single-stranded DNA cleaving enzyme is not particularly limited, and examples thereof include cleavase. In this method, an oligonucleotide probe having a sequence complementary to the flap, which is labeled with reporter fluorescence and quencher fluorescence, is then hybridized with the flap. Then, the intensity of the emitted fluorescence is measured. Then, the intensity of the measured fluorescence is compared with that of the control. Examples of such a method include the Invader method.

In still another method, first, a DNA or cDNA sample is prepared from a biological sample. Then, the DNA containing a mutation site of a PTDSS2 gene region is amplified. Subsequently, the amplificated DNA is dissociated into single strands, and only one strand of the dissociated single-stranded DNAs is separated. Then, the extension reaction is performed on each base from near the base of the mutation site of the PTDSS2 gene region, and the pyrophosphoric acid generated at this time is allowed to enzymatically emit light to measure the intensity of luminescence. Subsequently, the intensity of the measured fluorescence is compared with that of the control. Examples of such a method include the Pyrosequencing method.

In still another method, first, a DNA or cDNA sample is prepared from a biological sample. Then, the DNA containing a mutation site of a PTDSS2 gene region is amplified. Then, "an oligonucleotide primer having a base sequence complementary to the base adjacent 3' to the base of a mutation site of a PTDSS2 gene region and the base sequence 3' to the base" is prepared. Then, a single base extension reaction is performed in the presence of fluorescently labeled nucleotides using the amplified DNA as a template with the prepared primer. Subsequently, the polarization of the fluorescence is measured. Then, the polarization of the fluorescence measured is compared with that of the control. Examples of such a method include the AcycloPrime method.

In still another method, first, a DNA or cDNA sample is prepared from a biological sample. Then, the DNA containing a mutation site of a PTDSS2 gene region is amplified. Then, "an oligonucleotide primer having a base sequence complementary to the base adjacent 3' to the base of the mutation site of the PTDSS2 gene region and the base sequence 3' to the base" is prepared. Then, a single base extension reaction is performed in the presence of fluorescently labeled nucleotides using the amplified DNA as a template with the prepared primer. Then, the base type used in the single base extension reaction is determined. Then, the determined base type is compared with that of the control. Examples of such a method include the SNuPE method.

When the mutation is associated with the amino acid change (e.g., substitution, deletion, and insertion) in PSS2, the sample prepared from the biological sample may be protein. In this case, a method for using a molecule (e.g., antibody) specifically binds to the site where an amino acid change is caused by the mutation can be used to detect the mutation.

The compound of the present invention or a pharmaceutically acceptable salt thereof may be used in combination with other anti-tumor agents. Examples thereof include alkylating agents, antimetabolites, antitumor antibiotics, anti-tumor plant components, BRM (biological response modifiers), hormones, vitamins, anti-tumor antibodies, molecular target drug, and other anti-tumor agents.

More specific examples of alkylating agents include alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin and ranimustine; busulfan, improsulfan tosilate, and dacarbazine.

Examples of antimetabolites include purine antimetabolites such as 6-mercaptopurine, 6-thioguanine, and thioinosine; pyrimidine antimetabolites such as fluorouracil, tegafur, tegafur-uracil, carmofur, doxifluridine, broxuridine, cytarabine, and enocitabine; and folic acid antimetabolites such as methotrexate and trimethotrexate.

Examples of antitumor antibiotics include mitomycin C, bleomycin, peplomycin, daunorubicin, aclarubicin, doxorubicin, idarubicin, pirarubicin, THP-adriamycin, 4'-epidoxorubicin or epirubicin, chromomycin A3, and actinomycin D.

Examples of anti-tumor plant components include vinca alkaloids such as vindesine, vincristine, and vinblastine; taxanes such as paclitaxel and docetaxel; and epipodophyllotoxins such as etoposide and teniposide.

Examples of the BRM include tumor necrosis factor and indomethacin.

Examples of hormones include hydrocortisone, dexamethasone, methylprednisolone, prednisolone, prasterone, betamethasone, triamcinolone, oxymetholone, nandrolone, methenolone, fosfestrol, ethinyl estradiol, chlormadinone, mepitiostane, and medroxyprogesterone.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, ipilimumab, nivolumab, pembrolizumab, avelumab, pidilizumab, atezolizumab, ramucirumab, imatinib mesylate, dasatinib, gefitinib, erlotinib, osimertinib, sunitinib, lapatinib, dabrafenib, trametinib, cobimetinib, pazopanib, palbociclib, panobinostat, sorafenib, crizotinib, vemurafenib, quizartinib, bortezomib, carfilzomib, ixazomib, midostaurin, and gilteritinib.

Examples of other anti-tumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, sizofiran, picibanil, procarbazine, pipobroman, neocarzinostatin, hydroxyurea, ubenimex, thalidomide, lenalidomide, pomalidomide, eribulin, tretinoin, and krestin.

The pharmaceutical composition of the present invention contains the compound of the present invention or a pharmaceutically acceptable salt and a pharmaceutically acceptable carrier, and can be administered as various injections such as intravenous injection, intramuscular injection, and subcutaneous injection, or by various methods such as oral administration or percutaneous administration. The pharmaceutically acceptable carrier means a pharmaceutically acceptable material (e.g., an excipient, a diluent, an additive, and a solvent) involved in transport of the compound of the present invention or the composition containing the compound of the present invention from a certain organ or body part to another organ or body part.

A formulation containing the compound of the present invention or a pharmaceutically acceptable salt thereof as an active substance is prepared using additives such as a carrier and an excipient used for conventional formulations. Administration of the compound of the present invention may be oral administration in the form of tablets, pills, capsules, granules, powders, liquids, or the like, or parenteral administration in the form of injections (e.g., intravenous and intramuscular), suppositories, transdermal agents, nasal agents, inhalation agents, or the like. The dosage and frequency of administration of the compound of the present invention is appropriately determined according to each case in consideration of symptoms, age or sex of the subject to be administered, and the like. The dosage is commonly 0.001 mg/kg to 100 mg/kg per administration per adult in the case of oral administration, and is commonly 0.0001 mg/kg to 10 mg/kg per administration per adult in the case of intravenous administration. The frequency of administration is commonly once to six times daily or once daily to once per seven days.

The solid formulation of the present invention for oral administration may be tablets, powders, granules, or the like. Such formulations are manufactured according to an ordinary method by mixing one or more active materials with an inactive excipient, a lubricant, a disintegrant, a solubilizing aid, and the like. The excipient may be, for example, lactose, mannitol, or glucose. The lubricant may be, for example, magnesium stearate. The disintegrant may be, for example, sodium carboxymethyl starch. The tablets or pills may be coated with sugar coating or stomach-soluble or enteric coating, if necessary.

The liquid formulation for oral administration may be pharmaceutically acceptable emulsions, liquids, suspensions, syrups, elixirs, or the like. Such formulations contain generally used inactive solvents (e.g., purified water and ethanol), and may further contain solubilizing agents, moistening agents, suspending agents, sweetening agents, flavoring agents, flavoring agents, or preservatives.

The injection for parenteral administration may be sterile aqueous or non-aqueous liquids, suspensions, or emulsions. The aqueous solvent for injection may be, for example, distilled water or saline. The non-aqueous solvent for injection may be, for example, propyleneglycol, polyethylene glycol, plant oils such as olive oil, alcohols such as ethanol, or polysorbate 80 (name in Pharmacopeia). Such a formulation may further contain an isotonic agent, a preservative, a moistening agent, an emulsifying agent, a dispersing agent, a stabilizing agent, or a solubilizing aid. For example, these formulations may be sterilized by filtration through a bacteria-retaining filter, blending with a fungicide, or irradiation. Also, a composition obtained by dissolving or suspending a sterile solid composition in sterile water or an injection solvent before use can be used as these formulations.

EXAMPLES

Hereinafter, the present invention will be described further in detail by way of Reference Examples and Examples, but the scope of the present invention is not limited thereto and they should not be construed as limiting, in any way. As used herein, reagents, solvents, and starting materials not specifically described are readily available from commercial sources.

Column chromatography was performed either using a commercial packed column and an automated preparative purification system (e.g., SP1 manufactured by Biotage Japan Ltd., EPCLC-W-Prep2XY manufactured by YAMAZEN CORPORATION, and Purif-α2 manufactured by SHOKO SCIENCE CO., LTD.), or using silica gel SK-85 manufactured by Merck or Chromatorex NH of FUJI SILYSIA CHEMICAL LTD. as silica gel for column, and only a plurality of solvent types used as mobile phase was mentioned. Reverse phase high performance liquid chromatography (reverse phase HPLC) was performed using a reverse phase column (Develosil Combi-RP-5) manufactured by Nomura Chemical Co., Ltd., and an acetonitrile/water system containing 0.1% formic acid was used as a mobile phase. Elution was performed under observation by thin-layer chromatography (TLC) employing silica gel 60 $F_{254}$ or 60 $NH_2$ $F_{254}$s manufactured by Merck, $NH_2$ silica gel 60 $F_{254}$ plate manufactured by FUJIFILM Wako Pure Chemical Corporation, or CHROMATOREX NH TLC manufactured by FUJI SILYSIA CHEMICAL LTD as a TLC plate, the mobile phase used for the column chromatography as a developing solvent, and a UV detector or a color reagent as the detection method.

Preparative thin-layer chromatography (PTLC) was performed using silica gel 60 $F_{254}$ plate manufactured by Merck, or silica gel 70 $PF_{254}$ plate or $NH_2$ silica gel 60 $F_{254}$ plate manufactured by FUJIFILM Wako Pure Chemical Corporation, and only a plurality of solvent types used as mobile phase was mentioned.

The "optical resolution using two columns connected" in Examples refers to the optical resolution carried out by connecting two columns of the same type in series. For example, the "optical resolution using two Daicel Corporation CHIRALFLASH® IC (20 μm, 30 mmφ×100 mmL) connected" refers to the optical resolution carried out by connecting two CHIRALFLASH® IC (20 μm, 30 mmφ×100 mmL) manufactured by Daicel Corporation in series.

Purification, separation, and optical resolution were conducted according to the conditions determined based on the common knowledge and skill of the synthetic organic chemistry (e.g., the amount of solvent, solvent ratio, exchange timing thereof, and gradient method), unless specifically indicated in Reference Examples and Examples.

The abbreviations used in Reference Examples and Examples have the following meanings.

Me=methyl, Et=ethyl, SEM=2-(trimethylsilyl)ethoxymethyl group, Ms=methanesulfonyl, HATU=O-(7-azabenzotriazol-1-yl)-N,N,N',N'-tetramethyluroniumhexafluorophosphate (CAS number: 148893-10-1), EDCI=1-(3-dimethylaminopropyl)-3-ethylcarbodiimide hydrochloride (CAS number: 25952-53-8), and DBU=1,8-diazabicyclo [5.4.0]-7-undecene (CAS number: 6674-22-2).

The proton nuclear magnetic resonance spectrum ($^1$H-NMR) was measured using 400 MHz manufactured by JEOL Ltd., or 400 MHz nuclear magnetic resonance apparatus manufactured by Varian Medical Systems, Inc. The notations of spectral data indicate meaningful peaks and are shown with a chemical shift (which is shown as relative ppm (δ) using tetramethylsilane as a standard substance), the number of protons, the multiplicity of peak splitting (which is shown as s: singlet; d: doublet; t: triplet; q: quartet; quint: quintet; m: multiplet; br: broad, br s: broad singlet; and the like), and if it can be explicitly shown, the spin coupling constant is shown as J value (unit: Hz). The $^1$H-NMR (CDCl$_3$) shows the δ (ppm) of the peaks in the $^1$H-NMR in chloroform-d, and the $^1$H-NMR (DMSO-D$_6$) shows the δ (ppm) of the peaks in the $^1$H-NMR in dimethylsulfoxide-d$_6$.

The mass spectrum (MS m/z) was measured using electrospray ionization (ESI) or atmospheric pressure chemical ionization (APCI). The mass spectrum data shows the maximum ionization peak (which matches the maximum absorption peak, in most cases) after passage through a reverse phase high performance liquid chromatography column (Agilent system; column: Develosil Combi-RP-5, 2.0×50 mm, Cadenza CD-C18, 3.0×75 mm, or ZORBAX SB-C18, 1.8 μm, 2.1×50 mm; solvent: acetonitrile/water system containing 0.1% formic acid or acetonitrile/water system containing 0.01% trifluoroacetic acid).

The instrument and measurement conditions in the powder X-ray diffraction measurement in Examples are as follows.
Model name: Rigaku Rint TTR-III
Sample holder: non-reflective sample holder
Sample: q.s.
X-ray generation conditions: 50 kV, 300 mA
Wavelength: 1.54 angstrom (copper Kα, radiation)
Measurement temperature: room temperature
Scanning rate: 20°/min
Scanning range: 2 to 400
Sampling width: 0.02°
Analysis procedure: A few mg of the test substance was collected with a spatula, placed on a non-reflective sample holder, and flattened with a medical paper. Thereafter, the peak pattern was analyzed under the aforementioned conditions.

In Reference Examples and Examples below, the notations of geometrical isomers are described according to the following criteria, for convenience. (1) In the structural formula of a compound that may have a geometrical isomer, the wavy line represents a bond that does not particularly specify any geometrical isomer. (2) When there is no particular description after the compound name of the compound that may have a geometrical isomer, it indicates that the compound does not particularly specify any geometrical isomer.

In Reference Examples and Examples below, the notations of enantiomers, racemates, and mixtures of diastereomers are described according to the following criteria, for convenience. (1) In the structural formula of a compound having one asymmetric carbon, when * is attached to the asymmetric carbon, it indicates that the compound represented by the structural formula is an enantiomer. In the structural formula of a compound having one asymmetric carbon, when * is not attached to the asymmetric carbon and no particular stereochemical notation (e.g., wedge bond) is given, it indicates that the compound represented by the structural formula is a racemate. In the structural formula of a compound having two asymmetric carbons, when * is not attached to any asymmetric carbons and no particular stereochemical notation (e.g., wedge bond) is given, it indicates that the compound represented by the structural formula is a mixture of diastereomers. (2) When "(enantiomer)" is attached after the compound name of a compound having one asymmetric carbon, it indicates that the compound represented by the compound name is an enantiomer. When no "(enantiomer)" is attached after the compound name of the compound having one asymmetric carbon and no particular stereochemical notation (e.g., the notation of the specific rotation is attached before the compound name) is given, it indicates that the compound represented by the compound name is a racemate. When "(mixture of diastereomers)" is attached after the compound name of a compound having two asymmetric carbons, it indicates that the compound represented by the compound name is a mixture of diastereomers. (3) When "(+)-" or "(−)-" is attached before the compound name, it indicates that the compound represented by the compound name is an enantiomer having a specific rotation of (+) or (−).

Reference Example 1

Ethyl 2,4-dioxo-4-(2-oxo-2,3-dihydro-1,3-benzoxazol-7-yl)butanoate

[Chemical Formula 89]

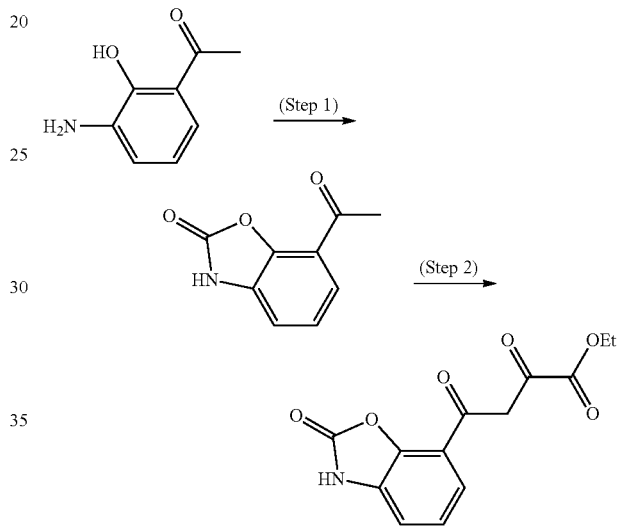

(Step 1) 7-Acetyl-1,3-benzoxazol-2(3H)-one

To a solution of 3-amino-2-hydroxyacetophenone (15.0 g) in tetrahydrofuran (150 mL), 1,1'-carbonyldiimidazole (17.7 g) was added at room temperature, and the mixture was stirred at the same temperature for 20 hours. The reaction mixture was concentrated under reduced pressure, methanol (120 mL) and 2 M-hydrochloric acid (120 mL) were added to the residue obtained, and the mixture was stirred at room temperature for 2 hours and then allowed to stand overnight. The precipitated solid was collected by filtration, washed three times with a methanol-water (1:1) mixed solution (30 mL), and then dried under reduced pressure to obtain the title compound (16.4 g) as a solid.

$^1$H-NMR (DMSO-D$_6$) δ: 2.65 (3H, s), 7.25 (1H, dd, J=7.8, 7.4 Hz), 7.33 (1H, d, J=7.4 Hz), 7.53 (1H, d, J=7.8 Hz), 11.96 (1H, br s).

(Step 2) Ethyl 2,4-dioxo-4-(2-oxo-2,3-dihydro-1,3-benzoxazol-7-yl) butanoate

To a suspension of the compound obtained in the above step 1 (5.00 g) in tetrahydrofuran (250 mL), potassium tert-butoxide (6.97 g) was added at room temperature, and the mixture was stirred at the same temperature for 30 minutes. Then, diethyl oxalate (4.95 g) was added, and the mixture was further stirred at the same temperature for 2 hours. After acetic acid (323 μL) was added to the reaction mixture, the mixture was concentrated under reduced pressure. Ethyl acetate and 10%-citric acid aqueous solution was added to the residue obtained, and the mixture was stirred at room temperature for 20 minutes. The organic layer and the aqueous layer were separated, the aqueous layer obtained was extracted with ethyl acetate, and the combined organic layers were washed with water and brine, and then dried over anhydrous sodium sulfate. After filtration, the solvent was distilled off under reduced pressure, the residue obtained was suspended in ethyl acetate (50 mL)-n-hexane (50 mL), and the mixture was stirred at room temperature for 1 hour and a half. The precipitated solid was collected by filtration, washed three times with an ethyl acetate-n-hexane (1:1) mixed solution (10 mL), and then dried under reduced pressure to obtain the title compound (6.86 g) as a solid.

$^1$H-NMR (DMSO-D$_6$) δ: 1.32 (3H, t, J=7.0 Hz), 4.33 (2H, q, J=7.0 Hz), 7.18-7.24 (1H, m), 7.27-7.41 (2H, m), 7.63-7.69 (1H, m), 12.08 (1H, br s).

Reference Example 2

Ethyl 4-(5-fluoro-2-oxo-2,3-dihydro-1,3-benzoxazol-7-yl)-2,4-dioxobutanoate

[Chemical Formula 90]

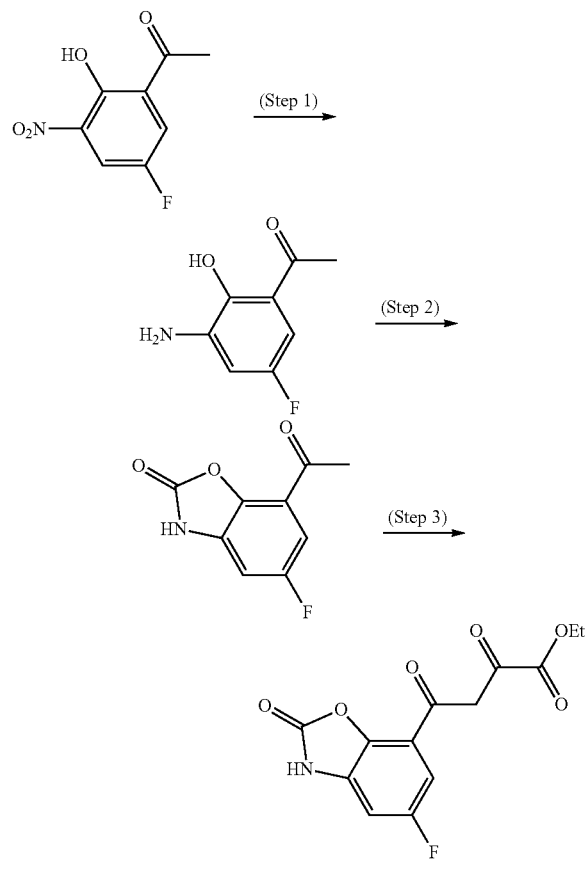

(Step 1) 1-(3-Amino-5-fluoro-2-hydroxyphenyl)ethan-1-one

To a solution of 5'-fluoro-2'-hydroxy-3'-nitroacetophenone (938 mg, CAS number: 70978-39-1) in methanol (80 mL), rhodium 5% on carbon (72.0 mg) was added at room temperature, and the mixture was stirred under a hydrogen atmosphere at the same temperature for 7 hours. After insoluble materials were removed by filtration through a pad of Celite, the solvent was distilled off under reduced pressure to obtain the crude title compound (792 mg) as a solid.

$^1$H-NMR (CDCl$_3$) δ: 2.58 (3H, s), 4.08 (2H, br s), 6.63 (1H, dd, J=9.7, 2.4 Hz), 6.77 (1H, dd, J=9.1, 2.4 Hz), 12.27 (1H, s).

(Step 2) 7-Acetyl-5-fluoro-1,3-benzoxazol-2(3H)-one

To a solution of the compound obtained in the above step 1 (835 mg) in tetrahydrofuran (50 mL), 1,1'-carbonyldiimidazole (1.12 g) was added at 0° C., and the mixture was stirred at room temperature for 3 days. The reaction mixture was diluted with a chloroform-methanol (9:1) mixed solution, and the organic layer obtained was washed with brine, and then dried over anhydrous magnesium sulfate. After filtration, the solvent was distilled off under reduced pressure, and the residue obtained was subjected to silica gel column chromatography (n-hexane/ethyl acetate) to obtain a mixture containing the title compound (887 mg) as a solid.

(Step 3) Ethyl 4-(5-fluoro-2-oxo-2,3-dihydro-1,3-benzoxazol-7-yl)-2,4-dioxobutanoate To a solution of the compound obtained in the above step 2 (870 mg) in tetrahydrofuran (55 mL), 55%-sodium hydride (dispersed in liquid paraffin) (611 mg) was added at room temperature, and the mixture was stirred at the same temperature for 10 minutes. Then, diethyl oxalate (0.66 mL) was added, and the mixture was further stirred at 70° C. for 3 hours. The reaction mixture was cooled to 0° C., ethyl acetate, 1 M-hydrochloric acid (20.0 mL), and water were added, and the mixture was stirred. Then, the organic layer was separated, and the organic layer obtained was dried over anhydrous magnesium sulfate. After filtration, the solvent was distilled off under reduced pressure, and the solid obtained was washed with an n-hexane-ethyl acetate mixed solution to obtain the title compound (898 mg) as a solid.

$^1$H-NMR (DMSO-D$_6$) δ: 1.31 (3H, t, J=7.4 Hz), 4.33 (2H, q, J=7.4 Hz), 7.20 (1H, s), 7.27-7.43 (2H, m), 12.29 (1H, br s).

Reference Example 3

Ethyl 4-(4-fluoro-2-oxo-2,3-dihydro-1,3-benzoxazol-7-yl)-2,4-dioxobutanoate

[Chemical Formula 91]

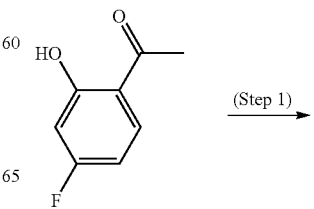

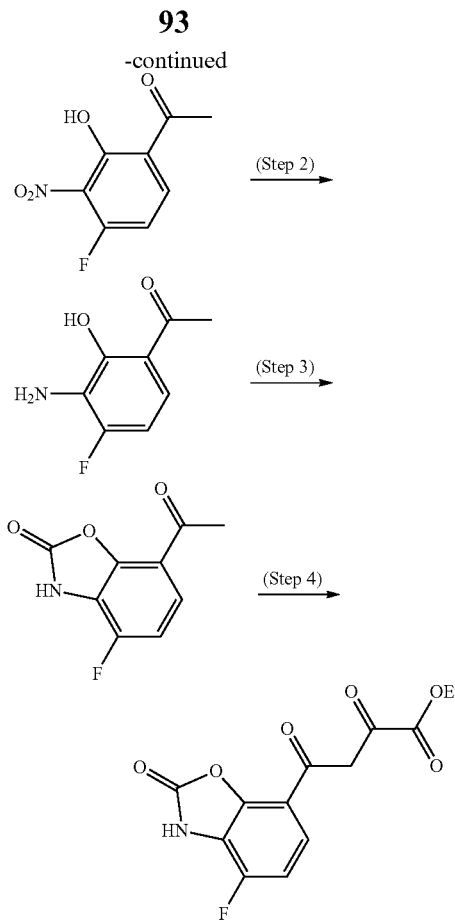

(Step 1) 1-(4-Fluoro-2-hydroxy-3-nitrophenyl)ethan-1-one

After 64% sulfuric acid (10 mL) was added to 4'-fluoro-2'-hydroxyacetophenone (2.00 g, CAS number: 1481-27-2), concentrated nitric acid (69%) (0.75 mL) was added dropwise at 0° C., and the mixture was stirred at the same temperature for 30 minutes. The reaction mixture was slowly poured into ice water and then extracted with ethyl acetate, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (845 mg) as a solid.

$^1$H-NMR (CDCl$_3$) δ: 2.67 (3H, s), 6.82 (1H, dd, J=9.1, 8.5 Hz), 7.92 (1H, dd, J=9.1, 5.5 Hz), 13.30 (1H, d, J=1.2 Hz).

(Step 2) 1-(3-Amino-4-fluoro-2-hydroxyphenyl)ethan-1-one

A mixture of the compound obtained in the above step 1 (658 mg), zinc (powder) (987 mg), methanol (55 mL), and acetic acid (14 mL) was stirred at room temperature for 30 minutes. Water was added to the reaction mixture, insoluble materials were removed by filtration through a pad of Celite, and the filtrate was concentrated under reduced pressure. Then, the mixture was extracted with dichloromethane, and the organic layer obtained was washed with a saturated aqueous sodium hydrogen carbonate solution, and then dried over anhydrous magnesium sulfate. After filtration, the solvent was distilled off under reduced pressure, and the residue obtained was purified by silica gel column chromatography (n-hexane/ethyl acetate) to obtain the title compound (396 mg) as a solid.

$^1$H-NMR (CDCl$_3$) δ: 2.60 (3H, s), 3.85 (2H, br s), 6.62 (1H, dd, J=9.7, 9.1 Hz), 7.14 (1H, dd, J=9.1, 5.5 Hz), 12.68 (1H, d, J=1.8 Hz).

(Step 3) 7-Acetyl-4-fluoro-1,3-benzoxazol-2(3H)-one

The compound obtained in the above step 2 (390 mg) was used as a manufacturing raw material, and the same procedure as that in step 2 of Reference Example 2 was performed to obtain the title compound (251 mg) as a solid.

$^1$H-NMR (DMSO-D$_6$) δ: 2.63 (3H, s), 7.16-7.27 (1H, m), 7.54-7.63 (1H, m), 12.64 (1H, br s).

(Step 4) Ethyl 4-(4-fluoro-2-oxo-2,3-dihydro-1,3-benzoxazol-7-yl)-2,4-dioxobutanoate To a solution of the compound obtained in the above step 3 (202 mg) in tetrahydrofuran (20 mL), a 1.17 M-lithium hexamethyldisilazane/tetrahydrofuran solution (2.0 mL) was added dropwise at −78° C., and the mixture was stirred at the same temperature for 10 minutes. Then, diethyl oxalate (180 μL) was added, and the mixture was gradually heated to room temperature and stirred overnight. Ethyl acetate, 1 M-hydrochloric acid (10.0 mL), and water were added to the reaction mixture, and the mixture was stirred. Then, the organic layer was separated, and the organic layer obtained was dried over anhydrous magnesium sulfate. After filtration, the solvent was distilled off under reduced pressure, and the residue obtained was sequentially purified by silica gel column chromatography (n-hexane/ethyl acetate) and reverse phase HPLC to obtain the title compound (102 mg) as a solid.

$^1$H-NMR (DMSO-D$_6$) δ: 1.31 (3H, t, J=7.3 Hz), 4.33 (2H, q, J=7.3 Hz), 7.19 (1H, s), 7.29 (1H, dd, J=9.7, 9.1 Hz), 7.72 (1H, dd, J=9.1, 5.5 Hz), 12.73 (1H, br s).

Reference Example 4

Ethyl 2,4-dioxo-4-(2-oxo-5-phenoxy-2,3-dihydro-1,3-benzoxazol-7-yl)butanoate

[Chemical Formula 92]

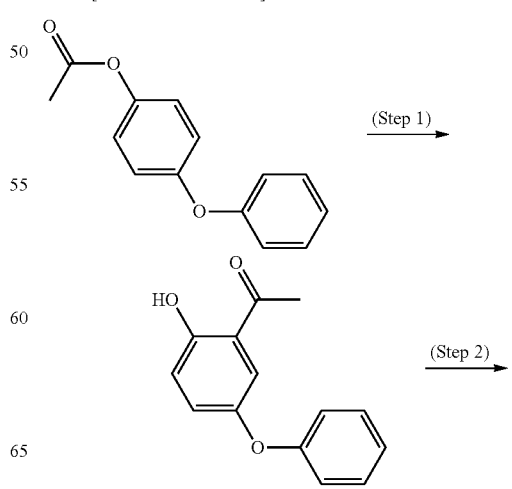

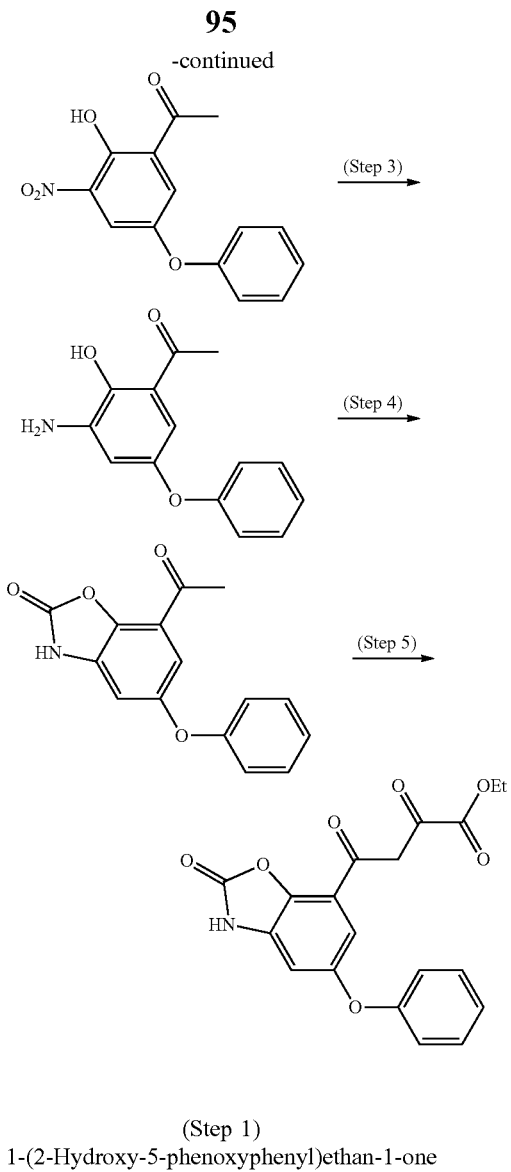

(Step 1)
1-(2-Hydroxy-5-phenoxyphenyl)ethan-1-one

A mixture of 4-phenoxyphenyl acetate (WO 2010/021680 A2) (6.25 g) and aluminum chloride (6.39 g) was stirred at 70° C. for 2 hours and a half and then further stirred at 140° C. for 1 hour. The reaction mixture was cooled to room temperature, and ice water (30 mL) was added dropwise. Then, the mixture was extracted with chloroform, and the organic layer obtained was dried over anhydrous sodium sulfate. After insoluble materials were removed by filtration through a pad of Celite, the solvent was distilled off under reduced pressure, and the residue obtained was purified by silica gel column chromatography (n-hexane/ethyl acetate) to obtain the title compound (1.51 g) as a solid.

$^1$H-NMR (CDCl$_3$) δ: 2.58 (3H, s), 6.95 (2H, d, J=8.5 Hz), 6.99 (1H, d, J=9.1 Hz), 7.08 (1H, t, J=7.3 Hz), 7.22 (1H, dd, J=9.1, 3.0 Hz), 7.33 (2H, dd, J=8.5, 7.3 Hz), 7.42 (1H, d, J=3.0 Hz), 12.04 (1H, s).

(Step 2) 1-(2-Hydroxy-3-nitro-phenoxyphenyl)ethan-1-one

To a solution of the compound obtained in the above step 1 (1.47 g) in acetic acid (1.0 mL), concentrated nitric acid (69%) (5.0 mL) was added dropwise at room temperature, and the mixture was stirred at the same temperature for 3 hours. The reaction mixture was slowly poured into ice water, the mixture was then extracted with ethyl acetate, and the organic layer obtained was dried over anhydrous sodium sulfate. After filtration, the solvent was distilled off under reduced pressure, and the residue obtained was sequentially purified by silica gel column chromatography (n-hexane/ethyl acetate) and reverse phase HPLC to obtain the title compound (562 mg) as a solid.

$^1$H-NMR (CDCl$_3$) δ: 2.68 (3H, s), 7.00 (2H, d, J=8.5 Hz), 7.19 (1H, t, J=7.3 Hz), 7.40 (2H, dd, J=8.5, 7.3 Hz), 7.76 (1H, d, J=3.0 Hz), 7.85 (1H, d, J=3.0 Hz), 12.62 (1H, s).

(Step 3) 1-(3-Amino-2-hydroxy-5-phenoxyphenyl)ethan-1-one

The compound obtained in the above step 2 (551 mg) was used as a manufacturing raw material, and the same procedure as that in step 2 of Reference Example 3 was performed to obtain the title compound (268 mg) as a solid.

MS (m/z): 244 (M+H)$^+$.

(Step 4) 7-Acetyl-5-phenoxy-1,3-benzoxazol-2(3H)-one

To a solution of the compound obtained in the above step 3 (268 mg) in tetrahydrofuran (12 mL), 1,1'-carbonyldiimidazole (268 mg) was added at 0° C., and the mixture was stirred at room temperature for 1 day. The reaction mixture was concentrated under reduced pressure, and the residue obtained was purified by silica gel column chromatography (n-hexane/ethyl acetate) to obtain the title compound (178 mg) as a solid. $^1$H-NMR (CDCl$_3$) δ: 2.75 (3H, s), 6.96 (1H, d, J=2.4 Hz), 7.00 (2H, d, J=8.5 Hz), 7.16 (1H, t, J=7.3 Hz), 7.31 (1H, d, J=2.4 Hz), 7.37 (2H, dd, J=8.5, 7.3 Hz).

(Step 5) Ethyl 2,4-dioxo-4-(2-oxo-5-phenoxy-2,3-dihydro-1,3-benzoxazol-7-yl)butanoate The compound obtained in the above step 4 (176 mg) was used as a manufacturing raw material, and the same procedure as that in step 4 of Reference Example 3 was performed to obtain the title compound (80.7 mg) as a solid.

$^1$H-NMR (DMSO-D$_6$) δ: 1.30 (3H, t, J=7.3 Hz), 4.32 (2H, q, J=7.3 Hz), 7.04-7.24 (6H, m), 7.43 (2H, t, J=7.9 Hz), 12.11 (1H, br s).

Reference Example 5

Ethyl 4-(3-acetamidephenyl)-2,4-dioxobutanoate

[Chemical Formula 93]

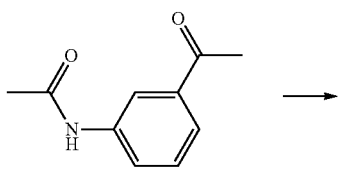

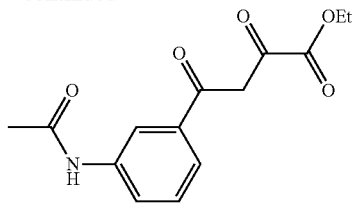

To a solution of 3'-acetamideacetophenone (500 mg, CAS number: 7463-31-2) in tetrahydrofuran (35 mL), 55%-sodium hydride (dispersed in liquid paraffin) (369 mg) was added, and the mixture was stirred at room temperature for 40 minutes. Then, diethyl oxalate (1.3 mL) was added thereto, and the mixture was further stirred at 70° C. for 1 hour and a half. The reaction mixture was cooled to room temperature, acetic acid (565 µL) and water were added, and the mixture was extracted with ethyl acetate. The organic layer obtained was washed with brine, and then dried over anhydrous sodium sulfate. After filtration, the solvent was distilled off under reduced pressure, and the residue obtained was washed with a 2-propanol-water mixed solution and water, and then dried under reduced pressure to obtain the title compound (788 mg) as a solid.

$^1$H-NMR (CDCl$_3$) δ: 1.42 (3H, t, J=7.3 Hz), 2.22 (3H, s), 4.41 (2H, q, J=7.3 Hz), 7.05 (1H, s), 7.33 (1H, br s), 7.47 (1H, t, J=7.9 Hz), 7.73 (1H, d, J=7.9 Hz), 7.93 (1H, d, J=7.9 Hz), 8.00 (1H, br s).

Reference Example 6

1-(2-Methoxy-1-{[2-(trimethylsilyl)ethoxy]methyl}-1H-benzimidazol-4-yl)ethan-1-one

[Chemical Formula 94]

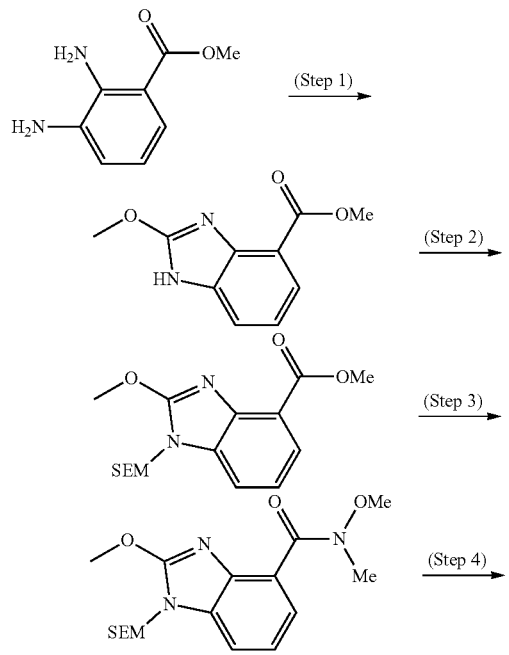

(Step 1) Methyl 2-methoxy-1H-benzimidazole-4-carboxylate

A mixture of methyl 2,3-diaminobenzoate (708 mg, CAS number: 107582-20-7), tetramethoxymethane (850 µL), and acetic acid (5.0 mL) was stirred at room temperature for 3 hours. The reaction mixture was concentrated under reduced pressure, and the residue obtained was purified by silica gel column chromatography (chloroform/ethyl acetate) to obtain the title compound (719 mg) as a solid.

$^1$H-NMR (CDCl$_3$) δ: 3.96-4.00 (3H, m), 4.19-4.23 (3H, m), 7.17-7.24 (1H, m), 7.71-7.78 (2H, m), 9.54 (1H, br s).

(Step 2) Methyl 2-methoxy-1-{[2-(trimethylsilyl)ethoxy]methyl}-1H-benzimidazole-4-carboxylate To a solution of the compound obtained in the above step 1 (719 mg) in dichloromethane (8.0 mL), N,N-diisopropylethylamine (1.20 mL) and 2-(chloromethoxy)ethyl trimethylsilane (918 µL) were added at room temperature, and the mixture was stirred at the same temperature for 3 days. Then, N,N-diisopropylethylamine (304 µL) and 2-(chloromethoxy)ethyl trimethylsilane (184 µL) were added, and the mixture was further stirred at the same temperature for 3 hours. The reaction mixture was diluted with dichloromethane, and the organic layer obtained was washed with a saturated aqueous sodium hydrogen carbonate solution, and then dried over anhydrous sodium sulfate. After filtration, the solvent was distilled off under reduced pressure, and the residue obtained was purified by silica gel column chromatography (n-hexane/ethyl acetate) to obtain the title compound (761 mg) as an oil.

$^1$H-NMR (CDCl$_3$) δ: −0.10 (9H, s), 0.79 (2H, t, J=8.3 Hz), 3.33 (2H, t, J=8.3 Hz), 3.95 (3H, s), 4.23 (3H, s), 5.74 (2H, s), 7.21 (1H, t, J=8.0 Hz), 7.62 (1H, dd, J=8.0, 1.2 Hz), 7.71 (1H, dd, J=8.0, 1.2 Hz).

Step 3

N,2-Dimethoxy-N-methyl-1-{[2-(trimethylsilyl)ethoxy]methyl}-1H-benzimidazole-4-carboxamide To a solution of the compound obtained in the above step 2 (761 mg) in tetrahydrofuran (15 mL)-water (5.0 mL), lithium hydroxide monohydrate (142 mg) was added at room temperature, and the mixture was stirred at the same temperature for 2 days. Then, lithium hydroxide monohydrate (48.0 mg) was added, and the mixture was further stirred at the same temperature for 1 day. To the reaction mixture, 1 M-hydrochloric acid was added, and the mixture was extracted with chloroform and dried over anhydrous sodium sulfate. After filtration, the solvent was distilled off under reduced pressure, a mixture of the residue obtained and N,O-dimethylhydroxyamine hydrochloride (331 mg, CAS number: 6638-79-5), 1-hydroxybenzotriazole (306 mg), EDCI (650 mg), triethylamine (940 µL), and dichloromethane (20 mL) was stirred at room temperature for 3 days. The reaction mixture was diluted with chloroform, and the organic layer obtained was washed with a saturated aqueous sodium hydrogen carbonate solution, and then dried over anhydrous sodium sulfate. After filtration, the solvent was distilled off under reduced pressure, and the residue obtained was purified by silica gel column chromatography (chloroform/ethyl acetate) to obtain the title compound (657 mg) as an oil.

$^1$H-NMR (CDCl$_3$) δ: −0.03 (9H, s), 0.86 (2H, t, J=8.5 Hz), 3.17-3.98 (8H, m), 4.22 (3H, s), 5.45 (2H, s), 7.10-7.24 (2H, m), 7.57-7.64 (1H, m).

Step 4

1-(2-Methoxy-1-{[2-(trimethylsilyl)ethoxy]methyl}-1H-benzimidazol-4-yl)ethan-1-one To a solution of the compound obtained in the above step 3 (657 mg) in tetrahydrofuran (15 mL), a 0.98 M-methyl magnesium bromide/tetrahydrofuran solution (3.70 mL) was added at 0° C., the mixture was stirred at room temperature for 2 hours. Then, a 0.98 M-methyl magnesium bromide/tetrahydrofuran solution (3.00 mL) was added at 0° C., and the mixture was further stirred at room temperature for 2 hours. Subsequently, a 0.98 M-methyl magnesium bromide/tetrahydrofuran solution (2.00 mL) was added to the reaction mixture at 0° C., and the mixture was stirred at room temperature for 2 hours. The reaction mixture was cooled to 0° C., and a saturated ammonium chloride aqueous solution and water were added. The mixture was extracted with ethyl acetate, and the organic layer obtained was dried over anhydrous sodium sulfate. After filtration, the solvent was distilled off under reduced pressure, and the residue obtained was purified by silica gel column chromatography (chloroform/ethyl acetate) to obtain the title compound (436 mg) as an oil.

$^1$H-NMR (CDCl$_3$) δ: −0.09 (9H, s), 0.77 (2H, t, J=7.3 Hz), 2.67 (3H, s), 3.28 (2H, t, J=7.3 Hz), 4.23 (3H, s), 5.58 (2H, s), 7.20-7.26 (1H, m), 7.48 (1H, d, J=7.9 Hz), 7.71 (1H, d, J=7.9 Hz).

Reference Example 7

Ethyl 2,4-dioxo-4-(2-oxo-2,3-dihydro-1,3-benzothiazol-7-yl)butanoate

[Chemical Formula 95]

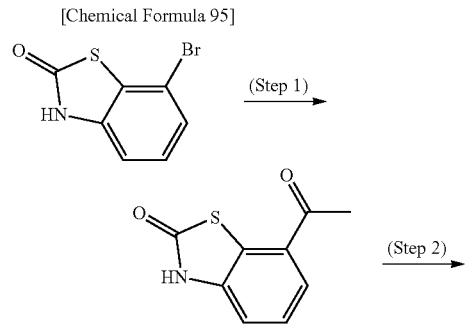

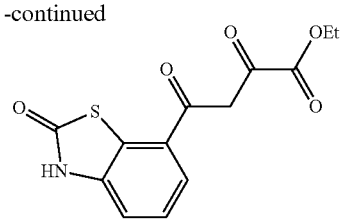

(Step 1) 7-Acetyl-1,3-benzothiazol-2(3H)-one

A mixture of 7-bromo-1,3-benzothiazol-2(3H)-one (460 mg, CAS number: 1188047-07-5), tributyl(1-ethoxyvinyl)tin (1.0 mL), bis(triphenylphosphine)palladium(II) dichloride (140 mg), and 1,4-dioxane (10 mL) was stirred under microwave irradiation at 100° C. for 4 hours, and then cooled to room temperature, 5 M-hydrochloric acid (1.2 mL) was added, and the mixture was further stirred at the same temperature for 16 hours. Water was added to the reaction mixture, and the mixture was extracted with ethyl acetate. The organic layer obtained was washed with brine, and then dried over anhydrous sodium sulfate. After filtration, the solvent was distilled off under reduced pressure, and the residue was purified by silica gel column chromatography (dichloromethane/methanol). Then, the solid obtained was washed with a dichloromethane-n-hexane mixed solution to obtain the title compound (287 mg) as a solid.

$^1$H-NMR (CDCl$_3$) δ: 2.70 (3H, s), 7.35-7.45 (2H, m), 7.77 (1H, dd, J=7.3, 1.2 Hz), 9.73 (1H, s).

(Step 2) Ethyl 2,4-dioxo-4-(2-oxo-2,3-dihydro-1,3-benzothiazol-7-yl)butanoate

To a suspension of the compound obtained in the above step 1 (285 mg) in tetrahydrofuran (6 mL), potassium tert-butoxide (364 mg) was added at room temperature, and the mixture was stirred at the same temperature for 30 minutes. Then, diethyl oxalate (240 µL) and tetrahydrofuran (2 mL) were added, and the mixture was further stirred at the same temperature for 2 hours. Subsequently, diethyl oxalate (120 µL) was added to the reaction mixture at room temperature, and the mixture was stirred at the same temperature for 45 minutes. Then, potassium tert-butoxide (99 mg) was added, and the mixture was further stirred at the same temperature for 45 minutes. Acetic acid (68 µL), water, and 1 M-hydrochloric acid (4 mL) were sequentially added to the reaction mixture, and the mixture was extracted with ethyl acetate. The organic layer obtained was washed with brine, and then dried over anhydrous sodium sulfate. After filtration, the solvent was distilled off under reduced pressure, and the solid obtained was washed with an ethyl acetate-n-hexane mixed solution to obtain the title compound (298 mg) as a solid.

$^1$H-NMR (DMSO-D$_6$) δ: 1.32 (3H, t, J=7.0 Hz), 4.33 (2H, q, J=7.1 Hz), 7.26 (1H, s), 7.42-7.52 (2H, m), 8.07 (1H, d, J=7.9 Hz), 12.17 (1H, s).

Reference Example 8

3-(Cyclobutyloxy)benzaldehyde

[Chemical Formula 96]

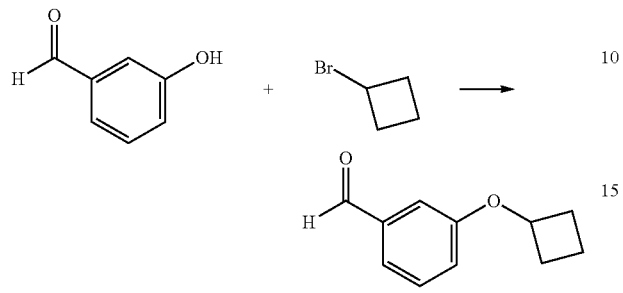

To a suspension of 3-hydroxybenzaldehyde (611 mg, CAS number: 100-83-4) and cesium carbonate (3.26 g) in acetonitrile (30 mL), bromocyclobutane (944 μL) was added at room temperature, and the mixture was stirred at 80° C. for 4 hours and a half. Then, bromocyclobutane (472 μL) was added, and the mixture was further stirred at the same temperature for 5 hours. After the reaction mixture was cooled to room temperature, water was added, the mixture was extracted with ethyl acetate, and the organic layer obtained was dried over anhydrous sodium sulfate. After filtration, the solvent was distilled off under reduced pressure, and the residue obtained was purified by silica gel column chromatography (n-hexane/dichloromethane, and then, n-hexane/ethyl acetate) to obtain the title compound (423 mg) as an oil.
$^1$H-NMR (CDCl$_3$) δ: 1.65-1.78 (1H, m), 1.83-1.94 (1H, m), 2.12-2.24 (2H, m), 2.45-2.54 (2H, m), 4.66-4.75 (1H, m), 7.08-7.13 (1H, m), 7.27-7.29 (1H, m), 7.40-7.47 (2H, m), 9.96 (1H, s).

Reference Example 9

3-[(4,4-Difluorocyclohexyl)oxy]benzaldehyde

[Chemical Formula 97]

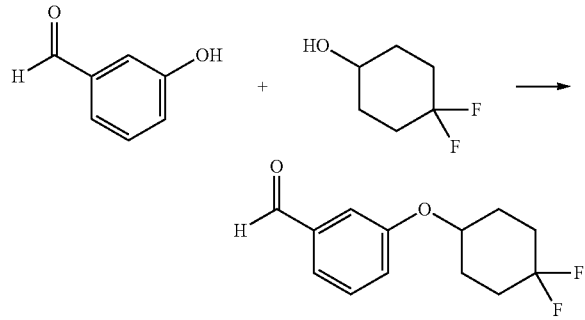

To a solution of 3-hydroxybenzaldehyde (343 mg, CAS number: 100-83-4), 4,4-difluorocyclohexanol (255 mg, CAS number: 22419-35-8), and triphenylphosphine (737 mg) in tetrahydrofuran (6.2 mL), diisopropyl azodicarboxylate (603 μL) was added at room temperature, and the mixture was stirred at the same temperature for 3 hours and a half. The solvent was distilled off under reduced pressure, and the residue obtained was purified by silica gel column chromatography (n-hexane/ethyl acetate) to obtain the title compound (78.0 mg) as an oil.
$^1$H-NMR (CDCl$_3$) δ: 1.89-2.24 (8H, m), 4.56-4.64 (1H, m), 7.16-7.22 (1H, m), 7.40-7.42 (1H, m), 7.45-7.49 (2H, m), 9.98 (1H, s).

Reference Example 10

3-Methyl-4-(4,4,4-trifluorobutoxy)benzaldehyde

[Chemical Formula 98]

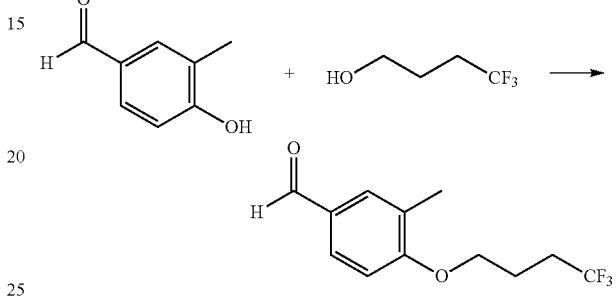

4-Hydroxy-3-methylbenzaldehyde (417 mg, CAS number: 15174-69-3) and 4,4,4-trifluorobutan-1-ol (323 μL, CAS number: 461-18-7) were used as manufacturing raw materials, and the same procedure as that in Reference Example 9 was performed to obtain the title compound (553 mg) as a solid.
$^1$H-NMR (CDCl$_3$) δ: 2.09-2.17 (2H, m), 2.27 (3H, s), 2.29-2.42 (2H, m), 4.13 (2H, t, J=6.1 Hz), 6.90 (1H, d, J=9.2 Hz), 7.68-7.75 (2H, m), 9.86 (1H, s).

Reference Example 11

4-Fluoro-3-(4,4,4-trifluorobutoxy)benzaldehyde

[Chemical Formula 99]

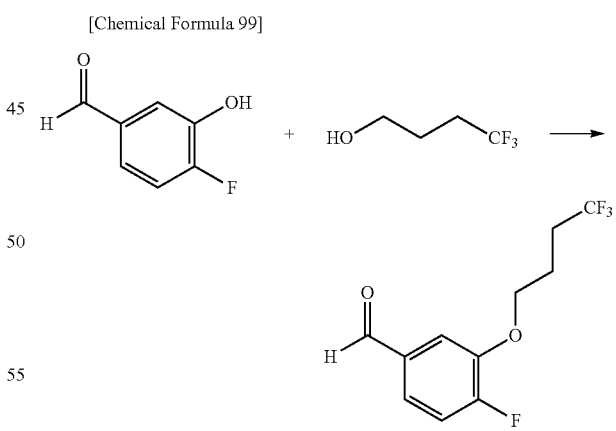

4-Fluoro-3-hydroxybenzaldehyde (523 mg, CAS number: 103438-85-3) and 4,4,4-trifluorobutan-1-ol (394 μL, CAS number: 461-18-7) were used as manufacturing raw materials, and the same procedure as that in Reference Example 9 was performed to obtain the title compound (401 mg) as an oil.
$^1$H-NMR (CDCl$_3$) δ: 2.08-2.20 (2H, m), 2.26-2.44 (2H, m), 4.12-4.19 (2H, m), 7.22-7.29 (1H, m), 7.43-7.54 (2H, m), 9.91 (1H, s).

Reference Example 12

4-{[3,5-Bis(trifluoromethyl)benzyl]oxy}benzaldehyde

[Chemical Formula 100]

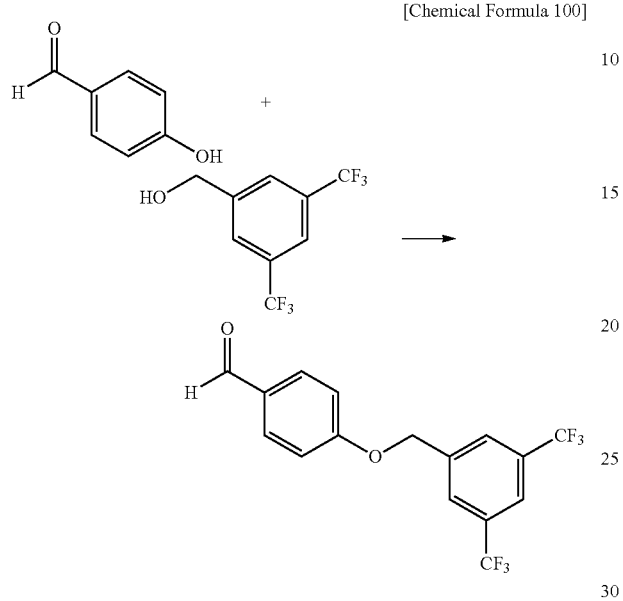

4-Hydroxybenzaldehyde (0.50 g, CAS number: 123-08-0) and [3,5-bis(trifluoromethyl)phenyl]methanol (1.1 g, CAS number: 32707-89-4) were used as manufacturing raw materials, di-tert-butyl azodicarboxylate (1.1 g) was used as an azodicarboxylic acid derivative, and the same procedure as that in Reference Example 9 was performed to obtain the title compound (1.25 g) as a solid.

$^1$H-NMR (CDCl$_3$) δ: 5.26 (2H, s), 7.10-7.13 (2H, m), 7.89-7.92 (5H, m), 9.93 (1H, s).

Reference Example 13

4-[(1R)-1-Phenylethoxy]benzaldehyde

[Chemical Formula 101]

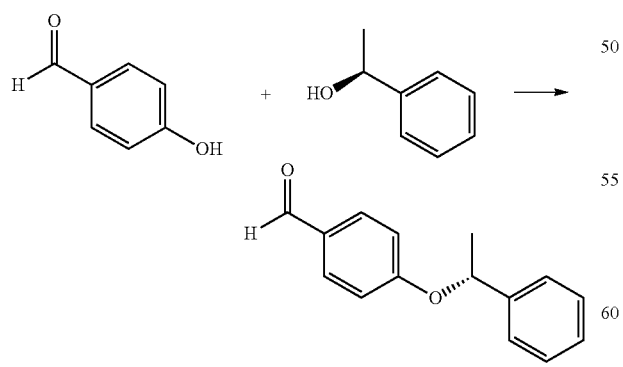

4-Hydroxybenzaldehyde (1.00 g, CAS number: 123-08-0) and (S)-(+)-1-phenylethyl alcohol (988 μL) were used as manufacturing raw materials, di-tert-butyl azodicarboxylate (2.26 g) was used as an azodicarboxylic acid derivative, and the same procedure as that in Reference Example 9 was performed to obtain the title compound (595 mg) as an oil.

$^1$H-NMR (CDCl$_3$) δ: 1.68 (3H, d, J=6.7 Hz), 5.41 (1H, q, J=6.7 Hz), 6.96 (2H, d, J=8.6 Hz), 7.24-7.39 (5H, m), 7.74 (2H, d, J=8.6 Hz), 11.46 (1H, s).

Reference Example 14

2-Fluoro-5-[(oxan-4-yl)oxy]benzaldehyde

[Chemical Formula 102]

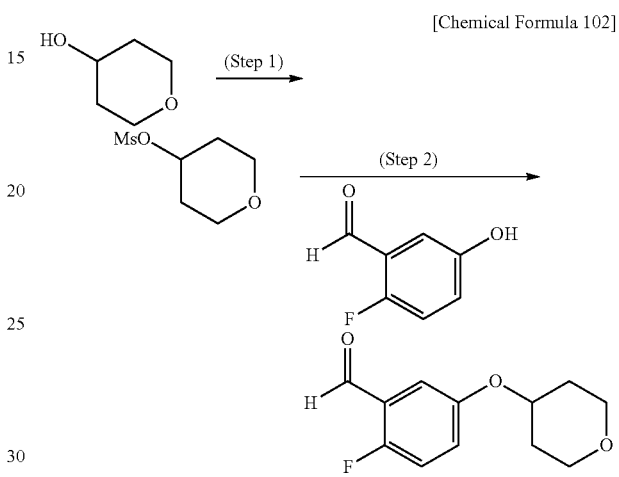

(Step 1) Oxan-4-yl methanesulfonate

To a solution of tetrahydro-4-pyranol (1.00 g, CAS number: 2081-44-9) in dichloromethane (20.0 mL), triethylamine (1.63 mL) and methanesulfonyl chloride (0.84 mL) was added at 0° C., and the mixture was stirred at the same temperature for 1 hour. The reaction mixture was diluted with ethyl acetate, washed with water and brine, and then dried over anhydrous sodium sulfate. After filtration, the solvent was distilled off under reduced pressure to obtain the crude title compound (1.59 g) as an oil.

$^1$H-NMR (CDCl$_3$) δ: 1.85-1.98 (2H, m), 2.04-2.13 (2H, m), 3.07 (3H, s), 3.55-3.61 (2H, m), 3.95-4.00 (2H, m), 4.90-4.97 (1H, m).

(Step 2) 2-Fluoro-5-[(oxan-4-yl)oxy]benzaldehyde

To a solution of the compound obtained in the above step 1 (1.00 g) and 2-fluoro-5-hydroxybenzaldehyde (650 mg, CAS number: 103438-84-2) in N,N-dimethylformamide (15 mL), potassium carbonate (962 mg) was added at room temperature, and the mixture was stirred at 90° C. for 11 hours. The reaction mixture was cooled to room temperature, water was added, and the mixture was extracted with ethyl acetate. The organic layer obtained was washed with brine, and then dried over anhydrous sodium sulfate. After filtration, the solvent was distilled off under reduced pressure, and the residue obtained was purified by silica gel column chromatography (n-hexane/ethyl acetate) to obtain the title compound (182 mg) as an oil.

$^1$H-NMR (CDCl$_3$) δ: 1.74-1.85 (2H, m), 2.00-2.09 (2H, m), 3.57-3.65 (2H, m), 3.96-4.04 (2H, m), 4.49-4.55 (1H, m), 7.11-7.21 (2H, m), 7.33-7.36 (1H, m), 10.36 (1H, s).

Reference Example 15

4-[(Oxan-4-yl)oxy]benzaldehyde

[Chemical Formula 103]

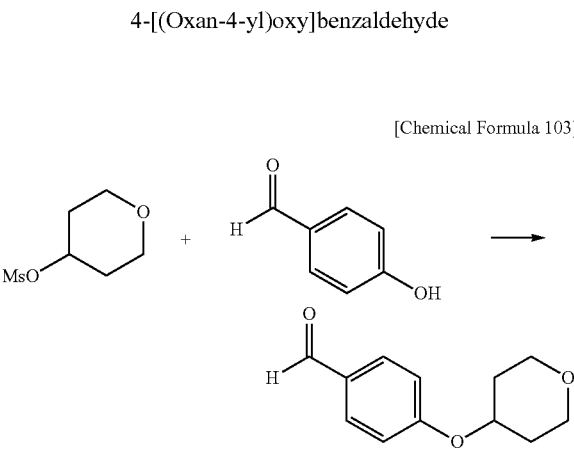

The compound obtained in step 1 of Reference Example 14 (1.2 g) and 4-hydroxybenzaldehyde (700 mg) were used as manufacturing raw materials, and the same procedure as that in step 2 of Reference Example 14 was performed to obtain the title compound (828 mg) as a solid.

$^1$H-NMR (CDCl$_3$) δ: 1.78-1.88 (2H, m), 2.02-2.10 (2H, m), 3.58-3.66 (2H, m), 3.96-4.03 (2H, m), 4.58-4.68 (1H, m), 7.01 (2H, d, J=7.9 Hz), 7.84 (2H, d, J=7.9 Hz), 9.88 (1H, s).

Reference Example 16

4-Chloro-3,5-dimethylbenzaldehyde

[Chemical Formula 104]

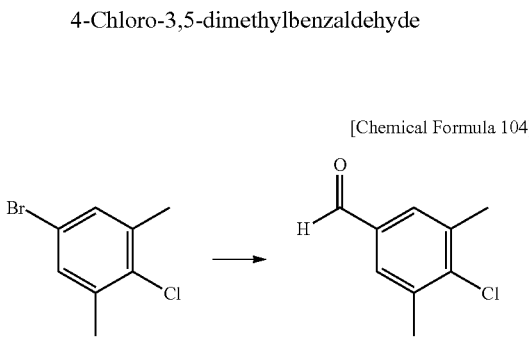

To a solution of 5-bromo-2-chloro-1,3-dimethylbenzene (878 mg, CAS number: 206559-40-2) in tetrahydrofuran (12 mL), a 1.6 M-n-butyllithium/n-hexane solution (2.45 mL) was added dropwise at −78° C., and the mixture was stirred at the same temperature for 30 minutes. Then, N,N-dimethylformamide (617 µL) was added dropwise, and the mixture was further stirred at the same temperature for 15 minutes and then stirred at room temperature for 30 minutes. To the reaction mixture, 1 M-hydrochloric acid (4 mL) and water were added, the mixture was extracted with ethyl acetate, and the organic layer obtained was washed with brine, and then dried over anhydrous sodium sulfate. After filtration, the solvent was distilled off under reduced pressure, and the residue obtained was purified by silica gel column chromatography (n-hexane/ethyl acetate) to obtain the title compound (352 mg) as a solid.

$^1$H-NMR (CDCl$_3$) δ: 2.46 (6H, s), 7.60 (2H, s), 9.93 (1H, s).

Reference Example 17

4-Hexylbenzaldehyde

[Chemical Formula 105]

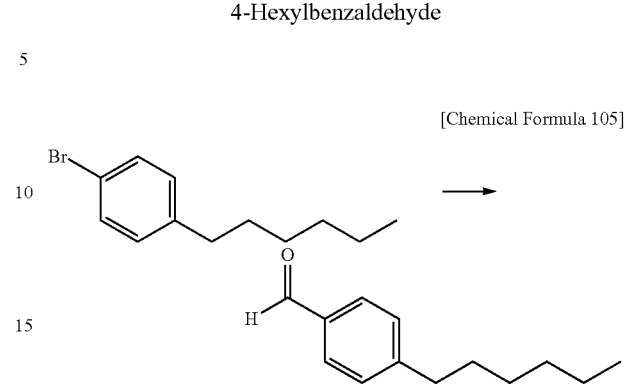

1-Bromo-4-hexylbenzene (965 mg, CAS number: 23703-22-2) was used as a manufacturing raw material, and the same procedure as that in Reference Example 16 was performed to obtain the title compound (577 mg) as an oil.

$^1$H-NMR (CDCl$_3$) δ: 0.88 (3H, t, J=7.0 Hz), 1.26-1.38 (6H, m), 1.59-1.68 (2H, m), 2.69 (2H, t, J=7.9 Hz), 7.34 (2H, d, J=7.9 Hz), 7.80 (2H, d, J=7.9 Hz), 9.97 (1H, s).

Reference Example 18

3-Butylbenzaldehyde

[Chemical Formula 106]

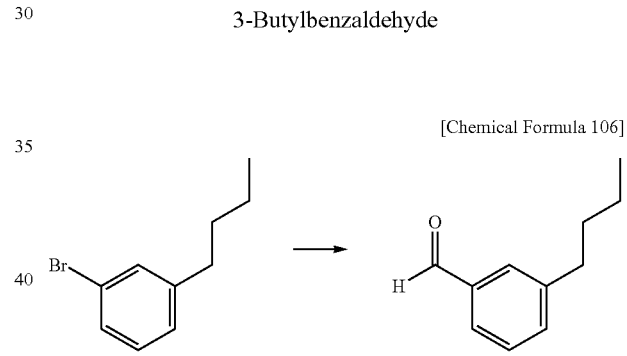

1-Bromo-3-butylbenzene (852 mg, CAS number: 54887-20-6) was used as a manufacturing raw material, and the same procedure as that in Reference Example 16 was performed to obtain the title compound (452 mg) as an oil.

$^1$H-NMR (CDCl$_3$) δ: 0.94 (3H, t, J=7.3 Hz), 1.32-1.42 (2H, m), 1.59-1.68 (2H, m), 2.70 (2H, t, J=7.6 Hz), 7.42-7.48 (2H, m), 7.67-7.72 (2H, m), 10.00 (1H, s).

Reference Example 19

4-Chloro-3-cyclopropylbenzaldehyde

[Chemical Formula 107]

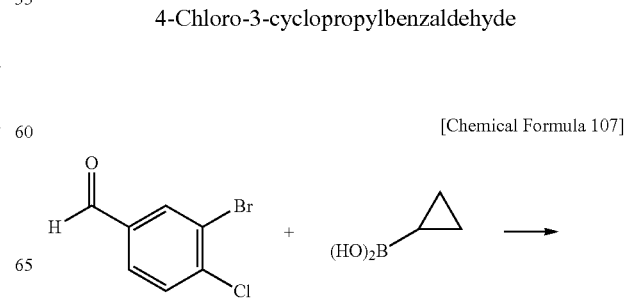

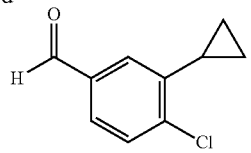

A mixture of 3-bromo-4-chlorobenzaldehyde (658 mg, CAS number: 86265-88-5), cyclopropylboronic acid (387 mg, CAS number: 411235-57-9), tetrakis(triphenylphosphine)palladium(0) (173 mg), tripotassium phosphate (955 mg), and 1,4-dioxane (4 mL) was stirred under microwave irradiation at 130° C. for 3 hours. The reaction mixture was cooled to room temperature, water was added, and the mixture was extracted with ethyl acetate. The organic layer obtained was washed with water and brine, and then dried over anhydrous sodium sulfate. After filtration, the solvent was distilled off under reduced pressure, and the residue obtained was purified by silica gel column chromatography (n-hexane/ethyl acetate) to obtain the title compound (491 mg) as an oil.

$^1$H-NMR (CDCl$_3$) δ: 0.74-0.80 (2H, m), 1.07-1.12 (2H, m), 2.20-2.28 (1H, m), 7.46 (1H, d, J=1.8 Hz), 7.52 (1H, d, J=7.9 Hz), 7.61 (1H, dd, J=7.9, 1.8 Hz), 9.94 (1H, s).

Reference Example 20

5-Chloro-4,6-dimethylpyrimidine-2-carbaldehyde

[Chemical Formula 108]

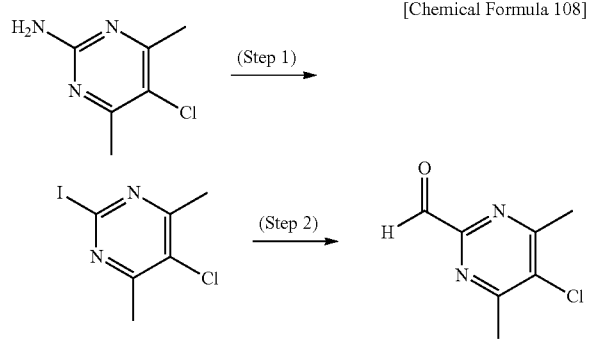

(Step 1) 5-Chloro-2-iodo-4,6-dimethylpyrimidine

To a suspension of 5-chloro-4,6-dimethyl-pyrimidine-2-amine (1.28 g, CAS number: 7749-61-3) in diiodomethane (6.5 mL), isoamyl nitrite (3.2 mL) was added dropwise at room temperature over 5 minutes, and the mixture was stirred at 65° C. for 75 minutes. The reaction mixture was cooled to room temperature, and purified by silica gel column chromatography (n-hexane/dichloromethane) to obtain the title compound (540 mg) as a solid.

$^1$H-NMR (CDCl$_3$) δ: 2.56 (6H, s).

(Step 2)
5-Chloro-4,6-dimethylpyrimidine-2-carbaldehyde

To a solution of the compound obtained in the above step 1 (535 mg) in tetrahydrofuran (10 mL), a 1.3 M-isopropyl magnesium chloride-lithium chloride complex/tetrahydrofuran solution (1.7 mL) was added dropwise at 0° C., and the mixture was stirred at the same temperature for 1 hour. Then, N,N-dimethylformamide (307 μL) was added dropwise, and the mixture was further stirred at the same temperature for 20 minutes, and then stirred at room temperature for 1 hour. Water was added to the reaction mixture, and the mixture was extracted with ethyl acetate. The organic layer obtained was washed with water and brine, and then dried over anhydrous sodium sulfate. After filtration, the solvent was distilled off under reduced pressure, and the residue was purified by silica gel column chromatography (dichloromethane/ethyl acetate) to obtain the title compound (32 mg) as an oil.

$^1$H-NMR (CDCl$_3$) δ: 2.73 (6H, s), 10.03 (1H, s).

Reference Example 21

3-Chloro-2-(trifluoromethoxy)phenol

[Chemical Formula 109]

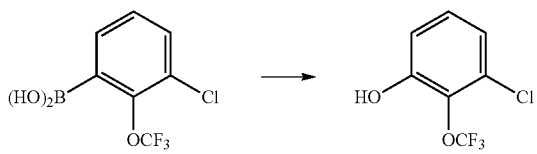

To a solution of 3-chloro-2-(trifluoromethoxy)phenylboronic acid (1.50 g, CAS number: 1942072-67-4) in acetone (15 mL), a solution of oxone (5.90 g) in water (15 mL) was added at room temperature, and the mixture was stirred at the same temperature for 1 hour and a half. Ethyl acetate and water were added to the reaction mixture, and the mixture was vigorously stirred, and then the organic layer was separated. Subsequently, 1 M-hydrochloric acid was added to the aqueous layer obtained, the mixture was extracted with ethyl acetate, and the combined organic layers were dried over anhydrous sodium sulfate. After filtration, the solvent was distilled off under reduced pressure, and the residue obtained was purified by silica gel column chromatography (n-hexane/ethyl acetate) to obtain the title compound (1.02 g) as an oil.

$^1$H-NMR (CDCl$_3$) δ: 5.71-5.91 (1H, m), 6.89-6.95 (1H, m), 6.96-7.02 (1H, m), 7.16-7.23 (1H, m).

Reference Example 22

3,5-Dichloro-4-(trifluoromethoxy)phenol

[Chemical Formula 110]

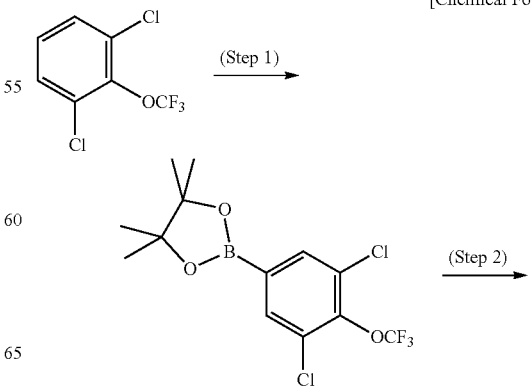

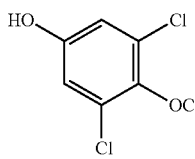

Step 1

2-[3,5-Dichloro-4-(trifluoromethoxy)phenyl]-4,4,5,5-tetramethyl-1,3,2-dioxaborolane A mixture of 2,6-dichloro(trifluoromethoxy)benzene (1.37 g, CAS number: 97608-49-6), bis(pinacolato)diboron (1.00 g), trans-2,6-diisopropyl-N-(2-pyridylmethylene)aniline (40 mg, CAS number: 908294-68-8), chloro(1,5-cyclooctadiene)iridium(I) dimer (61 mg, CAS number: 12112-67-3), and n-heptane (20 mL) was stirred at 105° C. for 4 hours. After the reaction mixture was cooled to room temperature, the solvent was distilled off under reduced pressure, and the residue obtained was purified by silica gel column chromatography (n-hexane/ethyl acetate) to obtain the title compound (1.83 g) as an oil.

$^1$H-NMR (CDCl$_3$) δ: 1.34 (12H, s), 7.79 (2H, s).

(Step 2) 3,5-Dichloro-4-(trifluoromethoxy)phenol

To a solution of the compound obtained in the above step 1 (1.83 g) in acetone (15 mL), a suspension of oxone (4.73 g) in water (15 mL) was added at room temperature, and the mixture was stirred at the same temperature for 30 minutes. Water was added to the reaction mixture, the mixture was extracted with ethyl acetate, and the organic layer obtained was washed with brine, and then dried over anhydrous sodium sulfate. After filtration, the solvent was distilled off under reduced pressure, and the residue obtained was purified by silica gel column chromatography (n-hexane/ethyl acetate) to obtain the title compound (1.17 g) as an oil.

$^1$H-NMR (CDCl$_3$) δ: 5.43 (1H, s), 6.88 (2H, s).

Reference Example 23

2-Fluoro-4-hydroxy-5-methylbenzaldehyde

[Chemical Formula 111]

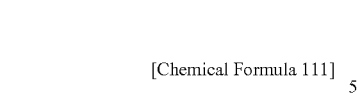

To a solution of 5-fluoro-2-methylphenol (693 mg, CAS number: 452-85-7) in dichloromethane (5 mL), a 1 M-titanium tetrachloride/dichloromethane solution (11 mL) and dichloro(methoxy)methane (534 μL) were added at 0° C., and the mixture was stirred at the same temperature for 1 hour. A saturated ammonium chloride aqueous solution was added to the reaction mixture, the mixture was extracted with dichloromethane, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (410 mg) as a solid.

$^1$H-NMR (CDCl$_3$) δ: 2.24 (3H, s), 5.83 (1H, s), 6.59 (1H, d, J=10.9 Hz), 7.66 (1H, d, J=7.9 Hz), 10.18 (1H, s).

Reference Example 24

4-Chloro-2-phenoxybenzaldehyde

[Chemical Formula 112]

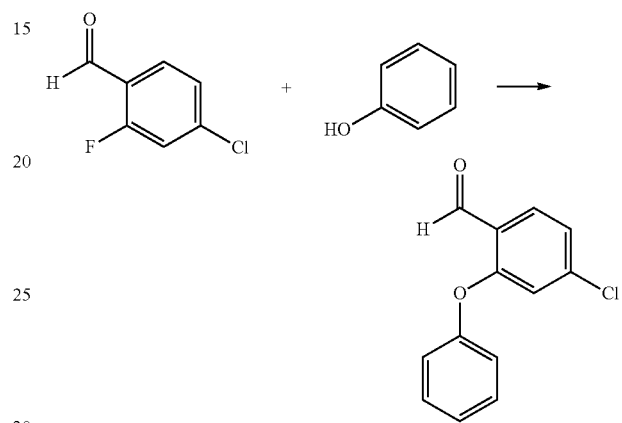

A mixture of 4-chloro-2-fluorobenzaldehyde (500 mg, CAS number: 61072-56-8), phenol (366 mg, CAS number: 108-95-2), potassium carbonate (654 mg), and N,N-dimethylformamide (11 mL) was stirred at 90° C. for 2 hours. The reaction mixture was cooled to room temperature, and then insoluble materials were removed by filtration through a pad of Celite. Toluene was added to the filtrate obtained, and the mixture was concentrated under reduced pressure. The residue obtained was purified by silica gel column chromatography (n-hexane/ethyl acetate) to obtain the title compound (565 mg) as an oil.

$^1$H-NMR (CDCl$_3$) δ: 6.85-6.88 (1H, m), 7.09-7.20 (3H, m), 7.25-7.31 (1H, m), 7.47 (2H, t, J=8.6 Hz), 7.90 (1H, d, J=8.6 Hz), 10.53 (1H, s), MS (m/z): 233.

Reference Example 25

4-[4-(Trifluoromethoxy)phenoxy]benzaldehyde

[Chemical Formula 113]

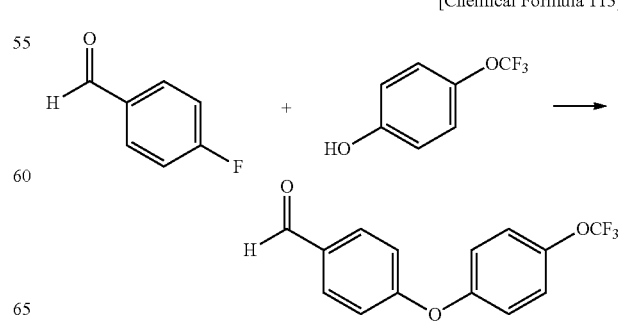

A mixture of 4-fluorobenzaldehyde (3.00 g, CAS number: 459-57-4), 4-(trifluoromethoxy)phenol (3.30 mL, CAS number: 828-27-3), potassium carbonate (3.79 g), and dimethylsulfoxide (9.0 mL) was stirred at 140° C. for 2 hours. The reaction mixture was cooled to room temperature, toluene and water were added, the mixture was vigorously stirred at room temperature, and then, the organic layer and the aqueous layer were separated. The organic layer obtained was washed with a 1 M-aqueous sodium hydroxide solution and water, and the solvent was distilled off under reduced pressure to obtain the title compound (6.69 g) as an oil.

$^1$H-NMR (CDCl$_3$) δ: 7.08 (2H, d, J=8.6 Hz), 7.11 (2H, d, J=8.6 Hz), 7.27 (2H, d, J=8.6 Hz), 7.88 (2H, t, J=4.3 Hz), 9.95 (1H, s).

Reference Example 26

4-[3-Chloro-4-(trifluoromethoxy)phenoxy]benzaldehyde

[Chemical Formula 114]

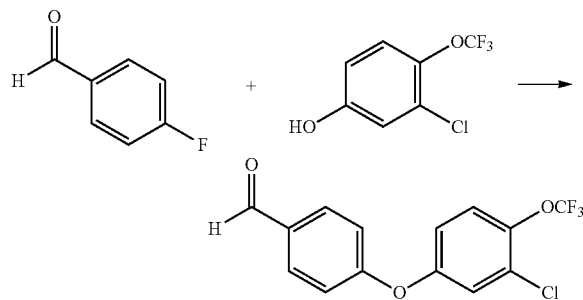

A mixture of 4-fluorobenzaldehyde (0.25 mL, CAS number: 459-57-4), 3-chloro-4-(trifluoromethoxy)phenol (529 mg, CAS number: 1000339-94-5), potassium carbonate (400 mg), and dimethylsulfoxide (3.5 mL) was stirred at 130° C. for 6 hours. The reaction mixture was cooled to room temperature, water was added, and the mixture was extracted twice with ethyl acetate. The organic layer obtained was washed with water and brine, and then dried over anhydrous sodium sulfate. After filtration, the solvent was distilled off under reduced pressure, and the residue obtained was purified by silica gel column chromatography (n-hexane/ethyl acetate) to obtain the title compound (645 mg) as an oil.

$^1$H-NMR (CDCl$_3$) δ: 7.01 (1H, dd, J=9.1, 3.0 Hz), 7.12 (2H, d, J=8.5 Hz), 7.20 (1H, d, J=3.0 Hz), 7.36 (1H, dd, J=9.1, 1.8 Hz), 7.91 (2H, d, J=8.5 Hz), 9.96 (1H, s).

Reference Example 27

4-[4-(Trifluoromethoxy)-3-(trifluoromethyl)phenoxy]benzaldehyde

[Chemical Formula 115]

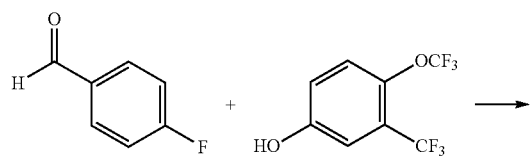

-continued

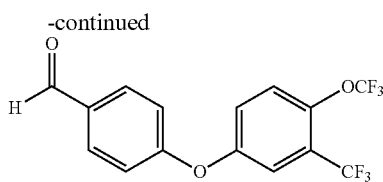

A mixture of 4-fluorobenzaldehyde (0.21 mL, CAS number: 459-57-4), 4-(trifluoromethoxy)3-(trifluoromethyl)phenol (504 mg, CAS number: 120355-08-0), potassium carbonate (488 mg), and dimethylsulfoxide (3.0 mL) was stirred at 140° C. for 6 hours. The reaction mixture was cooled to room temperature, water was added, and the mixture was extracted twice with ethyl acetate. The organic layer obtained was washed with water and brine, and then dried over anhydrous sodium sulfate. After filtration, the solvent was distilled off under reduced pressure, and the residue obtained was purified by silica gel column chromatography (n-hexane/ethyl acetate) to obtain the title compound (570 mg) as an oil.

$^1$H-NMR (CDCl$_3$) δ: 7.12 (2H, d, J=8.6 Hz), 7.28 (1H, dd, J=9.2, 3.1 Hz), 7.41 (1H, d, J=3.1 Hz), 7.45 (1H, d, J=9.2 Hz), 7.92 (2H, d, J=8.6 Hz), 9.98 (1H, s).

Reference Example 28

4-[3,5-Bis(trifluoromethyl)phenoxy]benzaldehyde

[Chemical Formula 116]

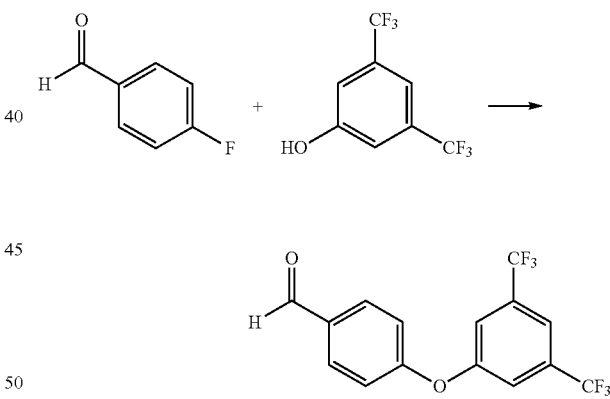

A mixture of 4-fluorobenzaldehyde (372 mg, CAS number: 459-57-4), 3,5-bis(trifluoromethyl)phenol (759 mg, CAS number: 349-58-6), potassium carbonate (456 mg), and N-methyl-2-pyrrolidone (3 mL) was stirred at 140° C. for 6 hours. The reaction mixture was cooled to room temperature, water was added, and the mixture was extracted twice with ethyl acetate. The organic layer obtained was washed with water and brine, and then dried over anhydrous sodium sulfate. After filtration, the solvent was distilled off under reduced pressure, and the residue obtained was purified by silica gel column chromatography (n-hexane/ethyl acetate) to obtain the title compound (678 mg) as an oil.

$^1$H-NMR (CDCl$_3$) δ: 7.16 (2H, d, J=8.5 Hz), 7.50 (2H, s), 7.70 (1H, s), 7.96 (2H, d, J=8.5 Hz), 10.00 (1H, s).

Reference Example 29

3-Chloro-4-(4-chlorophenoxy)benzaldehyde

[Chemical Formula 117]

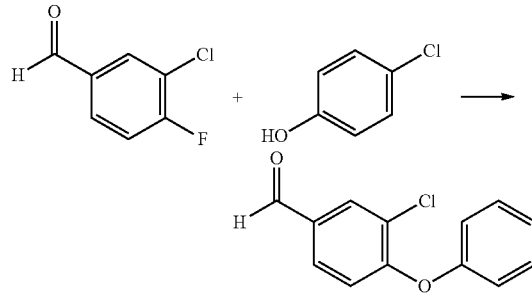

A mixture of 3-chloro-4-fluorobenzaldehyde (300 mg, CAS number: 34328-61-5), 4-chlorophenol (316 mg, CAS number: 106-48-9), sodium carbonate (301 mg), and dimethylsulfoxide (8.0 mL) was stirred at 130° C. for 7 hours. The reaction mixture was cooled to room temperature, ethyl acetate was added, and the organic layer obtained was washed with water, and then dried over anhydrous sodium sulfate. After filtration, the solvent was distilled off under reduced pressure, and the residue obtained was purified by silica gel column chromatography (n-hexane/ethyl acetate) to obtain the title compound (491 mg) as an oil.

$^1$H-NMR (CDCl$_3$) δ: 6.96 (1H, d, J=8.6 Hz), 6.99-7.04 (2H, m), 7.36-7.40 (2H, m), 7.71 (1H, dd, J=8.6, 1.8 Hz), 8.00 (1H, d, J=1.8 Hz), 9.91 (1H, s).

The same procedure as that in any one of Reference Examples 27 to 29 was performed to synthesize the following compounds (Table 1-1 to Table 1-7).

TABLE 1-1

| Reference Example No. | Manufacturing raw material 1 | Manufacturing raw material 2 | Structure of synthesized compound |
|---|---|---|---|
| 30 | [structure; CAS No. 577728-92-6] | [structure; CAS No. 108-95-2] | [structure] |
| 31 | [structure; CAS No. 459-57-4] | [structure; CAS No. 473917-15-6] | [structure] |
| 32 | [structure; CAS No. 459-57-48] | [structure; CAS No. 61721-07-1] | [structure] |
| 33 | [structure; CAS No. 63082-45-1] | [structure; CAS No. 1000339-94-5] | [structure] |
| 34 | [structure; CAS No. 459-57-4] | [structure; CAS No. 103467-50-1] | [structure] |

TABLE 1-1-continued

| Reference Example No. | Manufacturing raw material 1 | Manufacturing raw material 2 | Structure of synthesized compound |
|---|---|---|---|
| 35 | 4-fluorobenzaldehyde CAS No. 459-57-4 | 3-chloro-2-(trifluoromethoxy)phenol see Reference Example 21 | 4-(3-chloro-2-(trifluoromethoxy)phenoxy)benzaldehyde |

TABLE 1-2

| Reference Example No. | Manufacturing raw material 1 | Manufacturing raw material 2 | Structure of synthesized compound |
|---|---|---|---|
| 36 | 4-fluorobenzaldehyde CAS No. 459-57-4 | 2-methyl-4-(trifluoromethoxy)phenol CAS No. 129576-67-1 | 4-(2-methyl-4-(trifluoromethoxy)phenoxy)benzaldehyde |
| 37 | 4-fluorobenzaldehyde CAS No. 459-57-4 | 4-(trifluoromethoxy)benzenethiol CAS No. 169685-29-4 | 4-((4-(trifluoromethoxy)phenyl)thio)benzaldehyde |
| 38 | 4-fluorobenzaldehyde CAS No. 459-57-4 | 3-methyl-5-(trifluoromethyl)phenol CAS No. 934180-46-8 | 4-(3-methyl-5-(trifluoromethyl)phenoxy)benzaldehyde |
| 39 | 4-fluorobenzaldehyde CAS No. 459-57-4 | 4-(trifluoromethyl)phenol CAS No. 402-45-9 | 4-(4-(trifluoromethyl)phenoxy)benzaldehyde |
| 40 | 4-fluorobenzaldehyde CAS No. 459-57-4 | 4-((trifluoromethyl)thio)phenol CAS No. 461-84-7 | 4-(4-((trifluoromethyl)thio)phenoxy)benzaldehyde |
| 41 | 4-fluorobenzaldehyde CAS No. 459-57-4 | 3,5-dichloro-4-(trifluoromethoxy)phenol see Reference Example 22 | 4-(3,5-dichloro-4-(trifluoromethoxy)phenoxy)benzaldehyde |

TABLE 1-2-continued
step 2
42 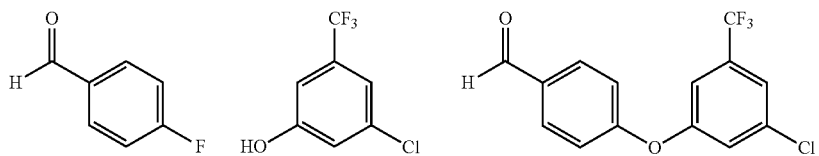
CAS No. 459-57-4    CAS No. 570391-18-3
TABLE 1-3
43 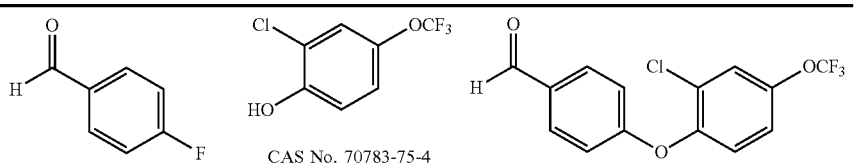
CAS No. 459-57-4    CAS No. 70783-75-4
44 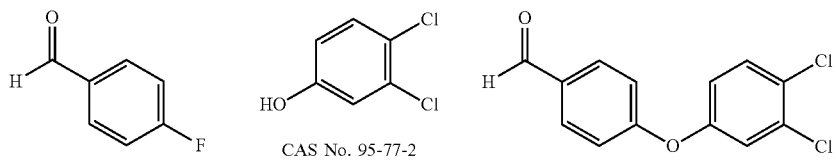
CAS No. 459-57-4    CAS No. 95-77-2
45 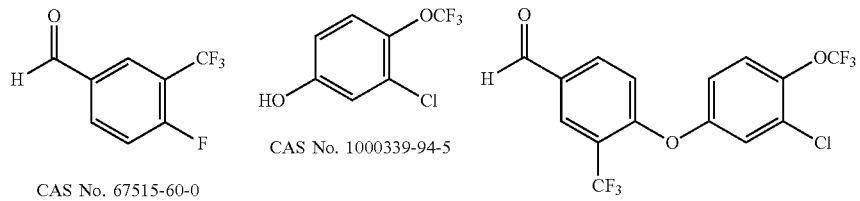
CAS No. 67515-60-0    CAS No. 1000339-94-5
46 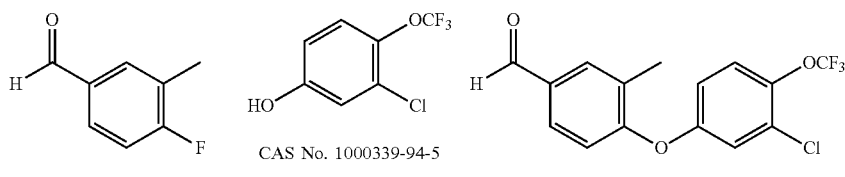
CAS No. 135427-08-6    CAS No. 1000339-94-5
47 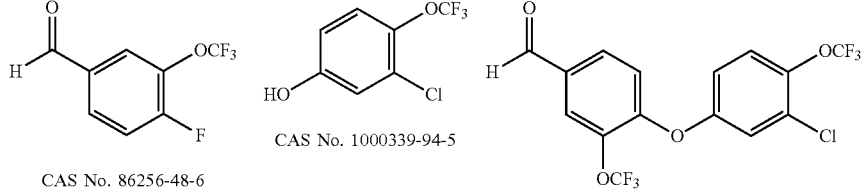
CAS No. 86256-48-6    CAS No. 1000339-94-5
48 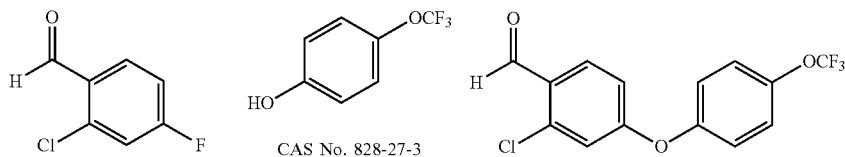
CAS No. 34194-36-5    CAS No. 828-27-3

TABLE 1-4
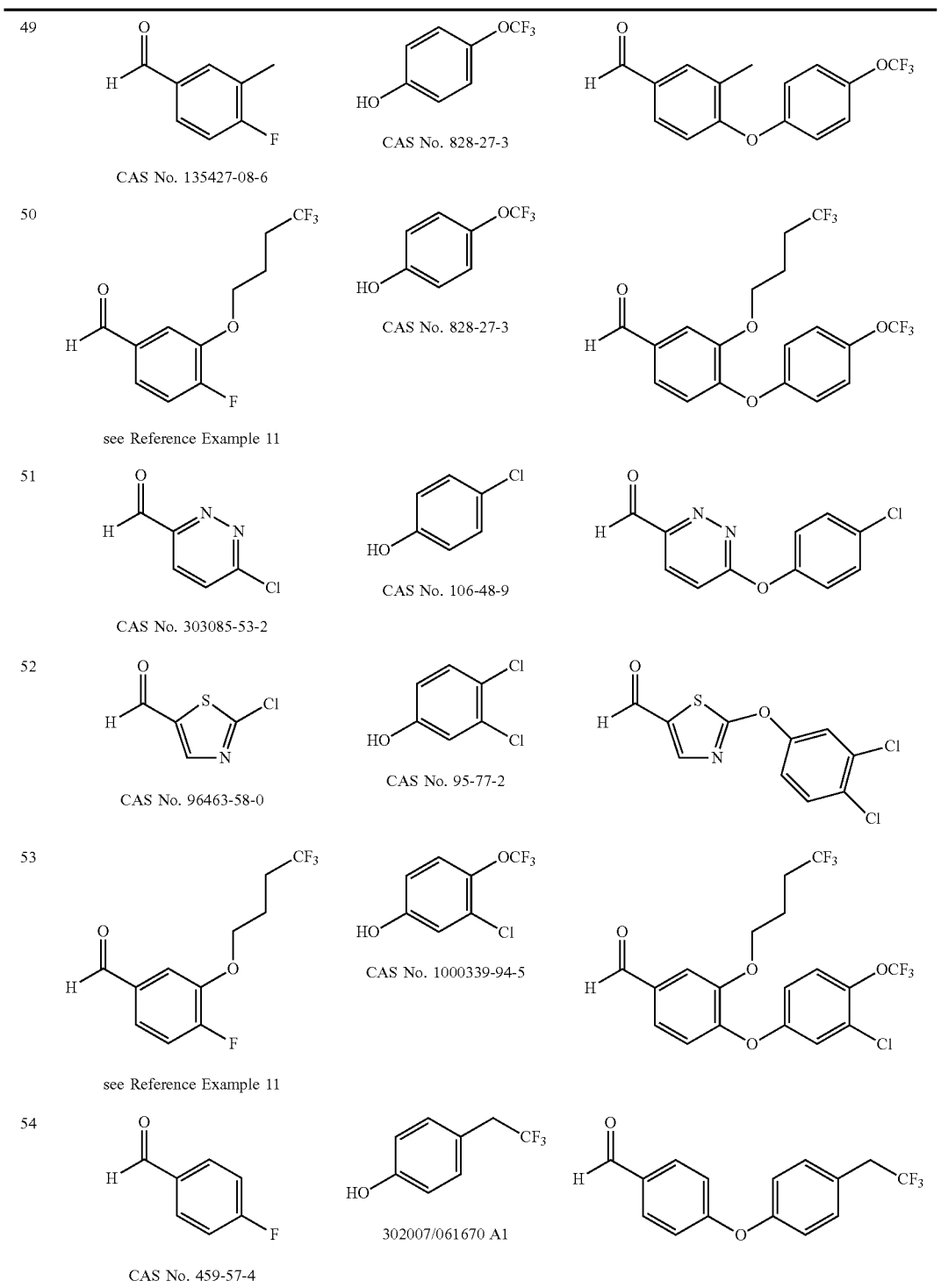
TABLE 1-5
| Reference Example No. | Name of synthesized compound | Synthetic method | Spectral data |
|---|---|---|---|
| 30 | 6-Phenoxypyridine-3-carbaldehyde | Reference Example 27 | $^1$H-NMR (CDCl$_3$) δ: 7.04 (1H, d, J = 8.5 Hz), 7.15-7.20 (2H, m), 7.27-7.32 (1H, m), 7.43-7.49 (2H, m) 8.19 (1H, dd, J = 8.5, |

TABLE 1-5-continued

| Reference Example No. | Name of synthesized compound | Synthetic method | Spectral data |
|---|---|---|---|
| | | | 2.4 Hz), 8.63 (1H, d, J = 2.4 Hz), 9.98 (1H, s). |
| 31 | 4-[3-Fluoro-4-(trifluoromethoxy)phenoxy]benzaldehyde | Reference Example 27 | $^1$H-NMR (CDCl$_3$) δ: 6.87 (1H, ddd, J = 9.1, 2.4, 1.2 Hz), 6.94 (1H, dd, J = 10.9, 2.4 Hz), 7.13 (2H, d) J = 8.5 Hz), 7.33 (1H, ddd, J = 9.7, 9.1, 1.2 Hz), 7.91 (2H, d, J = 8.5 Hz), 9.97 (1H, s). |
| 32 | 4-[4-Fluoro-3-(trifluoromethoxy)phenoxy]benzaldehyde | Reference Example 27 | $^1$H-NMR (CDCl$_3$) δ: 7.02 (1H, ddd, J = 9.2, 3.7, 3.1 Hz), 7.05-7.11 (3H, m), 7.25 (1H, t, J = 9.2 Hz), 7.89 (2H, d, J = 9.2 Hz), 9.95 (1H, s). |
| 33 | 4-[3-Chloro-4-(trifluoromethoxy)phenoxy]-2-methylbenzaldehyde | Reference Example 27 | $^1$H-NMR (CDCl$_3$) δ: 2.66 (3H, s), 6.84-6.87 (1H, m), 6.91-6.95 (1H, m), 6.97-7.02 (1H, m), 7.16-7.19 (1H, m), 7.31-7.40 (1H, m), 7.78-7.85 (1H, m), 10.18 (1H, s). |
| 34 | 4-{(2,2,3,3-Tetrafluoro-2,3-dihydro-1,4-benzodioxin-6-yl)oxy}benzaldehyde | Reference Example 27 | $^1$H-NMR (CDCl$_3$) δ: 6.84-6.94 (2H, m), 7.09 (2H, d. J = 8.6 Hz), 7.18 (1H, dd, J = 8.0, 1.2 Hz), 7.89 (2H, d, j = 8.6 Hz), 9.96 (1H, s). |
| 35 | 4-[3-Chloro-2-(trifluoromethoxy)phenoxy]benzaldehyde | Reference Example 27 | $^1$H-NMR (CDCl$_3$) δ: 7.01-7.13 (3H, m), 7.22-7.29 (1H, m), 7.13-7.39 (1H, m), 7.83-7.94 (2H, m), 9.95 (1H, s). |
| 36 | 4-[2-Methyl-4-(trifluoromethoxy)phenoxy]benzaldehyde | Reference Example 28 | $^1$H-NMR (CDCl$_3$) δ: 2.21 (3H, s), 6.95-7.04 (3H, m), 7.07-7.13 (1H, m), 7.17 (1H, s), 7.83-7.87 (2H, m), 9.93 (1H, s). |
| 37 | 4-{[4-(Trifluoromethoxy)phenyl]sulfanyl}benzaldehyde | Reference Example 28 | $^1$H-NMR (CDCl$_3$) δ: 7.27 (4H, d, J = 7.9 Hz), 7.52-7.57 (2H, m), 7.75 (2H, d, J = 7.9 Hz), 9.93 (1H, s). |
| 38 | 4-[3-Methyl-5-(trifluoromethyl)phenoxy-benzaldehyde | Reference Example 28 | $^1$H-NMR (CDCl$_3$) δ: 2.43 (3H, s), 7.06-7.11 (3H, m), 7.14 (1H, s), 7.29 (1H, s), 7.86-7.91 (2H, m), 9.95 (1H, s). |

TABLE 1-6

| 39 | 4-[4-(Trifluoromethyl)phenoxy]benzaldehyde | Example 28 | $^1$H-NMR (CDCl$_3$) δ: 7.11-7.20 (4H, m), 7.67 (2H, d, J = 9.1 Hz), 7.88-7.93 (2H, m), 9.97 (1H, s). |
|---|---|---|---|
| 40 | 4-{4-[(Trifluoromethyl)sulfanyl]phenoxy}benzaldehyde | Reference Example 28 | $^1$H-NMR (CDCl$_3$) δ: 7.08-7.17 (4H, m), 7.66-7.71 (2H, m), 7.88-7.93 (2H, m), 9.97 (1H, s). |
| 41 | 4-[3,5-Dichloro-4-(trifluoromethoxy)phenoxy]benzaldehyde | Reference Example 28 | $^1$H-NMR (CDCl$_3$) δ: 7.09 (2H, s), 7.16 (2H, d, J = 8.5 Hz), 7.94 (2H, d, J = 8.5 Hz), 9.99 (1H, s). |
| 42 | 4-[3-Chloro-5-(trifluoromethyl)phenoxy]benzaldehyde | Reference Example 28 | $^1$H-NMR (CDCl$_3$) δ: 7.12-7.16 (2H, m), 7.21-7.25 (2H, m), 7.45 (1H, s), 7.91-7.95 (2H, m, 9.98 (1H, s). |
| 43 | 4-[2-Chloro-4-(trifluoromethoxy)phenoxy]benzaldehyde | Reference Example 28 | $^1$H-NMR (CDCl$_3$) δ: 7.00-7.05 (2H, m), 7.15-7.23 (2H, m), 7.42 (1H, d, J = 2.4 Hz), 7.86-7.91 (2H, m), 9.95 (1H, s). |
| 44 | 4-(3,4-Dichlorophenoxy)fluorobenzaldehyde | Reference Example 29 | $^1$H-NMR (CDCl$_3$) δ: 6.95 (1H, dd, J = 8.6, 3.1 Hz), 7.07-7.12 (2H, m), 7.20 (1H, d, J = 3.1 Hz), 7.47 (1H, d, J = 8.6 Hz), 7.87-7.91 (2H, m), 9.96 (1H, s). |
| 45 | 4-[3-Chloro-4-(trifluoromethoxy)phenoxy]-3-(trifluoromethyl)benzaldehyde | Reference Example 29 | $^1$H-NMR (CDCl$_3$) δ: 7.01-7.10 (2H, m), 7.25 (1H, d, j = 3.0 Hz), 7.39 (1H, dd, J = 9.1, 1.2 Hz), 8.03 (1H, dd, J = 8.5, 1.8 Hz), 8.24 (1H, d, J = 1.8 Hz), 10.00 (1H, s). |
| 46 | 4-[3-Chloro-4-(trifluoromethoxy)phenoxy]-3-methylbenzaldehyde | Reference Example 29 | $^1$H-NMR (CDCl$_3$) δ: 2.35 (3H, s), 6.92 (1H, dd, J = 9.1, 3.0 Hz), 6.96 (1H, d, J = 7.9 Hz), 7.10 (1H, d, J = 3.0 Hz), 7.32 (1H, dd, J = 9.1, 1.2 Hz), 7.71 (1H, dd, J = 8.5, 1.8 Hz), 7.82 (1H, s), 9.95 (1H, s). |
| 47 | 4-[3-Chloro-4-(trifluoromethoxy)phenoxy]-3-(trifluoromethoxy)benzaldehyde | Reference Example 29 | $^1$H-NMR (CDCl$_3$) δ: 7. 00 (1H, dd, J = 9.1, 3.0 Hz), 7.11 (1H, d, J = 9.1 Hz), 7.20 (1H, d, J = 3.0 Hz), 7.34-7.39 (1H, m), 7.81 (1H, dd, J = 8.5, 1.8 Hz), 7.90 (1H, d, J = 1.8 Hz), 9.96 (1H, s). |
| 48 | 2-Chloro-4-[4-(trifluoromethoxy)phenoxy]benzaldehyde | Reference Example 29 | $^1$H-NMR (CDCl$_3$) δ: 6.95 (1H, dd, J = 8.5, 2.4 Hz), 6.99 (1H, d, J = 2.4 Hz), 7.07-7.15 (2H, m), 7.29 (2H, d, J = 9.2 Hz), 7.93 (1H, d, J = 8.5 Hz), 10.37 (1H, s). |

TABLE 1-7

| | | | |
|---|---|---|---|
| 49 | 3-Methyl-4-[4-(trifluoro-methoxy)phenoxy]benzaldehyde | Example 29 | ¹H-NMR (CDCl₃) δ: 2.37 (3H, s), 6.88 (1H, d, J = 8.6 Hz), 6.98-7.07 (2H, m), 7.20-7.27 (2H, m) 7.67 (1H, dd, J = 8.3, 2.1 Hz), 7.81 (1H, s), 9.93 (1H, s) |
| 50 | 3-(4,4,4-Trifluorobutoxy)-4-[4-(trifluoromethoxy)phenoxy]benzaldehyde | Reference Example 29 | ¹H-NMR (CDCl₃) δ: 1.88-2.05 (4H, m), 4.09 (2H, t, J = 6.5 Hz), 6.92-7.01 (2H, m), 7.06-7.22 (3H, m), 7.48-7.54 (2H, m), 9.93 (1H, s). |
| 51 | 6-(4-Chlorophenoxy)pyridazine-3-carbaldehyde | Reference Example 29 | ¹H-NMR (CDCl₃) δ: 7.18-7.22 (2H, m), 7.33 (1H, d, J = 9.2 Hz), 7.41-7.46 (2H, m), 8.08 (1H, d, J = 9.2 Hz), 10.25 (1H, s). |
| 52 | 2-(3,4-Dichlorophenoxy)-1,3-thiazol-5-carbaldehyde | Reference Example 29 | ¹H-NMR (CDCl₃) δ: 7.18-7.23 (1H, m), 7.49 (1H, d, J = 3.0 Hz), 7.54 (1H, d, J = 9.1 Hz), 7.91 (1H, s), 9.88 (1H, s). |
| 53 | 4-[3-Chloro-4-(trifluoromethoxy)phenoxy]-3-(4,4,4-trifluorobutoxy)benzaldehyde | Reference Example 29 | ¹H-NMR (CDCl₃) δ: 1.90-2.05 (4H, m), 4.09 (2H, t, J = 5.5 Hz), 6.88 (1H, dd, J = 8.8, 2.7 Hz), 7.02 (1H, d, J = 3.0 Hz), 7.21 (1H, d, J = 8.5 Hz), 7.26-7.31 (1H, m), 7.50-7.54 (2H, m), 9.95 (1H, s). |
| 54 | 4-[4-(2,2,2-Trifluoroethyl)phenoxy]benzaldehyde | Reference Example 27 | ¹H-NMR (CDCl₃) δ: 3.39 (2H, q, J = 10.6 Hz), 7.04-7.11 (4H, m), 7.34 (2H, d, J = 8.2 Hz), 7.87 (2H, d, J = 8.6 Hz), 9.94 (1H, s). |

Reference Example 55

3-[(5-Chloropyridin-2-yl)oxy]benzaldehyde

[Chemical Formula 118]

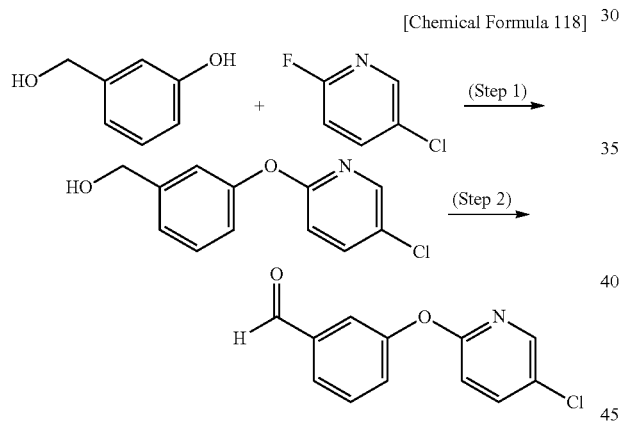

(Step 1) {3-[(5-Chloropyridin-2-yl)oxy]phenyl}methanol

A mixture of 3-(hydroxymethyl)phenol (660 mg, CAS number: 620-24-6), 5-chloro-2-fluoropyridine (534 μL, CAS number: 1480-65-5), cesium carbonate (2.25 g), and dimethylsulfoxide (15 mL) was stirred at 120° C. for 4 hours. The reaction mixture was cooled to room temperature, water was added, the mixture was extracted with ethyl acetate, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (840 mg) as an oil.

¹H-NMR (CDCl₃) δ: 1.72 (1H, t, J=6.1 Hz), 4.72 (2H, d, J=6.1 Hz), 6.90 (1H, d, J=8.5 Hz), 7.02-7.07 (1H, m), 7.15 (1H, s), 7.22 (1H, d, J=7.3 Hz), 7.40 (1H, t, J=7.9 Hz), 7.65 (1H, dd, J=8.5, 2.4 Hz), 8.12 (1H, d, J=2.4 Hz), MS (m/z): 236 (M+H)⁺.

(Step 2) 3-[(5-Chloropyridin-2-yl)oxy]benzaldehyde

To a solution of the compound obtained in the above step 1 (660 mg) in dichloromethane (5.0 mL), Dess-Martin periodinane (313 mg) was added at 0° C., and the mixture was stirred at the same temperature for 30 minutes. A saturated aqueous sodium hydrogen carbonate solution was added to the reaction mixture, the mixture was extracted with dichloromethane, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (132 mg) as a solid.

¹H-NMR (CDCl₃) δ: 6.97 (1H, d, J=8.5 Hz), 7.38-7.44 (1H, m), 7.59 (1H, t, J=7.9 Hz), 7.63-7.76 (3H, m), 8.12 (1H, d, J=3.1 Hz), 10.01 (1H, s).

Reference Example 56

2-Phenoxypyridine-4-carbaldehyde

[Chemical Formula 119]

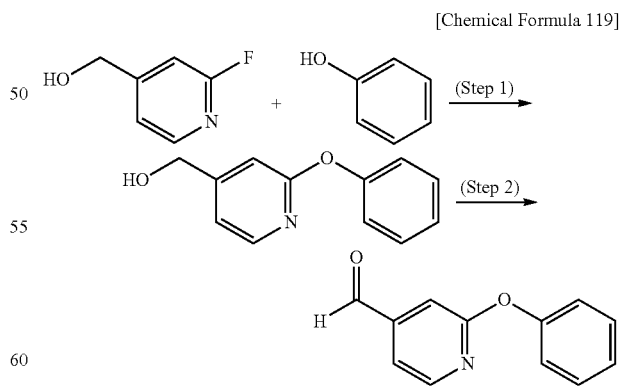

(Step 1) (2-Phenoxypyridin-4-yl)methanol

A mixture of (2-fluoropyridin-4-yl)methanol (1.00 g, CAS number: 131747-60-9), phenol (1.48 g, CAS number:

108-95-2), cesium carbonate (5.13 g), and dimethylsulfoxide (15 mL) was stirred under microwave irradiation at 120° C. for 1 hour. The reaction mixture was cooled to room temperature, diethyl ether was added, and the organic layer obtained was sequentially washed with water, a 1 M-aqueous sodium hydroxide solution, water, and brine, and dried over anhydrous sodium sulfate. After filtration, the solvent was distilled off under reduced pressure, and the residue obtained was purified by silica gel column chromatography (dichloromethane/ethyl acetate) to obtain the title compound (343 mg) as an oil.

$^1$H-NMR (CDCl$_3$) δ: 1.96 (1H, br s), 4.73 (2H, d, J=5.1 Hz), 6.91 (1H, d, J=0.8 Hz), 6.96-6.99 (1H, m), 7.13 (2H, d, J=8.2 Hz), 7.21 (1H, t, J=7.4 Hz), 7.40 (2H, dd, J=8.2, 7.4 Hz), 8.16 (1H, d, J=5.1 Hz).

(Step 2) 2-Phenoxypyridine-4-carbaldehyde

The compound obtained in the above step 1 (340 mg) was used as a manufacturing raw material, and the same procedure as that in step 2 of Reference Example 55 was performed to obtain the title compound (306 mg) as an oil.

$^1$H-NMR (CDCl$_3$) δ: 7.11-7.16 (2H, m), 7.20-7.25 (1H, m), 7.27-7.29 (1H, m), 7.37-7.44 (3H, m), 8.38 (1H, d, J=4.9 Hz), 10.02 (1H, s).

Reference Example 57

4-(4-Fluorophenoxy)pyridine-2-carbaldehyde

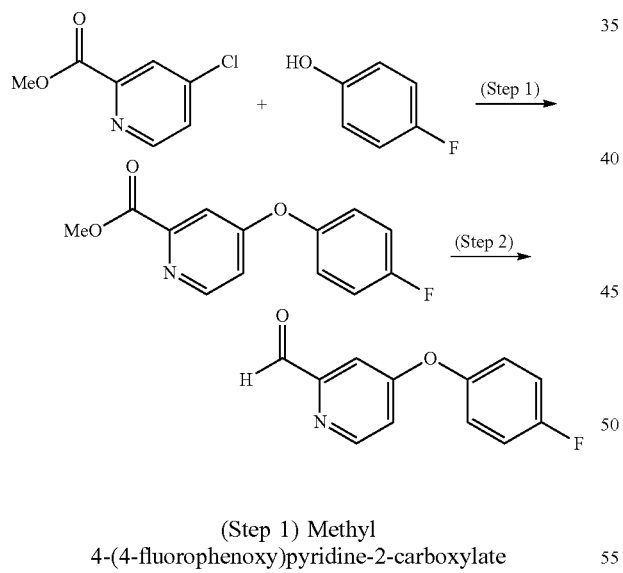

[Chemical Formula 120]

(Step 1) Methyl 4-(4-fluorophenoxy)pyridine-2-carboxylate

A mixture of methyl 4-chloropyridine-2-carboxylate (280 mg, CAS number: 24484-93-3), 4-fluorophenol (245 mg, CAS number: 371-41-5), sodium carbonate (386 mg), and dimethylsulfoxide (3.0 mL) was stirred at 120° C. for 9 hours. The reaction mixture was cooled to room temperature, iodomethane (181 μL) was added, and the mixture was stirred at room temperature for 3 hours. The reaction mixture was diluted with ethyl acetate, and the organic layer obtained was washed with water, and then dried over anhydrous sodium sulfate. After filtration, the solvent was distilled off under reduced pressure, and the residue obtained was purified by silica gel column chromatography (n-hexane/ethyl acetate) to obtain the title compound (85.0 mg) as an oil.

$^1$H-NMR (CDCl$_3$) δ: 3.99 (3H, s), 6.99 (1H, dd, J=5.5, 2.5 Hz), 7.04-7.20 (4H, m), 7.63 (1H, d, J=2.5 Hz), 8.59 (1H, d, J=5.5 Hz).

(Step 2) 4-(4-Fluorophenoxy)pyridine-2-carbaldehyde

To a solution of the compound obtained in the above step 1 (118 mg) in dichloromethane (5.0 mL), a 1.0 M-diisobutylaluminum hydride/toluene solution (0.70 mL) was added at −78° C., and the mixture was stirred at the same temperature for 30 minutes. A 1 M-aqueous sodium hydroxide solution was added to the reaction mixture at −78° C., the mixture was heated to room temperature, and insoluble materials were removed by filtration through a pad of Celite. The filtrate was concentrated under reduced pressure, and the residue obtained was purified by silica gel column chromatography (n-hexane/ethyl acetate) to obtain the title compound (53.0 mg) as an oil.

$^1$H-NMR (CDCl$_3$) δ: 7.05-7.18 (5H, m), 7.41 (1H, d, J=2.5 Hz), 8.64 (1H, d, J=5.5 Hz), 10.03 (1H, s).

Reference Example 58

5-(4-Fluorophenoxy)pyrazine-2-carbaldehyde

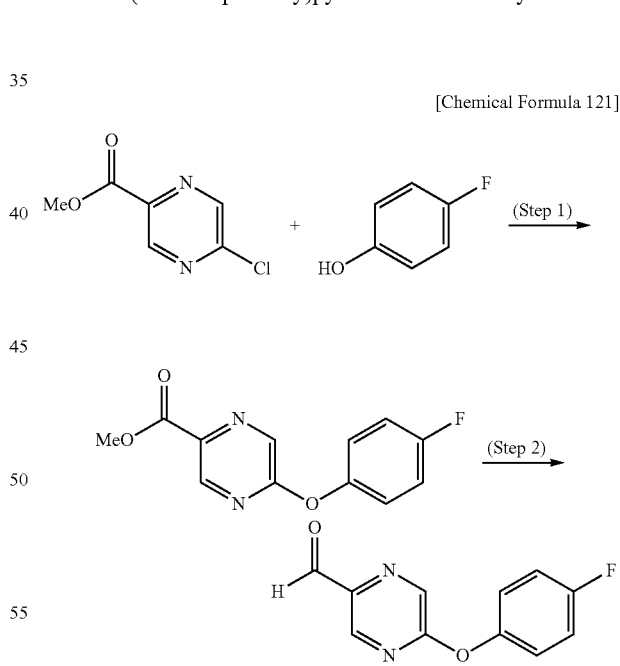

[Chemical Formula 121]

Methyl 5-chloropyrazine-2-carboxylate (222 mg, CAS number: 33332-25-1) and 4-fluorophenol (288 mg, CAS number: 371-41-5) were used as manufacturing raw materials, and the same procedure as that in step 1 and step 2 of Reference Example 57 was carried out to obtain the title compound (77.0 mg) as a solid.

$^1$H-NMR (CDCl$_3$) δ: 7.11-7.18 (4H, m), 8.54 (1H, d, J=1.2 Hz), 8.70 (1H, d, J=1.2 Hz), 10.09 (1H, s).

Reference Example 59

5-(4-Chlorophenoxy)pyridine-2-carbaldehyde

[Chemical Formula 122]

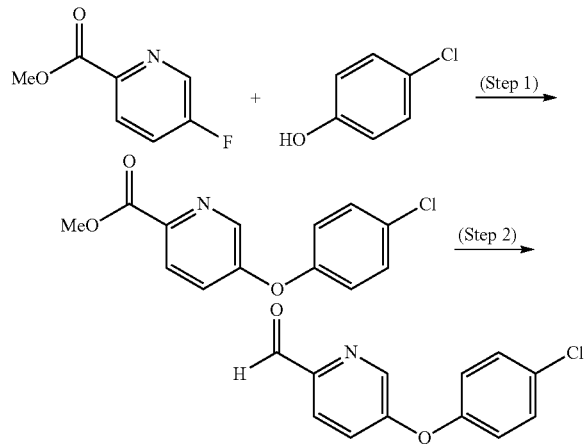

Methyl 5-fluoropyridine-2-carboxylate (234 mg, CAS number: 107504-07-4) and 4-chlorophenol (388 mg, CAS number: 106-48-9) were used as manufacturing materials, and the same procedure as that in step 1 and step 2 of Reference Example 57 was performed to obtain the title compound (235 mg) as an oil.

$^1$H-NMR (CDCl$_3$) δ: 7.03-7.12 (2H, m), 7.29-7.49 (3H, m), 7.96 (1H, d, J=8.5 Hz), 8.51 (1H, d, J=2.4 Hz), 10.03 (1H, s).

Reference Example 60

2-(4-Fluorophenoxy)pyrimidine-4-carbaldehyde

[Chemical Formula 123]

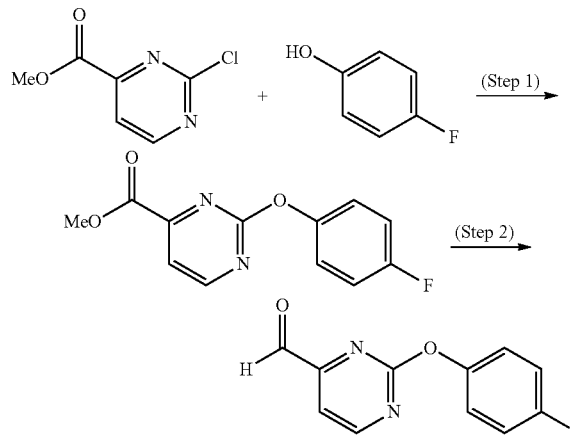

(Step 1) Methyl 2-(4-fluorophenoxy)pyrimidine-4-carboxylate

Methyl 2-chloropyrimidine-4-carboxylate (291 mg, CAS number: 149849-94-5) and 4-fluorophenol (283 mg, CAS number: 371-41-5) were used as manufacturing raw materials, and the same procedure as that in step 1 of Reference Example 57 was performed to obtain the title compound (193 mg) as a solid.

$^1$H-NMR (CDCl$_3$) δ: 4.02 (3H, s), 7.07-7.24 (4H, m), 7.73 (1H, d, J=4.9 Hz), 8.73 (1H, d, J=4.9 Hz). MS (m/z): 249 (M+H)$^+$.

(Step 2) 2-(4-Fluorophenoxy)pyrimidine-4-carbaldehyde

To a solution of the compound obtained in the above step 1 (193 mg) in methanol (4.0 mL)-tetrahydrofuran (4.0 mL), sodium borohydride (88.0 mg) was added at 0° C., and the mixture was stirred at room temperature for 90 minutes. After acetone was added to the reaction mixture, the mixture was concentrated under reduced pressure, water was added to the residue, the mixture was extracted with ethyl acetate, and the organic layer obtained was dried over anhydrous sodium sulfate. After filtration, the solvent was distilled off under reduced pressure, and the residue obtained was purified by silica gel column chromatography (chloroform/ethyl acetate). Subsequently, Dess-Martin periodinane (330 mg) was added to a solution of the solid obtained (130 mg) in dichloromethane (6.0 mL) at room temperature, and the mixture was stirred at the same temperature for 1 hour. A saturated aqueous sodium hydrogen carbonate solution was added to the reaction mixture, the mixture was extracted with dichloromethane, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (107 mg) as a solid.

$^1$H-NMR (CDCl$_3$) δ: 7.10-7.24 (4H, m), 7.56 (1H, d, J=4.9 Hz), 8.80 (1H, d, J=4.9 Hz), 9.92 (1H, s).

Reference Example 61

4-[4-(Trifluoromethanesulfonyl)phenoxy]benzaldehyde

[Chemical Formula 124]

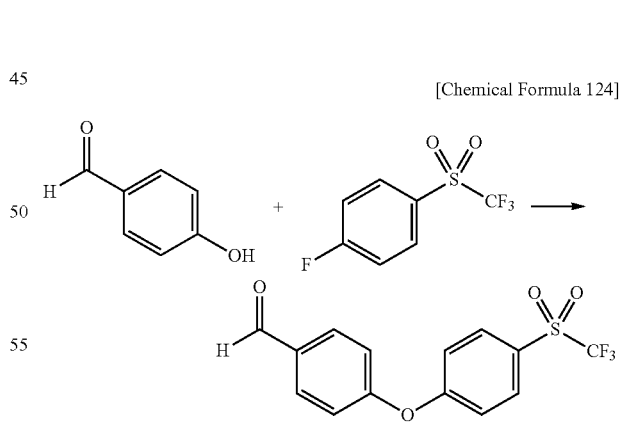

A mixture of 4-hydroxybenzaldehyde (176 mg, CAS number: 123-08-0), 1-fluoro-4-(trifluoromethanesulfonyl)benzene (274 mg, CAS number: 455-15-2), potassium carbonate (249 mg), and N,N-dimethylformamide (1.8 mL) was stirred at 50° C. for 7 hours. The reaction mixture was cooled to room temperature, water was added, and the mixture was extracted with ethyl acetate. The organic layer obtained was washed with water and brine, and then dried over anhydrous sodium sulfate. After filtration, the solvent was distilled off under reduced pressure, and the residue obtained was purified by silica gel column chromatography (n-hexane/ethyl acetate) to obtain the title compound (360 mg) as an oil.

$^1$H-NMR (CDCl$_3$) δ: 7.22-7.26 (4H, m), 7.97-8.06 (4H, m), 10.02 (1H, s).

Reference Example 62

4-{[4-(Trifluoromethyl)-1,3-thiazol-2-yl]oxy}benzaldehyde

[Chemical Formula 125]

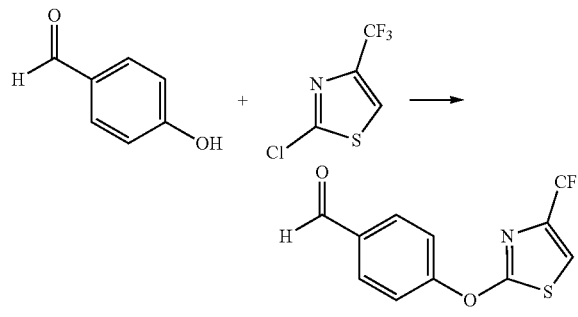

A mixture of 4-hydroxybenzaldehyde (298 mg, CAS number: 123-08-0), 2-chloro-4-(trifluoromethyl)-1,3-thiazole (229 mg, CAS number: 228119-52-6), sodium carbonate (259 mg), and dimethylsulfoxide (5.0 mL) was stirred at 120° C. for 2 hours. The reaction mixture was cooled to room temperature, ethyl acetate was added, and the organic layer obtained was washed with water, and then dried over anhydrous sodium sulfate. After filtration, the solvent was distilled off under reduced pressure, and the residue obtained was purified by silica gel column chromatography (n-hexane/ethyl acetate) to obtain the title compound (218 mg) as a solid.

$^1$H-NMR (CDCl$_3$) δ: 7.37-7.38 (1H, m), 7.49-7.55 (2H, m), 7.95-8.00 (2H, m), 10.02 (1H, s).

Reference Example 63

4-{[6-Chloro-4-(trifluoromethyl)pyridin-2-yl]oxy}benzaldehyde

[Chemical Formula 126]

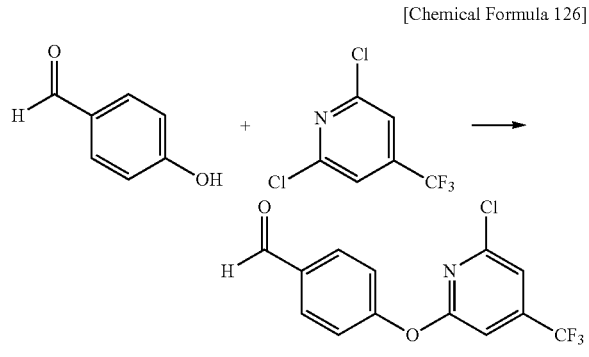

4-Hydroxybenzaldehyde (363 mg, CAS number: 123-08-0) and 2,6-dichloro-4-(trifluoromethyl)pyridine (459 μL, CAS number: 39890-98-7) was used as manufacturing raw materials, and the same procedure as that in Reference Example 62 was performed to obtain the title compound (746 mg) as an oil.

$^1$H-NMR (CDCl$_3$) δ: 7.14 (1H, s), 7.31-7.35 (3H, m), 7.96-8.00 (2H, m), 10.02 (1H, s).

Reference Example 64

4-[3-Methyl-4-(trifluoromethoxy)phenoxy]benzaldehyde

[Chemical Formula 127]

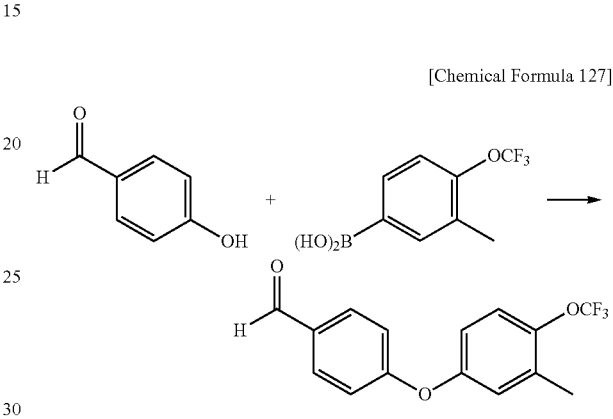

To a suspension of 4-hydroxybenzaldehyde (458 mg, CAS number: 123-08-0), 3-methyl-4-trifluoromethoxyphenylboronic acid (1.00 g, CAS number: 871362-79-7), copper (II) acetate (835 mg), and molecular sieve 4A (1.45 g) in dichloromethane (40 mL), pyridine (1.51 mL) was added at room temperature, and the mixture was stirred at the same temperature for 4 days. After insoluble materials were removed by filtration through a pad of Celite, the solvent was distilled off under reduced pressure, and diethyl ether was added to the residue. The organic layer obtained was sequentially washed with 1 M-hydrochloric acid, a 1 M-aqueous sodium hydroxide solution, water, and brine, and then dried over anhydrous sodium sulfate. After filtration, the solvent was distilled off under reduced pressure, and the residue obtained was purified by silica gel column chromatography (n-hexane/ethyl acetate) to obtain the title compound (295 mg) as an oil.

$^1$H-NMR (CDCl$_3$) δ: 2.33 (3H, s), 6.92 (1H, dd, J=9.2, 2.5 Hz), 6.97 (1H, d, J=2.5 Hz), 7.07 (2H, J=8.6 Hz), 7.24 (1H, dd, J=9.2, 1.2 Hz), 7.87 (2H, d, J=8.6 Hz), 9.94 (1H, s).

Reference Example 65

4-[3-Chloro-5-(trifluoromethoxy)phenoxy]benzaldehyde

[Chemical Formula 128]

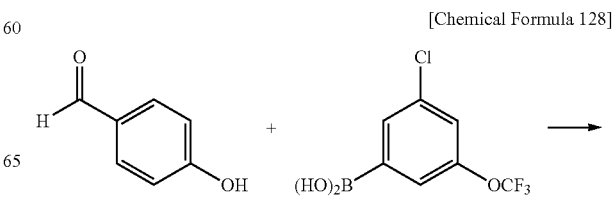

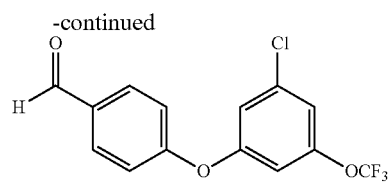

To a suspension of 3-chloro-5-(trifluoromethoxy)phenyl boronic acid (1.31 g, CAS number: 1451393-40-0), 4-hydroxybenzaldehyde (511 mg, CAS number: 123-08-0), copper(II) acetate (934 mg), and molecular sieve 4A (1.77 g) in dichloromethane (40 mL), pyridine (1.66 mL) was added at room temperature, and the mixture was stirred at the same temperature for 3 days. After insoluble materials were removed by filtration through a pad of Celite, the solvent was distilled off under reduced pressure, and diethyl ether was added to the residue. The organic layer obtained was sequentially washed with 1 M-hydrochloric acid, a 1 M-aqueous sodium hydroxide solution, water, and brine, and then dried over anhydrous sodium sulfate. After filtration, the solvent was distilled off under reduced pressure, and the residue obtained was purified by silica gel column chromatography (n-hexane/ethyl acetate) to obtain the title compound (295 mg) as an oil.

$^1$H-NMR (CDCl$_3$) δ: 6.82-6.88 (1H, m), 6.98-7.01 (1H, m), 7.05-7.09 (1H, m), 7.14 (2H, d, J=8.5 Hz), 7.92 (2H, d, J=8.5 Hz), 9.98 (1H, s).

Reference Example 66

3-(4-Fluorophenoxy)benzaldehyde

[Chemical Formula 129]

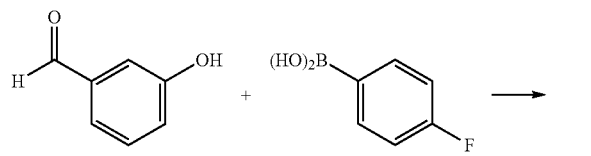

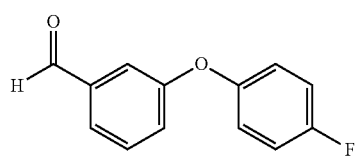

To a suspension of 3-hydroxybenzaldehyde (649 mg, CAS number: 100-83-4), 4-fluorophenylboronic acid (892 mg, CAS number: 1765-93-1), copper(II) acetate (965 mg), and molecular sieve 4A (800 mg) in dichloromethane (15 mL), triethylamine (3.70 mL) was added at room temperature, and the mixture was stirred at the same temperature overnight. After insoluble materials were removed by filtration through a pad of Celite, the solvent was distilled off under reduced pressure, and the residue obtained was purified by silica gel column chromatography (n-hexane/chloroform) to obtain the title compound (204 mg) as an oil.

$^1$H-NMR (CDCl$_3$) δ: 6.98-7.05 (2H, m), 7.08 (2H, dd, J=9.1, 7.9 Hz), 7.23-7.29 (1H, m), 7.41 (1H, d, J=1.2 Hz), 7.50 (1H, dd, J=7.9, 7.3 Hz), 7.60 (1H, dd, J=7.9, 1.2 Hz), 9.96 (1H, s).

Reference Example 67

4-(4-Chlorophenoxy)-2-fluorobenzaldehyde

[Chemical Formula 130]

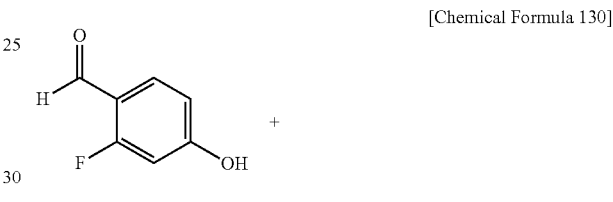

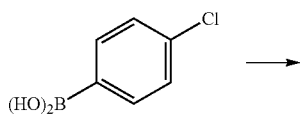

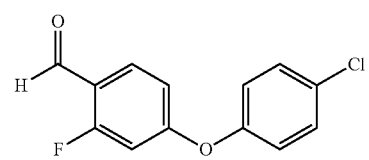 [SMILES: O=Cc1ccc(Oc2ccc(Cl)cc2)nn1]

To a suspension of 2-fluoro-4-hydroxybenzaldehyde (775 mg, CAS number: 348-27-6), 4-chlorophenylboronic acid (1.30 g, CAS number: 1679-18-1), copper(II) acetate (1.00 g), and molecular sieve 4A (1.50 g) in dichloromethane (50 mL), pyridine (2.20 mL) was added at room temperature, and the mixture was stirred at the same temperature for 6 days. After insoluble materials were removed by filtration through a pad of Celite, the solvent was distilled off under reduced pressure, and the residue obtained was purified by silica gel column chromatography (n-hexane/ethyl acetate and n-hexane/chloroform) to obtain the title compound (776 mg) as a solid.

$^1$H-NMR (CDCl$_3$) δ: 6.67 (1H, dd, J=11.6, 2.4 Hz), 6.83 (1H, dd, J=8.5, 2.4 Hz), 7.05 (2H, d, J=9.2 Hz), 7.41 (2H, d, J=9.2 Hz), 7.85 (1H, dd, J=8.5, 7.9 Hz), 10.24 (1H, s).

The same procedure as that in any one of Reference Examples 65 to 67 was performed to synthesize the following compounds (Table 2-1 to Table 2-3).

TABLE 2-1

| Reference Example No. | Manufacturing raw material 1 | Manufacturing raw material 2 | Structure of synthesized compound |
|---|---|---|---|
| 68 | CAS No. 123-08-0 | CAS No. 153254-09-2 | |
| 69 | CAS No. 123-08-0 | CAS No. 1204745-88-9 | |
| 70 | CAS No. 100-83-4 | CAS No. 139301-27-2 | |
| 71 | see Reference Example 23 | CAS No. 73852-19-4 | |
| 72 | CAS No. 348-27-6 | CAS No. 139301-27-2 | |
| 73 | see Reference Example 23 | CAS No. 139301-27-2 | |
| 74 | CAS No. 348-27-6 | CAS No. 73852-19-4 | |

TABLE 2-2

| 75 | 3-hydroxybenzaldehyde (CAS No. 100-83-4) | 2,4-bis(trifluoromethyl)phenylboronic acid (CAS No. 158254-09-2) | 3-[2,4-bis(trifluoromethyl)phenoxy]benzaldehyde |
| 76 | 2-fluoro-5-hydroxybenzaldehyde (CAS No. 103438-84-2) | phenylboronic acid (CAS No. 98-80-6) | 2-fluoro-5-phenoxybenzaldehyde |

TABLE 2-3

| Reference Example No | Name of synthesized compound | Synthetic method | Spectral data |
| --- | --- | --- | --- |
| 68 | 4-[2,4-Bis(trifluoromethyl)phenoxy]benzaldehyde | Reference Example 65 | $^1$H-NMR (CDCl$_3$) δ: 7.07-7.23 (3H, m), 7.75-7.83 (1H, m), 7.90-8.03 (3H, m), 9.98 (1H, s). |
| 69 | 4-[3,4-Bis(trifluoromethyl)phenoxy]benzaldehyde | Reference Example 67 | $^1$H-NMR (CDCl$_3$) δ: 7.16-7.21 (2H, m), 7.26-7.30 (1H, m), 7.52 (1H, d, J = 2.4 Hz), 7.86 (1H, d, J = 8.5 Hz), 7.93-7.98 (2H, m), 10.00 (1H, s). |
| 70 | 3-[4-(Trifluoromethoxy)phenoxy]benzaldehyde | Reference Example 66 | $^1$H-NMR (CDCl$_3$) δ: 7.02-7.07 (2H, m), 7.20-7.25 (2H, m), 7.28-7.32 (1H, m), 7.47-7.49 (1H, m) 7.54 (1H, t, J = 8.0 Hz), 7.63-7.66 (1H, m), 9.98 (1H, s). |
| 71 | 4-[3,5-Bis(trifluoromethyl)phenoxy]-2-fluoro-5-methylbenzaldehyde | Reference Example 67 | $^1$H-NMR (CDCl$_3$) δ: 2.30 (3H, s), 6.59 (1H, d, J = 10.9 Hz), 7.46 (2H, s), 7.72 (1H, s), 7.84 (1H, d, J = 7.9 Hz), 10.28 (1H, s). |
| 72 | 2-Fluoro-4-[4-(trifluoromethoxy)phenoxy]benzaldehyde | Reference Example 67 | $^1$H-NMR (CDCl$_3$) δ: 6.69 (1H, dd, J = 11.7, 2.5 Hz), 6.84 (1H, dd, J = 8.6, 2.5 Hz), 7.12 (2H, d, J = 9.2 Hz), 7.29 (2H, d, J = 9.2 Hz), 7.86 (1H, t, J = 8.6 Hz), 10.25 (1H, s). |
| 73 | 2-Fluoro-5-methyl-4-[4-(trifluoromethoxy)phenoxy]benzaldehyde | Reference Example 67 | $^1$H-NMR (CDCl$_3$) δ: 2.32 (3H, s), 6.46 (1H, d, J = 10.9 Hz), 7.08 (2H, d, J = 9.1 Hz), 7.27-7.30 (2H, m), 7.76 (1H, d, J = 7.9 Hz), 10.23 (1H, s). |
| 74 | 4-[3,5-Bis(trifluoromethyl)phenoxy]-2-fluorobenzaldehyde | Reference Example 67 | $^1$H-NMR (CDCl$_3$) δ: 6.79 (1H, dd, J = 11.5, 2.4 Hz), 6.89 (1H, dd, J = 8.5, 2.4 Hz), 7.53 (2H, s), 7.75 (1H, s), 7.94 (1H, t, J = 8.5 Hz), 10.29 (1H, s). |
| 75 | 3-[2,4-Bis(trifluoromethyl)phenoxy]benzaldehyde | Reference Example 65 | $^1$H-NMR (CDCl$_3$) δ: 7.01 (1H, d, J = 8.6 Hz), 7.38 (1H, ddd, J = 8.2, 2.3, 1.2 Hz), 7.57 (1H, dd, J = 2.3, 1.2 Hz), 7.62 (1H, dd, J = 8.2, 7.8 Hz), 7.71-7.76 (1H, m), 7.76 (1H, dt, J = 7.8, 1.2, Hz), 7.98 (1H, d, J = 1.6 Hz), 10.01 (1H, s). |
| 76 | 2-Fluoro-5-phenoxybenzaldehyde | Reference Example 67 | $^1$H-NMR (CDCl$_3$) δ: 6.99 (2H, d, J = 7.9 Hz), 7.12-7.20 (2H, m), 7.26-7.30 (1H, m), 7.36 (2H, t, J = 7.9 Hz), 7.41-7.45 (1H, m), 10.32 (1H, s). |

Reference Example 77

3-(4-Fluorophenoxy)-5-(trifluoromethyl)benzaldehyde

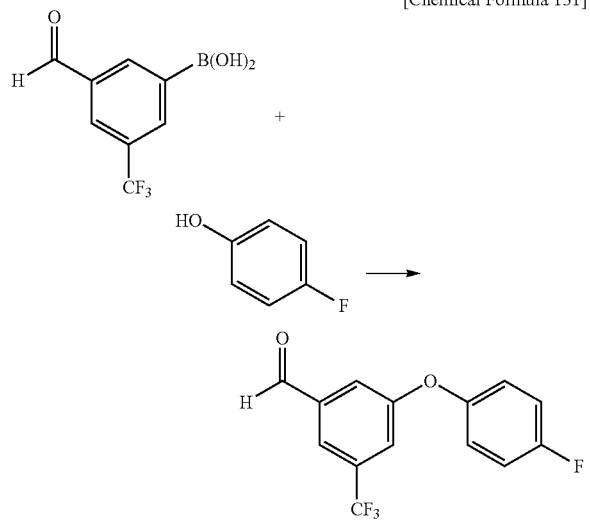

[Chemical Formula 131]

To a suspension of 3-formyl-5-(trifluoromethyl)phenylboronic acid (500 mg, CAS number: 1451393-24-0), 4-fluorophenol (309 mg, CAS number: 371-41-5), copper(II) acetate (417 mg), and molecular sieve 4A (0.3 g) in dichloromethane (5 mL), pyridine (923 μL) was added at room temperature, and the mixture was stirred at the same temperature for 22 hours. The reaction mixture was diluted with ethyl acetate, insoluble materials were removed by filtration through a pad of Celite, and then the solvent was distilled off under reduced pressure. The residue obtained was sequentially purified by silica gel column chromatography (n-hexane/ethyl acetate) and reverse phase HPLC to obtain the title compound (152 mg) as an oil.

$^1$H-NMR (CDCl$_3$) δ: 7.03-7.08 (2H, m), 7.10-7.16 (2H, m), 7.47 (1H, s), 7.55 (1H, s), 7.83 (1H, s), 9.99 (1H, s).

Reference Example 78

4-[3-Chloro-4-(trifluoromethoxy)phenoxy]-2-fluorobenzaldehyde

[Chemical Formula 132]

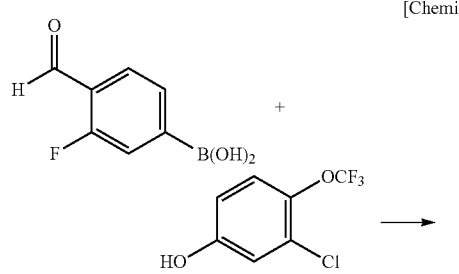

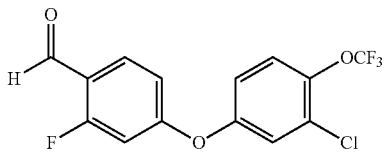

3-Fluoro-4-formylphenylboronic acid (432 mg, CAS number: 248270-25-9) and 3-chloro-4-(trifluoromethoxy)phenol (820 mg, CAS number: 1000339-94-5) were used as manufacturing raw materials, and the same procedure as that in Reference Example 77 was performed to obtain the title compound (571 mg) as an oil.

$^1$H-NMR (CDCl$_3$) δ: 6.74 (1H, dd, J=11.5, 2.4 Hz), 6.87 (1H, dd, J=8.5, 2.4 Hz), 7.04 (1H, dd, J=8.5, 2.4 Hz), 7.23 (1H, d, J=2.4 Hz), 7.38 (1H, dd, J=8.5, 1.2 Hz), 7.89 (1H, t, J=8.2 Hz), 10.27 (1H, s).

Reference Example 79

4-[(4,4-Difluoropiperidin-1-yl)methyl]benzaldehyde

[Chemical Formula 133]

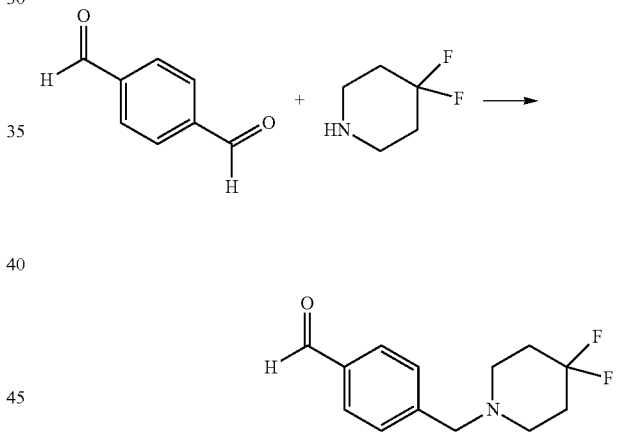

To a solution of terephthalaldehyde (1 g, CAS number: 623-27-8) in 1,2-dichloroethane (40 mL), 4,4-difluoropiperidine (0.9 mL, CAS number: 21987-29-1) and acetic acid (0.4 mL) were added at room temperature, and the mixture was stirred at the same temperature for 30 minutes. Then, sodium triacetoxyborohydride (1.5 g) was added, and the mixture was further stirred at the same temperature. The reaction mixture was diluted with ethyl acetate, the organic layer obtained was sequentially washed with a saturated aqueous sodium hydrogen carbonate solution, water, and brine, and then dried over anhydrous sodium sulfate. After filtration, the solvent was distilled off under reduced pressure, and the residue obtained was purified by silica gel column chromatography (n-hexane/ethyl acetate) to obtain the title compound (309 mg) as a solid.

$^1$H-NMR (CDCl$_3$) δ: 1.96-2.06 (4H, m), 2.56 (4H, t, J=5.5 Hz), 3.62 (2H, s), 7.51 (2H, d, J=8.5 Hz), 7.85 (2H, d, J=8.5 Hz), 10.01 (1H, s), MS (m/z): 240 (M+H)$^+$.

Reference Example 80

4-{[3-(Trifluoromethyl)-1,2-benzoxazol-5-yl]oxy}benzaldehyde

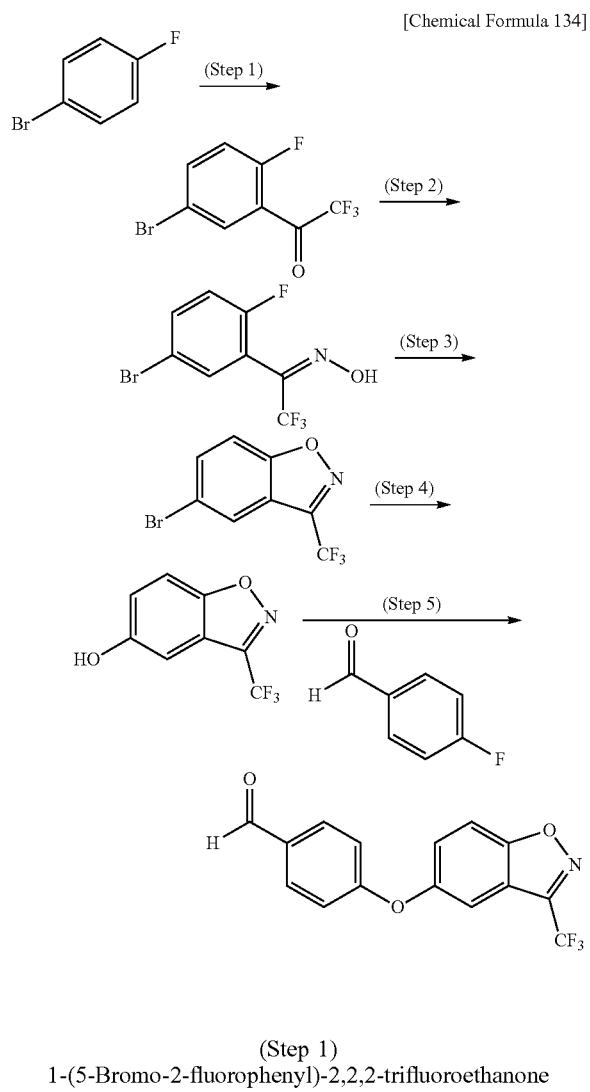

[Chemical Formula 134]

(Step 1)
1-(5-Bromo-2-fluorophenyl)-2,2,2-trifluoroethanone

To a solution of 4-bromofluorobenzene (1.8 mL, CAS number: 460-00-4) in tetrahydrofuran (10 mL), a 1.1 M-lithium diisopropylamide/n-hexane-tetrahydrofuran solution (17 mL) was added at −78° C., and the mixture was stirred at the same temperature for 1 hour. Then, a solution of ethyl trifluoroacetate (2.3 mL) in tetrahydrofuran (10 mL) was added, and the mixture was heated to 0° C. and stirred for 2 hours. A saturated ammonium chloride aqueous solution was added to the reaction mixture, the mixture was extracted with ethyl acetate, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (2.44 g) as a solid.

$^1$H-NMR (CDCl$_3$) δ: 7.12-7.18 (1H, m), 7.76-7.81 (1H, m), 7.98-8.01 (1H, m).

(Step 2) N-[1-(5-Bromo-2-fluorophenyl)-2,2,2-trifluoroethylidene]hydroxylamine

To a solution of the compound obtained in the above step 1 (2 g) in methanol (50 mL), hydroxylamine hydrochloride (3.9 g) and sodium acetate (5.7 g) were added, and the mixture was stirred at 60° C. for 24 hours. After insoluble materials were filtered off, the filtrate was diluted with ethyl acetate, and the organic layer obtained was washed with water, and then dried over anhydrous sodium sulfate. After filtration, the solvent was distilled off under reduced pressure to obtain the crude title compound (2.73 g) as an oil.

$^1$H-NMR (CDCl$_3$) δ: 7.03-7.12 (1H, m), 7.41-7.62 (2H, m), 8.69-9.07 (1H, m).

(Step 3) 5-Bromo-3-(trifluoromethyl)-1,2-benzoxazole

To a solution of the compound obtained in the above step 2 (2.1 g) in tetrahydrofuran (15 mL), DBU (0.77 mL) was added, and the mixture was stirred under microwave irradiation at 150° C. for 1 hour. The reaction mixture was cooled to room temperature, ethyl acetate was added, and the organic layer obtained was washed with water and brine, and then dried over anhydrous sodium sulfate. After filtration, the solvent was distilled off under reduced pressure, and the residue obtained was purified by silica gel column chromatography (n-hexane/dichloromethane) to obtain the title compound (1.49 g) as a solid.

$^1$H-NMR (CDCl$_3$) δ: 7.62 (1H, d, J=9.1 Hz), 7.79 (1H, dd, J=9.1, 1.8 Hz), 7.98 (1H, br s).

(Step 4) 3-(Trifluoromethyl)-1,2-benzoxazol-5-ol

A mixture of the compound obtained in the above step 3 (1.49 g), tris(dibenzylideneacetone)dipalladium(0) (0.13 g), 2-di-tert-butylphosphino-2',4',6'-triisopropylbiphenyl (0.12 g), potassium hydroxide (0.63 g), 1,4-dioxane (30 mL), and water (15 mL) was stirred at 80° C. for 12 hours. The reaction mixture was cooled to room temperature, and 1 M-hydrochloric acid was added to adjust the mixture to around neutrality. Then, the mixture was extracted with ethyl acetate, and the organic layer obtained was washed with brine, and then dried over anhydrous sodium sulfate. After filtration, the solvent was distilled off under reduced pressure, and the residue obtained was purified by silica gel column chromatography (n-hexane/ethyl acetate) to obtain the title compound (0.905 g) as a solid.

$^1$H-NMR (CDCl$_3$) δ: 5.32 (1H, br s), 7.14 (1H, d, J=1.8 Hz), 7.23 (1H, dd, J=8.8, 1.8 Hz), 7.58 (1H, d, J=8.8 Hz).

(Step 5) 4-{[3-(Trifluoromethyl)-1,2-benzoxazol-5-yl]oxy}benzaldehyde

A mixture of the compound obtained in the above step 4 (0.6 g), 4-fluorobenzaldehyde (0.5 mL, CAS number: 459-57-4), cesium carbonate (1.4 g), and dimethylsulfoxide (7 mL) was stirred under microwave irradiation at 130° C. for 1 hour. The reaction mixture was cooled to room temperature, water was added, and the mixture was extracted with ethyl acetate. The organic layer obtained was washed with brine, and then dried over anhydrous sodium sulfate. After filtration, the solvent was distilled off under reduced pressure, and the residue obtained was purified by silica gel column chromatography (n-hexane/ethyl acetate) to obtain the title compound (627 mg) as an oil.

¹H-NMR (CDCl₃) δ: 7.08 (2H, d, J=9.1 Hz), 7.45-7.49 (2H, m), 7.76 (1H, d, J=9.1 Hz), 7.90 (2H, d, J=9.1 Hz), 9.96 (1H, s), MS (m/z): 308 (M+H)⁺.

Reference Example 81

1-Phenyl-1H-indazole-5-carbaldehyde

[Chemical Formula 135]

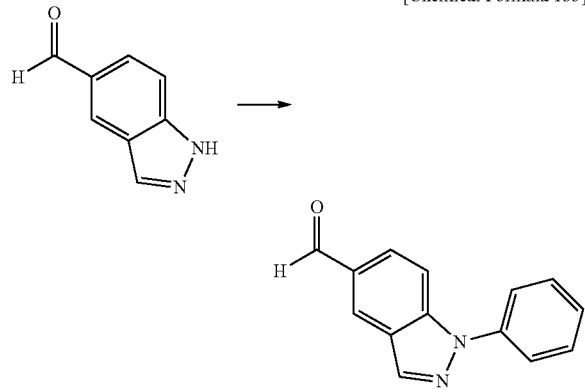

To a suspension of indazole-5-carboxyaldehyde (1.00 g), copper(I) iodide (262 mg), 1,10-phenanthroline (496 mg), and tripotassium phosphate (2.90 g) in toluene (10 mL), iodobenzene (763 μL) was added at room temperature, and the mixture was stirred under microwave irradiation at 130° C. for 2 hours. The reaction mixture was cooled to room temperature and then diluted with ethyl acetate, and insoluble materials were removed by filtration through a pad of Celite. Subsequently, water was added to the filtrate, the mixture was extracted with ethyl acetate, and the organic layer obtained was washed with water and brine, and then dried over anhydrous sodium sulfate. After filtration, the solvent was distilled off under reduced pressure, and the residue obtained was purified by silica gel column chromatography (n-hexane/ethyl acetate) to obtain the title compound (136 mg) as a solid.

¹H-NMR (CDCl₃) δ: 7.44 (1H, t, J=7.4 Hz), 7.59 (2H, dd, J=7.8, 7.4 Hz), 7.73 (2H, d, J=7.8 Hz), 7.82 (1H, d, J=8.6 Hz), 8.00 (1H, dd, J=8.6, 1.6 Hz), 8.35 (1H, m), 8.38 (1H, s), 10.10 (1H, s).

Reference Example 82

3-Anilinobenzaldehyde

[Chemical Formula 136]

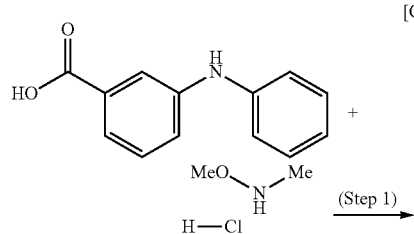

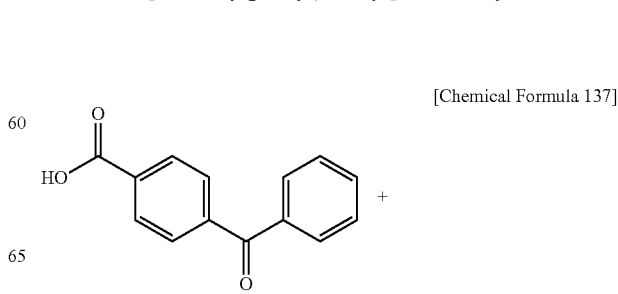

(Step 1) 3-Anilino-N-methoxy-N-methylbenzamide

To a solution of 3-(phenylamino)benzoic acid (250 mg, CAS number: 6025-56-5) and N,O-dimethylhydroxyamine hydrochloride (155 mg, CAS number: 6638-79-5) in dichloromethane (15 mL), HATU (502 mg) and triethylamine (0.2 mL) were added at room temperature, and the mixture was stirred at the same temperature for 16 hours. Water was added to the reaction mixture, the mixture was extracted with dichloromethane, and the organic layer obtained was washed with a saturated aqueous sodium hydrogen carbonate solution and brine, and then dried over anhydrous sodium sulfate. After filtration, the solvent was distilled off under reduced pressure, and the residue obtained was purified by silica gel column chromatography (n-hexane/ethyl acetate) to obtain the title compound (287 mg) as an oil.

¹H-NMR (CDCl₃) δ: 3.35 (3H, s), 3.58 (3H, s), 5.81-5.98 (1H, m), 6.91-7.00 (1H, m), 7.05-7.12 (2H, m), 7.12-7.20 (2H, m), 7.23-7.35 (4H, m).

(Step 2) 3-Anilinobenzaldehyde

To a solution of the compound obtained in the above step 1 (276 mg) in dichloromethane (5.0 mL), a 1.02 M-diisobutylaluminum hydride/toluene solution (1.60 mL) was added dropwise at 0° C., and the mixture was stirred at the same temperature for 3 hours. A 1 M-aqueous sodium hydroxide solution (0.3 mL) and anhydrous sodium sulfate (excess amount) were added to the reaction mixture at 0° C., and the mixture was stirred at room temperature for 30 minutes. After insoluble materials were removed by filtration through a pad of Celite, the solvent was distilled off under reduced pressure, and the residue obtained was purified by silica gel column chromatography (n-hexane/ethyl acetate) to obtain the title compound (173 mg) as a solid.

¹H-NMR (CDCl₃) δ: 5.87 (1H, br s), 6.98-7.05 (1H, m), 7.09-7.16 (2H, m), 7.27-7.35 (3H, m), 7.36-7.46 (2H, m), 7.53 (1H, s), 9.94 (1H, s).

Reference Example 83

4-[Methoxy(phenyl)methyl]benzaldehyde

[Chemical Formula 137]

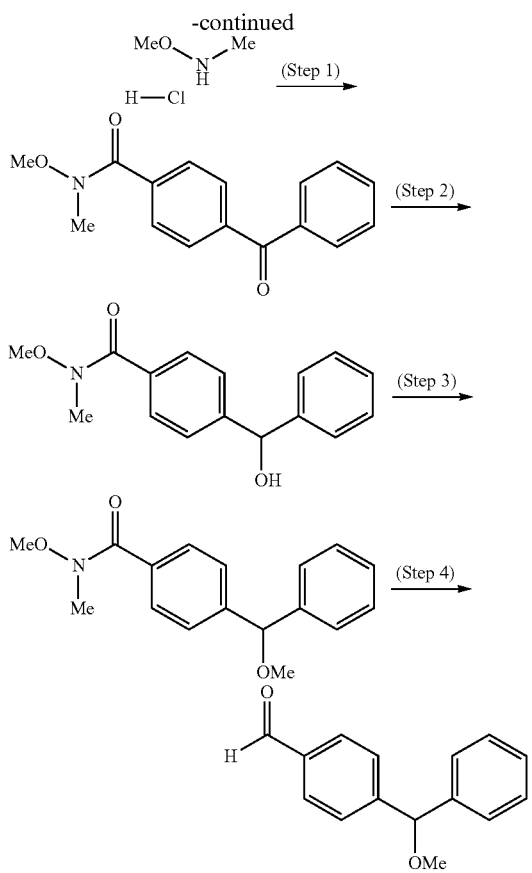

(Step 1) 4-Benzoyl-N-methoxy-N-methylbenzamide

4-Benzoylbenzoic acid (1.01 g, CAS number: 611-95-0) and N,O-dimethylhydroxyamine hydrochloride (461 mg, CAS number: 6638-79-5) were used as manufacturing raw materials, and the same procedure as that in step 1 of Reference Example 82 was performed to obtain the title compound (1.19 g) as an oil.

$^1$H-NMR (CDCl$_3$) δ: 3.40 (3H, s), 3.57 (3H, s), 7.46-7.54 (2H, m), 7.59-7.66 (1H, m), 7.75-7.86 (6H, m).

(Step 2) 4-[Hydroxy(phenyl)methyl]-N-methoxy-N-methylbenzamide

To a solution of the compound obtained in the above step 1 (300 mg) in methanol (7.0 mL), sodium borohydride (170 mg) was added at 0° C., and the mixture was stirred at the same temperature for 50 minutes. To the reaction mixture, 1 M-hydrochloric acid (0.7 mL) was added, the mixture was extracted with ethyl acetate, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (296 mg) as an oil.

$^1$H-NMR (CDCl$_3$) δ: 3.26 (3H, s), 3.50 (3H, s), 5.71-5.79 (1H, m), 7.18-7.40 (7H, m), 7.51-7.61 (2H, m).

(Step 3) N-Methoxy-4-[methoxy(phenyl)methyl]-N-methylbenzamide

To a solution of the compound obtained in the above step 2 (296 mg) in N,N-dimethylformamide (8.0 mL), 55%-sodium hydride (dispersed in liquid paraffin) (85.1 mg) was added at 0° C., and the mixture was stirred at the same temperature for 40 minutes. Then, iodomethane (180 μL) was added dropwise, and the mixture was stirred at the same temperature for 2 hours, and then further stirred at room temperature for 18 hours. Water was added to the reaction mixture, the mixture was extracted with ethyl acetate, and the organic layer obtained was dried over anhydrous sodium sulfate. After filtration, the solvent was distilled off under reduced pressure, and the residue obtained was purified by silica gel column chromatography (n-hexane/ethyl acetate) to obtain the title compound (71.0 mg) as an oil.

$^1$H-NMR (CDCl$_3$) δ: 3.34 (3H, s), 3.39 (3H, s), 3.54 (3H, s), 5.27 (1H, s), 7.23-7.30 (1H, m), 7.31-7.36 (4H, m), 7.37-7.41 (2H, m), 7.61-7.67 (2H, m).

(Step 4) 4-[Methoxy(phenyl)methyl]benzaldehyde

To a solution of the compound obtained in the above step 2 (71.0 mg) in dichloromethane (5.0 mL), a 1.02 M-diisobutylaluminum hydride/toluene solution (0.38 mL) was added dropwise at −78° C., and the mixture was stirred at the same temperature for 3 hours and a half A 1 M-aqueous sodium hydroxide solution (0.1 mL) and anhydrous sodium sulfate (excess amount) were added to the reaction mixture at −78° C., and the mixture was stirred at room temperature for 30 minutes. After insoluble materials were removed by filtration through a pad of Celite, the solvent was distilled off under reduced pressure, and the residue obtained was purified by silica gel column chromatography (n-hexane/ethyl acetate) to obtain the title compound (47.1 mg) as an oil.

$^1$H-NMR (CDCl$_3$) δ: 3.40 (3H, s), 5.30 (1H, s), 7.27-7.38 (5H, m), 7.51-7.58 (2H, m), 7.81-7.88 (2H, m), 9.98 (1H, s).

Reference Example 84

4-[Difluoro(phenyl)methyl]benzaldehyde

[Chemical Formula 138]

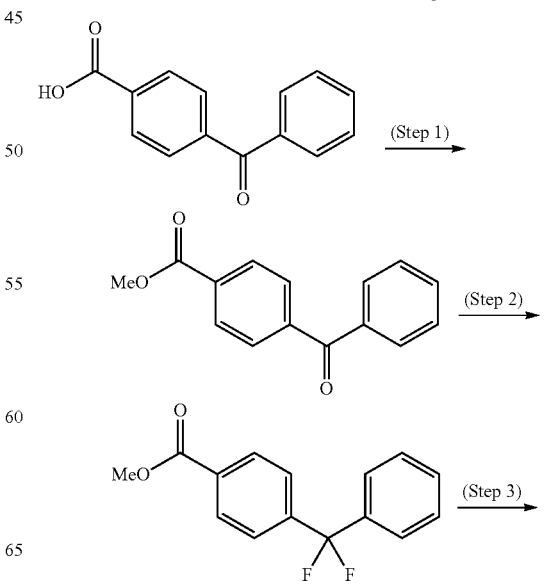

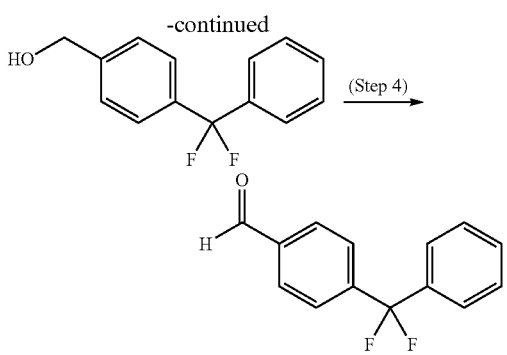

(Step 1) Methyl 4-benzoylbenzoate

To a suspension of 4-benzoylbenzoic acid (2.01 g, CAS number: 611-95-0) in methanol (10 mL), thionyl chloride (1.00 mL) was slowly added at 0° C., the mixture was stirred at the same temperature for 10 minutes, and then heated under reflux for 7 hours. The reaction mixture was cooled to room temperature, and then concentrated under reduced pressure. Dichloromethane was added to the residue, and the organic layer obtained was washed with water, and then dried over anhydrous sodium sulfate. After filtration, the solvent was distilled off under reduced pressure, and the residue obtained was purified by silica gel column chromatography (dichloromethane/ethyl acetate) to obtain the title compound (2.11 g) as a solid.

$^1$H-NMR (CDCl$_3$) δ: 3.98 (3H, s), 7.47-7.55 (2H, m), 7.58-7.68 (1H, m), 7.79-7.89 (4H, m), 8.13-8.19 (2H, m).

(Step 2) Methyl 4-[difluoro(phenyl)methyl]benzoate

To the compound obtained in the above step 1 (501 mg), bis(2-methoxyethyl)aminosulfur trifluoride (1.34 mL) was slowly added dropwise at room temperature, and the mixture was stirred at 90° C. for 24 hours. The reaction mixture was cooled to room temperature and diluted with dichloromethane, and the organic layer obtained was washed with water, and then dried over anhydrous sodium sulfate. After filtration, the solvent was distilled off under reduced pressure, and the residue obtained was purified by silica gel column chromatography (n-hexane/dichloromethane) to obtain the title compound (440 mg) as a solid.

$^1$H-NMR (CDCl$_3$) δ: 3.94 (3H, s), 7.39-7.52 (5H, m), 7.59 (2H, d, J=7.9 Hz), 8.09 (2H, d, J=7.9 Hz).

(Step 3) {4-[Difluoro(phenyl)methyl]phenyl}methanol

To a solution of the compound obtained in the above step 2 (416 mg) in tetrahydrofuran (10 mL), lithium hydridealuminum (94.9 mg) was added at 0° C., and the mixture was stirred at the same temperature for 1 hour and a half. A saturated aqueous magnesium sulfate solution (0.20 mL) was slowly added dropwise to the reaction mixture, and the mixture was stirred at the same temperature for 10 minutes, and then stirred at room temperature for 2 hours and a half. Magnesium sulfate was added to the reaction mixture, the mixture was diluted with ethyl acetate, and insoluble materials were filtered off. The solvent was distilled off under reduced pressure, and the residue obtained was purified by silica gel column chromatography (n-hexane/ethyl acetate) to obtain the title compound (340 mg) as a solid.

$^1$H-NMR (CDCl$_3$) δ: 1.73-1.85 (1H, m), 4.69-4.76 (2H, m), 7.34-7.46 (5H, m), 7.46-7.56 (4H, m).

(Step 4) 4-[Difluoro(phenyl)methyl]benzaldehyde

To a solution of the compound obtained in the above step 3 (320 mg) in dichloromethane (10 mL), manganese(IV) oxide (1.40 g) was added at room temperature, and the mixture was stirred at the same temperature for 3 days. The reaction mixture was diluted with dichloromethane, and insoluble materials were filtered off. Then, the solvent was distilled off under reduced pressure, and the residue obtained was purified by silica gel column chromatography (n-hexane/ethyl acetate) to obtain the title compound (247 mg) as a solid.

$^1$H-NMR (CDCl$_3$) δ: 7.40-7.54 (5H, m), 7.64-7.75 (2H, m), 7.90-7.98 (2H, m), 10.06 (1H, s).

Example 1

7-[5-(Cyclopropylmethyl)-4-(2-fluoro-5-phenoxy]phenyl)-6-oxo-1,4,5,6-tetrahydropyrrolo[3,4-c]pyrazol-3-yl-1,3-benzoxazol-2(3H)-one (enantiomer)

[Chemical Formula 139]

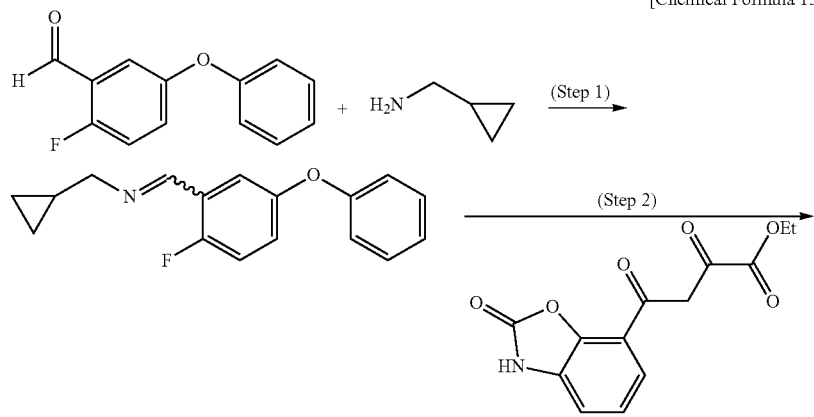

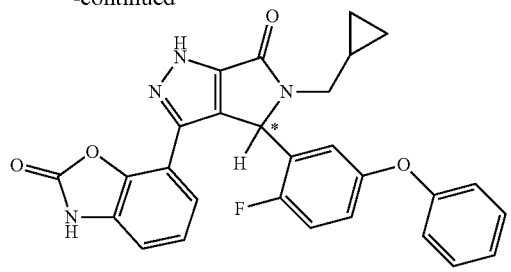

(Step 1) N-(Cyclopropylmethyl)-1-(2-fluoro-5-phenoxyphenyl)methanimine

A mixture of the compound obtained in Reference Example 76 (1.00 g), cyclopropylmethylamine (515 µL, CAS number: 2516-47-4), and ethanol (15 mL) was stirred at room temperature for 2 hours. The reaction mixture was concentrated under reduced pressure to obtain the crude title compound (1.24 g) as an oil.

$^1$H-NMR (CDCl$_3$) δ: 0.21-0.26 (2H, m), 0.51-0.57 (2H, m), 1.07-1.17 (1H, m), 3.50 (2H, d, J=6.7 Hz), 6.97 (2H, dd, J=8.5, 1.2 Hz), 7.02-7.07 (2H, m), 7.08-7.11 (1H, m), 7.32 (2H, dd, J=8.5, 7.3 Hz), 7.64-7.69 (1H, m), 8.53 (1H, s).

Step 2

7-[5-(Cyclopropylmethyl)-4-(2-fluoro-5-phenoxy]phenyl)-6-oxo-1,4,5,6-tetrahydropyrrolo[3,4-c]pyrazol-3-yl-1,3-benzoxazol-2(3H)-one (enantiomer)

A mixture of the compound obtained in the above step 1 (1.24 g), the compound obtained in step 2 of Reference Example 1 (1.00 g), and acetic acid (9.0 mL) was stirred at room temperature for 19 hours, and then the mixture was stirred at 90° C. for 15 minutes. Subsequently, the reaction mixture was cooled to room temperature, hydrazine monohydrate (524 µL) was added, and the mixture was stirred at 90° C. for 5 hours and a half. The reaction mixture was cooled to room temperature, ethyl acetate was added, the organic layer obtained was sequentially washed with water, a saturated aqueous sodium hydrogen carbonate solution, and brine, and then dried over anhydrous sodium sulfate. After filtration, the solvent was distilled off under reduced pressure, and the residue obtained was purified by silica gel column chromatography (n-hexane/ethyl acetate). The racemate obtained (1.34 g) was subjected to optical resolution [mobile phase: n-hexane/2-propanol=15/85, flow rate: 15 mL/minute, temperature: room temperature] by Daicel Corporation CHIRALPAK® IC (5 µm, 20 mmφ×250 mm), and the fraction eluted later in the main peaks was solidified with dichloromethane to obtain the title compound (410 mg).

$^1$H-NMR (DMSO-D$_6$) δ: 0.02-0.10 (1H, m), 0.18-0.25 (1H, m), 0.32-0.40 (1H, m), 0.41-0.49 (1H, m), 0.86-0.97 (1H, m), 2.72-2.80 (1H, m), 3.47-3.57 (1H, m), 6.14 (1H, s), 6.70 (2H, d, J=7.9 Hz), 6.75-6.91 (1H, m), 6.93-6.99 (1H, m), 7.00-7.25 (5H, m), 6.28 (2H, t, J=7.9 Hz), 11.65-11.88 (1H, m), 13.99-14.23 (1H, m), MS (m/z): 497 (M+H)$^+$.

Example 2

7-{4-[4-(4-Chlorophenoxy)phenyl]-5-(cyclopropylmethyl)-6-oxo-1,4,5,6-tetrahydro pyrrolo[3,4-c]pyrazol-3-yl}-1,3-benzoxazol-2(3H)-one (enantiomer)

[Chemical Formula 140]

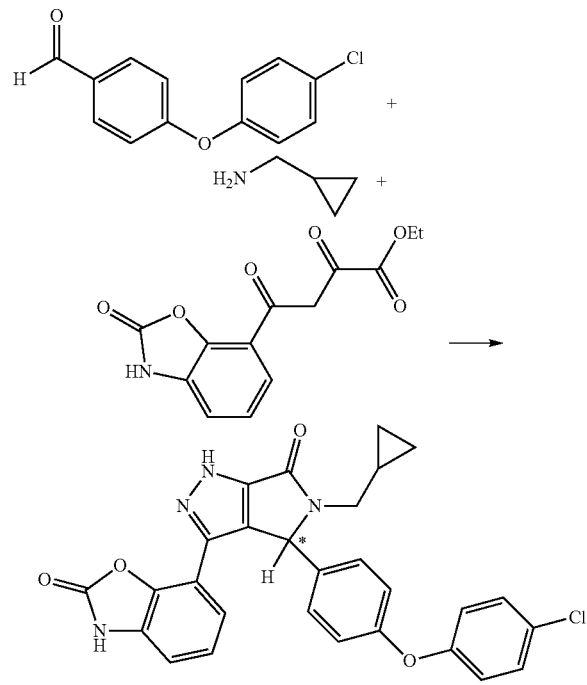

A mixture of 4-(4-chlorophenoxy)benzaldehyde (1.60 g, CAS number: 61343-99-5), the compound obtained in step 2 of Reference Example 1 (1.50 g), cyclopropylmethylamine (1.70 mL, CAS number: 2516-47-4), and acetic acid (11 mL) was stirred at room temperature for 24 hours, and then stirred at 90° C. for 1 hour. Subsequently, the reaction mixture was cooled to room temperature, hydrazine monohydrate (0.79 mL) was added, and the mixture was stirred at 90° C. for 6 hours. The reaction mixture was cooled to room temperature, and then hydrazine monohydrate (0.52 mL) was added, and the mixture was stirred at 90° C. for 8 hours. The reaction mixture was cooled to room temperature, ethyl acetate was added, and the organic layer obtained was sequentially washed with water, a saturated aqueous sodium hydrogen carbonate solution, and brine, and then dried over anhydrous sodium sulfate. After filtration, the solvent was distilled off under reduced pressure, and the residue obtained was purified by silica gel column chromatography (n-hexane/ethyl acetate) and solidified with dichloromethane to obtain a racemate (974 mg). Subsequently, the racemate obtained (60 mg) was subjected to optical resolution [mobile phase: n-hexane/tetrahydrofuran/ethanol=70/24/6, flow rate: 20 mL/minute, temperature: room temperature] by Daicel Corporation CHIRALPAK® IC (5 μm, 20 mmφ×250 mm), and the fraction eluted earlier in the main peaks was purified by silica gel column chromatography (n-hexane/ethyl acetate), and then solidified with an n-hexane-ethyl acetate mixed solution to obtain the title compound (15.8 mg).

$^1$H-NMR (DMSO-D$_6$) δ: 0.02-0.09 (1H, m), 0.17-0.25 (1H, m), 0.33-0.42 (1H, m), 0.44-0.53 (1H, m), 0.87-0.98 (1H, m), 2.52-2.59 (1H, m), 3.47-3.59 (1H, m), 5.95 (1H, s), 6.90 (2H, d, J=8.5 Hz), 6.95 (2H, d, J=9.2 Hz), 6.99-7.28 (5H, m), 7.40 (2H, d, J=8.5 Hz), 11.82 (1H, br s), 14.04 (1H, br s), MS (m/z): 513 (M+H)$^+$.

Example 3

7-[4-{3-[(5-Chloropyridin-2-yl)oxy]phenyl}-5-(cyclopropylmethyl)-6-oxo-1,4,5,6-tetrahydropyrrolo[3,4-c]pyrazol-yl]-1,3-benzoxazol-2(3H)-one Step 1

1-{3-[(5-Chloropyridin-2-yl)oxy]phenyl}-N-(cyclopropylmethyl)methanimine

To a solution of the compound obtained in step 2 of Reference Example 55 (132 mg) and cyclopropylmethylamine (97.0 μL, CAS number: 2516-47-4) in dichloromethane (5.0 mL), anhydrous magnesium sulfate (excess amount) was added at room temperature, and the mixture was stirred at the same temperature for 2 days. After insoluble materials were filtered off, the filtrate obtained was concentrated under reduced pressure to obtain the crude title compound (214 mg) as an oil.

$^1$H-NMR (CDCl$_3$) δ: 0.18-0.28 (2H, m), 0.48-0.58 (2H, m), 1.06-1.20 (1H, m), 3.49 (2H, d, J=6.1 Hz), 6.90 (1H, d, J=8.5 Hz), 7.19 (1H, dd, J=7.9, 2.4 Hz), 7.45 (1H, t, J=7.9 Hz), 7.55 (1H, d, J=2.4 Hz), 7.56 (1H, d=7.9 Hz), 7.65 (1H, dd, J=8.5, 2.4 Hz), 8.12 (1H, d, J=2.4 Hz), 8.26 (1H, s).

Step 2

7-[4-{3-[(5-Chloropyridin-2-yl)oxy]phenyl}-5-(cyclopropylmethyl)-6-oxo-1,4,5,6-tetrahydro pyrrolo [3,4-c]pyrazol-yl]-1,3-benzoxazol-2(3H)-one A mixture of the compound obtained in the above step 1 (214 mg), the compound obtained in step 2 of Reference Example 1 (100 mg), and 1,4-dioxane (4.0 mL) was stirred at room temperature for 15 hours. Subsequently, the reaction mixture was concentrated under reduced pressure, acetic acid (2.0 mL) and hydrazine monohydrate (70.0 μL) were sequentially added to the residue obtained, and the mixture was stirred at 100° C. for 2 hours. The reaction mixture was cooled to room temperature, and then concentrated under reduced pressure, chloroform was added to the residue, and

[Chemical Formula 141]

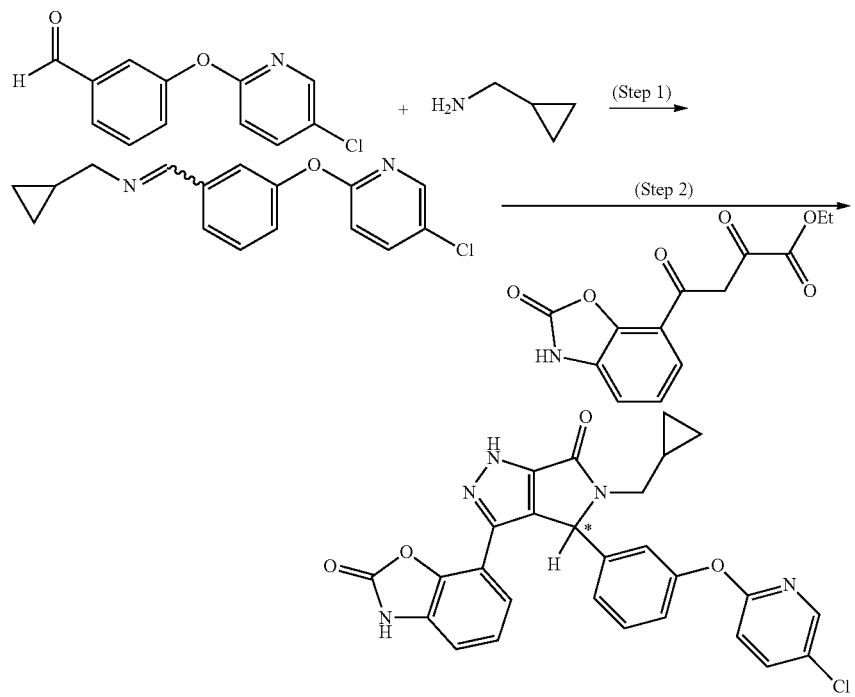

the organic layer obtained was washed with a saturated aqueous sodium hydrogen carbonate solution, and then dried over anhydrous sodium sulfate. After filtration, the solvent was distilled off under reduced pressure, and the residue obtained was purified by silica gel column chromatography (chloroform/ethyl acetate) to obtain the title compound (120 mg) as a solid.

$^1$H-NMR (DMSO-D$_6$) δ: 0.02-0.11 (1H, m), 0.16-0.25 (1H, m), 0.33-0.42 (1H, m), 0.43-0.51 (1H, m), 0.83-0.96 (1H, m), 2.49-2.57 (1H, m), 3.54-3.66 (1H, m), 5.97 (1H, s), 6.91-7.21 (6H, m), 7.22-7.36 (2H, m), 7.93 (1H, dd, J=8.8, 2.4 Hz), 8.06 (1H, d, J=2.4 Hz), 11.62-11.88 (1H, m), 14.00-14.27 (1H, m), MS (m/z): 514 (M+H)⁺.

Example 4

7-[5-(Cyclopropylmethyl)-6-oxo-4-(6-phenoxypyridin-3-yl)-1,4,5,6-tetrahydropyrrolo[3,4-c]pyrazol-3-yl]-1,3-benzoxazol-2(3H)-one

[Chemical Formula 142]

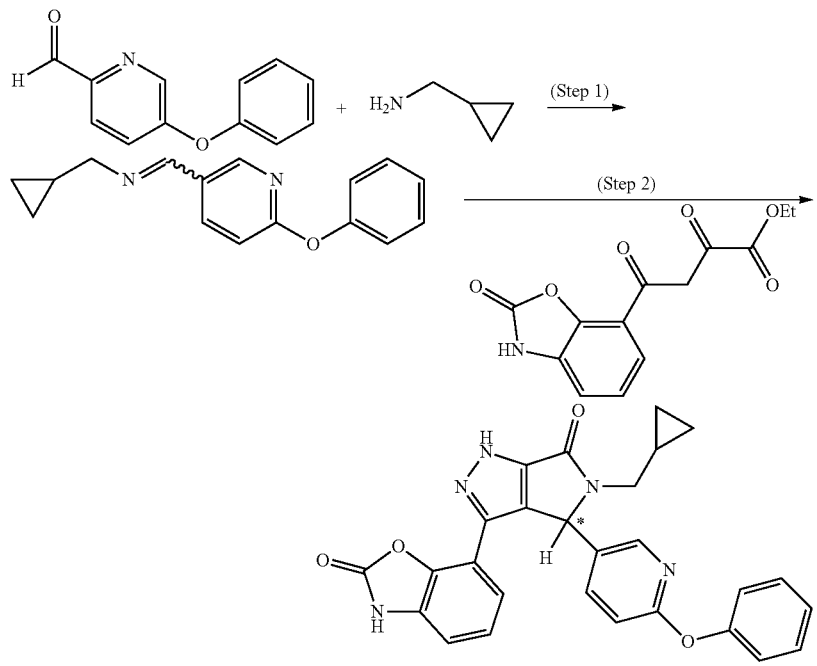

The compound obtained in Reference Example 30 (64.0 mg), cyclopropylmethylamine (55.0 μL, CAS number: 2516-47-4) and the compound obtained in step 2 of Reference Example 1 (86.0 mg) were used as manufacturing raw materials, and the same procedure as that in step 1 and step 2 of Example 3 was performed to obtain the title compound (79.0 mg) as a solid.

¹H-NMR (DMSO-D₆) δ: 0.00-0.08 (1H, m), 0.15-0.25 (1H, m), 0.31-0.53 (2H, m), 0.87-0.96 (1H, m), 2.58-2.68 (1H, m), 3.45-3.59 (1H, m), 6.00 (1H, s), 6.86 (1H, d, J=8.5 Hz), 6.97-7.48 (9H, m), 8.16 (1H, s), 11.66-11.94 (1H, m), 14.01-14.30 (1H, m), MS (m/z): 480 (M+H)⁺.

Example 5

7-[5-(Cyclopropylmethyl)-4-(2'-fluoro[1,1'-biphenyl]-4-yl)-6-oxo-1,4,5,6-tetrahydro pyrrolo[3,4-c]pyrazol-3-yl]-1,3-benzoxazol-2(3H)-one

[Chemical Formula 143]

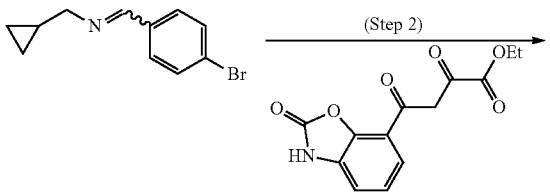

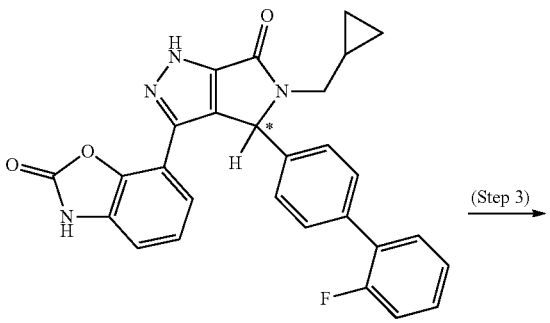

-continued

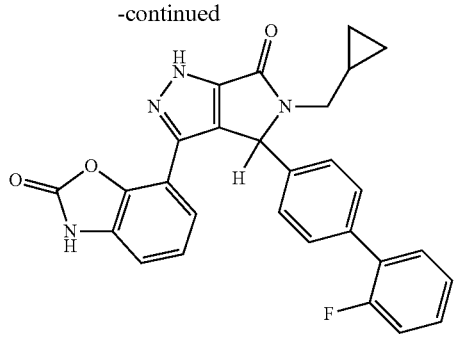

(Step 1)

1-(4-Bromophenyl)-N-(cyclopropylmethyl)methanimine

4-Bromobenzaldehyde (1.43 g, CAS number: 1122-91-4) and cyclopropylmethylamine (730 μL, CAS number: 2516-47-4) were used as manufacturing raw materials, and the same procedure as that in step 1 of Example 3 was performed to obtain the crude title compound (1.85 g) as an oil.

$^1$H-NMR (CDCl$_3$) δ: 0.21-0.29 (2H, m), 0.51-0.60 (2H, m), 1.07-1.21 (1H, m), 3.48 (2H, d, J=6.7 Hz), 7.49-7.65 (4H, m), 8.22 (1H, s).

Step 2

7-[4-(4-Bromophenyl)-5-(cyclopropylmethyl)-6-oxo-1,4,5,6-tetrahydropyrrolo[3,4-c]pyrazol-3-yl]-1,3-benzoxazol-2(3H)-one A mixture of the compound obtained in the above step 1 (1.85 g), the compound obtained in step 2 of Reference Example 1 (1.50 g), and 1,4-dioxane (15 mL) was stirred at 80° C. for 4 hours. The reaction mixture was cooled to room temperature, and then concentrated under reduced pressure, and the residue obtained was purified by silica gel column chromatography (chloroform/methanol). Subsequently, to a solution of the obtained intermediate in acetic acid (10 mL), hydrazine monohydrate (500 μL) was added at room temperature, and the mixture was stirred at 80° C. for 4 hours. The reaction mixture was cooled to room temperature and concentrated under reduced pressure, a chloroform-methanol (9:1) mixed solution was added to the residue, and the organic layer obtained was washed with a saturated aqueous sodium hydrogen carbonate solution, and then dried over anhydrous sodium sulfate. After filtration, the solvent was distilled off under reduced pressure, and the residue obtained was purified by silica gel column chromatography (chloroform/methanol), and then solidified with an n-hexane-ethyl acetate mixed solution to obtain the title compound (1.52 g).

$^1$H-NMR (DMSO-D$_6$) δ: −0.01-0.09 (1H, m), 0.14-0.24 (1H, m), 0.31-0.53 (2H, m), 0.81-0.95 (1H, m), 2.41-2.52 (1H, m), 3.49-3.64 (1H, m), 5.97 (1H, s), 6.95-7.35 (5H, m), 7.46 (2H, d, J=8.5 Hz), 11.84 (1H, br s), 14.09 (1H, br s), MS (m/z): 465 (M+H)$^+$.

Step 3

7-[5-(Cyclopropylmethyl)-4-(2'-fluoro[1,1'-biphenyl]-4-yl)-6-oxo-1,4,5,6-tetrahydropyrrolo[3,4-c]pyrazol-3-yl]-1,3-benzoxazol-2(3H)-one A mixture of the compound obtained in the above step 2 (70.0 mg), 2-fluorophenyl boronic acid (32.0 mg), tetrakis(triphenylphosphine)palladium(0) (17.0 mg), sodium carbonate (46.0 mg), water (0.50 mL), and 1,4-dioxane (3.0 mL) was stirred at 90° C. for 6 hours. The reaction mixture was cooled to room temperature, water was added, the mixture was extracted with chloroform, and the organic layer obtained was dried over anhydrous sodium sulfate. After filtration, the solvent was distilled off under reduced pressure, and a mixture of the residue obtained and 2-fluorophenyl boronic acid (32.0 mg), tetrakis(triphenylphosphine)palladium(0) (17.0 mg), sodium carbonate (46.0 mg), water (0.50 mL), and 1,4-dioxane (3.0 mL) was stirred at 90° C. for 2 hours. The reaction mixture was cooled to room temperature, water was added, the mixture was extracted with chloroform, and the organic layer obtained was dried over anhydrous sodium sulfate. After filtration, the solvent was distilled off under reduced pressure, the residue obtained was subjected to silica gel column chromatography (ethyl acetate/methanol and chloroform/methanol), and further purified by preparative thin-layer chromatography (chloroform/methanol), and solidified with n-hexane-dichloromethane to obtain the title compound (9.0 mg).

$^1$H-NMR (CDCl$_3$) δ: 0.11-0.66 (4H, m), 0.96-1.08 (1H, m), 2.58-2.68 (1H, m), 3.75-3.87 (1H, m), 5.93 (1H, s), 6.97-7.45 (9H, m), 7.51 (2H, d, J=7.3 Hz), MS (m/z): 481 (M+H)$^+$.

Example 6

7-{4-[3-(Cyclobutyloxy)phenyl]-5-(cyclopropylmethyl)-6-oxo-1,4,5,6-tetrahydropyrrolo[3,4-c]pyrazol-3-yl}-1,3-benzoxazol-2(3H)-one

[Chemical Formula 144]

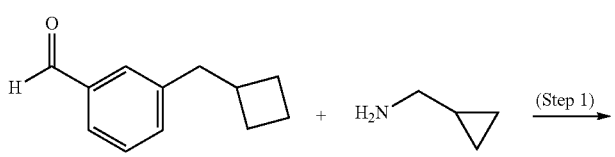

(Step 1)

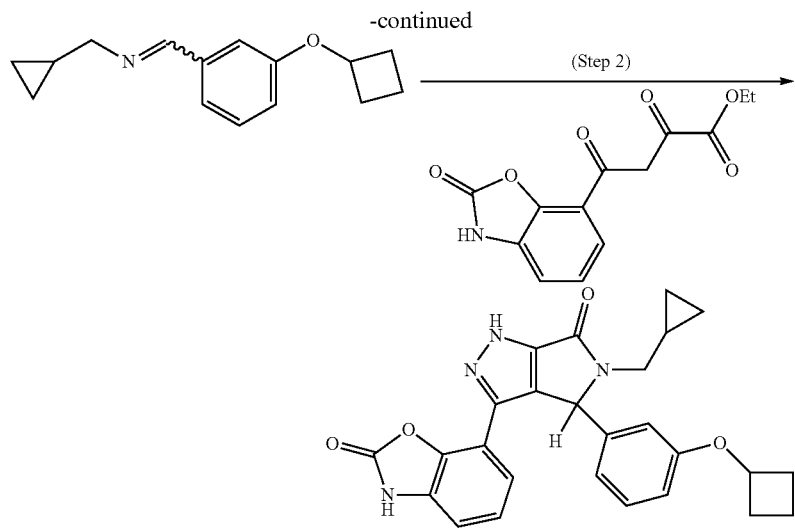

(Step 1) 1-[3-(Cyclobutyloxy)phenyl]-N-(cyclopropylmethyl)methanimine

To a solution of the compound obtained in Reference Example 8 (71 mg) in ethanol (1.3 mL), cyclopropylmethylamine (69 μL, CAS number: 2516-47-4) was added at room temperature, and the mixture was stirred at the same temperature for 2 days. The reaction mixture was concentrated under reduced pressure to obtain the crude title compound (93 mg) as an oil.

Step 2

7-{4-[3-(Cyclobutyloxy)phenyl]-5-(cyclopropylmethyl)-6-oxo-1,4,5,6-tetrahydropyrrolo[3,4-c]pyrazol-3-yl}-1,3-benzoxazol-2(3H)-one A mixture of the compound obtained in the above step 1 (91 mg), the compound obtained in step 2 of Reference Example 1 (83 mg), and 1,4-dioxane (3 mL) was stirred at room temperature for 22 hours. Subsequently, the reaction mixture was concentrated under reduced pressure, acetic acid (3 mL) and hydrazine monohydrate (58 μL) were sequentially added to the residue obtained, and the mixture was stirred at 90° C. for 3 hours and a half. The reaction mixture was cooled to room temperature, and then concentrated under reduced pressure, a saturated aqueous sodium hydrogen carbonate solution was added to the residue, the mixture was extracted with chloroform, and the organic layer obtained was dried over anhydrous sodium sulfate. After filtration, the solvent was distilled off under reduced pressure, and the residue obtained was purified by silica gel column chromatography (dichloromethane/methanol) to obtain the title compound (62 mg) as a solid.

$^1$H-NMR (DMSO-D$_6$) δ: 0.02-0.09 (1H, m), 0.15-0.22 (1H, m), 0.33-0.41 (1H, m), 0.44-0.53 (1H, m), 0.83-0.96 (1H, m), 1.53-1.66 (1H, m), 1.68-1.79 (1H, m), 1.86-1.98 (2H, m), 2.26-2.37 (2H, m), 2.41-2.48 (1H, m), 3.51-3.65 (1H, m), 4.50-4.60 (1H, m), 5.91 (1H, s), 6.58-6.72 (3H, m), 6.96-7.31 (4H, m), 11.86 (1H, s), 14.02 (1H, s), MS (m/z): 457 (M+H)$^+$.

Example 7

7-[5-(Cyclopropylmethyl)-4-{3-[(4,4-difluorocyclohexyl)oxy]phenyl}-6-oxo-1,4,5,6-tetrahydropyrrolo[3,4-c]pyrazol-3-yl]-1,3-benzoxazol-2(3H)-one

[Chemical Formula 145]

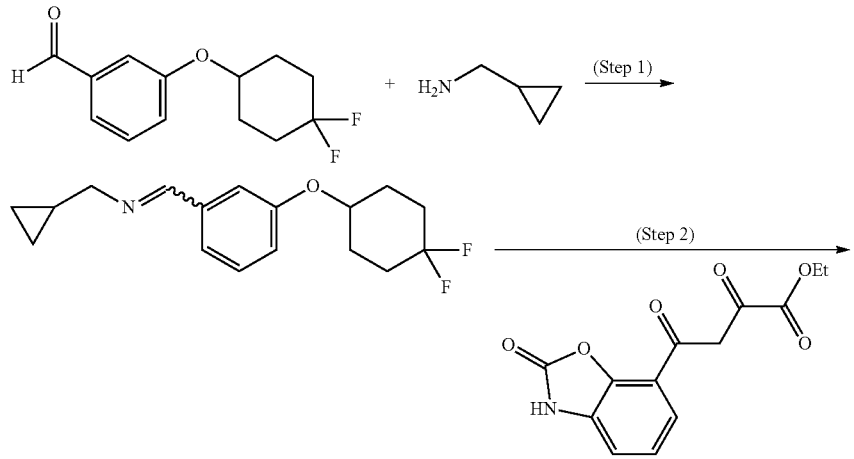

-continued

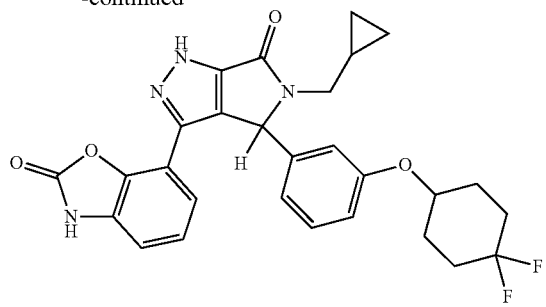

The compound obtained in Reference Example 9 (108 mg), cyclopropylmethylamine (116 μL, CAS number: 2516-47-4), and the compound obtained in step 2 of Reference Example 1 (80 mg) were used as manufacturing raw materials, and the same procedure as that in step 1 and step 2 of Example 6 was performed to obtain the title compound (85.7 mg) as a solid.

$^1$H-NMR (CDCl$_3$) δ: 0.13-0.20 (1H, m), 0.25-0.33 (1H, m), 0.42-0.50 (1H, m), 0.53-0.61 (1H, m), 0.95-1.06 (1H, m), 1.76-2.17 (8H, m), 2.57-2.66 (1H, m), 3.75-3.83 (1H, m), 4.42-4.44 (1H, m), 5.84 (1H, s), 6.76 (1H, s), 6.80-6.85 (1H, m), 6.90-6.94 (1H, m), 7.01-7.27 (4H, m), 11.98 (1H, s), MS (m/z): 521 (M+H)$^+$.

Example 8

7-[4-(4-Fluorophenyl)-6-oxo-5-(2,2,2-trifluoroethyl)-1,4,5,6-tetrahydropyrrolo[3,4-c]pyrazol-3-yl]-1,3-benzoxazol-2(3H)-one (enantiomer)

[Chemical Formula 146]

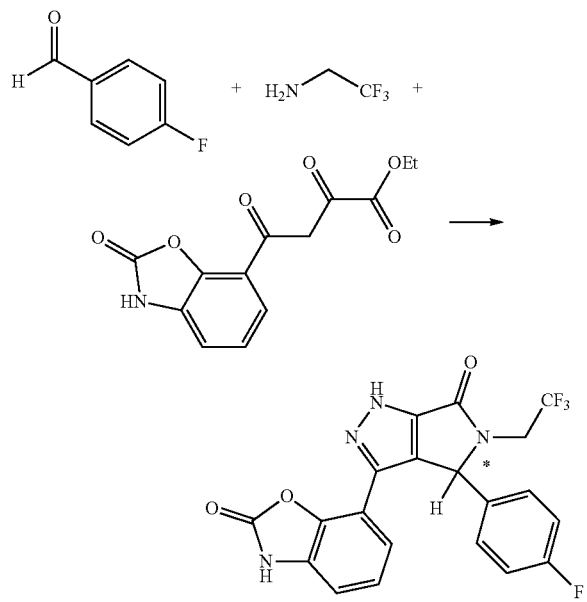

To a solution of 4-fluorobenzaldehyde (0.29 mL, CAS number: 459-57-4) and 2,2,2-trifluoroethylamine (0.22 mL, CAS number: 753-90-2) in dichloromethane (8.0 mL), anhydrous magnesium sulfate (excess amount) was added at room temperature, and the mixture was stirred at the same temperature for 1 day. Insoluble materials were filtered off, the filtrate obtained was diluted with dichloromethane, and then washed with water, and dried over anhydrous magnesium sulfate. After filtration, the solvent was distilled off under reduced pressure, a mixture of the oil obtained, the compound obtained in step 2 of Reference Example 1 (512 mg) and acetic acid (7.0 mL) was stirred at room temperature for 40 hours, and then stirred at 80° C. for 6 hours and a half. Subsequently, the reaction mixture was cooled to room temperature, hydrazine monohydrate (255 μL) was added, and the mixture was stirred at 100° C. for 13 hours. The reaction mixture was cooled to room temperature, and then concentrated under reduced pressure, a chloroform-methanol (9:1) mixed solution was added to the residue, and the organic layer obtained was washed with water and dried over magnesium sulfate. After filtration, the solvent was distilled off under reduced pressure, and the residue obtained was sequentially purified by silica gel column chromatography (dichloromethane/methanol) and reverse phase HPLC to obtain a racemate (299 mg) as a solid. Subsequently, the racemate obtained (50.0 mg) was subjected to optical resolution [mobile phase: n-hexane/tetrahydrofuran/ethanol=75/20/5, flow rate: 20 mL/minute, temperature: 35° C.] by Daicel Corporation CHIRALPAK® IC (5 μm, 20 mmφ×250 mm), and the fraction eluted earlier in the main peaks was purified by silica gel column chromatography (ethyl acetate/n-hexane) and solidified with an n-hexane-ethyl acetate mixed solution to obtain the title compound (13 mg).

$^1$H-NMR (DMSO-D$_6$) δ: 3.38-3.46 (1H, m), 4.43-4.55 (1H, m), 5.98 (1H, s), 6.92-7.40 (7H, m), 11.69-11.91 (1H, m), 14.30-14.48 (1H, m), MS (m/z): 433 (M+H)$^+$.

Example 9

7-[4-{2-Fluoro-5-[(oxan-4-yl)oxy]phenyl}-6-oxo-5-(2,2,2-trifluoroethyl)-1,4,5,6-tetrahydropyrrolo[3,4-c]pyrazol-3-yl]-1,3-benzoxazol-2(3H)-one

[Chemical Formula 147]

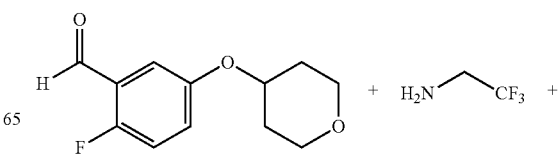

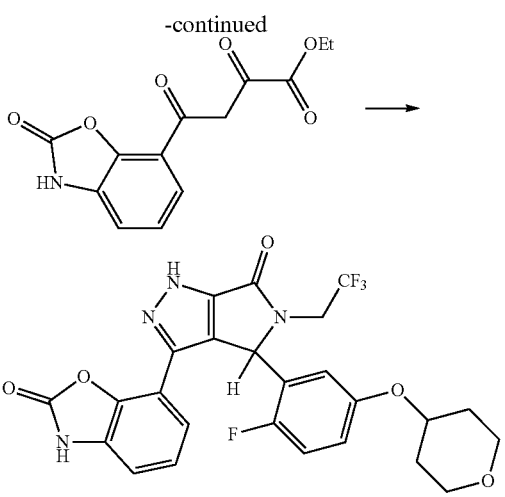

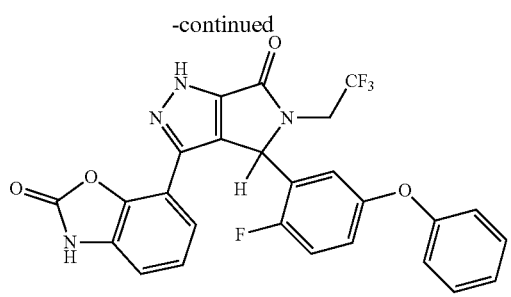

A mixture of the compound obtained in Reference Example 14 (74.0 mg), 2,2,2-trifluoroethylamine (29.0 µL, CAS number: 753-90-2), the compound obtained in step 2 of Reference Example 1 (70.0 mg), and acetic acid (2.0 mL) was stirred at 90° C. for 19 hours. Subsequently, the reaction mixture was cooled to room temperature, hydrazine monohydrate (37.0 µL) was added, and the mixture was stirred at 90° C. for 6 hours. The reaction mixture was cooled to room temperature, water was added, and the mixture was extracted with ethyl acetate. The organic layer obtained was washed with brine, and then dried over anhydrous sodium sulfate. After filtration, the solvent was distilled off under reduced pressure, and the residue obtained was sequentially purified by silica gel column chromatography (n-hexane/ethyl acetate) and reverse phase HPLC to obtain the title compound (64.3 mg) as a solid.

$^1$H-NMR (DMSO-D$_6$) δ: 1.35-1.47 (2H, m), 1.67-1.80 (2H, m), 3.37-3.45 (2H, m), 3.58-3.64 (1H, m), 3.74-3.79 (2H, m), 4.35-4.54 (2H, m), 6.10 (1H, s), 6.74-6.86 (1H, m), 6.89-6.92 (1H, m), 6.99-7.05 (2H, m), 7.14 (1H, t, J=7.9 Hz), 7.28 (1H, d, J=7.9 Hz), 11.83 (1H, br s), 14.32 (1H, br s), MS (ESI) m/z: 533 (M+H)$^+$.

Example 10

7-[4-(2-Fluoro-5-phenoxy]phenyl)-6-oxo-5-(2,2,2-trifluoroethyl)-1,4,5,6-tetrahydropyrrolo[3,4-c]pyrazol-3-yl-1,3-benzoxazol-2(3H)-one

[Chemical Formula 148]

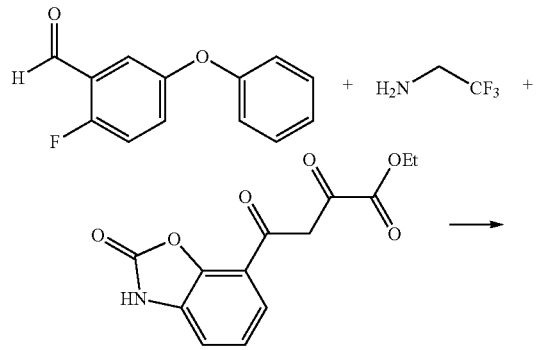

The compound obtained in Reference Example 76 (82.0 mg), 2,2,2-trifluoroethylamine (32.7 µL, CAS number: 753-90-2), and the compound obtained in step 2 of Reference Example 1 (70.0 mg) were used as manufacturing raw materials, and the same procedure as that in Example 9 was performed to obtain the title compound (45.8 mg) as a solid.

$^1$H-NMR (DMSO-D$_6$) δ: 3.68-3.80 (1H, in), 4.39-4.53 (1H, in), 6.17 (1H, s), 6.67-6.73 (2H, in), 6.81-6.92 (1H, in), 6.94-7.01 (1H, in), 7.05-7.13 (2H, in), 7.14-7.22 (2H, in), 7.23-7.33 (3H, in), 8.62 (1H, br s), 14.29 (1H, br s), MS (m/z): 525 (M+H)$^+$.

Example 11

7-[5-(2,2-Difluorobutyl)-4-(4-fluorophenyl)-6-oxo-1,4,5,6-tetrahydropyrrolo[3,4-c]pyrazol-3-yl]-1,3-benzoxazol-2(3H)-one

[Chemical Formula 149]

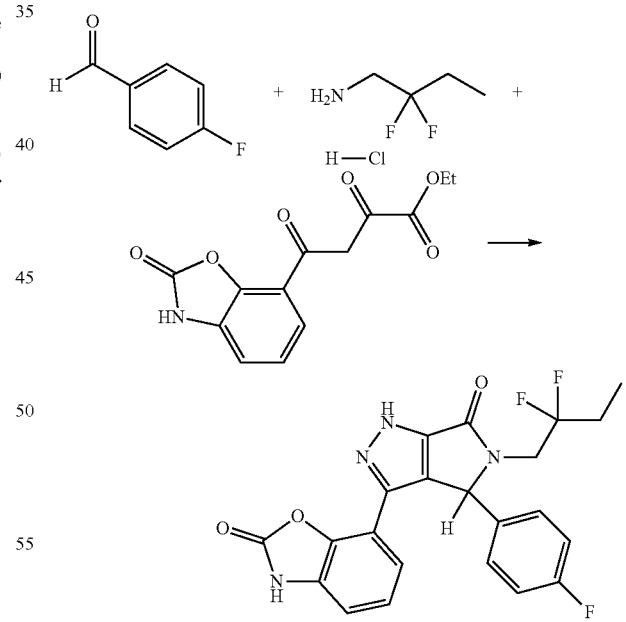

A mixture of 4-fluorobenzaldehyde (44 µL, CAS number: 459-57-4), 2,2-difluorobutane-1-amine hydrochloride (61 mg, CAS number: 1384428-33-4), the compound obtained in step 2 of Reference Example 1 (83 mg), triethylamine (233 µL), and acetic acid (3 mL) was stirred at 100° C. for 9 hours. Subsequently, the reaction mixture was cooled to room temperature, hydrazine monohydrate (58 µL) was added, and the mixture was stirred at 100° C. for 3 hours.

The reaction mixture was cooled to room temperature and then concentrated under reduced pressure, and a saturated aqueous sodium hydrogen carbonate solution was added to the residue. The mixture was extracted with dichloromethane, and the organic layer obtained was dried over anhydrous sodium sulfate. After filtration, the solvent was distilled off under reduced pressure, and the residue obtained was sequentially purified by silica gel column chromatography (dichloromethane/methanol) and reverse phase HPLC to obtain the title compound (25 mg) as a solid.

$^1$H-NMR (DMSO-D$_6$) δ: 0.97 (3H, t, J=7.3 Hz), 1.83-2.00 (2H, m), 2.70-2.83 (1H, m), 4.10-4.29 (1H, m), 5.99 (1H, s), 7.00-7.35 (7H, m), 11.82 (1H, s), 14.28 (1H, s), MS (m/z): 443 (M+H)$^+$.

Example 12

7-{5-[(1,3-Oxazol-2-yl)methyl]-6-oxo-4-(3-phenoxyphenyl)-1,4,5,6-tetrahydropyrrolo[3,4-c]pyrazol-3-yl}-1,3-benzoxazol-2(3H)-one

[Chemical Formula 150]

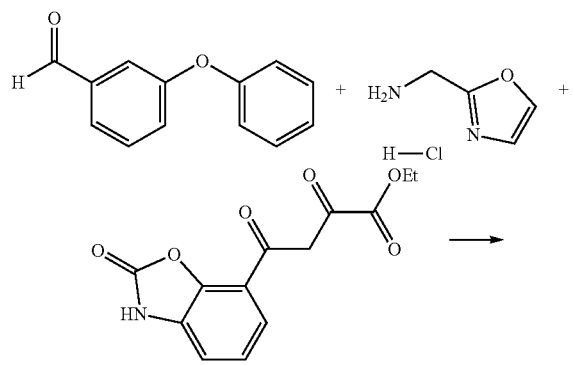

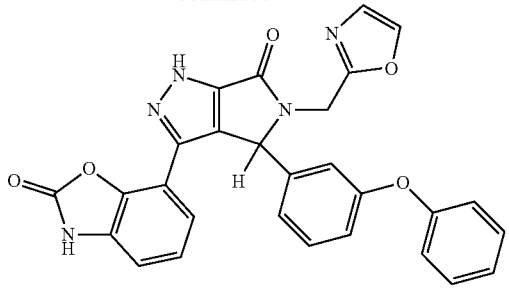

A mixture of 3-phenoxybenzaldehyde (88.0 μL, CAS number: 39515-51-0), 1-(1,3-oxazol-2-yl)methanamine hydrochloride (70.5 mg, CAS number: 1041053-44-4), and acetic acid (3.0 mL) was stirred at 100° C. for 2 hours and a half, and then cooled to room temperature. The compound obtained in step 2 of Reference Example 1 (103 mg) was added, and the mixture was further stirred at 100° C. for 37 hours. Subsequently, the reaction mixture was cooled to room temperature, hydrazine monohydrate (100 μL) was added, and the mixture was stirred at 100° C. for 9 hours. The reaction mixture was cooled to room temperature, and then concentrated under reduced pressure, a chloroform-methanol (9:1) mixed solution was added to the residue, and the organic layer obtained was washed with water, and then dried over magnesium sulfate. After filtration, the solvent was distilled off under reduced pressure, and the residue obtained was sequentially purified by silica gel column chromatography (dichloromethane/methanol) and reverse phase HPLC to obtain the title compound (24.6 mg) as a solid.

$^1$H-NMR (DMSO-D$_6$) δ: 4.03-4.18 (1H, m), 5.16-5.31 (1H, m), 5.80 (1H, s), 6.79-7.09 (10H, m), 7.11 (1H, s), 7.24-7.26 (2H, m), 7.63 (1H, s), 10.32 (1H, br s), 12.55 (1H, br s), MS (m/z): 506 (M+H)$^+$.

Example 13

7-{4-(2-Fluoro-5-phenoxyphenyl)-6-oxo-5-[(pyridin-2-yl)methyl]-1,4,5,6-tetrahydro pyrrolo[3,4-c]pyrazol-3-yl}-1,3-benzoxazol-2(3H)-one

[Chemical Formula 151]

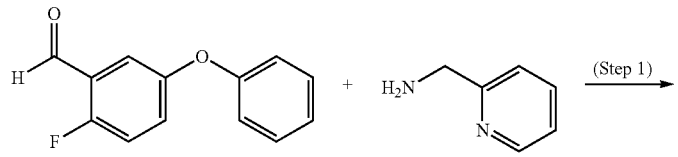

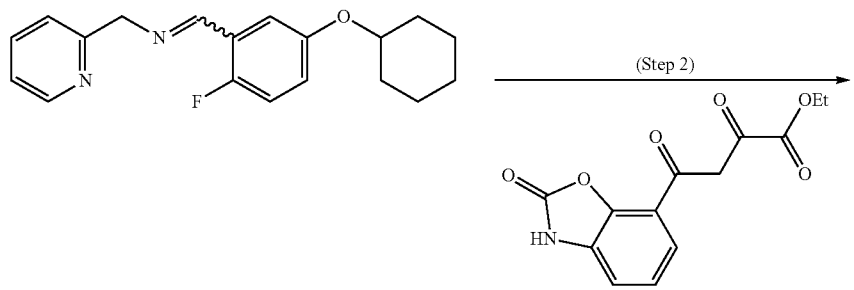

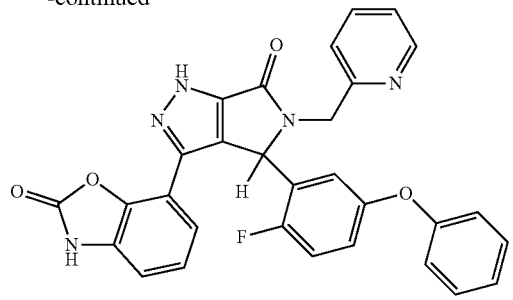

(Step 1) 1-(2-Fluoro-5-phenoxyphenyl)-N-[(pyridin-2-yl)methyl]methanimine

A mixture of the compound obtained in Reference Example 76 (181 mg), 2-(aminomethyl)pyridine (85.0 µL, CAS number: 3731-51-9), and ethanol (5.0 mL) was stirred at room temperature for 3 hours. The reaction mixture was concentrated under reduced pressure to obtain the crude title compound as an oil.

$^1$H-NMR (CDCl$_3$) δ: 4.96 (2H, s), 6.93-7.00 (2H, m), 7.05-7.12 (3H, m), 7.15-7.21 (1H, m), 7.29-7.35 (2H, m), 7.37-7.41 (1H, m), 7.64-7.70 (1H, m), 7.72-7.76 (1H, m), 8.55-8.60 (1H, m), 8.74 (1H, s).

Step 2

7-{4-(2-Fluoro-5-phenoxyphenyl)-6-oxo-5-[(pyridin-2-yl)methyl]-1,4,5,6-tetrahydropyrrolo[3,4-c]pyrazol-3-yl}-1,3-benzoxazol-2(3H)-one The compound obtained in the above step 1 and the compound obtained in step 2 of Reference Example 1 (188 mg) were used as manufacturing raw materials, and the same procedure as that in step 2 of Example 6 was performed to obtain the title compound (79.0 mg) as a solid.

$^1$H-NMR (DMSO-D$_6$) δ: 4.22 (1H, d, J=16.4 Hz), 4.94 (1H, d, J=16.4 Hz), 6.07 (1H, s), 6.60-6.68 (2H, m), 6.68-6.76 (1H, m), 6.86-6.92 (1H, m), 7.00-7.11 (3H, m), 7.12-7.21 (1H, m), 7.21-7.33 (5H, m), 7.68-7.78 (1H, m), 8.42-8.50 (1H, m), 11.73 (1H, br s), 14.17 (1H, br s), MS (m/z): 534 (M+H)$^+$.

Example 14

N-{3-[4-(2-Fluoro-5-phenoxy]phenyl)-6-oxo-5-(2,2,2-trifluoroethyl)-1,4,5,6-tetrahydropyrrolo[3,4-c]pyrazol-3-ylphenyl}acetamide

[Chemical Formula 152]

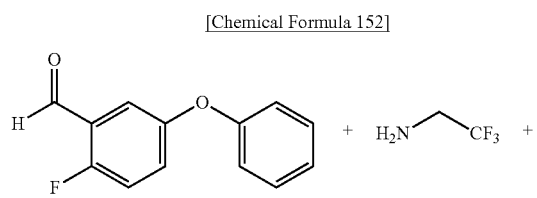

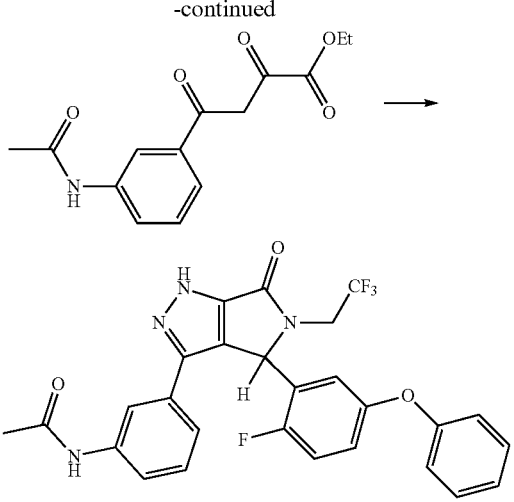

The compound obtained in Reference Example 76 (76.0 mg), 2,2,2-trifluoroethylamine (30.6 µL, CAS number: 753-90-2), and the compound obtained in Reference Example 5 (70.0 mg) were used as manufacturing raw materials, and the same procedure as that in Example 9 was performed to obtain the title compound (53.6 mg) as a solid.

$^1$H-NMR (CDCl$_3$) δ: 2.19 (3H, s), 3.26-3.38 (1H, m), 4.49-4.62 (1H, m), 6.10 (1H, s), 6.64-6.81 (3H, m), 6.83-6.89 (1H, m), 6.90-6.95 (1H, m), 7.01-7.11 (2H, m), 7.18-7.28 (3H, m), 7.78-7.82 (1H, m), 7.89 (1H, s), 8.72 (1H, br s), 13.71 (1H, br s), MS m/z: 525 (M+H)$^+$.

Example 15

7-[4-(4-Fluorophenyl)-6-oxo-5-(2,2,2-trifluoroethyl)-1,4,5,6-tetrahydropyrrolo[3,4-c]pyrazol-3-yl]-5-phenoxy-1,3-benzoxazol-2(3H)-one

[Chemical Formula 153]

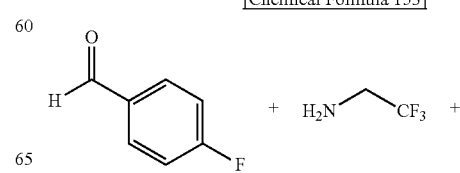

-continued

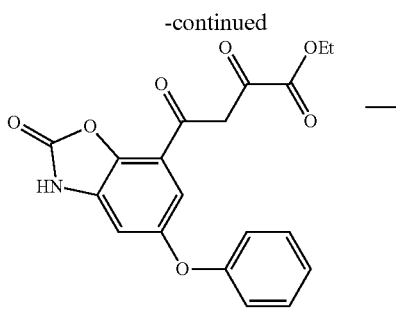

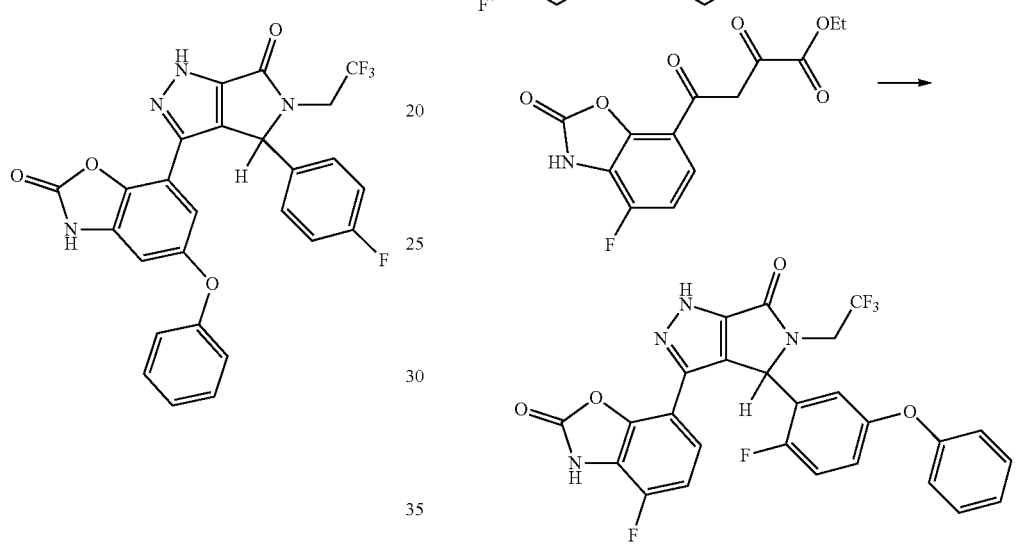

To a solution of 4-fluorobenzaldehyde (40.0 μL, CAS number: 459-57-4) and 2,2,2-trifluoroethylamine (30.0 μL, CAS number: 753-90-2) in dichloromethane (5.0 mL), anhydrous magnesium sulfate (excess amount) was added at room temperature, and the mixture was stirred at the same temperature for 1 day. Insoluble materials were filtered off, dichloromethane was added to the filtrate, and the organic phase obtained was washed with water, and then dried over anhydrous magnesium sulfate. After filtration, the solvent was distilled off under reduced pressure, and a mixture of the residue obtained, the compound obtained in step 5 of Reference Example 4 (50.4 mg), and acetic acid (4.0 mL) was stirred at 100° C. for 24 hours. Subsequently, the reaction mixture was cooled to room temperature, hydrazine monohydrate (35.0 μL) was added, and the mixture was stirred at 100° C. for 6 hours and a half. The reaction mixture was cooled to room temperature, and then concentrated under reduced pressure. A chloroform-methanol (9:1) mixed solution was added to the residue, and the organic layer obtained was washed with water, and then dried over magnesium sulfate. After filtration, the solvent was distilled off under reduced pressure, the residue obtained was sequentially purified by silica gel column chromatography (dichloromethane/methanol) and reverse phase HPLC to obtain the title compound (22.3 mg) as a solid.

$^1$H-NMR (DMSO-D$_6$) δ: 2.92-3.07 (1H, m), 4.44-4.60 (1H, m), 5.72 (1H, s), 6.52-6.61 (1H, m), 6.77-6.93 (5H, m), 6.96-7.04 (2H, m), 7.10-7.20 (1H, m), 7.28-7.39 (2H, m), 9.80 (1H, br s), MS (m/z): 525 (M+H)$^+$.

Example 16

4-Fluoro-7-[4-(2-fluoro-5-phenoxy]phenyl)-6-oxo-5-(2,2,2-trifluoroethyl)-1,4,5,6-tetrahydropyrrolo[3,4-c]pyrazol-3-yl-1,3-benzoxazol-2(3H)-one

[Chemical Formula 154]

The compound obtained in Reference Example 76 (93.1 mg), 2,2,2-trifluoroethylamine (34.0 μL, CAS number: 753-90-2), and the compound obtained in step 4 of Reference Example 3 (45.7 mg) were used as manufacturing raw materials, and the same procedure as that in Example 15 was carried out to obtain the title compound (52.0 mg) as a solid.

$^1$H-NMR (DMSO-D$_6$) δ: 3.23-3.37 (1H, m), 4.52-4.68 (1H, m), 6.21 (1H, s), 6.67-6.75 (1H, m), 6.75-6.81 (2H, m), 6.89-6.97 (2H, m), 7.02-7.14 (3H, m), 7.20-7.25 (2H, m), 9.19 (1H, s), 12.02 (1H, br s), MS (m/z): 543 (M+H)$^+$.

Example 17

7-[4-(4-Chloro-3-ethylphenyl)-5-(2,2-difluoropropyl)-6-oxo-1,4,5,6-tetrahydropyrrolo[3,4-c]pyrazol-3-yl]-1,3-benzoxazol-2(3H)-one (enantiomer)

[Chemical Formula 155]

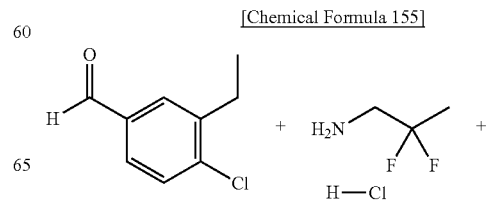

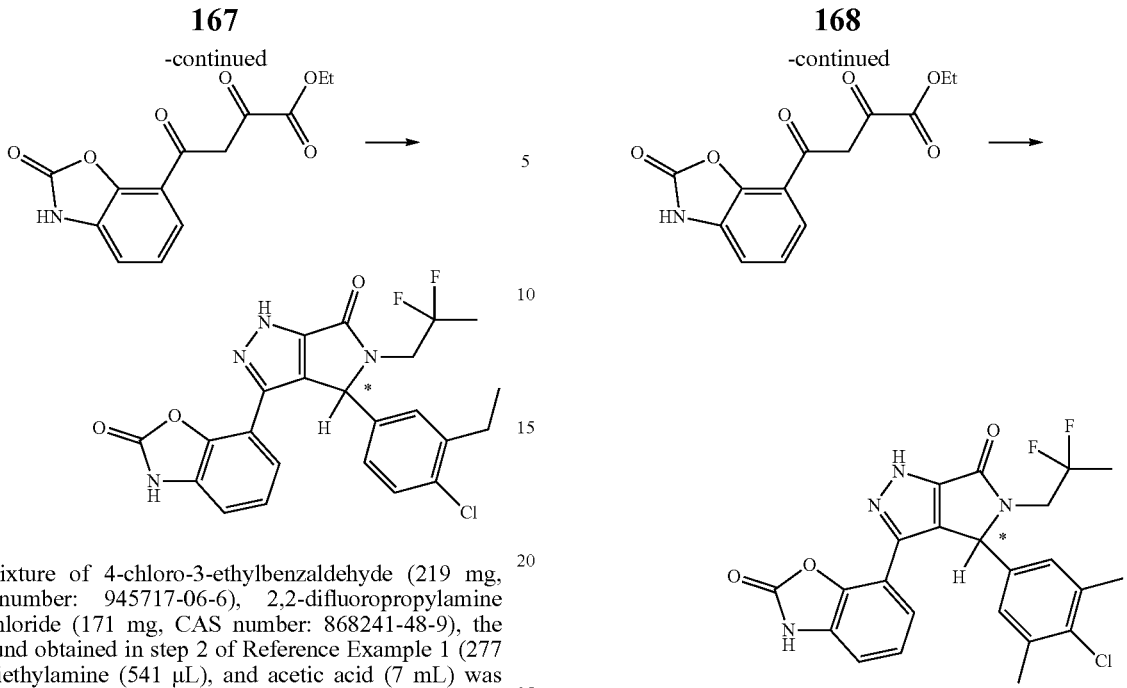

A mixture of 4-chloro-3-ethylbenzaldehyde (219 mg, CAS number: 945717-06-6), 2,2-difluoropropylamine hydrochloride (171 mg, CAS number: 868241-48-9), the compound obtained in step 2 of Reference Example 1 (277 mg), triethylamine (541 μL), and acetic acid (7 mL) was stirred at 50° C. for 30 minutes, and then stirred at 90° C. for 8 hours. Subsequently, the reaction mixture was cooled to room temperature, hydrazine monohydrate (146 μL) was added, and the mixture was stirred at 100° C. for 4 hours. The reaction mixture was cooled to room temperature, and water and a 1 M-aqueous sodium hydroxide solution were added to adjust the mixture to around neutrality. Then, the mixture was extracted with ethyl acetate, and the organic layer obtained was washed with brine, and then dried over anhydrous sodium sulfate. After filtration, the solvent was distilled off under reduced pressure, and the residue obtained was sequentially purified by silica gel column chromatography (dichloromethane/methanol) and reverse phase HPLC. The racemate obtained was subjected to optical resolution using two Daicel Corporation CHIRALFLASH® IC (20 μm, 30 mmφ×100 mmL) connected [mobile phase: n-hexane/tetrahydrofuran/ethanol=72/24/2 to 72/24/5 (0 to 30 minutes), flow rate: 12 mL/minute, temperature: room temperature], the fraction eluted earlier in the main peaks was solidified with an n-hexane-ethyl acetate mixed solution to obtain the title compound (77 mg).

$^1$H-NMR (DMSO-D$_6$) δ: 1.04 (3H, t, J=7.6 Hz), 1.64 (3H, t, J=19.4 Hz), 2.53-2.69 (2H, m), 2.77-2.92 (1H, m), 4.08-4.28 (1H, m), 5.96 (1H, s), 6.76-6.87 (1H, m), 6.96-7.41 (5H, m), 11.87 (1H, s), 14.28 (1H, s), MS (m/z): 473 (M+H)$^+$.

Example 18

7-[4-(4-Chloro-3,5-dimethylphenyl)-5-(2,2-difluoropropyl)-6-oxo-1,4,5,6-tetrahydro pyrrolo[3,4-c]pyrazol-3-yl]-1,3-benzoxazol-2(3H)-one (enantiomer)

[Chemical Formula 156]

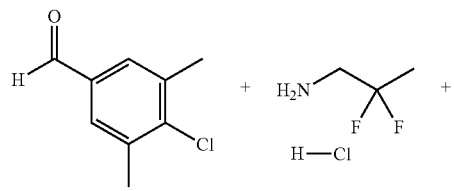

A mixture of the compound obtained in Reference Example 16 (202 mg), 2,2-difluoropropylamine hydrochloride (158 mg, CAS number: 868241-48-9), triethylamine (499 μL), and acetic acid (5 mL) was stirred at room temperature for 1 hour, and then the compound obtained in step 2 of Reference Example 1 (277 mg) and acetic acid (2 mL) were added. The mixture was stirred at the same temperature for 4 days, and then stirred at 90° C. for 3 hours. Subsequently, the reaction mixture was cooled to room temperature, hydrazine monohydrate (146 μL) was added, and the mixture was stirred at 100° C. for 3 hours and a half. The reaction mixture was cooled to room temperature, and water and a 1 M-aqueous sodium hydroxide solution were added to adjust the mixture to around neutrality. Then, the mixture was extracted with ethyl acetate, and the organic layer obtained was washed with brine, and then dried over anhydrous sodium sulfate. After filtration, the solvent was distilled off under reduced pressure, and the residue obtained was sequentially purified by silica gel column chromatography (dichloromethane/methanol) and reverse phase HPLC. The racemate obtained was subjected to optical resolution using two Daicel Corporation CHIRALFLASH® IC (20 μm, 30 mmφ×100 mmL) connected [mobile phase: n-hexane/tetrahydrofuran/ethanol=72/24/3 to 72/24/4 (0 to 40 minutes), flow rate: 14 mL/minute, temperature: room temperature], and the fraction eluted earlier in the main peaks was solidified with an n-hexane-ethyl acetate mixed solution to obtain the title compound (89 mg).

$^1$H-NMR (DMSO-D$_6$) δ: 1.64 (3H, t, J=19.4 Hz), 2.20 (6H, s), 2.75-2.90 (1H, m), 4.07-4.28 (1H, m), 5.91 (1H, s), 6.97 (2H, s), 7.02-7.42 (3H, m), 11.87 (1H, s), 14.26 (1H, s), MS (m/z): 473 (M+H)$^+$.

The same procedure as that in Example 18 was performed to synthesize the following compounds (Table 3-1 and Table 3-2).

TABLE 3-1
| Example No. | Manufacturing raw material | Structure of synthesized compound |
|---|---|---|
| 19 | 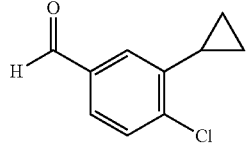 [SMILES: O=Cc1ccc(Cl)c(C2CC2)c1]<br>see Reference Example 19 | 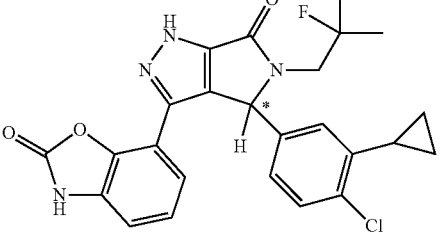 |
| 20 | 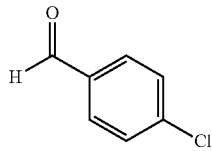<br>CAS No. 104-88-1 | 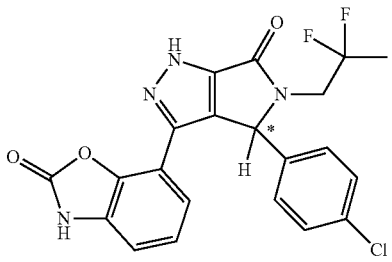 [SMILES: CC(F)(F)CN1C(=O)c2[nH]nc(-c3cccc4[nH]c(=O)oc34)c2C1c1ccc(Cl)cc1] |
| 21 | 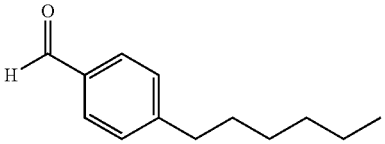<br>see Reference Example 17 | 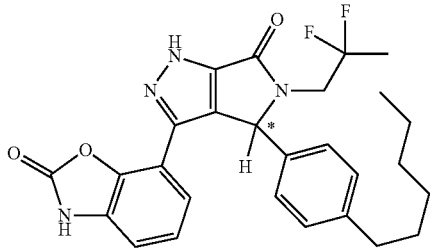 [SMILES: CCCCCCc1ccc(C2c3c(-c4cccc5[nH]c(=O)oc45)n[nH]c3C(=O)N2CC(C)(F)F)cc1] |
| 22 | 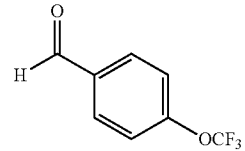<br>CAS No. 659-28-9 | 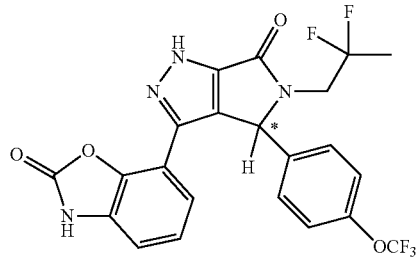 [SMILES: CC(F)(F)CN1C(=O)c2[nH]nc(-c3cccc4[nH]c(=O)oc34)c2C1c1ccc(OC(F)(F)F)cc1] |
| 23 | 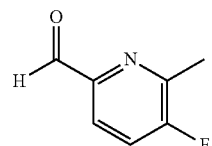<br>CAS No. 884495-34-5 | 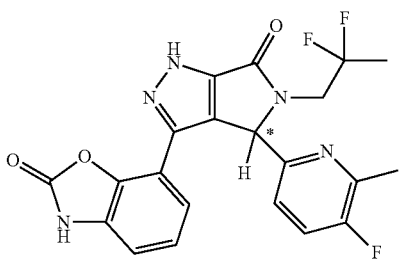 [SMILES: Cc1nc(C2c3c(-c4cccc5[nH]c(=O)oc45)n[nH]c3C(=O)N2CC(C)(F)F)ccc1F] |

TABLE 3-1-continued

| Example No. | Manufacturing raw material | Structure of synthesized compound |
|---|---|---|
| 24 | 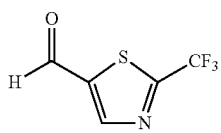  CAS No. 903130-38-1 | 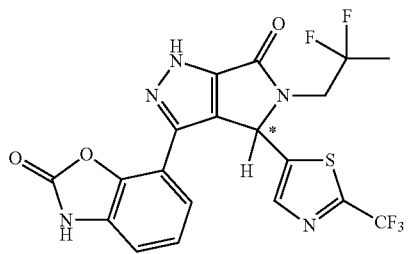 [SMILES: CC(F)(F)CN1C(=O)c2[nH]nc(-c3cccc4[nH]c(=O)oc34)c2C1c1cnc(C(F)(F)F)s1] |

TABLE 3-2

| Example No | Name of synthesized compound | Spectral data |
|---|---|---|
| 19 | 7-[4-(4-Chloro-3-cyclopropylphenyl)-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 0.38-0.54 (1H, m), 0.63-0.76 (1H, m), 0.92-1.03 (2H, m), 1.63 (3H, t, J = 19.1 Hz), 2.02-2.12 (1H, m), 2.75-2.89 (1H, m), 4.07-4.27 (1H, m,), 5.93 (1H, s), 6.61-6.72 (1H, m), 6.85-7.42 (5H, m), 11.92 (1H, s), 14.27 (1H, s)., MS (m/z): 485 (M+H)$^+$. |
| 20 | 7-[4-(4-Chlorophenyl)-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.64 (3H, t, J = 19.1 Hz), 2.75-2.90 (1H, m), 4.06-4.26 (1H, m), 5.99 (1H, s), 6.96-7.40 (7H, m), 11.85 (1H, s), 14.27 (1H, s)., MD (m/z): 445 (M+H)$^+$. |
| 21 | 7-[(4)-5-(2,2-Difluoropropyl)-4-(4-hexylphenyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 0.79 (3H, t, J = 6.7 Hz), 1.19 (6H, s), 1.40-1.52 (2H, m), 1.64 (3H, t, J = 19.4 Hz), 2.43-2.49 (2H, m), 2.69-2.81 (1H, m), 4.03-4.26 (1H, m), 5.94 (1H, s), 6.92-7.38 (7H, m), 11.82 (1H, s), 14.22 (1H, s)., MS (m/z): 495 (M+H)$^+$. |
| 22 | 7-{5-(2,2-Difluoropropyl)-6-oxo-4-[4-(trifluoromethoxy)phenyl]-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.1 Hz), 2.76-2.91 (1H, m), 4.08-4.27 (1H, m), 6.03 (1H, s), 6.98-7.36 (7H, m), 11.83 (1H, s), 14.28 (1H, s)., MS (m/z): 495 (M+H)$^+$. |
| 23 | 7-[5-(2,2-Difluoropropyl)-4-(5-fluoro-6-methylpyridin-2-yl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.63 (3H, t, J = 19.1 Hz), 2.25 (3H, d, J = 2.4 Hz), 2.85-3.00 (1H, m), 4.10-4.27 (1H, m), 6.06 (1H, s), 6.99-7.36 (4H, m), 7.54-7.64 (1H, m), 11.83 (1H, s), 14.16 (1H, s)., MS (m/z) 444 (M+H)$^+$. |
| 24 | 7-{5-(2,2-Difluoropropyl)-6-oxo-4-[2-(trifluoromethyl)-1,3-thiazol-5-yl]-1,4,5,6-tetrahydropyrrolo[3,4-c]pyrazol-3-yl}-1,3-benzoxazol-2(3H)-one (enantiomer) | $^1$H-NMR (DMSO-D$_6$) δ: 1.68 (3H, t, J = 19.4 Hz), 3.26-3.32 (1H, m), 4.17-4.26 (1H, m), 6.50 (1H, s), 7.07-7.12 (1H, m), 7.18-7.24 (1H, m), 7.45 (1H, d, J = 7.9 Hz), 8.19 (1H, s), 11.88 (1H, br s), 14.46 (1H, br s)., MS (m/z): 486 (M+H)$^+$. |

Example 25

7-{(5-(2,2-Difluoropropyl)-4-[3-methyl-4-(4,4,4-trifluorobutoxy)phenyl]-6-oxo-1,4,5,6-tetrahydropyrrolo[3,4-c]pyrazol-3-yl}-1,3-benzoxazol-2(3H)-one (enantiomer)

[Chemical Formula 157]

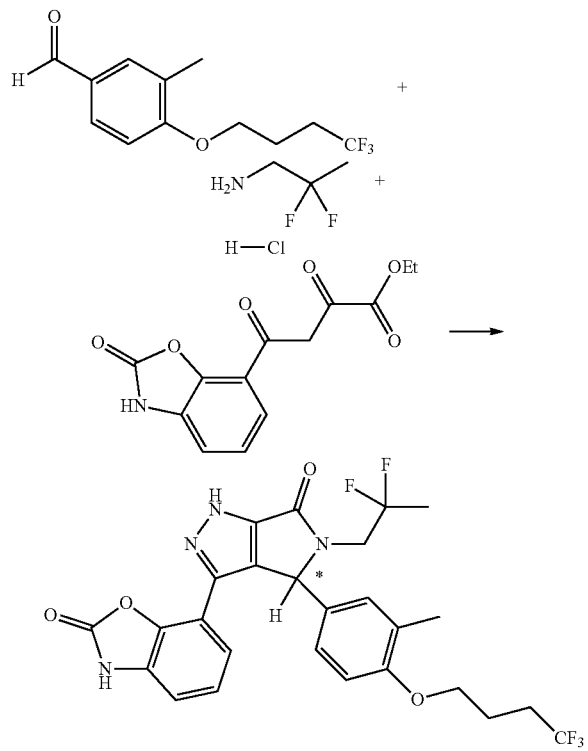

A mixture of the compound obtained in Reference Example 10 (160 mg), 2,2-difluoropropylamine hydrochloride (85.0 mg, CAS number: 868241-48-9), the compound obtained in step 2 of Reference Example 1 (150 mg), triethylamine (225 μL), and acetic acid (3.0 mL) was stirred at 80° C. for 16 hours. Subsequently, the reaction mixture was cooled to room temperature, hydrazine monohydrate (79.0 μL) was added, and the mixture was stirred at 100° C. for 2 hours. The reaction mixture was cooled to room temperature, and then concentrated under reduced pressure, ethyl acetate was added to the residue, and the organic layer obtained was washed with a saturated aqueous sodium hydrogen carbonate solution, and then dried over anhydrous sodium sulfate. After filtration, the solvent was distilled off under reduced pressure, and the residue obtained was sequentially purified by silica gel column chromatography (chloroform/ethyl acetate) and reverse phase HPLC. The racemate obtained was subjected to optical resolution using two Daicel Corporation CHIRALFLASH® IA (20 μm, 30 mmφ×100 mmL) connected [mobile phase: n-hexane/tetrahydrofuran/ethanol=75/20/5, flow rate: 14 mL/minute, temperature: room temperature], and the fraction eluted later in the main peaks was solidified with an n-hexane-ethyl acetate mixed solution to obtain the title compound (30.0 mg).

$^1$H-NMR (DMSO-D$_6$) δ: 1.63 (3H, t, J=19.1 Hz), 1.82-1.95 (2H, m), 2.01 (3H, s), 2.28-2.47 (2H, m), 2.66-2.86 (1H, m), 3.94 (2H, t, J=6.1 Hz), 4.02-4.23 (1H, m), 5.88 (1H, s), 6.77-6.85 (2H, m), 6.90-7.20 (3H, m), 7.25-7.36 (1H, m), 11.83 (1H, br s), 14.20 (1H, br s), MS (m/z): 551 (M+H)$^+$.

Example 26

7-[4-(5-Chloro-4,6-dimethylpyrimidine-2-yl)-5-(2,2-difluoropropyl)-6-oxo-1,4,5,6-tetrahydropyrrolo[3,4-c]pyrazol-3-yl]-1,3-benzoxazol-2(3H)-one

[Chemical Formula 158]

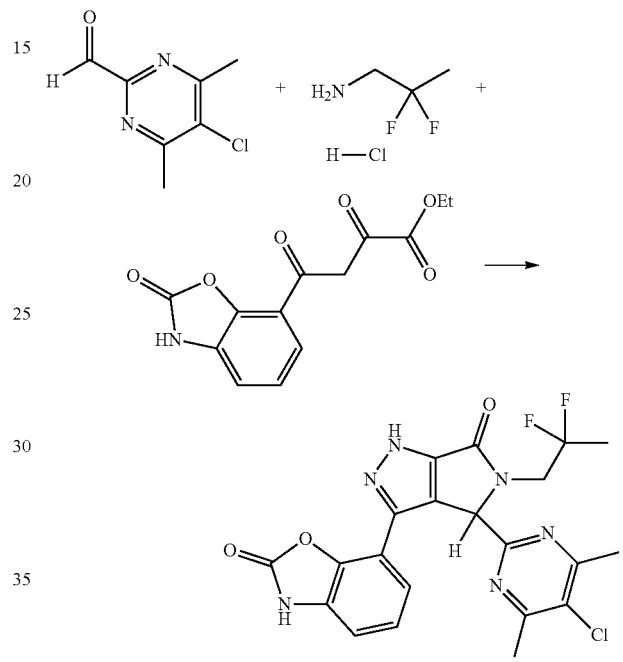

A mixture of the compound obtained in step 2 of Reference Example 20 (27 mg), 2,2-difluoropropylamine hydrochloride (23 mg, CAS number: 868241-48-9), the compound obtained in step 2 of Reference Example 1 (48 mg), triethylamine (97 μL), and acetic acid (1.6 mL) was stirred at 90° C. for 2 hours. Subsequently, the reaction mixture was cooled to room temperature, hydrazine monohydrate (23 μL) was added, and the mixture was stirred at 100° C. for 6 hours. The reaction mixture was cooled to room temperature, and then concentrated under reduced pressure. Water, a 1 M-aqueous sodium hydroxide solution, and a saturated aqueous sodium hydrogen carbonate solution were added to the residue obtained to adjust the mixture to around neutrality. Then, the mixture was extracted with ethyl acetate, and the organic layer obtained was washed with brine, and then dried over anhydrous sodium sulfate. After filtration, the solvent was distilled off under reduced pressure, and the residue obtained was sequentially purified by silica gel column chromatography (dichloromethane/methanol) and reverse phase HPLC to obtain the title compound (24 mg) as a solid.

$^1$H-NMR (DMSO-D$_6$) δ: 1.65 (3H, t, J=19.1 Hz), 2.35 (6H, s), 3.36-3.44 (1H, m), 4.14-4.35 (1H, m), 6.05 (1H, s), 6.98-7.37 (3H, m), 11.82 (1H, s), 14.10 (1H, s), MS (m/z): 475 (M+H)$^+$.

The same procedure as that in Example 26 was performed to synthesize the following compounds (Table 4-1 and Table 4-2).

TABLE 4-1

| Example No | Manufacturing raw material | Structure of synthesized compound |
|---|---|---|
| 27 | 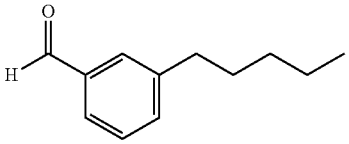 see Reference Example 18 | 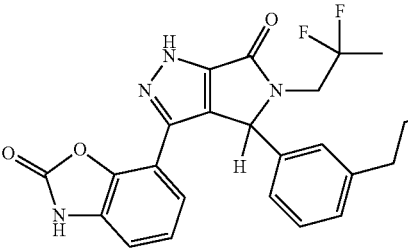 |
| 28 | 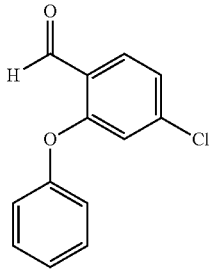 [SMILES: O=Cc1ccc(Cl)cc1Oc1ccccc1] see Reference Example 24 | 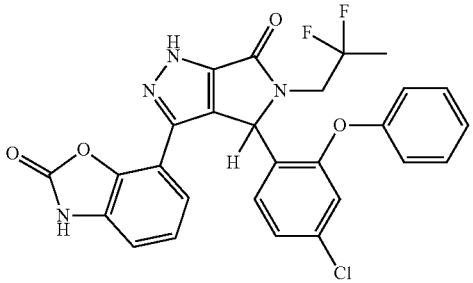 [SMILES: CC(F)(F)CN1C(=O)c2[nH]nc(-c3cccc4[nH]c(=O)oc34)c2C1c1ccc(Cl)cc1Oc1ccccc1] |
| 29 | 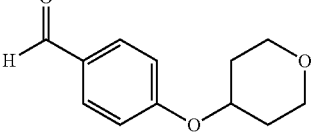 see Reference Example 15 | 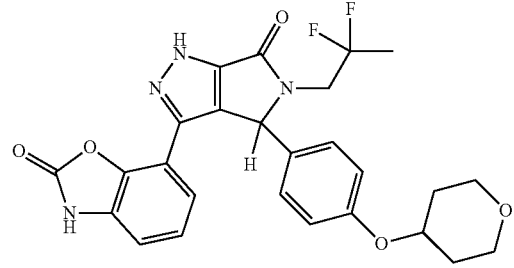 [SMILES: CC(F)(F)CN1C(=O)c2[nH]nc(-c3cccc4[nH]c(=O)oc34)c2C1c1ccc(OC2CCOCC2)cc1] |

TABLE 4-2

| Example No | Name of synthesized compound | Spectral data |
|---|---|---|
| 27 | 7-[4-(3-Butylphenyl)-5-(2,2-difluoropropyl)-6-oxo-1,4,5,6-tetrahydropyrrolo[3,4-c]pyrazol-3-yl]-1,3-benzoxazol-2(3H)-one | $^1$H-NMR (DMSO-D$_6$) δ: 0.79 (3H, t, J = 7.3 Hz), 1.02-1.14 (2H, m), 1.33-1.44 (2H, m), 1.64 (3H, t, J = 19.1 Hz), 2.46 (2H, t, J = 7.3 Hz), 2.71-2.86 (1H, m), 4.09-4.27 (1H, m), 5.94 (1H, s), 6.74-7.36 (7H, m), 11.85 (1H, s), 14.22 (1H, s)., MS (m/z): 467 (M+H)$^+$. |
| 28 | 7-[4-(4-Chloro-2-phenoxyphenyl)-5-(2,2-difluoropropyl)-6-oxo-1,4,5,6-tetrahydropyrrolo[3,4-c]pyrazol-3-yl]-1,3-benzoxazol-2(3H)-one | $^1$H-NMR (DMSO-D$_6$) δ: 1.63 (3H, t, J = 19.0 Hz), 2.97-3.21 (1H, m), 4.07-4.27 (1H, m), 5.82-7.93 (12H, m), 11.81 (1H, br s), 14.00 (1H, br s)., MS (m/z): 537 (M+H)$^+$. |
| 29 | 7-[5-(2,2-Difluoropropyl)-4-{4-[oxan-4-yl)oxy]phenyl}-6-oxo-1,4,5,6-tetrahydropyrrolo[3,4-c]pyrazol-3-yl]-1,3-benzoxazol-2(3H)-one | $^1$H-NMR (DMSO-D$_6$) δ: 1.60-1.84 (5H, m), 1.95-2.06 (2H, m), 2.88-3.05 (1H, m), 3.54-3.63 (2H, m), 3.94-4.03 (2H, m), 4.23-4.34 (1H, m), 4.44-4.54 (1H, m.), 5.88 (1H, s), 6.85-7.23 (6H, m), 8.12 (1H, s), 9.88 (1H, br s), 13.53 (1H, br s)., MS (m/z): 511 (M+H)$^+$. |

Example 30

(−)-7-[5-(2,2-Difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one

[Chemical Formula 159]

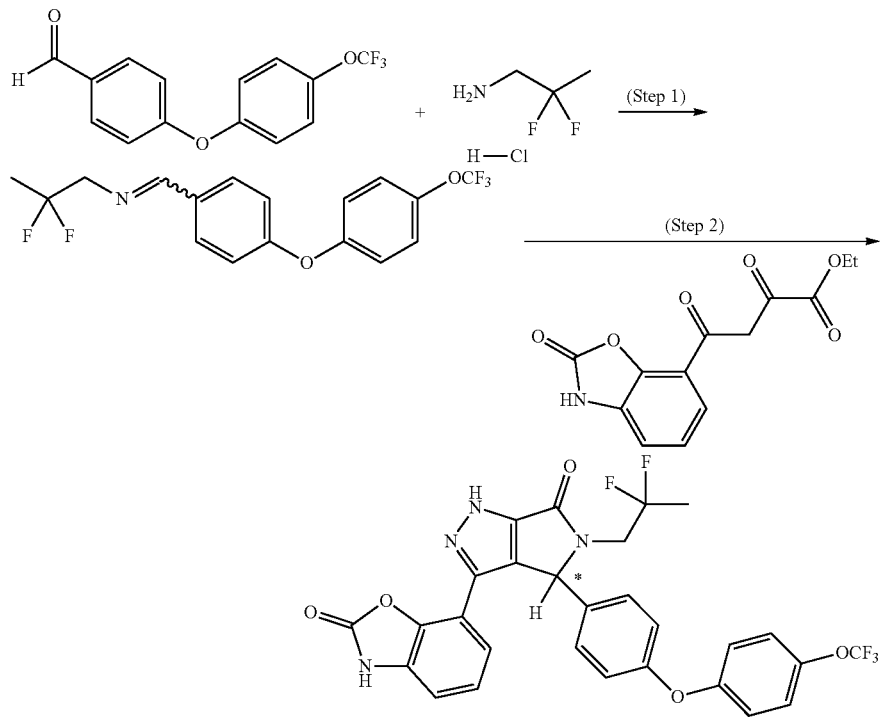

Step 1

N-(2,2-Difluoropropyl)-1-{4-[4-(trifluoromethoxy)phenoxy]phenyl}methanimine

To a suspension of the compound obtained in Reference Example 25 (6.69 g) and 2,2-difluoropropylamine hydrochloride (3.33 g, CAS number: 868241-48-9) in tetrahydrofuran (30 mL), water (3.0 mL) and triethylamine (3.60 mL) were added at room temperature, and the mixture was stirred at the same temperature for 22 hours. The reaction mixture was diluted with ethyl acetate and sequentially washed with water, a saturated aqueous sodium hydrogen carbonate solution, and brine, and then dried over anhydrous sodium sulfate. After filtration, the solvent was distilled off under reduced pressure to obtain the crude title compound (8.23 g) as an oil.

$^1$H-NMR (CDCl$_3$) δ: 1.75 (3H, t, J=18.8 Hz), 3.90 (2H, t, J=13.3 Hz), 7.01-7.07 (4H, m), 7.22 (2H, dd, J=9.0, 0.8 Hz), 7.76 (2H, d, J=9.0 Hz), 8.28 (1H, s).

Step 2

(−)-7-[5-(2,2-Difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzoxazol-2(3H)-one A mixture of the compound obtained in the above step 1 (8.23 g), the compound obtained in step 2 of Reference Example 1 (4.87 g), and acetic acid (50 mL) was stirred at room temperature for 22 hours, and then the mixture was stirred at 100° C. for 7 hours. The reaction mixture was cooled to room temperature, hydrazine monohydrate (1.70 mL) was added, and the mixture was stirred at 100° C. for 2 hours. The reaction mixture was cooled to room temperature, water (25 mL) was added, and the mixture was stirred at room temperature for 30 minutes, further stirred at 70° C. for 40 minutes, and then stirred at room temperature for 6 hours. The precipitated solid was collected by filtration, washed twice with an ethanol-water (1:1) mixed solution, and dried under reduced pressure to obtain the crude product as a solid. The crude product obtained was dissolved in ethyl acetate (40 mL), n-hexane (10 mL) was slowly added, and the mixture was allowed to stand at room temperature for 2 hours. Then, n-hexane (10 mL) was further slowly added, and the mixture was allowed to stand at room temperature overnight. The precipitated solid was collected by filtration, washed three times with an n-hexane-ethyl acetate mixed solution (1:1), and then dried under reduced pressure to obtain a racemate (7.82 g) as a solid. Subsequently, the racemate obtained (5.00 g) was subjected to optical resolution using two Daicel Corporation CHIRALFLASH® IC (20 μm, 30 mmφ×100 mmL) connected [mobile phase: n-hexane/tetrahydrofuran/ethanol=70/27/3, flow rate: 12 mL/minute, temperature: room temperature], and the fraction eluted earlier in the main peaks (the retention time in two columns connected: 8.0 minutes) was solidified with an n-hexane-ethyl acetate mixed solution to obtain the title compound (2.30 g).

$^1$H-NMR (DMSO-D$_6$) δ: 1.66 (3H, t, J=19.5 Hz), 2.80-2.95 (1H, m), 4.07-4.27 (1H, m), 5.98 (1H, s), 6.94 (2H, d, J=8.6 Hz), 7.01-7.08 (3H, m), 7.10-7.19 (3H, m), 7.26-7.33

(1H, m), 7.36 (2H, dd, J=9.0, 0.8 Hz), 11.84 (1H, br s), 14.24 (1H, br s), MS (m/z): 587 (M+H)$^+$, [α]$^{20}_D$: −297 (c=1.00, MeOH).

Example 31

(−)-7-[4-{4-[3-Chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one

[Chemical Formula 160]

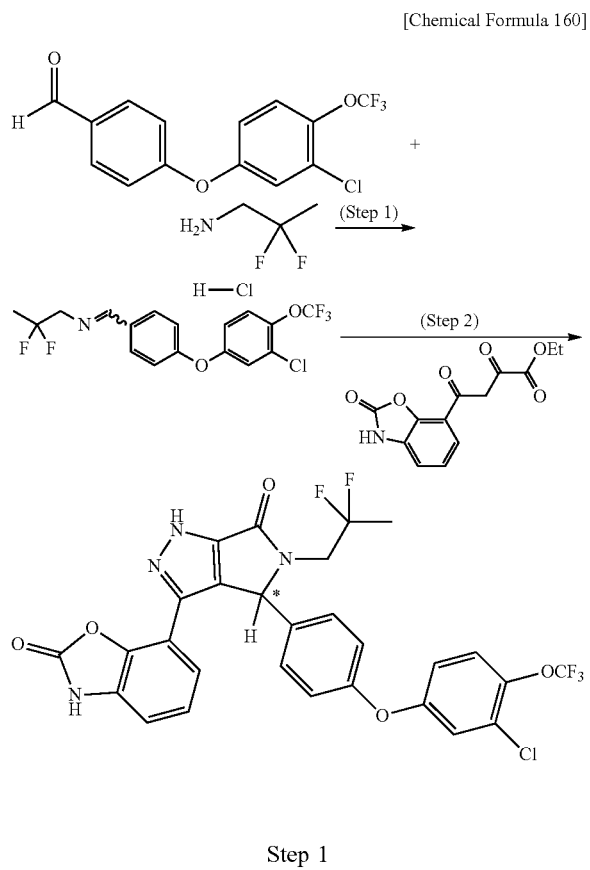

Step 1

1-{4-[3-Chloro-4-(trifluoromethoxy)phenoxy]phenyl}-N-(2,2-difluoropropyl)methanimine To a suspension of the compound obtained in Reference Example 26 (365 mg) and 2,2-difluoropropylamine hydrochloride (200 mg, CAS number: 868241-48-9) in dichloromethane (8.0 mL), triethylamine (250 μL) and anhydrous magnesium sulfate (excess amount) was added at room temperature, and the mixture was stirred at the same temperature for 5 days. Insoluble materials were filtered off, the filtrate obtained was diluted with dichloromethane and washed twice with water, and then dried over anhydrous magnesium sulfate. After filtration, the solvent was distilled off under reduced pressure to obtain the crude title compound (457 mg) as an oil.

$^1$H-NMR (CDCl$_3$) δ: 1.76 (3H, t, J=19.0 Hz), 3.91 (2H, t, J=12.3 Hz), 6.95 (1H, dd, J=9.2, 3.1 Hz), 7.06 (2H, J=8.6 Hz), 7.12 (1H, d, J=3.1 Hz), 7.30 (1H, dd, J=9.2, 1.2 Hz), 7.80 (2H, J=8.6 Hz), 8.29 (1H, s).

Step 2

(−)-7-[4-{4-[3-Chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one A mixture of the compound obtained in the above step 1 (457 mg), the compound obtained in step 2 of Reference Example 1 (292 mg), and acetic acid (8.0 mL) was stirred at room temperature for 40 hours, and then stirred at 80° C. for 6 hours and a half. Subsequently, the reaction mixture was cooled to room temperature, hydrazine monohydrate (255 μL) was added, and the mixture was stirred at 100° C. for 10 hours. The reaction mixture was cooled to room temperature, and then concentrated under reduced pressure, a chloroform-methanol (9:1) mixed solution was added to the residue, and the organic layer obtained was washed twice with water, and then dried over magnesium sulfate. After filtration, the solvent was distilled off under reduced pressure, and the residue obtained was sequentially purified by silica gel column chromatography (dichloromethane/methanol) and reverse phase HPLC. The racemate obtained (416 mg) was subjected to optical resolution using two Daicel Corporation CHIRALFLASH® IC (20 μm, 30 mmφ×100 mmL) connected [mobile phase: n-hexane/tetrahydrofuran/ethanol=75/25/2 (0 to 5 minutes) to 75/25/5 (5 to 60 minutes), flow rate: 14 mL/minute, temperature: room temperature], and the fraction eluted earlier in the main peaks (the retention time in two columns connected: 30 minutes) was purified by silica gel column chromatography (n-hexane/ethyl acetate) to obtain the title compound (172 mg).

$^1$H-NMR (DMSO-D$_6$) δ: 1.66 (3H, t, J=19.4 Hz), 2.84-2.99 (1H, m), 4.07-4.28 (1H, m), 5.99 (1H, s), 6.96-7.09 (4H, m), 7.11-7.23 (3H, m), 7.23-7.37 (2H, m), 7.54 (1H, dd, J=9.1, 1.2 Hz), 11.82 (1H, br s), 14.25 (1H, br s), MS (m/z): 621 (M+H)$^+$, [α]$^{20}_D$: −268 (c=1.01, MeOH).

Example 32

(−)-7-[5-(2,2-Difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one

[Chemical Formula 161]

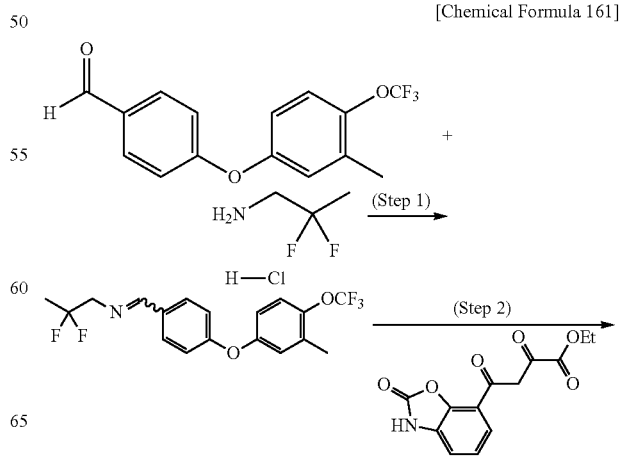

-continued

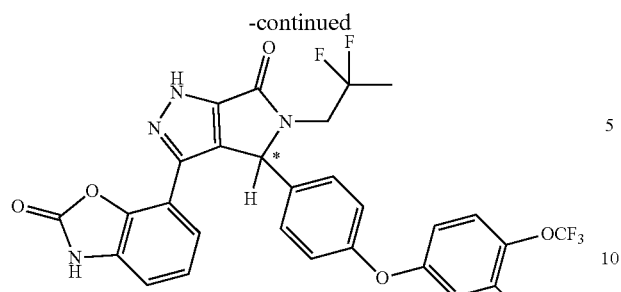

Step 1

N-(2,2-Difluoropropyl)-1-{4-[3-methyl-4-(trifluoromethoxy)phenoxy]phenyl}methanimine To a suspension of the compound obtained in Reference Example 64 (278 mg) and 2,2-difluoropropylamine hydrochloride (163 mg, CAS number: 868241-48-9) in dichloromethane (8.0 mL), triethylamine (190 µL) and anhydrous magnesium sulfate (excess amount) were added at room temperature, and the mixture was stirred at the same temperature for 5 days. Insoluble materials were filtered off, the filtrate obtained was diluted with dichloromethane, washed twice with water, and then dried over anhydrous magnesium sulfate. After filtration, the solvent was distilled off under reduced pressure to obtain the crude title compound (347 mg) as an oil.

$^1$H-NMR (CDCl$_3$) δ: 1.75 (3H, t, J=19.4 Hz), 2.30 (3H, s), 3.89 (2H, d, J=12.9 Hz), 6.87 (1H, dd, J=8.6, 3.1 Hz), 6.92 (1H, d, J=3.1 Hz), 7.02 (2H, d, J=9.2 Hz), 7.19 (1H, dd, J=8.6, 1.2 Hz), 7.75 (2H, d, J=9.2 Hz), 8.29 (1H, s).

Step 2

(−)-7-[5-(2,2-Difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one A mixture of the compound obtained in the above step 1 (347 mg), the compound obtained in step 2 of Reference Example 1 (220 mg), and acetic acid (8.0 mL) was stirred at room temperature for 41 hours, and then stirred at 80° C. for 9 hours. Subsequently, the reaction mixture was cooled to room temperature, hydrazine monohydrate (192 µL) was added, and the mixture was stirred at 100° C. for 8 hours and a half. The reaction mixture was cooled to room temperature and concentrated under reduced pressure, a chloroform-methanol (9:1) mixed solution was added to the residue, and the organic layer obtained was washed twice with water, and then dried over magnesium sulfate. After filtration, the solvent was distilled off under reduced pressure, the residue obtained was sequentially purified by silica gel column chromatography (dichloromethane/methanol) and reverse phase HPLC. The racemate obtained (272 mg) was subjected to optical resolution using two Daicel Corporation CHIRALFLASH® IC (20 µm, 30 mmφ×100 mmL) connected [mobile phase: n-hexane/tetrahydrofuran/ethanol=75/25/2 (0 to 5 minutes) to 75/25/5 (5 to 60 minutes), flow rate: 14 mL/minute, temperature: room temperature], and the fraction eluted earlier in the main peaks (the retention time in two columns connected: 36 minutes) was purified by silica gel column chromatography (n-hexane/ethyl acetate) to obtain the title compound (128 mg).

$^1$H-NMR (DMSO-D$_6$) δ: 1.67 (3H, t, J=19.0 Hz), 2.21 (3H, s), 2.78-2.98 (1H, m), 4.08-4.32 (1H, m), 5.97 (1H, s), 6.85 (1H, dd, J=9.2, 3.1 Hz), 6.92 (2H, d, J=8.6 Hz), 6.98 (1H, d, J=3.1 Hz), 7.02-7.22 (4H, m), 7.29 (2H, d, J=8.6 Hz), 11.62-11.95 (1H, m), 14.11-14.41 (1H, m), MS (m/z): 601 (M+H)$^+$, $[α]^{20}_D$: −289 (c=1.00, MeOH).

Example 33

(−)-7-[5-(2,2-Difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one

[Chemical Formula 162]

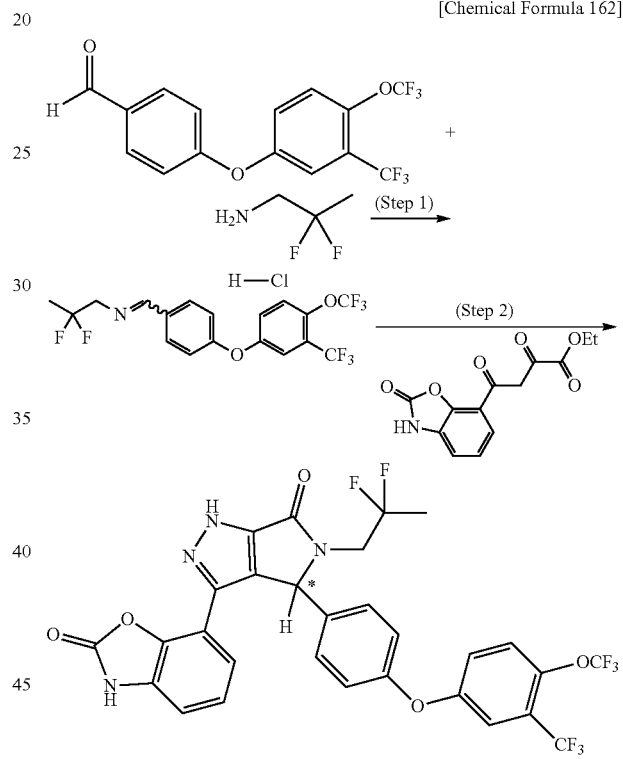

Step 1

N-(2,2-Difluoropropyl)-1-{4-[4-(trifluoromethoxy)-3-(trifluoromethyl)phenoxy]phenyl}methanimine To a suspension of the compound obtained in Reference Example 27 (356 mg) and 2,2-difluoropropylamine hydrochloride (193 mg, CAS number: 868241-48-9) in dichloromethane (6.0 mL), triethylamine (250 µL) and anhydrous magnesium sulfate (excess amount) were added at room temperature, and the mixture was stirred at the same temperature for 6 days. Insoluble materials were filtered off, the filtrate obtained was diluted with dichloromethane, washed twice with water, and then dried over anhydrous magnesium sulfate. After filtration, the solvent was distilled off under reduced pressure to obtain the crude title compound (434 mg) as an oil.

183

$^1$H-NMR (CDCl$_3$) δ: 1.76 (3H, t, J=18.8 Hz), 3.91 (2H, t, J=13.4 Hz), 7.07 (2H, d, J=8.5 Hz), 7.21 (1H, dd, J=9.1, 3.0 Hz), 7.34 (1H, d, J=3.0 Hz), 7.40 (1H, d, J=9.1 Hz), 7.81 (2H, d, J=8.5 Hz), 8.31 (1H, s).

Step 2

(−)-7-[5-(2,2-Difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one A mixture of the compound obtained in the above step 1 (434 mg), the compound obtained in step 2 of Reference Example 1 (263 mg), and acetic acid (5.0 mL) was stirred at room temperature for 42 hours, and then stirred at 80° C. for 10 hours. Subsequently, the reaction mixture was cooled to room temperature, hydrazine monohydrate (230 μL) was added, and the mixture was stirred at 100° C. for 9 hours. The reaction mixture was cooled to room temperature, and then concentrated under reduced pressure, a chloroform-methanol (9:1) mixed solution was added to the residue, and the organic layer obtained was washed twice with water, and then dried over magnesium sulfate. After filtration, the solvent was distilled off under reduced pressure, and the residue obtained was sequentially purified by silica gel column chromatography (dichloromethane/methanol) and reverse phase HPLC. The racemate obtained (263 mg) was subjected to optical resolution using two Daicel Corporation CHIRALFLASH® IC (20 μm, 30 mmφ×100 mmL) connected [mobile phase: n-hexane/tetrahydrofuran/ethanol=75/25/2 (0 to 5 minutes) to 75/25/5 (5 to 60 minutes), flow rate: 14 mL/minute, temperature: room temperature], and the fraction eluted earlier in the main peaks (the retention time in two columns connected: 29 minutes) was purified by silica gel column chromatography (n-hexane/ethyl acetate) to obtain the title compound (116 mg).

$^1$H-NMR (DMSO-D$_6$) δ: 1.65 (3H, t, J=19.4 Hz), 2.79-2.99 (1H, m), 4.08-4.26 (1H, m), 6.00 (1H, s), 6.95-7.11 (3H, m), 7.12-7.24 (3H, m), 7.25-7.42 (3H, m), 7.64 (1H, d, J=9.1 Hz), 11.59-11.97 (1H, m), 14.13-14.45 (1H, m), MS (m/z): 655 (M+H)$^+$, [α]$^{20}$$_D$: −264 (c=1.00, MeOH).

Example 34

(−)-7-[4-{4-[3-Chloro-5-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one

[Chemical Formula 163]

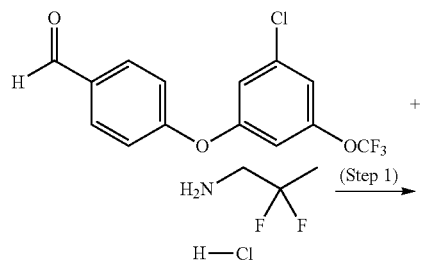

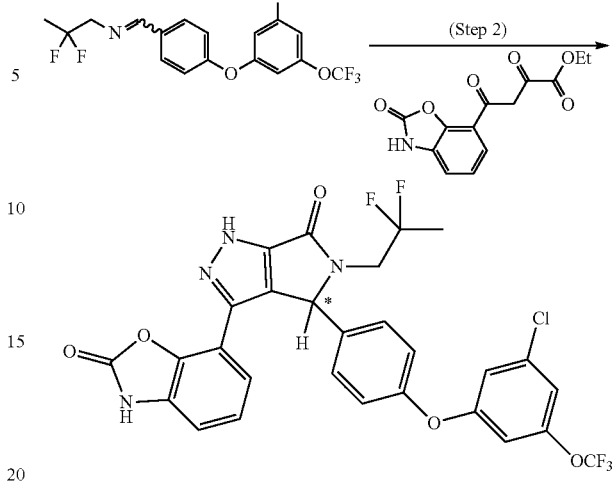

Step 1

1-{4-[3-Chloro-5-(trifluoromethoxy)phenoxy]phenyl}-N-(2,2-difluoropropyl)methanimine To a suspension of the compound obtained in Reference Example 65 (859 mg) and 2,2-difluoropropylamine hydrochloride (495 mg, CAS number: 868241-48-9) in dichloromethane (18.0 mL), triethylamine (700 μL) and anhydrous magnesium sulfate (excess amount) were added at room temperature, and the mixture was stirred at the same temperature for 4 days. Insoluble materials were filtered off, the filtrate obtained was diluted with dichloromethane, washed twice with water, and then dried over anhydrous magnesium sulfate. After filtration, the solvent was distilled off under reduced pressure to obtain the crude title compound (1.05 g) as an oil.

$^1$H-NMR (CDCl$_3$) δ: 1.76 (3H, t, J=18.8 Hz), 3.92 (2H, t, J=13.4 Hz), 6.79 (1H, s), 6.93 (1H, s), 7.00 (1H, s), 7.09 (2H, d, J=8.5 Hz), 7.81 (2H, d, J=8.5 Hz), 8.32 (1H, s).

Step 2

(−)-7-[4-{4-[3-Chloro-5-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one A mixture of the compound obtained in the above step 1 (1.05 g), the compound obtained in step 2 of Reference Example 1 (708 mg), and acetic acid (8.0 mL) was stirred at room temperature for 15 hours, and then stirred at 80° C. for 9 hours. Subsequently, the reaction mixture was cooled to room temperature, hydrazine monohydrate (620 μL) was added, and the mixture was stirred at 100° C. for 9 hours and a half. The reaction mixture was cooled to room temperature, and then concentrated under reduced pressure, a chloroform-methanol (9:1) mixed solution was added to the residue, and the organic layer obtained was washed twice with water, and then dried over magnesium sulfate. After filtration, the solvent was distilled off under reduced pressure, and the residue obtained was sequentially purified by silica gel column chromatography (dichloromethane/methanol) and reverse phase HPLC to obtain a racemate (1.08 g). Subsequently, the racemate obtained (626 mg) was subjected to optical resolution using two Daicel Corporation CHIRALFLASH® IC (20 μm, 30 mmφ×100 mmL) connected [mobile phase: n-hexane/tetrahydrofuran/ethanol=70/27/3, flow rate: 12 mL/minute, temperature: room temperature], and the fraction eluted earlier in the main peaks (the retention time in two columns connected: 18 minutes) was purified by silica gel column chromatography (n-hexane/ethyl acetate) to obtain the title compound (275 mg) as a solid.

$^1$H-NMR (DMSO-D$_6$) δ: 1.65 (3H, t, J=19.4 Hz), 2.87-3.02 (1H, m), 4.07-4.28 (1H, m), 5.99 (1H, s), 6.89 (1H, s), 6.99-7.08 (4H, m), 7.09-7.24 (3H, m), 7.25-7.34 (2H, m), 11.79 (1H, br s), 14.27 (1H, br s), MS (m/z): 621 (M+H)$^+$, [α]$^{20}_D$: −270 (c=0.533, MeOH).

The same procedure as that in step 1 and step 2 of Example 34 was performed to synthesize the following compounds (Table 5-1 to Table 5-4).

TABLE 5-1

| Example No | Manufacturing raw material | Structure of synthesized compound |
|---|---|---|
| 35 | 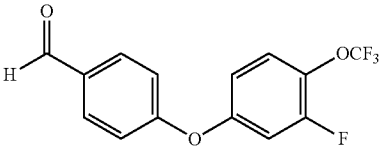 [SMILES: O=Cc1ccc(Oc2ccc(OC(F)(F)F)c(F)c2)cc1] see Reference Example 31 | 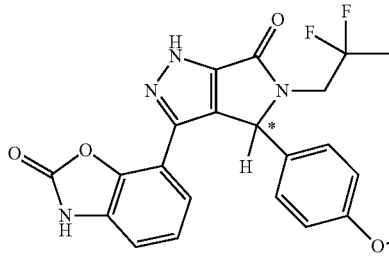 |
| 36 | 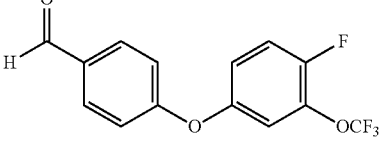 see Reference Example 32 | 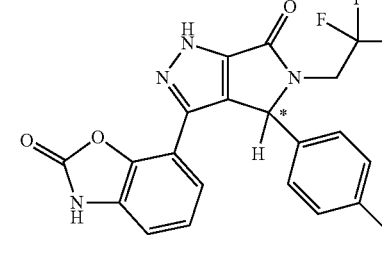 |
| 37 | 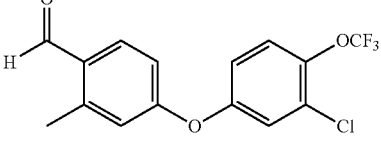 see Reference Example 33 | 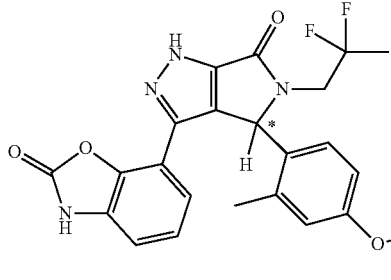 |
| 38 | 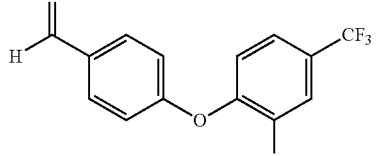 see Reference Example 68 | 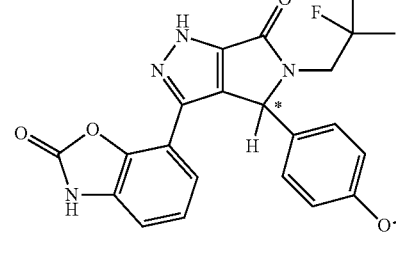 |

TABLE 5-2

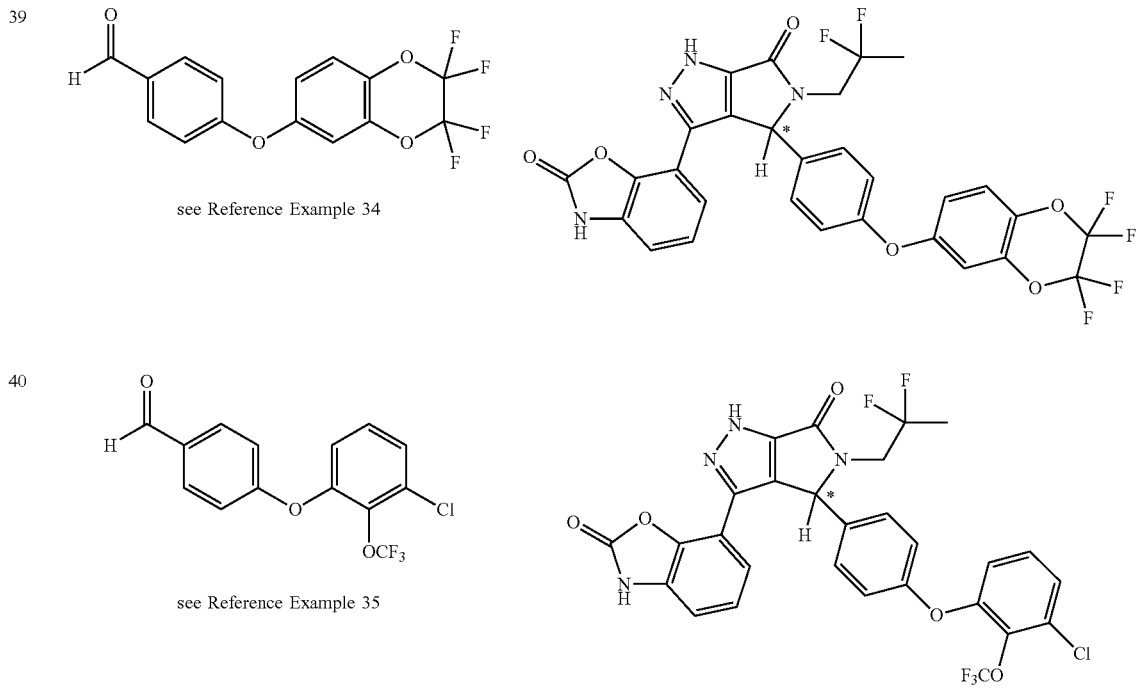

TABLE 5-3

| Example No | Name of synthesized compound | Spectral data |
| --- | --- | --- |
| 35 | 7-{5-(2,2-Difluoropropyl)-4-{4-[3-fluoro-4-(trifluoro-methoxy)phenoxy]phenyl}-6-oxo-1,4,5,6-tetrahydro-pyrrolo[3,4-c]pyrazol-3-yl]-1,3-benzoxazol-2(3H)-one (enantiomer) | $^{1}$H-NMR (DMSO-D$_{6}$) δ: 1.56 (3H, t, j = 19.4 Hz), 2.82-3.01 (1H, m). 4.08-4.30 (1H, m), 6.00 (1H, s), 6.84 (1H, dd, J = 9.1, 1.8 Hz), 6.94-7.23 (7H, m), 7.24-7.39 (1H, m), 7.55 (1H, t, J = 9.1 Hz), 11.84 (1H, br s), 14.29 (1H, br s)., MS (m/z): 605 (M+H)$^{+}$. |
| 36 | 7-[5-(2,2-Difluoropropyl)-4-{4-[4-fluoro-3-(trifluoro-methoxy)phenoxy]phenyl}-6-oxo-1,4,5,6-tetrahydro-pyrrolo[3,4-c]pyrazol-3-yl]-1,3-benzoxazol-2(3H)-one (enantiomer) | $^{1}$H-NMR (DMSO-D$_{6}$) δ: 1.66 (3H, t, J = 19.4 Hz), 2.80-2.98 (1H, m), 4.05-4.30 (1H, m), 5.99 (1H, s), 6.91-7.02 (2H, m), 7.02-7.22 (6H, m), 7.25-7.39 (1H, m), 7.44-7.57 (1H, m), 11.65-11.94 (1H, m), 1.414-14.39 (1H, m)., MS (m/z): 605 (M+H)$^{+}$. |
| 37 | 7-[4-{4-[3-Chloro-4-(trifluoro-methoxy)phenoxy]-2-methylphenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^{1}$H-NMR (DMSO-D$_{6}$) δ: 1.66 (3H, t, J = 19. 4 Hz), 2.51 (3H, s), 2.80-3.06 (1H, m), 3.97-4.31 (1H, m), 6.05 (0.36H, s), 6.22 (0.64H, s), 6.54-6.64 (0.6H, m), 6.71-6.82 (1H, m), 6.87-7.30 (6H, m), 7.49-7.84 (1.36H, m), 11.63-11.95 (1H, m), 14.09-14.45 (1H, m)., MS (m/z): 635 (M+H)$^{+}$. |
| 38 | 7-[4-{4-[2,4-Bis(trifluoro-methyl)phenoxy]phenyl}-5-(2,2-difluoropropyl)-6-oxo-1,4,5,6-tetra-hydropyrrolo[3,4-c]pyrazol-3-yl]-1,3-benzoxazol-2(3H)-one (enantiomer) | $^{1}$H-NMR (DMSO-D$_{6}$) δ: 1.67 (3H, t, J = 19.4 Hz), 2.83-3.00 (1H, m), 4.11-4.30 (1H, m), 6.02 (1H, s), 6.97-7.29 (8H, m), 7.92-8.01 (1H, m), 8.03-8.11 (1H, m), 11.69-11.96 (1H, m), 14.19-14.41 (1H, m)., MS (m/z): 639 (M+H)$^{+}$. |
| 39 | 7-[5-(2,2-Difluoropropyl)-6-oxo-4-{4-[(2,2,3,3-tetrafluoro-2,3-dihydro-1,4-benzodioxin-6-yl)oxy]phenyl}-1,4,5,6-tetrahydropyrrolo[3,4-c]pyrazol-3-yl]-1,3-benzoxazol-2(3H)-one (enantiomer) | $^{1}$H-NMR (DMSO-D$_{6}$) δ: 1.66 (3H, t, J = 19.0 Hz), 2.78-2.99 (1H, m), 4.03-4.32 (1H, m), 5.98 (1H, s), 6.92 (1H, dd, J = 9.2, 2.5 Hz), 6.96 (2H, d, J = 9. 2 Hz), 7.04-7.20 (5H, m), 7.25-7.39 (1H, m), 7.47 (1H, J = 9.2 Hz), 11.84 (1H, br s), 14.13-14.44 (1H, m)., MS (m/z): 632 (M+H)$^{+}$. |

TABLE 5-4

| 40 | 7-[4-{4-[3-Chloro-2-(trifluoromethoxy) phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.67 (3H, t, J = 19.4 Hz), 2.80-2.95 (1H, m), 4.07-4.31 (1H, m), 5.99 (1H, s), 6.92-7.10 (4H, m), 7.11-7.22 (3H, m), 7.24-7.33 (1H, m), 7.35-7.46 (2H, m), 11.66-11.92 (1H, m), 14.17-14.38 (1H, m)., MS (m/z): 621 (M + H)$^+$. |

Example 41

7-{4-[4-(4-Chlorophenoxy)phenyl]-5-(2,2-difluoropropyl)-6-oxo-1,4,5,6-tetrahydro pyrrolo[3,4-c]pyrazol-3-yl}-5-fluoro-1,3-benzoxazol-2(3H)-one (enantiomer)

[Chemical Formula 164]

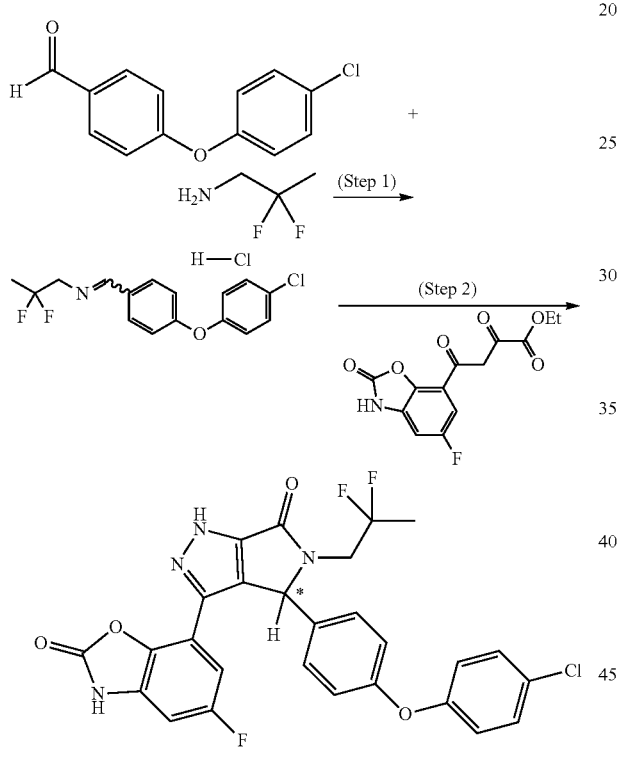

(Step 1) 1-[4-(4-Chlorophenoxy)phenyl]-N-(2,2-difluoropropyl)methanimine

To a solution of 4-(4-chlorophenoxy)benzaldehyde (209 mg, CAS number: 61343-99-5) and 2,2-difluoropropylamine hydrochloride (143 mg, CAS number: 868241-48-9) in ethanol (5.0 mL), triethylamine (160 μL) was added at room temperature, and the mixture was stirred at the same temperature for 19 hours. The solvent was distilled off under reduced pressure, ethyl acetate was added to the residue, and the organic layer obtained was washed with water, and then dried over anhydrous magnesium sulfate. After filtration, the solvent was distilled off under reduced pressure to obtain the crude title compound (138 mg) as an oil.

$^1$H-NMR (CDCl$_3$) δ: 1.75 (3H, t, J=18.8 Hz), 3.89 (2H, t, J=13.4 Hz), 6.98 (2H, d, J=9.1 Hz), 7.01 (2H, d, J=9.1 Hz), 7.33 (2H, d, J=9.1 Hz), 7.75 (2H, d, J=9.1 Hz), 8.27 (1H, s).

Step 2

7-{4-[4-(4-Chlorophenoxy)phenyl]-5-(2,2-difluoropropyl)-6-oxo-1,4,5,6-tetrahydropyrrolo[3,4-c]pyrazol-3-yl}-5-fluoro-1,3-benzoxazol-2(3H)-one (enantiomer)

The compound obtained in the above step 1 (138 mg) and the compound obtained in step 3 of Reference Example 2 (211 mg) were used as manufacturing raw materials, and the same procedure as that in step 2 of Example 34 was performed to obtain the title compound (101 mg) as a solid.

$^1$H-NMR (DMSO-D$_6$) δ: 1.65 (3H, t, J=19.4 Hz), 2.79-2.96 (1H, m), 4.04-4.27 (1H, m), 5.98 (1H, s), 6.89-7.04 (5H, m), 7.05-7.20 (3H, m), 7.41 (2H, d, J=8.5 Hz), 12.03 (1H, br s), 14.29 (1H, br s), MS (m/z): 555 (M+H)$^+$.

Example 42

(−)-7-[4-{4-[3,5-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one

[Chemical Formula 165]

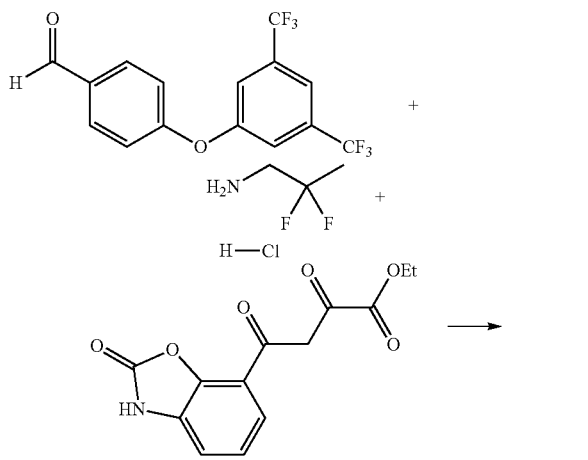

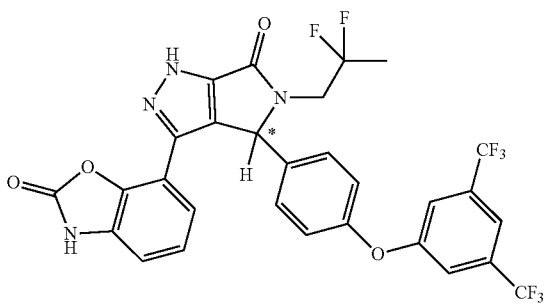

A mixture of the compound obtained in Reference Example 28 (348 mg), 2,2-difluoropropylamine hydrochloride (126 mg, CAS number: 868241-48-9), triethylamine (399 µL), and acetic acid (4 mL) was stirred at room temperature for 1 hour, and then the compound obtained in step 2 of Reference Example 1 (222 mg) and acetic acid (1 mL) were added. The mixture was further stirred at the same temperature for 3 days, and then stirred at 90° C. for 6 hours. Subsequently, the reaction mixture was cooled to room temperature, hydrazine monohydrate (116 µL) was added, and the mixture was stirred at 100° C. for 3 hours. The reaction mixture was cooled to room temperature, water and a 1 M-aqueous sodium hydroxide solution were added to adjust the mixture to around neutrality. Then, the mixture was extracted twice with ethyl acetate, and the organic layer obtained was washed with brine, and then dried over anhydrous sodium sulfate. After filtration, the solvent was distilled off under reduced pressure, and the residue obtained was sequentially purified by silica gel column chromatography (dichloromethane/methanol) and reverse phase HPLC. The racemate obtained was subjected to optical resolution using two Daicel Corporation CHIRALFLASH® IC (20 µm, 30 mmφ×100 mmL) connected [mobile phase: n-hexane/tetrahydrofuran/ethanol=72/24/2 to 72/24/5 (0 to 60 minutes), flow rate: 14 mL/minute, temperature: room temperature], and the fraction eluted earlier in the main peaks (the retention time in two columns connected: 21 minutes) was solidified with an n-hexane-ethyl acetate-diethyl ether mixed solution to obtain the title compound (80 mg).

$^1$H-NMR (DMSO-D$_6$) δ: 1.64 (3H, t, J=19.2 Hz), 2.89-3.03 (1H, m), 4.03-4.29 (1H, m), 6.00 (1H, s), 6.95-7.10 (3H, m), 7.12-7.36 (4H, m), 7.53 (2H, s), 7.84 (1H, s), 11.82 (1H, br s), 14.26 (1H, br s), MS (m/z): 639 (M+H)$^+$, [α]$^{20}_D$: −264 (c=1.01, MeOH).

In the process of the optical resolution in Example 42, (+)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one was obtained from the fraction eluted later in the main peaks ($^1$H-NMR: the same as the compound of Example 42, [α]$^{20}_D$: +258 (c=1.00, MeOH), IC$_{50}$ in Test Example 1: >5 uM).

Absolute Configuration

The absolute configuration of the compound of Example 42 was confirmed to be the configuration represented by formula (13A) by the methods shown in (i) to (iv). (i) Diastereomeric salts were obtained from the synthesis intermediate obtained in the synthesis process of Example 42 and a commercially available optically active compound, (ii) the single crystal of one diastereomeric salt was subjected to single crystal X-ray crystallography to determine the absolute configuration of this diastereomeric salt, (iii) this diastereomeric salt was converted to a free intermediate, and then the remaining steps in Example 42 were performed, and (iv) $^1$H-NMR and the retention times in the chiral column were compared using the compound of Example 42 as a standard.

[Formula 1]

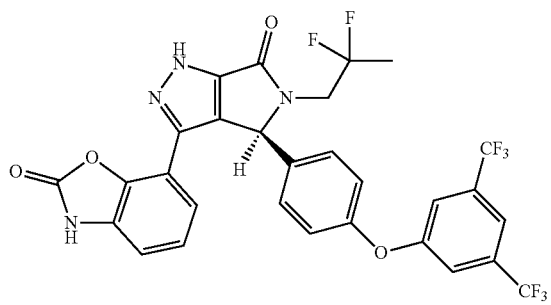

(13A)

The name of the compound represented by formula (13A) is

7-[(4S)-4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one.

As used herein, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one and 7-[(4S)-4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one indicate the same compound.

Tautomer

The compound obtained in a similar manner as Example 42 was subjected to single crystal X-ray crystallography, so that it was found that the compound of Example 42 shows a structure represented by formula (13B):

[Formula 2]

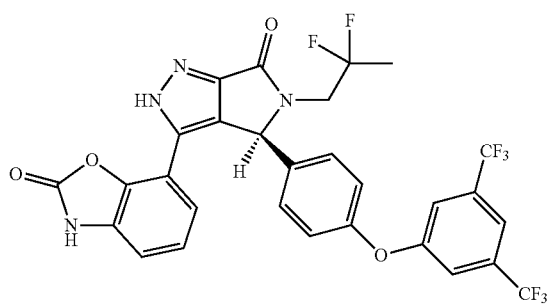

(13B)

in the single crystal. The name of the compound represented by formula (13B) is 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one.

The compound represented by formula (13B):

[Formula 3]

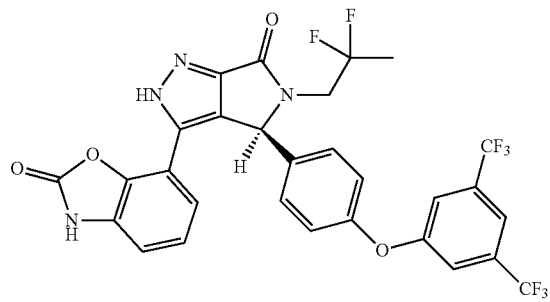

(13B)

and the compound represented by formula (13A):

[Formula 4]

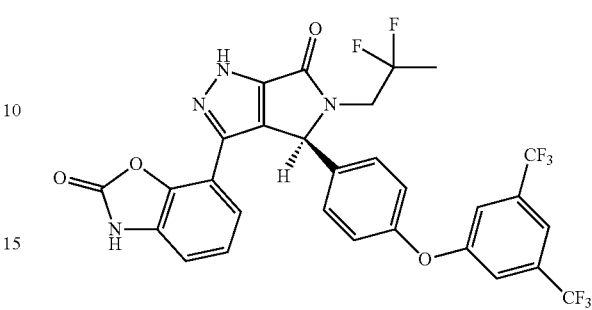

(13A)

are in a tautomeric relationship.

In general, tautomers may isomerize into each other depending on the temperature, pH, liquid phase/solid phase, and when the tautomers are solutions, depending on the type of the solvent, and therefore, it is considered that the compound represented by formula (13B) may isomerize into the compound represented by formula (13A) according to the changes in the above various physicochemical conditions.

The same procedure as that in Example 42 was performed to synthesize the following compounds (Table 6-1 to Table 6-4).

TABLE 6-1

| Example No | Manufacturing raw material | Structure of synthesized compound |
|---|---|---|
| 43 | see Reference Example 36 | |
| 44 | see Reference Example 37 | |

TABLE 6-1-continued
| Example No | Manufacturing raw material | Structure of synthesized compound |
|---|---|---|
| 45 | 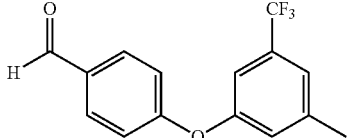<br>see Reference Example 38 | |
| 46 | 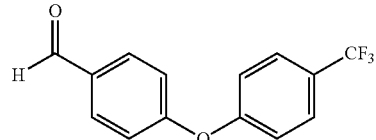<br>see Reference Example 39 | |
| 47 | 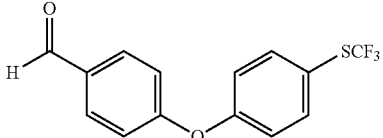<br>see Reference Example 40 | |
TABLE 6-2
| 48 | 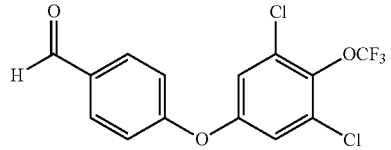 [SMILES: O=Cc1ccc(Oc2cc(Cl)c(OC(F)(F)F)c(Cl)c2)cc1]<br>see Reference Example 41 | |
| 49 | 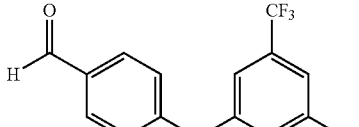<br>see Reference Example 42 | |

TABLE 6-2-continued

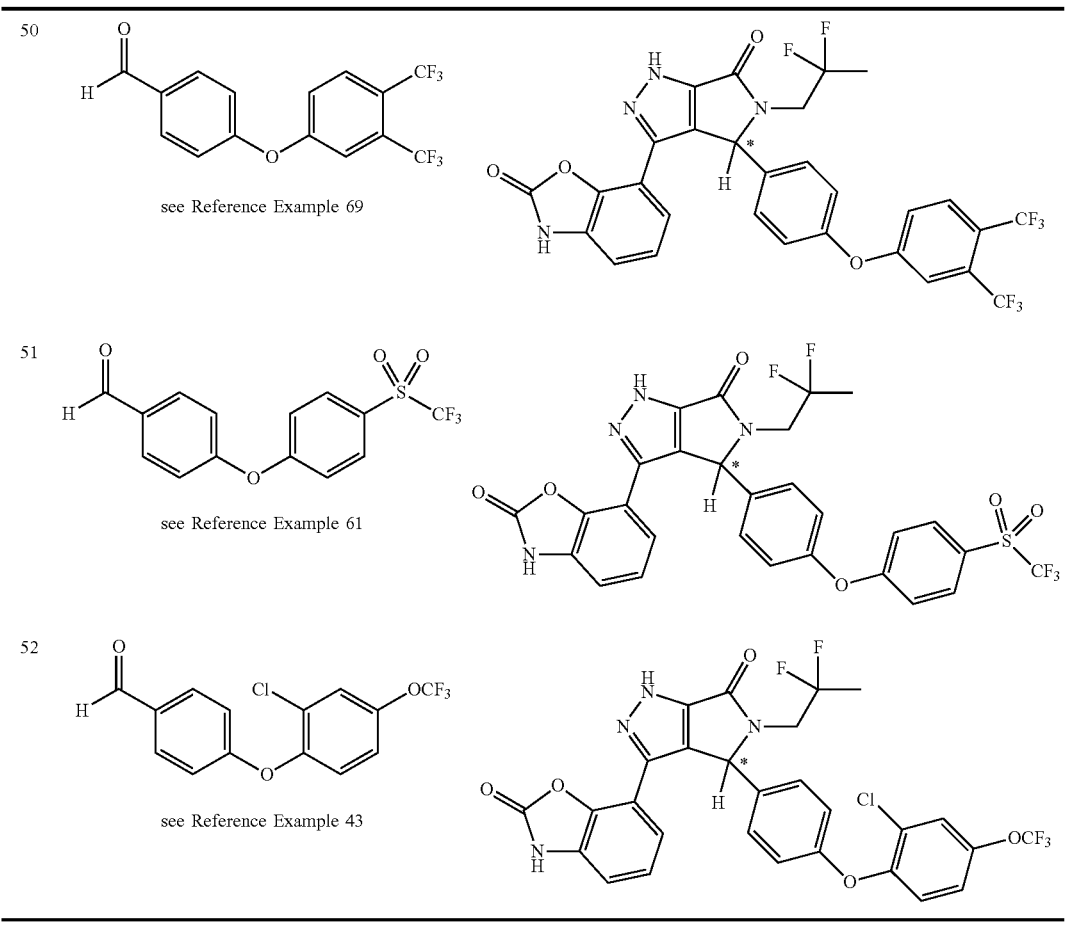

| 50 | see Reference Example 69 | |
| 51 | see Reference Example 61 | |
| 52 | see Reference Example 43 | |

TABLE 6-3

| Example No | Name of synthesized compound | Spectral data |
|---|---|---|
| 43 | 7-[5-(2,2-Difluoropropyl)-4-{4-[2-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one (enantiomer) | $^1$H-NMR (DMSO-$D_6$) δ: 1.65 (3H, t, J = 19.2 Hz), 2.11 (3H, s), 2.79-2.93 (1H, m), 4.04-4.28 (1H, m), 5.96 (1H, s), 6.80-7.36 (10H, m), 11.83 (1H, s)., 14.24 (1H, s)., MS (m/z): 601 (M + H)$^+$. |
| 44 | 7-[5-(2,2-Difluoropropyl)-6-oxo-4-(4-{[4-(trifluoromethoxy)phenyl]sulfanyl}phenyl)-1,4,5,6-tetrahydropyrrolo[3,4-c]pyrazol-3-yl]-1,3-benzoxazol-2(3H)-one (enantiomer) | $^1$H-NMR (DMSO-$D_6$) δ: 1.65 (3H, t, J = 19.1 Hz), 2.78-2.94 (1H, m), 4.03-4.29 (1H, m), 5.97 (1H, s), 6.98-7.37 (11H, m), 11.83 (1H, s), 14.26 (1H, s)., MS (m/z): 603 (M + H)$^+$. |
| 45 | 7-[5-(2,2-Difluoropropyl)-4-{4-[3-methyl-5-(trifluoromethyl)phenoxy]phenyl}-6-oxo-1,4,5,6-tetrahydropyrrolo[3,4-c]pyrazol-3-yl]-1,3-benzoxazol-2(3H)-one (enantiomer) | $^1$H-NMR (DMSO-$D_6$) δ: 1.65 (3H, t, J = 19.1 Hz), 2.33 (3H, s), 2.83-2.99 (1H, m), 4.04-4.30 (1H, m), 5.98 (1H, s), 6.91-7.36 (10H, m), 11.82 (1H, s), 14.24 (1H, s)., MS (m/z): 585 (M + H)$^+$. |
| 46 | 7-[5-(2,2-Difluoropropyl)-6-oxo-4-{4-[4-(trifluoromethyl)phenoxy]phenyl}-1,4,5,6-tetrahydropyrrolo[3,4-c]pyrazol-3-yl]-1,3-benzoxazol-2(3H)-one (enantiomer) | $^1$H-NMR (DMSO-$D_6$)δ: 1.66 (3H, t, J = 19.1 Hz), 2.83-2.98 (1H, m), 4.06-4.30 (1H, m), 5.99 (1H, s), 6.98-7.38 (9H, m), 7.71 (2H, d, J = 8.5 Hz), 11.84 (1H, s), 14.26 (1H, s)., MS (m/z): 571 (M + H)$^+$. |
| 47 | 7-[5(2,2-Difluoropropyl)-6-oxo-4-(4-{4-[(trifluoromethyl)sulfanyl]phenoxy}phenyl)-1,4,5,6-tetrahydropyrrolo[3,4-c]pyrazol-3-yl]-1,3-benzoxazol-2(3H)-one (enantiomer) | $^1$H-HMR (DMSO-$D_6$)δ: 1.66 (3H, t, J = 19.4 Hz), 2.83-2.98 (1H, m), 4.07-4.29 (1H, m), 5.99 (1H, s), 6.95-7.39 (9H, m), 7.68 (2H, d, J = 8.5 Hz), 11.84 (1H, s), 14.26 (1H, s)., MS (m/z): 603 (M + H)$^+$. |

TABLE 6-4

| | | |
|---|---|---|
| 48 | 7-[4-{4-[3,5-Dichloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.1 Hz), 2.89-3.02 (1H, m), 4.08-4.27 (1H, m), 5.99 (1H, s), 6.96-7.22 (6H, m), 7.23 (2H, s), 7.24-7.37 (1H, m), 11.81 (1H, s), 14.25 (1H, s)., MS (m/z): 655 (M + H)$^+$. |
| 49 | 7-[4-{4-[3-Chloro-5-(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.1 Hz), 2.86-3.03 (1H, m), 4.06-4.28 (1H, m), 5.99 (1H, s), 6.95-7.35 (9H, m), 7.61 (1H, s), 11.82 (1H, s), 14.25 (1H, s)., MS (m/z): 605 (M + H)$^+$. |
| 50 | 7-[4-{4-[3,4-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.66 (3H, t, J = 19.4 Hz), 2.80-3.02 (1H, m), 4.08-4.29 (1H, m), 6.01 (1H, s), 6.98-7.38 (8H, m), 7.44 (1H, d, J = 2.4 Hz,), 7.99 (1H, d, J = 9.1 Hz), 11.83 (1H, br s), 14.27 (1H, br s), MS (m/z): 639 (M + H)$^+$. |
| 51 | 7-[5-(2,2-Difluoropropyl)-6-oxo-4-{4[4-(trifluoromethanesulfonyl)phenoxy]phenyl}-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.67 (3H, t, J = 19.2 Hz) 2.87-3.00 (1H, m), 4.10-4.29 (1H, m), 6.03 (1H, s), 7.00-7.36 (9H, m), 8.08 (2H, d, J = 9.2 Hz), 11.85 (1H, s), 14.28 (H, s)., MS (m/z): 635 (M + H)$^+$. |
| 52 | 7-[4-{4-[2-Chloro-4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.2 Hz) 2.80-2.92 (1H, m), 4.07-4.27 (1H, m), 5.98, (1H, s), 6.90-7.39 (9H, m), 7.74 (1H, d, J = 2.4 Hz), 11.84 (1H, s), 14.25 (1H, s)., MS (m/z): 621 (M + H)$^+$. |

Example 53

(−)-7-{5-(2,2-Difluoropropyl)-4-[3-(4-fluorophenoxy)phenyl]-6-oxo-1,4,5,6-tetrahydropyrrolo[3,4-c]pyrazol-3-yl}-1,3-benzoxazol-2(3H)-one

[Chemical Formula 166]

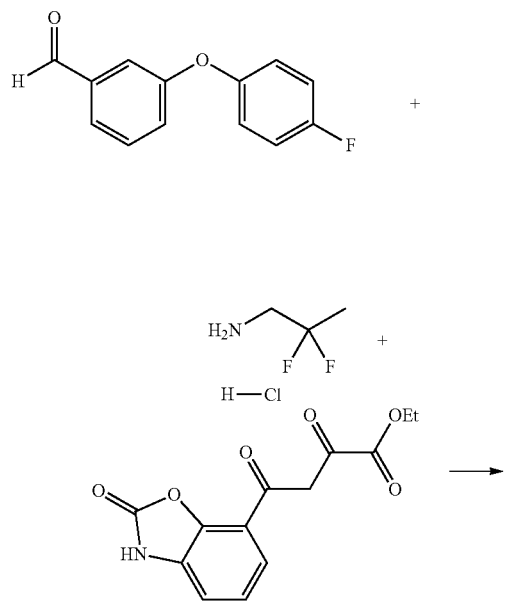

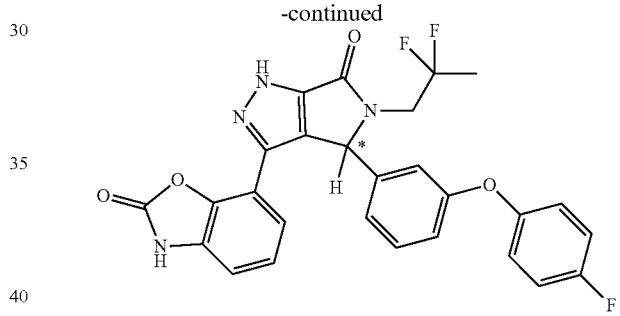

-continued

A mixture of the compound obtained in Reference Example 66 (101 mg), 2,2-difluoropropylamine hydrochloride (62.0 mg, CAS number: 868241-48-9), the compound obtained in step 2 of Reference Example 1 (68.0 mg), triethylamine (135 μL), and acetic acid (3.0 mL) was stirred at room temperature for 3 days. Then, hydrazine monohydrate (70.0 μL) was added, and the mixture was further stirred at 100° C. for 2 hours. The reaction mixture was cooled to room temperature, and then concentrated under reduced pressure, ethyl acetate was added to the residue, and the organic layer obtained was washed with a saturated aqueous sodium hydrogen carbonate solution, and then dried over anhydrous sodium sulfate. After filtration, the solvent was distilled off under reduced pressure, the residue obtained was purified by silica gel column chromatography (chloroform/ethyl acetate), and then solidified with an n-hexane-ethyl acetate mixed solution to obtain a racemate (102 mg). Subsequently, the racemate obtained (99.0 mg) was subjected to optical resolution by Daicel Corporation CHIRALPAK® IA (5 μm, 20 mmφ×250 mm) [mobile phase: n-hexane/tetrahydrofuran/ethanol=82/14/4, flow rate: 20 mL/minute, temperature: 35° C.], and the fraction eluted later in the main peaks was solidified with an n-hexane-ethyl acetate mixed solution to obtain the title compound (36.0 mg).

$^1$H-NMR (DMSO-D$_6$) δ: 1.64 (3H, t, J=19.3 Hz), 2.83-3.00 (1H, m), 4.05-4.30 (1H, m), 5.95 (1H, s), 6.70-6.94 (5H, m), 7.01-7.11 (1H, m), 7.12-7.22 (3H, m), 7.24-7.35 (2H, m), 11.82 (1H, br s), 14.24 (1H, br s), MS (m/z): 521 (M+H)$^+$, [α]$^{20}_D$: −296 (c=1.00, MeOH).

Example 54

7-{5-(2,2-Difluoropropyl)-4-[3-(4-fluorophenoxy)-5-(trifluoromethyl)phenyl]-6-oxo-1,4,5,6-tetrahydro-pyrrolo[3,4-c]pyrazol-3-yl}-1,3-benzoxazol-2(3H)-one (enantiomer)

[Chemical Formula 167]

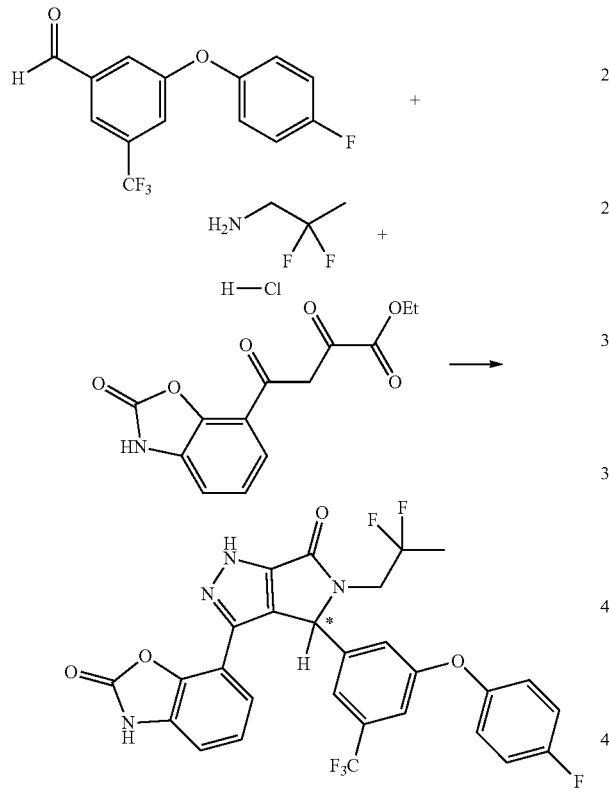

A mixture of the compound obtained in Reference Example 77 (150 mg), 2,2-difluoropropylamine hydrochloride (70 mg, CAS number: 868241-48-9), triethylamine (220 μL), and acetic acid (2.4 mL) was stirred at room temperature for 1 hour. Then, the compound obtained in step 2 of Reference Example 1 (133 mg) and acetic acid (1.2 mL) were added, and the mixture was further stirred at the same temperature for 2 hours, and then stirred at 90° C. for 7 hours and a half. Subsequently, the reaction mixture was cooled to room temperature, hydrazine monohydrate (70 μL) was added, and the mixture was stirred at 100° C. for 3 hours and a half. The reaction mixture was cooled to room temperature, water and a 1 M-aqueous sodium hydroxide solution were added to adjust the mixture to around neutrality. Then, the mixture was extracted with ethyl acetate, and the organic layer obtained was washed with brine and dried over anhydrous sodium sulfate. After filtration, the solvent was distilled off under reduced pressure, and the residue obtained was sequentially purified by silica gel column chromatography (dichloromethane/methanol) and reverse phase HPLC to obtain a racemate (154 mg). Subsequently, the racemate obtained (70 mg) was subjected to optical resolution by Daicel Corporation CHIRALPAK® IA (5 μm, 20 mmφ×250 mm) [mobile phase: n-hexane/tetrahydrofuran/ethanol=85/12/3, flow rate: 20 mL/minute, temperature: 35° C.], and the fraction eluted earlier in the main peaks was solidified with ethyl acetate-n-hexane-diethyl ether to obtain the title compound (28 mg).

$^1$H-NMR (DMSO-D$_6$) δ: 1.63 (3H, t, J=19.1 Hz), 3.01-3.12 (1H, m), 4.07-4.30 (1H, m), 6.05 (1H, s), 6.85-7.42 (10H, m), 11.86 (1H, s), 14.30 (1H, s), MS (m/z): 589 (M+H)$^m$.

Example 55

7-[5-(2,2-Difluoropropyl)-6-oxo-4-{3-[4-(trifluoromethoxy)phenoxy]phenyl}-1,4,5,6-tetrahydropyrrolo[3,4-c]pyrazol-3-yl]-1,3-benzoxazol-2(3H)-one (enantiomer)

[Chemical Formula 168]

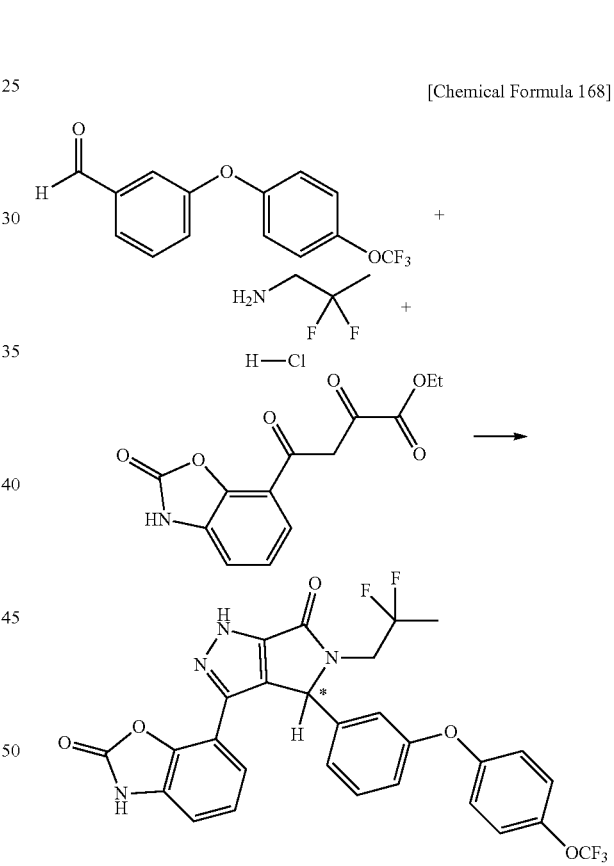

The compound obtained in Reference Example 70 (158 mg), 2,2-difluoropropylamine hydrochloride (80.0 mg, CAS number: 868241-48-9), and the compound obtained in step 2 of Reference Example 1 (130 mg) were used as manufacturing raw materials, and the same procedure as that in Example 54 was performed to obtain the title compound (21.0 mg) as a solid.

$^1$H-NMR (DMSO-D$_6$) δ: 1.64 (3H, t, J=19.0 Hz), 2.84-3.01 (1H, m), 4.09-4.29 (1H, m), 5.97 (1H, s), 6.78-7.22 (7H, m), 7.26-7.40 (4H, m), 11.81 (1H, br s), 14.25 (1H, br s), MS (m/z): 587 (M+H)$^+$.

Example 56

7-{5-(2,2-Difluoropropyl)-4-[3-(4-fluorophenoxy)phenyl]-6-oxo-1,4,5,6-tetrahydropyrrolo[3,4-c]pyrazol-3-yl}-5-fluoro-1,3-benzoxazol-2(3H)-one (enantiomer)

[Chemical Formula 169]

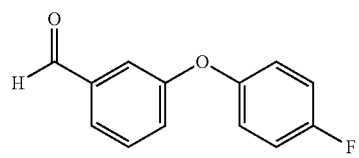

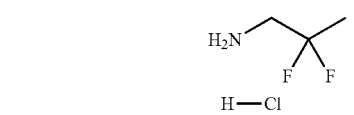

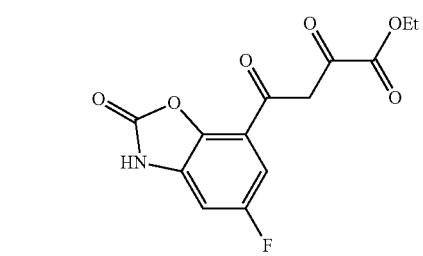

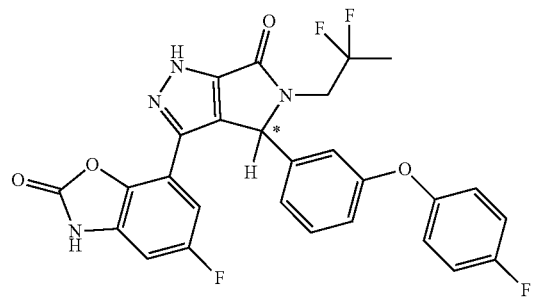

The compound obtained in Reference Example 66 (105 mg), 2,2-difluoropropylamine hydrochloride (64.0 mg, CAS number: 868241-48-9), and the compound obtained in step 3 of Reference Example 2 (110 mg) were used as manufacturing raw materials, and the same procedure as that in Example 54 was performed to obtain the title compound (37.0 mg) as a solid.

$^1$H-NMR (DMSO-D$_6$) δ: 1.64 (3H, t, J=19.3 Hz), 2.82-2.99 (1H, m), 4.07-4.31 (1H, m), 5.97 (1H, s), 6.72-6.94 (5H, m), 6.95-7.21 (4H, m), 7.30 (1H, t, J=8.0 Hz), 12.05 (1H, br s), 14.23-14.55 (1H, m), MS (m/z): 539 (M+H)$^+$.

Example 57

(−)-7-{4-[4-(4-Chlorophenoxy)phenyl]-5-(2,2-difluoropropyl)-6-oxo-1,4,5,6-tetrahydropyrrolo[3,4-c]pyrazol-3-yl}-1,3-benzoxazol-2(3H)-one

[Chemical Formula 170]

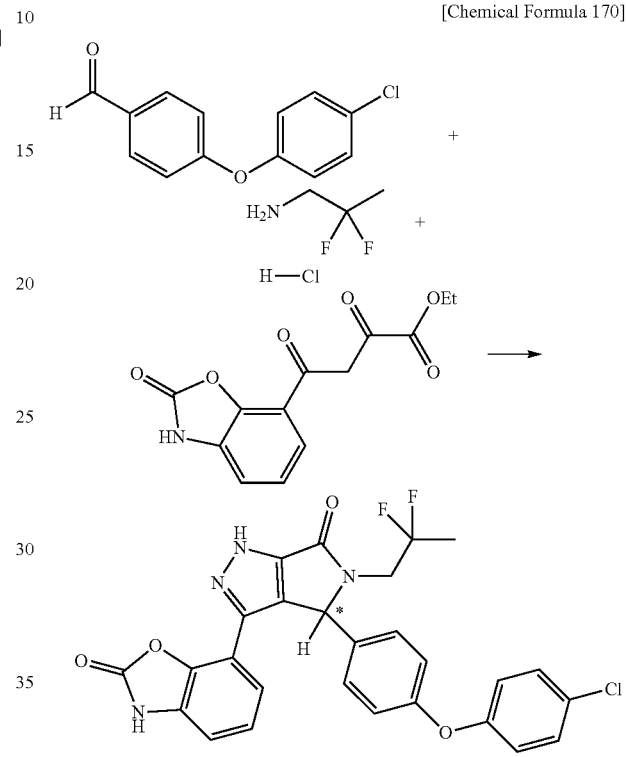

A mixture of 4-(4-chlorophenoxy)benzaldehyde (126 mg, CAS number: 61343-99-5), 2,2-difluoropropylamine hydrochloride (72.0 mg, CAS number: 868241-48-9), the compound obtained in step 2 of Reference Example 1 (100 mg), triethylamine (150 μL), and acetic acid (2.4 mL) was stirred at room temperature for 7 hours, and then hydrazine monohydrate (52.0 μL) was added, and the mixture was further stirred at 90° C. for 2 hours and a half. The reaction mixture was cooled to room temperature, and then diluted with ethyl acetate, the organic layer obtained was washed with water, and the solvent was distilled off under reduced pressure. The residue obtained was sequentially purified by silica gel column chromatography (n-hexane/ethyl acetate) and reverse phase HPLC, and then solidified with ethyl acetate-n-hexane to obtain a racemate (27.9 mg). Subsequently, the racemate obtained (22.8 mg) was subjected to optical resolution [mobile phase: n-hexane/tetrahydrofuran/ethanol=80/16/4, flow rate: 20 mL/minute, temperature: 40° C.] by Daicel Corporation CHIRALPAK® IC (5 μm, 20 mmφ×250 mm), and the fraction eluted earlier in the main peaks (retention time: 12.8 minutes) was purified by silica gel column chromatography (n-hexane/ethyl acetate), and then solidified with an n-hexane-ethyl acetate mixed solution to obtain the title compound (10.4 mg).

$^1$H-NMR (DMSO-D$_6$) δ: 1.66 (3H, t, J=19.5 Hz), 2.79-2.92 (1H, m), 4.09-4.26 (1H, m), 5.97 (1H, s), 6.91 (2H, d, J=9.2 Hz), 6.97 (2H, J=9.2 Hz), 7.01-7.21 (4H, m), 7.25-

7.35 (1H, m), 7.40 (2H, d, J=9.2 Hz), 11.84 (1H, br s), 12.24 (1H, br s), MS (m/z): 537 (M+H)$^+$, [α]$^{20}_D$: −324 (c=1.01, MeOH).

Example 58

(−)-7-{4-[4-(4-Chlorophenoxy)-2-fluorophenyl]-5-(2,2-difluoropropyl)-6-oxo-1,4,5,6-tetrahydropyrrolo[3,4-c]pyrazol-3-yl}-1,3-benzoxazol-2(3H)-one

[Chemical Formula 171]

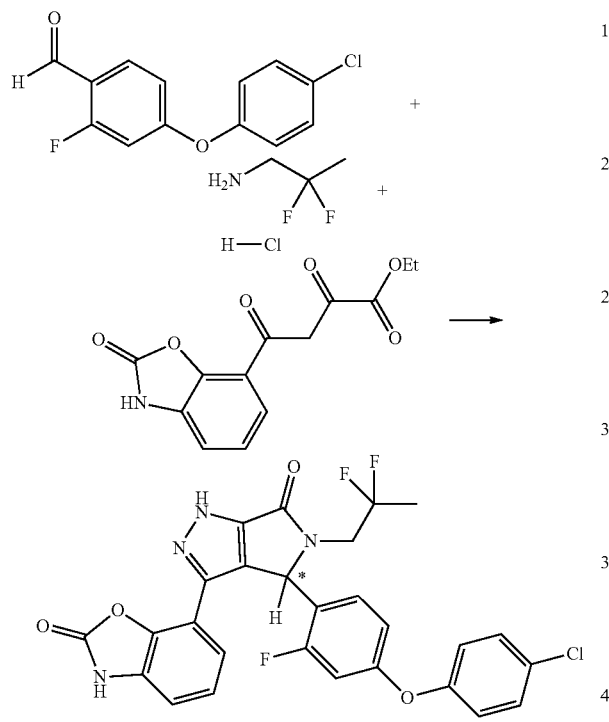

A mixture of the compound obtained in Reference Example 67 (376 mg), 2,2-difluoropropylamine hydrochloride (296 mg, CAS number: 868241-48-9), triethylamine (314 μL), and ethanol (4.0 mL) was stirred at room temperature for 3 hours. The reaction mixture was diluted with ethyl acetate, the organic layer obtained was sequentially washed with water, a saturated aqueous sodium hydrogen carbonate solution, and brine, and then dried over anhydrous sodium sulfate. After filtration, the solvent was distilled off under reduced pressure, and a mixture of the oil obtained (499 mg), the compound obtained in step 2 of Reference Example 1 (150 mg), and acetic acid (4.0 mL) was stirred at room temperature for 2 days. Then, hydrazine monohydrate (131 μL) was added, and the mixture was further stirred at 100° C. for 7 hours. The reaction mixture was cooled to room temperature, toluene was added, and then the mixture was concentrated under reduced pressure. Water was added to the residue obtained, and the mixture was extracted with ethyl acetate. The organic layer obtained was washed with a saturated aqueous sodium hydrogen carbonate solution and brine, and then dried over anhydrous sodium sulfate. After filtration, the solvent was distilled off under reduced pressure, the residue was purified by silica gel column chromatography (n-hexane/ethyl acetate), and then the solid obtained was washed with an n-hexane-ethyl acetate mixed solution to obtain a racemate (200 mg). Subsequently, the racemate obtained (168 mg) was subjected to optical resolution [mobile phase: n-hexane/tetrahydrofuran/ethanol=80/16/4, flow rate: 20 mL/minute, temperature: 40° C.] by Daicel Corporation CHIRALPAK® IC (5 μm, 20 mmφ×250 mm), and the fraction eluted earlier in the main peaks (retention time: 19 minutes) was solidified with an n-hexane-ethyl acetate mixed solution to obtain the title compound (63.0 mg).

$^1$H-NMR (DMSO-D$_6$) δ: 1.65 (3H, t, J=19.1 Hz), 2.94-3.08 (1H, m), 4.07-4.28 (1H, m), 6.15 (1H, s), 6.69-6.76 (1H, m), 6.78-6.86 (1H, m), 7.00-7.33 (6H, m), 7.44 (2H, d, J=8.6 Hz), 11.81 (1H, br s), 14.21 (1H, br s), MS (m/z): 555 (M+H)$^+$, [α]$^{20}_D$: −273 (c=0.919, MeOH).

Example 59

7-[4-[4-(3,4-Dichlorophenoxy)phenyl]-5-(2,2-difluoropropyl)-6-oxo-1,4,5,6-tetrahydropyrrolo[3,4-c]pyrazol-3-yl]-1,3-benzoxazol-2(3H)-one (enantiomer)

[Chemical Formula 172]

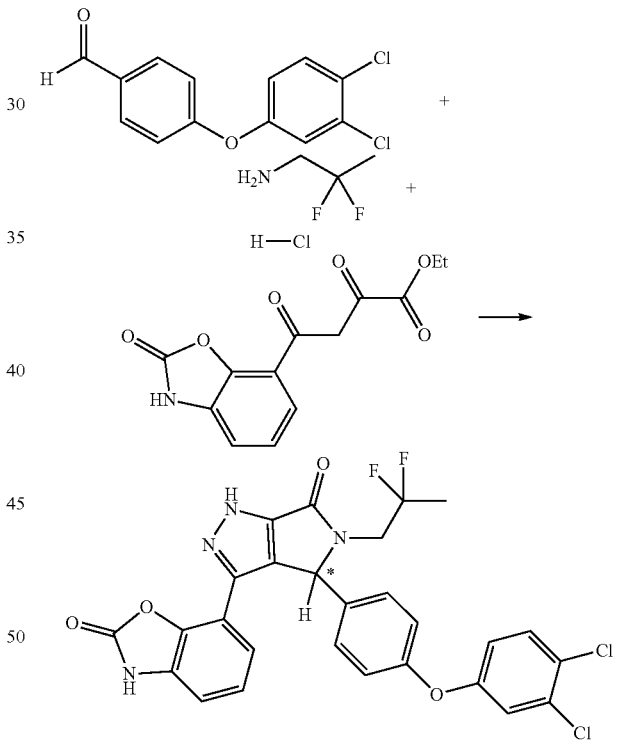

A mixture of the compound obtained in Reference Example 44 (128 mg), 2,2-difluoropropylamine hydrochloride (68.0 mg, CAS number: 868241-48-9), the compound obtained in step 2 of Reference Example 1 (111 mg), triethylamine (222 μL), and acetic acid (3.0 mL) was stirred at room temperature for 5 days. Then, hydrazine monohydrate (58.0 μL) was added, and the mixture was further stirred at 100° C. for 3 hours. The reaction mixture was cooled to room temperature and concentrated under reduced pressure, ethyl acetate was added to the residue, and the organic layer obtained was washed with a saturated aqueous sodium hydrogen carbonate solution, and then dried over anhydrous sodium sulfate. After filtration, the solvent was distilled off under reduced pressure, the residue was purified by silica gel column chromatography (chloroform/ethyl acetate) to obtain an intermediate. The intermediate obtained was dissolved in a tetrahydrofuran (2.0 mL)-ethanol (2.0 mL) mixed solution, a 1 M-aqueous sodium hydroxide solution (1.5 mL) was added at room temperature, and the mixture was stirred at the same temperature for 2 days. To the reaction mixture, 1 M-hydrochloric acid was added, the mixture was extracted with ethyl acetate, and the organic layer obtained was washed with a saturated aqueous sodium hydrogen carbonate solution, and then dried over anhydrous sodium sulfate. After filtration, the solvent was distilled off under reduced pressure, the racemate obtained (110 mg) was subjected to optical resolution [mobile phase: n-hexane/tetrahydrofuran/ethanol=80/16/4, flow rate: 20 mL/minute, temperature: 40° C.] by Daicel Corporation CHIRALPAK® IC (5 μm, 20 mmφ×250 mm), and the fraction eluted earlier in the main peaks was solidified with an n-hexane-ethyl acetate mixed solution to obtain the title compound (47.0 mg).

$^1$H-NMR (DMSO-D$_6$) δ: 1.65 (3H, t, J=19.0 Hz), 2.82-2.97 (1H, m), 4.08-4.26 (1H, m), 5.98 (1H, s), 6.95 (1H, dd, J=8.6, 2.5 Hz), 6.97 (2H, J=8.6 Hz), 7.00-7.20 (4H, m), 7.23 (1H, d, J=2.4 Hz), 7.25-7.34 (1H, m), 7.60 (1H, d, J=8.6 Hz), 11.82 (1H, br s), 14.25 (1H, br s), MS (m/z): 571 (M+H)$^+$.

Example 60

7-{4-[3-Chloro-4-(4-chlorophenoxy)phenyl]-5-(2,2-difluoropropyl)-6-oxo-1,4,5,6-tetrahydropyrrolo[3,4-c]pyrazol-3-yl}-1,3-benzoxazol-2-(3H)-one (enantiomer)

[Chemical Formula 173]

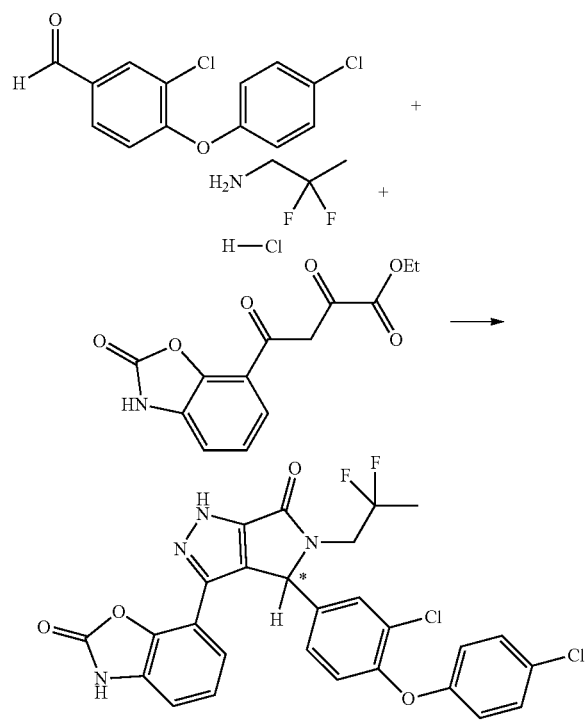

The compound obtained in Reference Example 29 (150 mg), 2,2-difluoropropylamine hydrochloride (80.0 mg, CAS number: 868241-48-9), and the compound obtained in step 2 of Reference Example 1 (130 mg) were used as manufacturing raw materials, and the same procedure as that in Example 59 was performed to obtain the title compound (13.0 mg).

$^1$H-NMR (DMSO-D$_6$) δ: 1.66 (3H, t, J=19.0 Hz), 2.92-3.09 (1H, m), 4.08-4.29 (1H, m), 5.98 (1H, s), 6.85-7.23 (6H, m), 7.28-7.46 (4H, m), 11.85 (1H, br s), 14.28 (1H, br s), MS (m/z): 571 (M+H)$^+$.

Example 61

7-[4-{4-[3-Chloro-4-(trifluoromethoxy)phenoxy]-3-(trifluoromethyl)phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer)

[Chemical Formula 174]

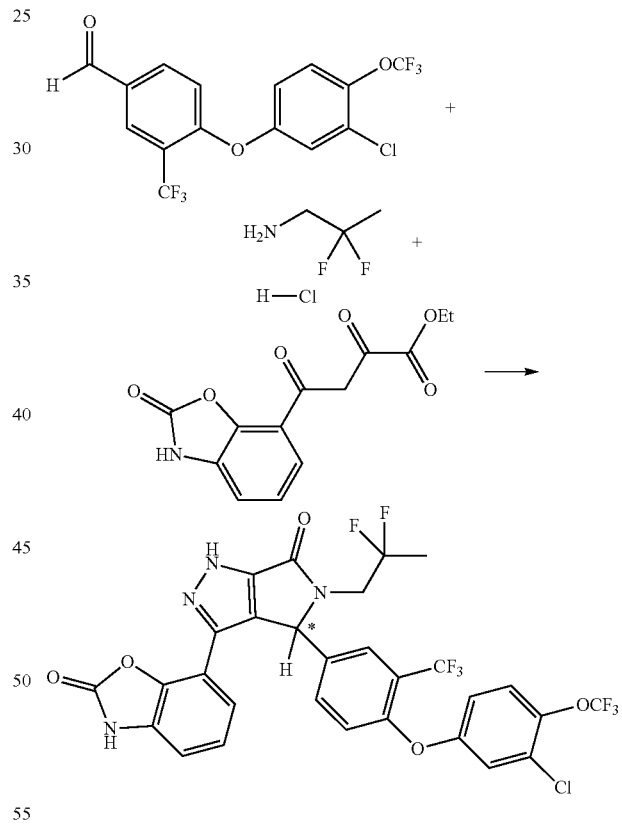

The compound obtained in Reference Example 45 (278 mg), 2,2-difluoropropylamine hydrochloride (95.0 mg, CAS number: 868241-48-9), and the compound obtained in step 2 of Reference Example 1 (200 mg) were used as manufacturing raw materials, and the same procedure as that in Example 59 was performed to obtain the title compound (47.0 mg).

$^1$H-NMR (DMSO-D$_6$) δ: 1.66 (3H, t, J=19.4 Hz), 2.98-3.15 (1H, m), 4.07-4.30 (1H, m), 6.08 (1H, s), 6.98-7.42 (7H, m), 7.58 (1H, d, J=9.1 Hz), 7.69 (1H, s), 11.87 (1H, br s), 14.32 (1H, br s), MS (m/z): 689 (M+H)$^+$.

Example 62

7-[4-{4-[3,5-Bis(trifluoromethyl)phenoxy]-2-fluoro-5-methylphenyl}-5-(2,2-difluoropropyl)-6-oxo-1,4,5,6-tetrahydropyrrolo[3,4-c]pyrazol-3-yl]-1,3-benzoxazol-2(3H)-one (enantiomer)

[Chemical Formula 175]

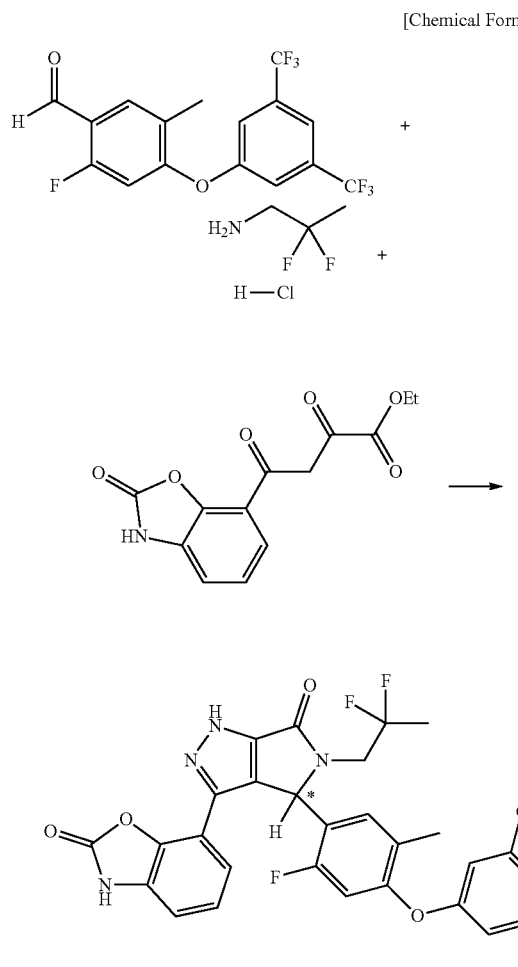

A mixture of the compound obtained in Reference Example 71 (268 mg), 2,2-difluoropropylamine hydrochloride (123 mg, CAS number: 868241-48-9), triethylamine (300 μL), and acetic acid (3.0 mL) was stirred at room temperature for 2 hours. Then, the compound obtained in step 2 of Reference Example 1 (200 mg) was added, and the mixture was further stirred at 80° C. for 24 hours. Subsequently, the reaction mixture was cooled to room temperature, hydrazine monohydrate (105 μL) was added, and the mixture was stirred at 100° C. for 3 hours. The reaction mixture was cooled to room temperature, and then concentrated under reduced pressure, ethyl acetate was added to the residue, and the organic layer obtained was washed with a saturated aqueous sodium hydrogen carbonate solution, and then dried over anhydrous sodium sulfate. After filtration, the solvent was distilled off under reduced pressure, the residue obtained was sequentially purified by silica gel column chromatography (chloroform/methanol) and reverse phase HPLC. The racemate obtained was subjected to optical resolution using two Daicel Corporation CHIRAL-FLASH® IC (20 μm, 30 mmφ×100 mmL) connected [mobile phase: n-hexane/tetrahydrofuran/ethanol=73/24/3, flow rate: 14 mL/minute, temperature: room temperature], and the fraction eluted earlier in the main peaks was purified by silica gel column chromatography (chloroform/methanol), and then solidified with an n-hexane-ethyl acetate mixed solution to obtain the title compound (29.0 mg).

$^1$H-NMR (DMSO-D$_6$) δ: 1.64 (3H, t, J=19.4 Hz), 2.04 (3H, s), 3.08-3.24 (1H, m), 4.06-4.27 (1H, m), 6.14 (1H, s), 6.94 (1H, d, J=10.9 Hz), 6.99-7.39 (4H, m), 7.49 (2H, s), 7.85 (1H, s), 11.84 (1H, br s), 14.23 (1H, br s), MS (m/z): 671 (M+H)$^+$.

The same procedure as that in Example 62 was performed to synthesize the following compounds (Table 7-1 to Table 7-4).

TABLE 7-1

| Example No | Manufacturing raw material | Structure of synthesized compound |
|---|---|---|
| 63 | see Reference Example 72 | |

TABLE 7-1-continued
| Example No | Manufacturing raw material | Structure of synthesized compound |
|---|---|---|
| 64 | 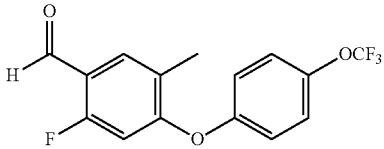 [SMILES: Cc1cc(C=O)c(F)cc1Oc1ccc(OC(F)(F)F)cc1] see Reference Example 73 | |
| 65 | 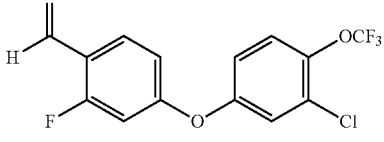 see Reference Example 78 | |
| 66 | 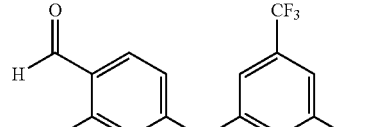 see Reference Example 74 | |
| 67 | 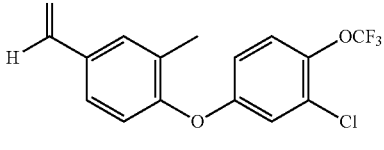 see Reference Example 46 | |
TABLE 7-2
| 68 | 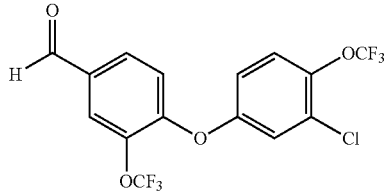 [SMILES: O=Cc1ccc(Oc2ccc(OC(F)(F)F)c(Cl)c2)c(OC(F)(F)F)c1] see Reference Example 47 | |

TABLE 7-2-continued

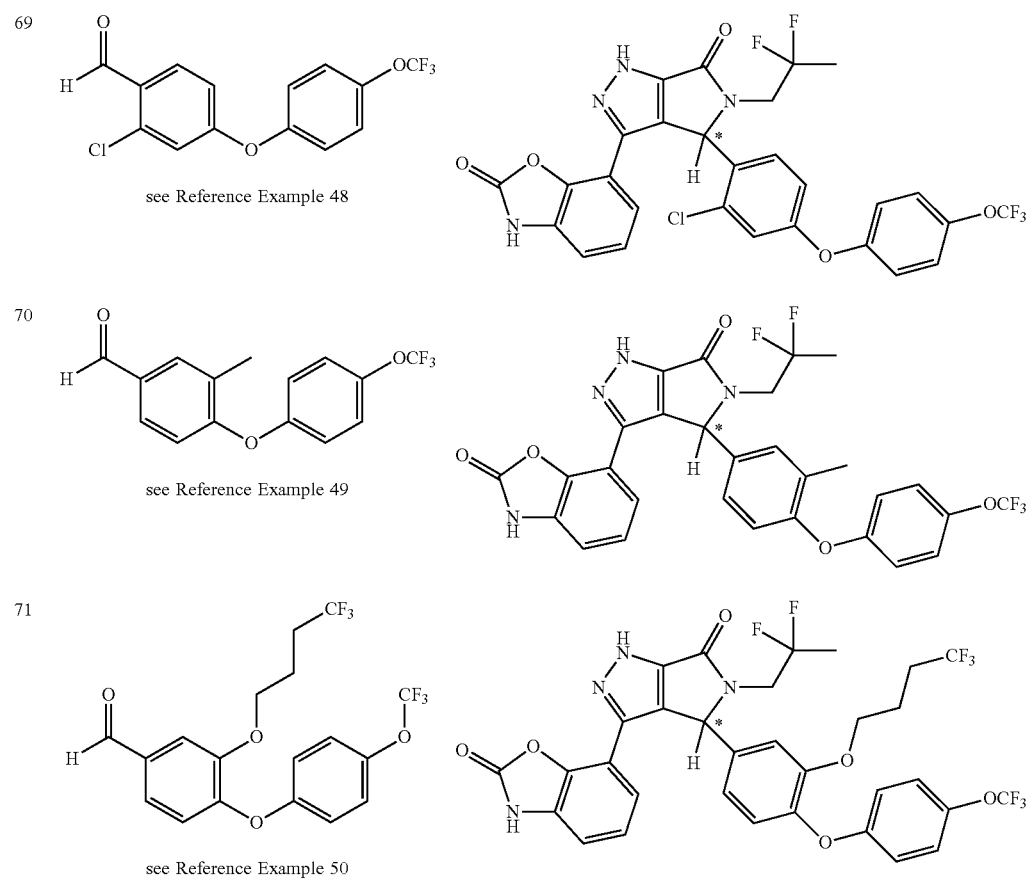

TABLE 7-3

| Example No | Name of synthesized compound | Spectral data |
|---|---|---|
| 63 | 7-[5-(2,2-Difluoropropyl)-4-{2-fluoro-4-[4-(trifluoromethoxy)phenoxy]phenyl}-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.3 Hz), 2.88-3.12 (1H, m), 4.04-4.29 (1H, m), 6.16 (1H, s), 6.76 (1H, dd, J = 8.6, 2.5 Hz), 6.86 (1H, dd, J = 12.3, 2.5 Hz), 6.99-7.32 (6H, m), 7.39 (2H, d, J = 9.2 Hz), 11.82 (1H, br s), 14.21 (1H, br s)., MS (m/z): 605 (M + H)$^+$. |
| 64 | 7-[5-(2,2-Difluoropropyl)-4-{2-fluoro-5-methyl-4-[4-(trifluoromethoxy)phenoxy]phenyl}-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$): δ 1.66 (3H, t, J = 19.1 Hz), 2.04 (3H, s), 2.98-3.16 (1H, m), 4.07-4.32 (1H, m), 6.12 (1H, s), 6.69 (1H, d, J = 10.9 Hz), 6.98 (2H, d, J = 9.1 Hz), 7.01-7.32 (4H, m), 7.36 (2H, d, J = 9.1 Hz), 11.84 (1H, br s), 14.21 (1H, br s)., MS (m/z): 619 (M + H)$^+$. |
| 65 | 7-[4-{4-[3-Chloro-4-(trifluoromethoxy)phenoxy]-2-fluorophenyl}-5-(2,2-difluoropropyl)-6-oxo-1,4,5,6-tetrahydropyrrolo[3,4-c]pyrazol-3-yl]-1,-benzoxazol-2(3H)-one (enantiomer) | $^1$H-NMR (DMSO-D$_6$) δ: 1.65 (3H, t, J = 19.1 Hz), 2.95-3.15 (1H, m), 4.06-4.30 (1H, m), 6.17 (1H, s), 6.80-6.87 (1H, m), 6.92-7.00 (1H, m), 7.02-7.32 (5H, m), 7.36 (1H, d, J = 2.4 Hz), 7.57 (1H, d, J = 9.1 Hz), 11.82 (1H, br s), 14.22 (1H, br s)., MS (m/z): 639 (M + H)$^+$. |
| 66 | 7-[4-{4-[3,5-Bis(trifluoromethyl)phenoxy]-2-fluorophenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.63 (3H, t, J = 19.1 Hz), 3.04-3.19 (1H, m), 4.06-4.25 (1H, m), 6.18 (1H, s), 6.86-6.94 (1H, m), 7.00-7.34 (5H, m), 7.65 (2H, s), 7.89 (1H, s), 11.81 (1H, br s), 14.23 (1H, br s)., MS (m/z): 657 (M + H)$^+$. |
| 67 | 7-[4-{4-[3-Chloro-4-(trifluoromethoxy)phenoxy]-3-methylphenyl}-5-(2,2-difluoropropyl)-6-oxo-1,4,5,6- | $^1$H-NMR (DMSO-D$_6$) δ: 1.66 (3H, t, J = 19.1 Hz), 2.05 (3H, s), 2.85-3.04 (1H, m), 4.06-4.32 (1H, m), 5.95 (1H, s), 6.82-6.92 (2H, |

TABLE 7-3-continued

| Example No | Name of synthesized compound | Spectral data |
|---|---|---|
| | tetrahydropyrrolo[3,4-c]pyrazol-3-yl]-1,3-benzoxazol-2(3H)-one (enantiomer) | m), 6.93-7.38 (6H, m)., 7.51 (1H, d, J = 9.1 Hz), 11.83 (1H, br s), 14.24 (1H, br s)., MS (m/z): 635 (M + H)$^+$. |

TABLE 7-4

| | | |
|---|---|---|
| 68 | 7-[4-{4-[3-Chloro-4-(trifluoromethoxy)phenoxy]-3-(trifluoromethoxy)phenoxy}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.1 Hz), 2.98-3.16 (1H, m), 4.08-4.29 (1H, m), 6.03 (1H, s), 6.94-7.48 (8H, m), 7.57 (1H, d, J = 9.1 Hz), 11.86 (1H, br s), 14,29 (1H, br s)., MS (m/z): 705 (M + H)$^+$. |
| 69 | 7-[4-{2-Chloro-4-[4-(trifluoromethoxy)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.65 (3H, t, J = 19.1 Hz), 2.87-3,05 (1H, m), 4.00-4.29 (1H, m), 6.09 (0.42H, s), 6.40 (0.58H, s), 6.69-7.77 (10H, m), 11.65-11.97 (1H, m), 14.03-14.44 (1H, m)., MS (m/z): 621 (M + H)$^+$. |
| 70 | 7-[5-(2,2-Difluoropropyl)-4-{3-methyl-4-[4-(trifluoromethoxy)phenoxy]phenyl}-6-oxo-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.66 (3H, t, J = 19.2 Hz), 2.05 (3H, s), 2.84-2.99 (1H, m), 4.06-4.28 (1H, m), 5.94 (1H, s), 6.76-7.39 (10H, m), 11.83 (1H, br s), 14.24 (1H, br s)., MS (m/z): 601 (M + H)$^+$. |
| 71 | 7-[5-(2,2-Difluoropropyl)-6-oxo-4-{3-(4,4,4-trifluorobutoxy)-4-[4-(trifluoromethoxy)phenoxy]phenyl}-1,4,5,6-tetrahydropyrrolo[3,4-c]pyrazol-3-yl]-1,3-benzoxazol-2(3H)-one (enantiomer) | $^1$H-NMR (DMSO-D$_6$) δ: 1.56-1.74 (5H, m), 1.75-1.94 (2H, m), 2.94-3.10 (1H, m), 3.84 (2H, t, J = 5.5 Hz), 4.08-4.31 (1H, m), 5.97 (1H, s), 6.65-6.74 (1H, m), 6.79 (2H, d, J = 9.1 Hz), 6.84-6.96 (1H, m), 7.00-7.41 (6H, m), 11.86 (1H, br s), 14.25 (1H, br s)., MS (m/z): 713 (M + H)$^+$. |

Example 72

7-[5-(2,2-Difluoropropyl)-6-oxo-4-(2-phenoxypyridin-4-yl)-1,4,5,6-tetrahydropyrrolo[3,4-c]pyrazol-3-yl]-1,3-benzoxazol-2(3H)-one

[Chemical Formula 176]

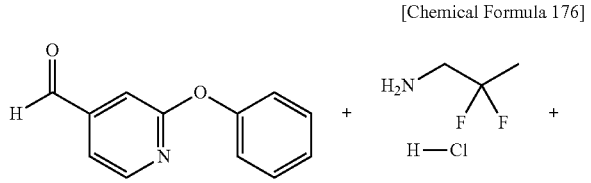

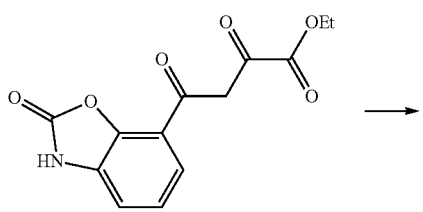

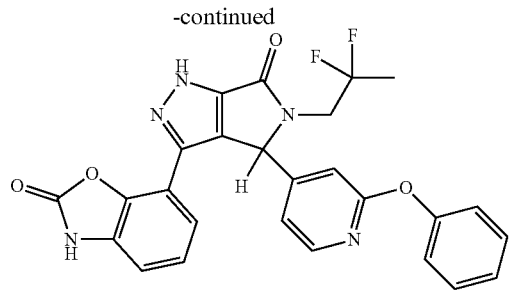

-continued

A mixture of the compound obtained in Reference Example 56 (108 mg), 2,2-difluoropropylamine hydrochloride (118 mg, CAS number: 868241-48-9), sodium carbonate (506 mg), and dichloromethane (5.0 mL) was stirred at room temperature for 27 hours. After insoluble materials were filtered off, the solvent was distilled off under reduced pressure, and a mixture of the oil obtained, the compound obtained in step 2 of Reference Example 1 (100 mg), and acetic acid (3.0 mL) was stirred at 90° C. for 1 hour and a half. Subsequently, the reaction mixture was cooled to room temperature, hydrazine monohydrate (52.0 µL) was added, and the mixture was stirred at 90° C. for 7 hours. The reaction mixture was cooled to room temperature and concentrated under reduced pressure, chloroform was added to the residue, and the organic layer obtained was washed with a saturated aqueous sodium hydrogen carbonate solution, and then dried over anhydrous sodium sulfate. After filtration, the solvent was distilled off under reduced pressure, the residue obtained was purified by silica gel column chromatography (chloroform/methanol and chloroform/ethyl acetate), and then solidified with an n-hexane-ethyl acetate mixed solution to obtain the title compound (111 mg).

$^1$H-NMR (DMSO-D$_6$) δ: 1.66 (3H, t, J=19.2 Hz), 2.94-3.11 (1H, m), 4.11-4.33 (1H, m), 6.01 (1H, s), 6.72-6.88 (2H, m), 6.97-7.24 (5H, m), 7.32-7.44 (3H, m), 8.02 (1H, d, J=4.9 Hz), 11.88 (1H, br s), 14.33 (1H, br s), MS (m/z): 504 (M+H)$^+$.

Example 73

7-{5-(2,2-Difluoropropyl)-4-[2-(4-fluorophenoxy)pyrimidine-4-yl]-6-oxo-1,4,5,6-tetrahydropyrrolo[3,4-c]pyrazol-3-yl}-1,3-benzoxazol-2(3H)-one

[Chemical Formula 177]

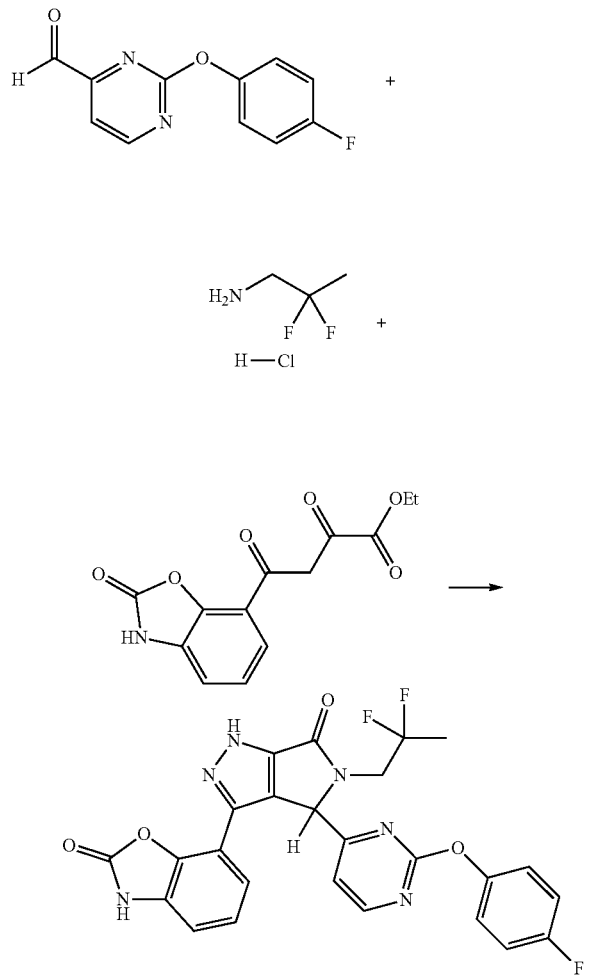

The compound obtained in Reference Example 60 (107 mg), 2,2-difluoropropylamine hydrochloride (130 mg, CAS number: 868241-48-9), and the compound obtained in step 2 of Reference Example 1 (110 mg) were used as manufacturing raw materials, and the same procedure as that in Example 72 was performed to obtain the title compound (101 mg) as a solid.

$^1$H-NMR (DMSO-D$_6$) δ: 1.63 (3H, t, J=19.2 Hz), 3.10-3.25 (1H, m), 4.08-4.27 (1H, m), 6.03 (1H, s), 7.00-7.29 (7H, m), 7.36-7.47 (1H, m), 8.56 (1H, d, J=4.9 Hz), 11.86 (1H, br s), 14.27 (1H, br s), MS (m/z): 523 (M+H)$^+$.

Example 74

7-{5-(2,2-Difluoropropyl)-4-[5-(4-fluorophenoxy)pyrazine-2-yl]-6-oxo-1,4,5,6-tetra hydropyrrolo[3,4-c]pyrazol-3-yl}-1,3-benzoxazol-2(3H)-one

[Chemical Formula 178]

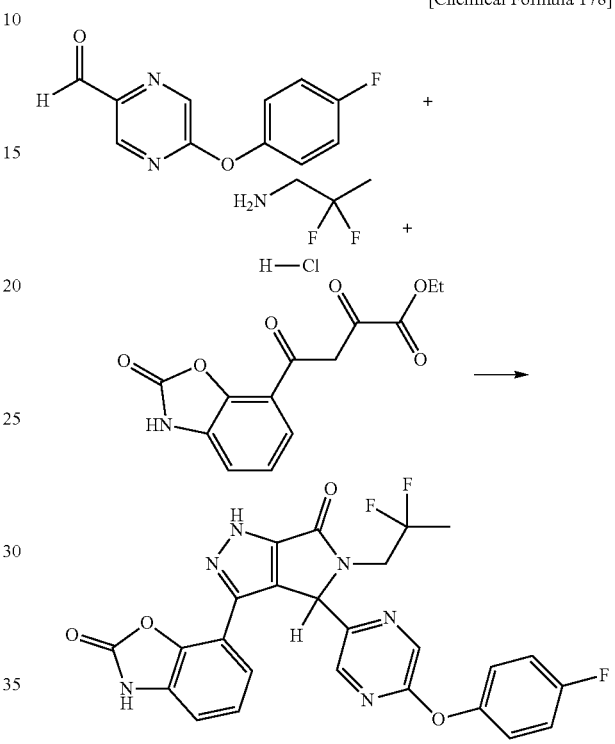

A mixture of the compound obtained in Reference Example 58 (70.0 mg), 2,2-difluoropropylamine hydrochloride (63.0 mg, CAS number: 868241-48-9), triethylamine (133 μL), and ethanol (5.0 mL) was stirred at room temperature for 5 hours. The reaction mixture was diluted with ethyl acetate, and the organic layer obtained was washed with a saturated aqueous sodium hydrogen carbonate solution and dried over anhydrous sodium sulfate. After filtration, the solvent was distilled off under reduced pressure, and a mixture of the oil obtained, the compound obtained in step 2 of Reference Example 1 (88.0 mg), and acetic acid (3.0 mL) was stirred at 100° C. for 1 hour and a half. Subsequently, the reaction mixture was cooled to room temperature, and then hydrazine monohydrate (62.0 μL) was added, and the mixture was stirred at 100° C. for 1 hour and a half. The reaction mixture was cooled to room temperature, and then concentrated under reduced pressure, ethyl acetate was added to the residue, and the organic layer obtained was washed with a saturated aqueous sodium hydrogen carbonate solution, and then dried over anhydrous sodium sulfate. After filtration, the solvent was distilled off under reduced pressure, and the solid obtained was washed with ethyl acetate to obtain the title compound (82.0 mg) as a solid.

$^1$H-NMR (DMSO-D$_6$) δ: 1.63 (3H, t, J=19.2 Hz), 2.94-3.08 (1H, m), 4.07-4.24 (1H, m), 6.15 (1H, s), 7.00-7.47 (7H, m), 8.24 (1H, br s), 8.39 (1H, d, J=1.8 Hz), 11.84 (1H, br s), 14.22 (1H, br s), MS (m/z): 523 (M+H)$^+$.

Example 75

7-{4-[6-(4-Chlorophenoxy)pyridazine-3-yl]-5-(2,2-difluoropropyl)-6-oxo-1,4,5,6-tetrahydropyrrolo[3,4-c]pyrazol-3-yl}-1,3-benzoxazol-2(3H)-one

[Chemical Formula 179]

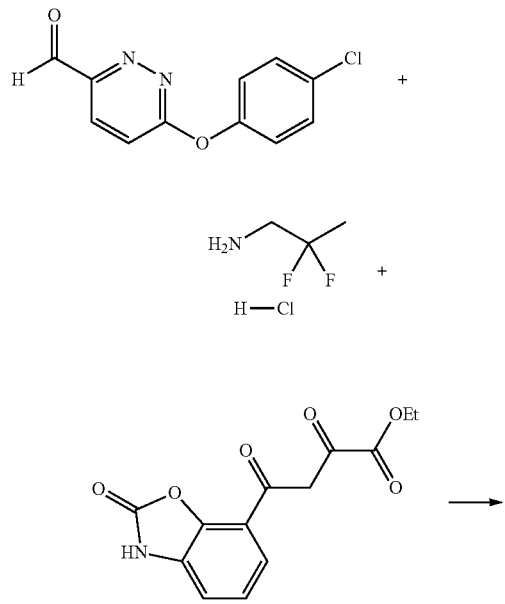

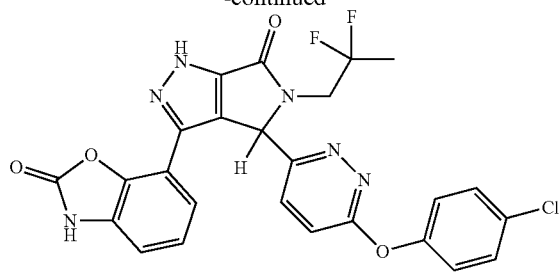

A mixture of the compound obtained in Reference Example 51 (77.0 mg), 2,2-difluoropropylamine hydrochloride (43 mg, CAS number: 868241-48-9), the compound obtained in step 2 of Reference Example 1 (90.0 mg), triethylamine (182 µL), and acetic acid (3.0 mL) was stirred at room temperature for 17 hours, and then hydrazine monohydrate (64.0 µL) was added, and the mixture was further stirred at 100° C. for 2 hours. The reaction mixture was cooled to room temperature, and then concentrated under reduced pressure, and the residue obtained was purified by silica gel column chromatography (dichloromethane/methanol) and reverse phase HPLC, and then solidified with an n-hexane-ethyl acetate mixed solution to obtain the title compound (78.0 mg).

$^1$H-NMR (DMSO-$D_6$) δ: 1.63 (3H, t, J=19.1 Hz), 3.02-3.19 (1H, m), 4.06-4.25 (1H, m), 6.21 (1H, s), 7.01-7.33 (5H, m), 7.39-7.51 (3H, m), 7.58 (1H, d, J=9.1 Hz), 11.82 (1H, br s), 14.24 (1H, br s), MS (m/z): 539 (M+H)$^+$.

The same procedure as that in Example 75 was performed to synthesize the following compounds (Table 8-1 and Table 8-2).

TABLE 8-1

| Example No | Manufacturing raw material | Structure of synthesized compound |
|---|---|---|
| 76 | 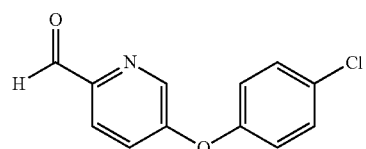<br>see Reference Example 52 | 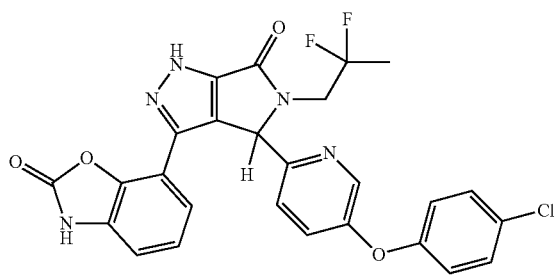 [SMILES: CC(F)(F)CN1C(=O)c2[nH]nc(-c3cccc4[nH]c(=O)oc34)c2C1c1ccc(Oc2ccc(Cl)cc2)cn1] |
| 77 | see Reference Example 59 | |

TABLE 8-1-continued

| Example No | Manufacturing raw material | Structure of synthesized compound |
|---|---|---|
| 78 | 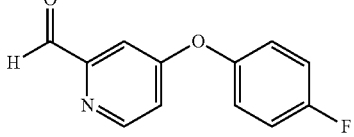 see Reference Example 57 | 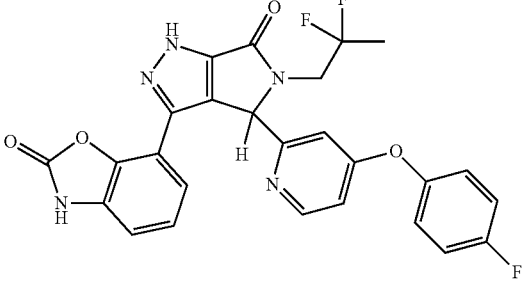 |
| 79 | 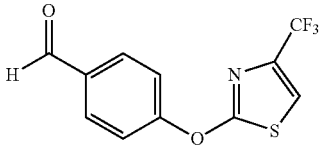 [SMILES: O=Cc1ccc(Oc2nc(C(F)(F)F)cs2)cc1] see Reference Example 62 | 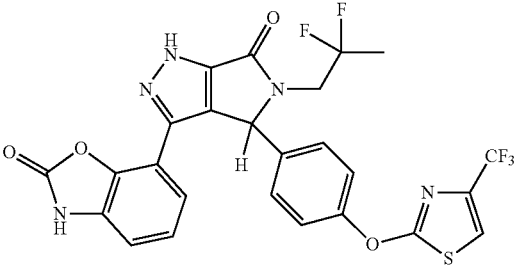 [SMILES: CC(F)(F)CN1C(=O)c2[nH]nc(-c3cccc4[nH]c(=O)oc34)c2C1c1ccc(Oc2nc(C(F)(F)F)cs2)cc1] |
| 80 | 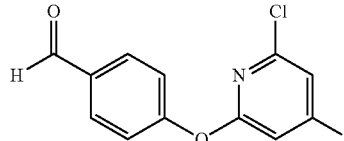 see Reference Example 63 | 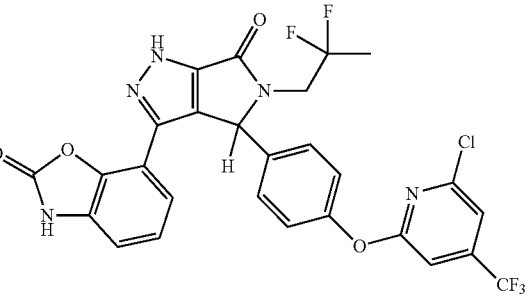 |

TABLE 8-2

| Example No | Name of synthesized compound | Spectral data |
|---|---|---|
| 76 | 7-{4-[2-(3,4-Dichlorophenoxy)-1,3-thiazol-5-yl]-5-(2,2-difluoropropyl)-6-oxo-1,4,5,6-tetrahydropyrrolo[3,4-c]pyrazol-3-yl]-1,3-benzoxazol-2(3H)-one | $^1$H-NMR (DMSO-D$_6$) δ: 1.68 (3H, t, J = 19.1 Hz), 3.20-3.33 (1H, m), 4.14-4.32 (1H, m), 5.25 (1H, s), 7.06-7.28 (2H, m), 7.34 (1H, dd, J = 9.1, 3.0 Hz), 7.39-7.47 (2H, m), 7.69 (1H, d, J = 9.1 Hz), 7.71 (1H, d, J = 3.0 Hz), 11.90 (1H, br s), 14.37 (1H, br s)., MS (m/s): 578 (M + H)$^+$. |
| 77 | 7-{4-[5-(4-Chlorophenoxy)pyridin-2-yl]-5-(2,2-difluoropropyl)-6-oxo-1,4,5,6-tetrahydropyrrolo[3,4-c]pyrazol-3-yl]-1,3-benzoxazol-2(3H)-one | $^1$H-NMR (DMSO-D$_6$) δ: 1.64 (3H, t, J = 19.1 Hz), 2.85-3.04 (1H, m), 4.05-4.30 (1H, m), 6.09 (1H, s), 6.98-7.34 (5H, m), 7.37-7.49 (4H, m), 8.25 (1H, d, J = 2.4 Hz), 11.82 (1H, br s), 14.15 (1H, br s)., MS (m/z): 538 (M + H)$^+$. |

TABLE 8-2-continued

| Example No | Name of synthesized compound | Spectral data |
|---|---|---|
| 78 | 7-{5-(2,2-Difluoropropyl)-4-[4-(4-fluorophenoxy)pyridin-2-yl]-6-oxo-1,4,5,6-tetrahydropyrrolo[3,4-c]pyrazol-3-yl}-1,3-benzoxazol-2(3H)-one | $^1$H-NMR (DMSO-D$_6$) δ: 1.63 (3H, t, J = 19.0 Hz), 2.86-3.03 (1H, m), 4.08-4.28 (1H, m), 6.00 (1H, s), 6.79 (1H, dd, J = 5.5, 2.5 Hz), 6.91-7.00 (1H, m), 7.06-7.22 (4H, m), 7.25-7.39 (3H, m), 8.29 (1H, d, J = 5.5 Hz), 11.82 (1H, br s), 14.13 (1H, br s)., MS (m/z): 522 (M + H)$^+$. |
| 79 | 7-[5-(2,2-Difluoropropyl)-6-oxo-4-(4-{[4-(trifluoromethyl)-1,3-thiazol-2-yl]oxy}phenyl)-1,4,5,6-tetrahydropyrrolo[3,4-c]pyrazol-3-yl]-1,3-benzoxazol-2(3H)-one | $^1$H-NMR (DMSO-D$_6$) δ: 1.65 (3H, t, J = 19.0 Hz), 2.82-2.99 (1H, m), 4.07-4.30 (1H, m), 6.02 (1H, s), 6.96-7.40 (7H, m), 7.96-7.98 (1H, m), 11.82 (1H, br s), 14.27 (1H, br s)., MS (m/z): 578 (M + H)$^+$. |
| 80 | 7-[4-(4-{[6-Chloro-4-(trifluoromethyl)pyridin-2-yl]oxy}phenyl)-5-(2,2-difluoropropyl)-6-oxo-1,4,5,6-tetrahydropyrrolo[3,4-c]pyrazol-3-yl]-1,3-benzoxazol-2(3H)-one | $^1$H-NMR (DMSO-D$_6$) δ: 1.66 (3H, t, J = 19.4 Hz), 2.80-2.98 (1H, m), 4.12-4.32 (1H m), 6.02 (1H, s), 7.00-7.04 (1H, m), 7.09-7.28 (6H, m), 7.38 (1H, s), 7.71 (1H, s), 11.82 (1H, br s), 14.25 (1H, br s)., MS (m/z); 606 (M + H)$^+$. |

Example 81

7-[4-{4-[3-Chloro-4-(trifluoromethoxy)phenoxy]-3-(4,4,4-trifluorobutoxy)phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer)

[Chemical Formula 180]

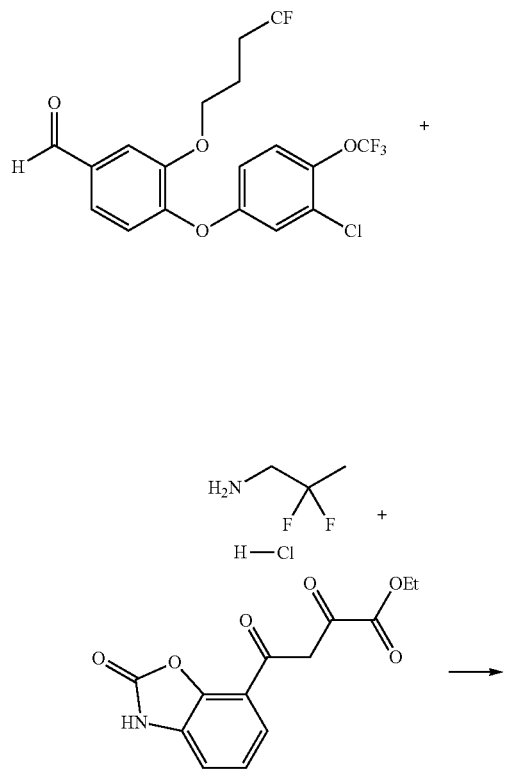

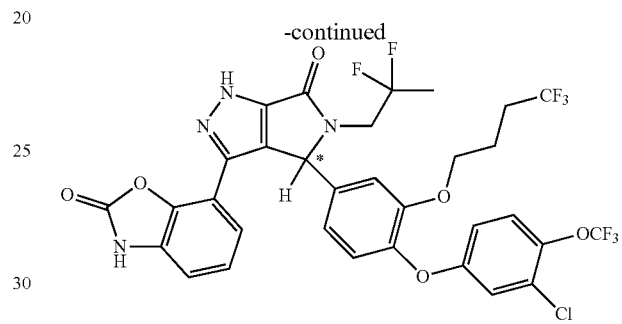

A mixture of the compound obtained in Reference Example 53 (0.33 g), 2,2-difluoropropylamine hydrochloride (95 mg, CAS number: 868241-48-9), triethylamine (0.3 mL), and acetic acid (4.5 mL) was stirred at room temperature for 2 hours and a half, and then the compound obtained in step 2 of Reference Example 1 (166 mg) was added, and the mixture was further stirred at the same temperature for 30 minutes, and then stirred at 80° C. for 30 hours. Subsequently, the reaction mixture was cooled to room temperature, hydrazine monohydrate (90 μL) was added, and the mixture was stirred at 100° C. for 3 hours. The reaction mixture was cooled to room temperature, and then concentrated under reduced pressure. Water and a saturated aqueous sodium hydrogen carbonate solution were added to the residue, the mixture was extracted with ethyl acetate, and the organic layer obtained was washed with brine, and then dried over anhydrous sodium sulfate. After filtration, the solvent was distilled off under reduced pressure, and the residue obtained was sequentially purified by silica gel column chromatography (dichloromethane/methanol) and reverse phase HPLC. The racemate obtained was subjected to optical resolution using two Daicel Corporation CHIRALFLASH® IC (20 μm, 30 mmφ×100 mmL) connected [mobile phase: n-hexane/tetrahydrofuran/ethanol=72/24/2 to 72/24/5 (0 to 60 minutes), flow rate: 14 mL/minute, temperature: room temperature], and the fraction eluted earlier in the main peaks was solidified with an n-hexane-diethyl ether mixed solution to obtain the title compound (53.0 mg).

$^1$H-NMR (DMSO-D$_6$) δ: 1.59-1.86 (7H, m), 2.97-3.07 (1H, m), 3.83-3.86 (2H, m), 4.11-4.24 (1H, m), 5.95 (1H, s), 6.67-7.44 (9H, m), 11.84 (1H, s), 14.22 (1H, s), MS (m/z): 747 (M+H)$^+$.

The same procedure as that in Example 81 was performed to synthesize the following compounds (Table 9-1 and Table 9-2).

TABLE 9-1

| Example No | Manufacturing raw material | Structure of synthesized compound |
|---|---|---|
| 82 | see Reference Example 12 | |
| 83 | see Reference Example 79 | |
| 84 | see Reference Example 80 | |

TABLE 9-2

| Example No | Name of synthesized compound | Spectral data |
|---|---|---|
| 82 | 7-[4-(4-{[3,5-Bis(trifluoromethyl) benzyl]oxy}phenyl)-5-(2,2-difluoropropyl)-6-oxo-1,4,5,6-tetrahydro pyrrolo[3,4-c]pyrazol-3-yl]-1,3-benzoxazol-2(3H)-one (enantiomer) | $^1$H-NMR (DMSO-D$_6$) δ: 1.64 (3H, t, J = 19.1 hz), 2.72-2.82 (1H, m), 4.08-4.22 (1H, m), 5.21 (2H, s), 5.94 (1H, s), 6.95-7.30 (7H, m), 8.08-8.11 (3H, m), 11.82 {1H, br s), 14.22-14.30 (1H, m)., MS m/z: 653 (M + H)$^+$. |
| 83 | 7-[4-{4-[(4,4-Difluoropiperidin-1-yl)methyl]phenyl}-5-(2,2-difluoropropyl)-6-oxo-1,4,5,6-tetrahydro-pyrrolo[3,4-c]pyrazol-3-yl]-1,3-benzoxazol-2(3H)-one (enantiomer) | $^1$H-NMR (DMSO-D$_6$) δ: 1.64 (3H, t, J = 19.1 Hz), 1.85-1.94 (4H, m), 2.35-2.39 (4H, m), 2.75-2.84 (1H, m), 3.44 (2H, s), 4.10-4.22 1H, m), 5.95 (1H, s), 7.00-7.25 (7H, m), 11.79 (1H, br s), 14.24 (1H, br s)., MS m/z: 544 (M + H)$^+$. |
| 84 | 7-[5-(2,2-Difluoropropyl)-6-oxo-4-(4-{[3-(trifluoromethyl)-1,2-benzoxazol-5-yl]oxy}phenyl)-1,4,5,6-tetrahydropyrrolo[3,4-c] pyrazol-3-yl]-1,3-benzoxazol-2(3H)-one(enantiomer) | $^1$H-NMR (DMSO-D$_6$) δ: 1.65 (3H, t, J = 19.1 hz), 2.83-2.93 (1H, m), 4.11-4.23 (1H, m), 5.98 (1H, s), 6.95-7.40 (8H, m), 7.56 (1H, dd, J = 9.1, 2.4 Hz), 8.04 (1H, d, J = 9.1 Hz), 11.83 (1H, br s), 14.25 (1H, br s)., MS m/z: 612 (M + H)$^+$. |

Example 85

7-[5-(2,2-Difluoropropyl)-6-oxo-4-{4-[(1R)-1-phenylethoxy]phenyl}-1,4,5,6-tetrahydropyrrolo[3,4-c]pyrazol-3-yl]-1,3-benzoxazol-2(3H)-one (enantiomer)

[Chemical Formula 181]

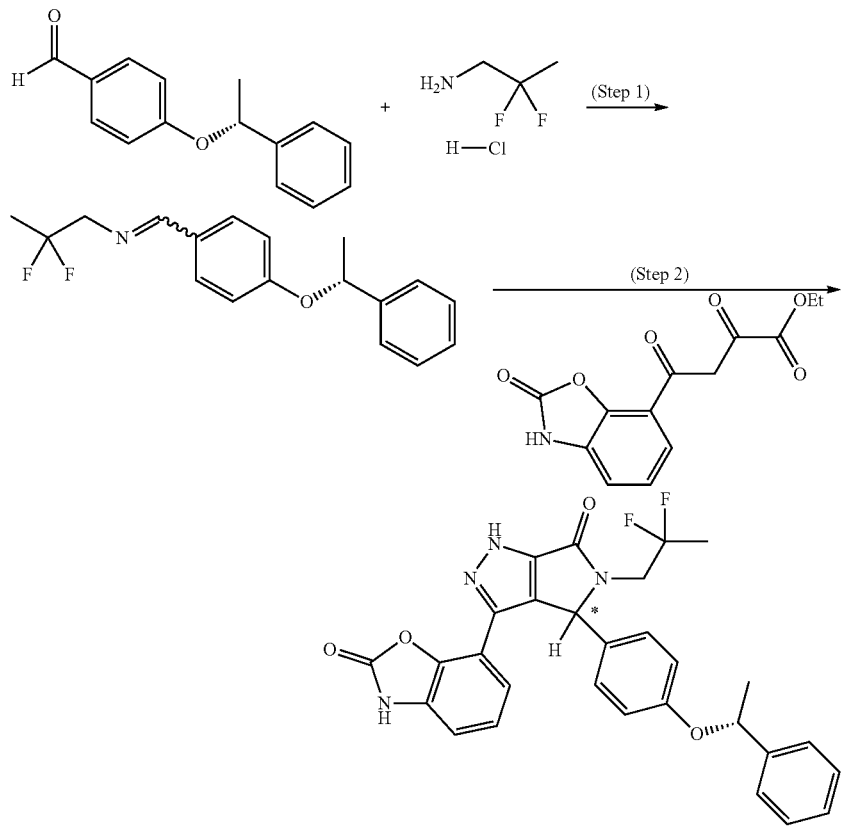

(Step 1) N-(2,2-Difluoropropyl)-1-{4-[(1R)-1-phenoxyethoxy]phenyl}methanimine

To a suspension of the compound obtained in Reference Example 13 (150 mg) and 2,2-difluoropropylamine hydrochloride (131 mg, CAS number: 868241-48-9) in tetrahydrofuran (6.0 mL), triethylamine (139 µL) was added at room temperature, and the mixture was stirred at the same temperature for 22 hours. The reaction mixture was diluted with ethyl acetate and sequentially washed with water, a saturated aqueous sodium hydrogen carbonate solution, and brine, and then dried over anhydrous sodium sulfate. After filtration, the solvent was distilled off under reduced pressure to obtain the crude title compound (189 mg) as an oil.

Step 2

7-[5-(2,2-Difluoropropyl)-6-oxo-4-{4-[(1R)-1-phenylethoxy]phenyl}-1,4,5,6-tetrahydropyrrolo[3,4-c]pyrazol-3-yl]-1,3-benzoxazol-2(3H)-one (enantiomer)

A mixture of the compound obtained in the above step 1 (189 mg), the compound obtained in step 2 of Reference Example 1 (100 mg), and acetic acid (4.0 mL) was stirred at room temperature for 20 hours, and then stirred at 100° C. for 6 hours. Subsequently, the reaction mixture was cooled to room temperature, hydrazine monohydrate (52.5 µL) was added, and the mixture was stirred at 100° C. for 8 hours. The reaction mixture was cooled to room temperature, toluene was added, and then the mixture was concentrated under reduced pressure. A saturated aqueous sodium hydrogen carbonate solution was added to the residue, and the mixture was extracted with ethyl acetate. The organic layer obtained was washed with a saturated aqueous sodium hydrogen carbonate solution and brine, and then dried over anhydrous sodium sulfate. After filtration, the solvent was distilled off under reduced pressure, and the residue obtained was purified by silica gel column chromatography (dichloromethane/methanol, and then, n-hexane/ethyl acetate). The racemate obtained was subjected to optical resolution using two Daicel Corporation CHIRALFLASH® IC (20 µm, 30 mmφ×100 mmL) connected [mobile phase: n-hexane/tetrahydrofuran/ethanol=70/27/3, flow rate: 12 mL/minute, temperature: room temperature], and the fraction eluted earlier in the main peaks was purified by reverse phase HPLC, and then solidified with an n-hexane-ethyl acetate mixed solution to obtain the title compound (15.1 mg).

¹H-NMR (DMSO-D₆) δ: 1.46 (3H, d, J=6.3 Hz), 1.60 (3H, t, J=19.2 Hz), 2.65-2.78 (1H, m), 4.00-4.19 (1H, m), 5.41 (1H, q, J=6.3 Hz), 5.86 (1H, s), 6.79 (2H, d, J=8.6 Hz), 6.88-6.96 (2H, m), 6.98-7.06 (1H, m), 7.07-7.16 (1H, m), 7.18-7.26 (2H, m), 7.27-7.32 (2H, m), 7.33-7.37 (2H, m), 11.81 (1H, br s), MS (m/z): 531 (M+H)⁺.

The same procedure as that in Example 85 was performed to synthesize the following compounds (Table 10-1 and Table 10-2).

TABLE 10-1

| Example No | Manufacturing raw material | Structure of synthesized compound |
|---|---|---|
| 86 | 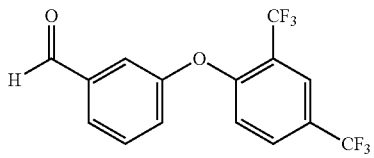 [SMILES: O=Cc1cccc(Oc2ccc(C(F)(F)F)cc2C(F)(F)F)c1] see Reference Example 75 | 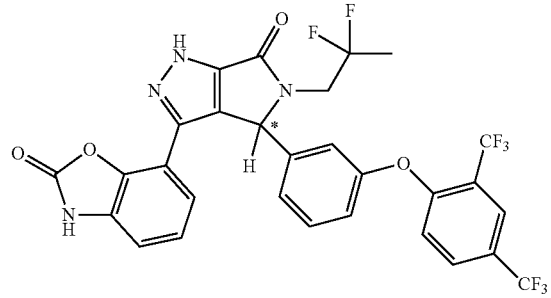 [SMILES: CC(F)(F)CN1C(=O)c2[nH]nc(-c3cccc4[nH]c(=O)oc34)c2C1c1cccc(Oc2ccc(C(F)(F)F)cc2C(F)(F)F)c1] |
| 87 | 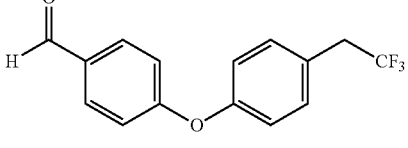 see Reference Example 54 | 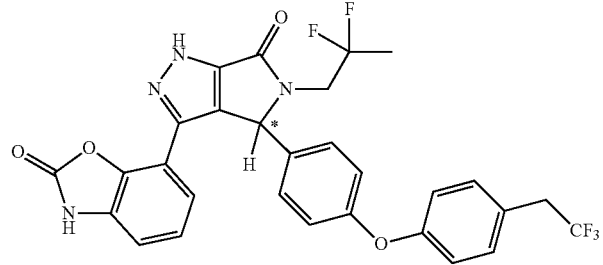 [SMILES: CC(F)(F)CN1C(=O)c2[nH]nc(-c3cccc4[nH]c(=O)oc34)c2C1c1ccc(Oc2ccc(CC(F)(F)F)cc2)cc1] |

TABLE 10-2

| Example No | Name of synthesized compound | Spectral data |
|---|---|---|
| 86 | 7-[4-{3-[2,4-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (enantiomer) | ¹H (DMSO-D₆) δ: 1.65 (3H, t, J = 19.2 Hz), 2.90-3.07 (1H, m), 4.10-4.31 1H, m), 5.99 (1H, s), 6.74-6.83 (1H, m), 6.92-7.20 (5H, m), 7.27-7.43 (2H, m), 7.88 (1H, dd, J = 9.0, 2.3 Hz), 8.07 (1H, s), 11.70 (0.27H, s), 11.82 (0.73H, s)., MS (m/z): 639 (M + H)⁺. |
| 87 | 7-[5-(2,2-Difluoropropyl)-6-oxo-4-{4-[4-(2,2,2-trifluoroethyl)phenoxy]phenyl}-1,4,5,6-tetrahydropyrrolo[3,4-c]pyrazol-3-yl]-1,3-benzoxazol-2(3H)-one (enantiomer) | ¹H-NMR (DMSO-D₆) δ: 1.65 (3H, t, J = 19.6 Hz), 2.79-2.93 (1H, m), 3.62 (2H, q, J = 11.4 Hz), 4.07-4.27 (1H, m), 5.97 (1H, s), 6.90 (2H, d, J = 8.6 Hz), 6.94 (2H, d, J = 8.6 Hz), 6.98-7.19 (4H, m), 7.24-7.31 (1H, m), 7.33 (2H, d, J = 9.0 Hz), 11.84 (1H, br s)., MS (m/z): 585 (M + H)⁺. |

Example 88

7-[5-(2,2-Difluoropropyl)-6-oxo-4-(1-phenyl-1H-indazol-5-yl)-1,4,5,6-tetrahydropyrrolo[3,4-c]pyrazol-3-yl]-1,3-benzoxazol-2(3H)-one

[Chemical Formula 182]

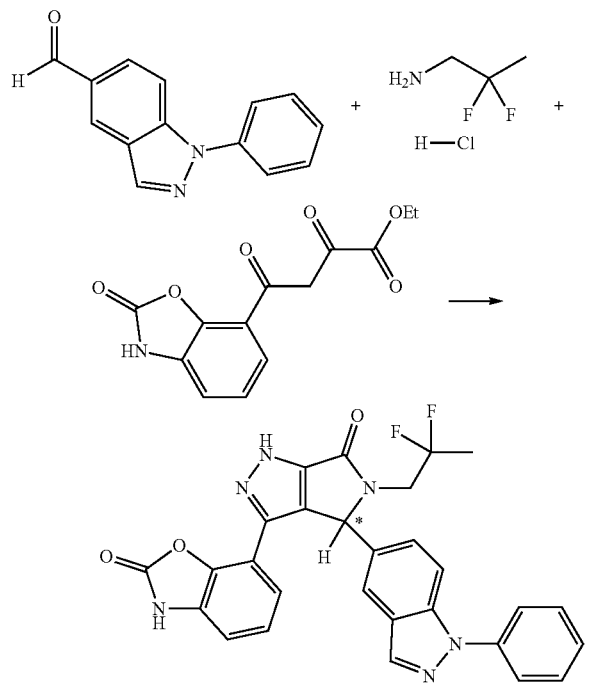

To a solution of the compound obtained in Reference Example 81 (78.0 mg) and 2,2-difluoropropylamine hydrochloride (50 mg, CAS number: 868241-48-9) in ethanol (2.5 mL), triethylamine (105 μL) was added at room temperature, and the mixture was stirred at the same temperature for 18 hours. The solvent was distilled off under reduced pressure, a mixture of the residue obtained and the compound obtained in step 2 of Reference Example 1 (70.0 mg) and acetic acid (2.5 mL) was stirred at 90° C. for 17 hours. Subsequently, the reaction mixture was cooled to room temperature, hydrazine monohydrate (37 μL) was added, and the mixture was stirred at 90° C. for 2 hours. The reaction mixture was cooled to room temperature, and then diluted with ethyl acetate, and the organic layer obtained was washed with water, and then dried over magnesium sulfate. After filtration, the solvent was distilled off under reduced pressure, and the residue obtained was sequentially purified by silica gel column chromatography (n-hexane/ethyl acetate) and reverse phase HPLC to obtain the title compound (59.1 mg) as a solid.

$^1$H-NMR (DMSO-D$_6$) δ: 1.64 (3H, t, J=19.0 Hz), 2.74-2.88 (1H, m), 4.06-4.25 (1H, m), 6.14 (1H, s), 6.89-7.18 (3H, m), 7.27-7.41 (2H, m), 7.51-7.58 (2H, m), 7.65-7.74 (3H, m), 7.81 (1H, s), 8.32-8.35 (1H, m), 11.79 (1H, s), 14.27 (1H, s), MS (m/z): 527 (M+H)$^+$.

Example 89

7-[4-(3-Anilinophenyl)-5-(2,2-difluoropropyl)-6-oxo-1,4,5,6-tetrahydropyrrolo[3,4-c]pyrazol-3-yl]-1,3-benzoxazol-2(3H)-one

[Chemical Formula 183]

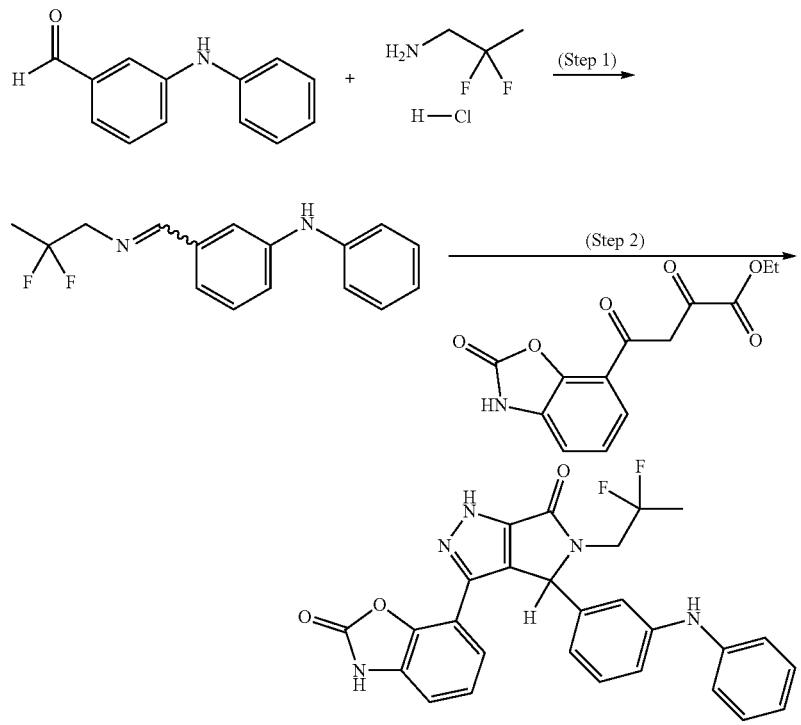

(Step 1) 3-{[(2,2-Difluoropropyl)imino]methyl}-N-phenylaniline

To a solution of the compound obtained in step 2 of Reference Example 82 (66.3 mg) and 2,2-difluoropropylamine hydrochloride (70.4 mg, CAS number: 868241-48-9) in ethanol (5.0 mL), triethylamine (90.0 μL) was added, and the mixture was stirred at room temperature for 4 hours. The reaction mixture was concentrated under reduced pressure, ethyl acetate was added to the residue, and the organic layer obtained was washed with a saturated aqueous sodium hydrogen carbonate solution and brine, and then dried over anhydrous sodium sulfate. After filtration, the solvent was distilled off under reduced pressure to obtain the crude title compound (121 mg) as an oil.

$^1$H-NMR (CDCl$_3$) δ: 1.74 (3H, t, J=19.4 Hz), 3.84-3.94 (2H, m), 5.78 (1H, br s), 6.94-7.00 (1H, m), 7.06-7.11 (2H, m), 7.14-7.19 (1H, m), 7.24-7.33 (4H, m), 7.47 (1H, s), 8.24 (1H, s).

Step 2

7-[4-(3-Anilinophenyl)-5-(2,2-difluoropropyl)-6-oxo-1,4,5,6-tetrahydropyrrolo[3,4-c]pyrazol-3-yl]-1,3-benzoxazol-2(3H)-one A mixture of the compound obtained in the above step 1, the compound obtained in step 2 of Reference Example 1 (92.4 mg), and acetic acid (5.0 mL) was stirred at room temperature for 40 hours, and then hydrazine monohydrate (81.0 μL) was added, and the mixture was further stirred at 100° C. for 8 hours. The reaction mixture was cooled to room temperature and concentrated under reduced pressure, a chloroform-methanol (9:1) mixed solution was added to the residue, and the organic layer obtained was washed with water, and then dried over magnesium sulfate. After filtration, the solvent was distilled off under reduced pressure, the residue obtained was sequentially purified by silica gel column chromatography (dichloromethane/methanol) and reverse phase HPLC to obtain the title compound (105 mg) as a solid.

$^1$H-NMR (DMSO-D$_6$) δ: 1.65 (3H, t, J=19.4 Hz), 2.81-2.94 (1H, m), 4.10-4.26 (1H, m), 5.89 (1H, s), 6.62-6.69 (2H, m), 6.77-6.83 (1H, m), 6.87-6.97 (3H, m), 7.02-7.09 (1H, m), 7.10-7.22 (4H, m), 7.26-7.35 (1H, m), 8.17 (1H, s), 11.83 (1H, br s), 14.23 (1H, br s), MS (m/z): 502 (M+H)$^+$.

Example 90

7-[5-(2,2-Difluoropropyl)-4-{4-[methoxy(phenyl)methyl]phenyl}-6-oxo-1,4,5,6-tetrahydropyrrolo[3,4-c]pyrazol-3-yl]-1,3-benzoxazol-2(3H)-one (mixture of diastereomers)

[Chemical Formula 184]

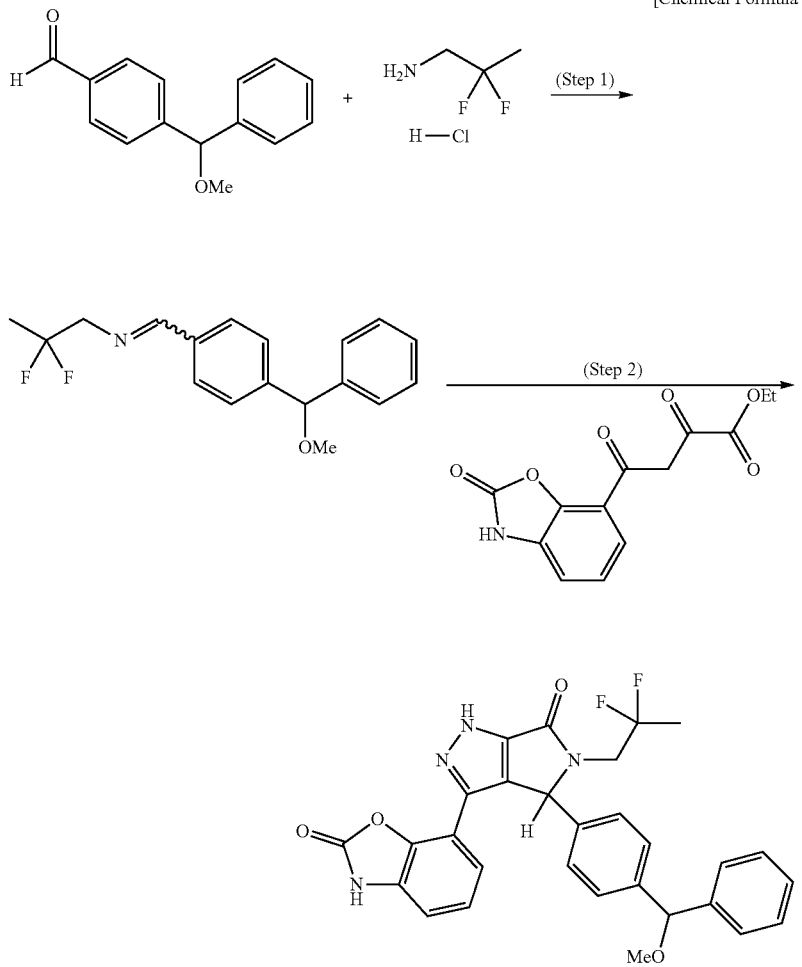

Step 1

N-(2,2-Difluoropropyl)-1-{4-[methoxy(phenyl)methyl]phenyl}methanimine

The compound obtained in Reference Example 83 (47.0 mg), 2,2-difluoropropylamine hydrochloride (42.6 mg, CAS number: 868241-48-9), and the compound obtained in step 2 of Reference Example 1 (49.8 mg) were used as manufacturing raw materials, and the same procedure as that in step 1 of Example 34 was performed to obtain the crude title compound (100 mg) as an oil.

$^1$H-NMR (CDCl$_3$) δ: 1.73 (3H, t, J=18.8 Hz), 3.39 (3H, s), 3.89 (2H, t, J=12.8 Hz), 5.27 (1H, s), 7.22-7.38 (4H, m), 7.42 (2H, d, J=8.7 Hz), 7.73 (2H, d, J=8.7 Hz), 8.28 (1H, s).

Step 2

7-[5-(2,2-Difluoropropyl)-4-{4-[methoxy(phenyl)methyl]phenyl}-6-oxo-1,4,5,6-tetrahydropyrrolo[3,4-c]pyrazol-3-yl]-1,3-benzoxazol-2(3H)-one (mixture of diastereomers)

The compound obtained in the above step 1 (100 mg) was used as a manufacturing raw material, and the same procedure as that in step 2 of Example 89 was performed to obtain the title compound (35.7 mg) as a solid.

$^1$H-NMR (DMSO-D$_6$) δ: 1.62 (3H, t, J=19.4 Hz), 2.67-2.85 (1H, m), 3.16 (3H, s), 4.03-4.27 (1H, m), 5.25 (1H, s), 5.94 (1H, s), 6.95-7.15 (4H, m), 7.16-7.34 (8H, m), 11.80 (1H, br s), 14.23 (1H, br s), MS (m/z): 531 (M+H)$^+$.

Example 91

7-[4-{4-[Difluoro(phenyl)methyl]phenyl}-5-(2,2-difluoropropyl)-6-oxo-1,4,5,6-tetra hydropyrrolo[3,4-c]pyrazol-3-yl]-1,3-benzoxazol-2(3H)-one

[Chemical Formula 185]

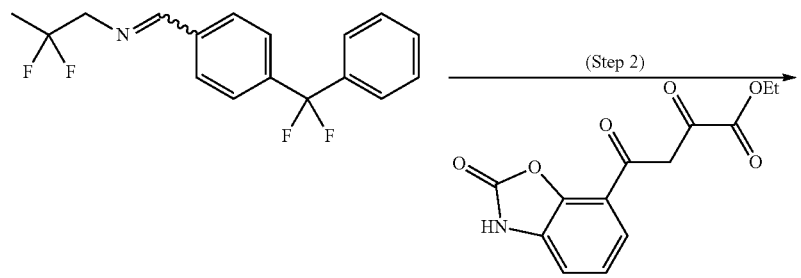

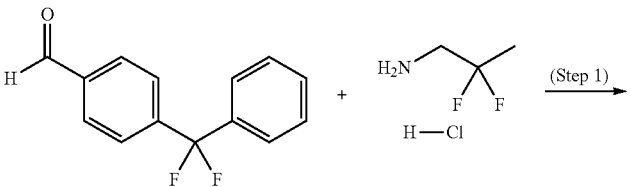

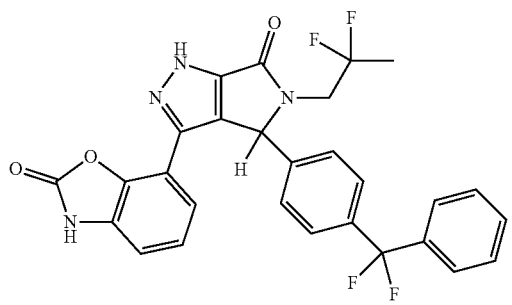

237

(Step 1) 1-{4-[Difluoro(phenyl)methyl]phenyl}-N-(2,2-difluoropropyl)methanimine

The compound obtained in Reference Example 84 (234 mg) and 2,2-difluoropropylamine hydrochloride (198 mg, CAS number: 868241-48-9) were used as manufacturing raw materials, and the same procedure as that in step 1 of Example 34 was performed to obtain the crude title compound (308 mg) as an oil.

$^1$H-NMR (CDCl$_3$) δ: 1.68-1.85 (3H, m), 3.84-3.98 (2H, m), 7.36-7.46 (3H, m), 7.46-7.53 (2H, m), 7.55-7.61 (2H, m), 7.77-7.86 (2H, m), 8.34 (1H, s).

(Step 2) 7-[4-{4-[Difluoro(phenyl)methyl]phenyl}-5-(2,2-difluoropropyl)-6-oxo-1,4,5,6-tetrahydropyrrolo[3,4-c]pyrazol-3-yl]-1,3-benzoxazol-2(3H)-one

The compound obtained in the above step 1 (308 mg) and the compound obtained in step 2 of Reference Example 1 (260 mg) were used as manufacturing raw materials, and the same procedure as that in step 2 of Example 89 was performed to obtain the title compound (296 mg) as a solid.

$^1$H-NMR (DMSO-D$_6$) δ: 1.66 (3H, t, J=19.2 Hz), 2.75-2.92 (1H, m), 4.09-4.30 (1H, m), 6.04 (1H, s), 6.95-7.18 (2H, m), 7.21-7.36 (3H, m), 7.38-7.56 (7H, m), 11.61-11.96 (1H, br m), 14.17-14.47 (1H, br m), MS (m/z): 537 (M+H)$^+$.

Example 92

N-{3-[4-(4-Chlorophenyl)-5-(2,2-difluoropropyl)-6-oxo-1,4,5,6-tetrahydropyrrolo[3,4-c]pyrazol-3-yl]phenyl}formamide

[Chemical Formula 186]

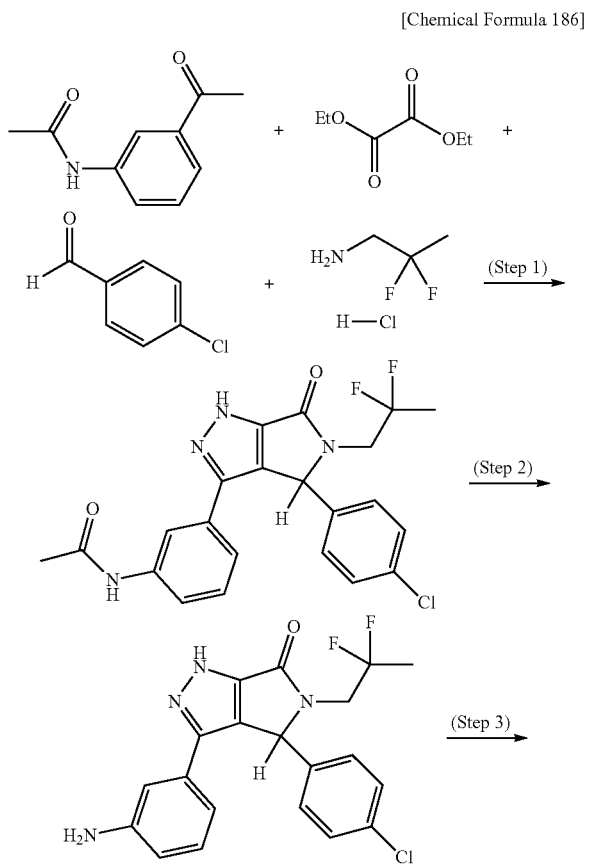

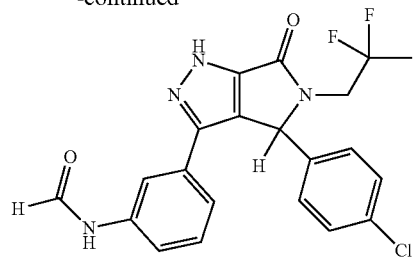

Step 1

N-{3-[4-(4-Chlorophenyl)-5-(2,2-difluoropropyl)-6-oxo-1,4,5,6-tetrahydropyrrolo[3,4-c]pyrazol-3-yl]phenyl}acetamide

To a solution of 3-acetamideacetophenone (142 mg, CAS number: 7463-31-2) in tetrahydrofuran (10 mL), 60%-sodium hydride (dispersed in liquid paraffin) (105 mg) was added at room temperature, and the mixture was stirred at the same temperature for 5 minutes, and then diethyl oxalate (152 μL) was added, and the mixture was further stirred at 70° C. for 40 minutes. The reaction mixture was cooled to room temperature, and then concentrated under reduced pressure, acetic acid (8 mL) was added to the residue obtained, and the mixture was stirred at room temperature for 5 minutes. Subsequently, 4-chlorobenzaldehyde (225 mg), 2,2-difluoropropylamine hydrochloride (210 mg, CAS number: 868241-48-9), and triethylamine (665 μL) were sequentially added to the reaction mixture at room temperature, and the mixture was stirred at 100° C. for 7 hours. The reaction mixture was cooled to room temperature, hydrazine monohydrate (155 μL) was added, and the mixture was stirred at 100° C. for 4 hours and a half. The reaction mixture was cooled to room temperature, and then concentrated under reduced pressure, and a 1 M-aqueous sodium hydroxide solution was added to the residue to adjust the mixture to around neutrality. Then, the mixture was extracted with dichloromethane, and the organic layer obtained was dried over anhydrous sodium sulfate. After filtration, the solvent was distilled off under reduced pressure, and the residue obtained was sequentially purified by silica gel column chromatography (dichloromethane/methanol) and reverse phase HPLC to obtain the title compound (89 mg) as a solid.

$^1$H-NMR (CDCl$_3$) δ: 1.65 (3H, t, J=18.5 Hz), 2.21 (3H, s), 2.82-2.96 (1H, m), 4.17-4.34 (1H, m), 5.80 (1H, s), 6.80 (1H, d, J=7.9 Hz), 7.13-7.22 (3H, m), 7.33 (2H, d, J=8.5 Hz), 7.64 (1H, d, J=7.9 Hz), 7.88 (1H, s), 8.26 (1H, s), MS (m/z): 445 (M+H)$^+$.

Step 2

3-(3-Aminophenyl)-4-(4-chlorophenyl)-5-(2,2-difluoropropyl)-4,5-dihydropyrrolo[3,4-c]pyrazol-6(1H)-one

A mixture of the compound obtained in the above step 1 (59 mg), ethanol (2 mL), and concentrated hydrochloric acid (1 mL) was stirred at 75° C. for 4 hours. The reaction mixture was cooled to room temperature, and then a 1 M-aqueous sodium hydroxide solution and a saturated aqueous sodium hydrogen carbonate solution were sequentially added, the mixture was extracted with dichloromethane, and the organic layer obtained was dried over anhydrous sodium sulfate. After filtration, the solvent was distilled off under reduced pressure to obtain the title compound (53 mg) as a solid.

$^1$H-NMR (CDCl$_3$) δ: 1.66 (3H, t, J=18.8 Hz), 2.81-2.93 (1H, m), 3.80 (2H, s), 4.19-4.36 (1H, m), 5.75 (1H, s), 6.56-6.63 (2H, m), 6.76 (1H, s), 7.03-7.08 (1H, m), 7.17 (2H, d, J=8.5 Hz), 7.35 (2H, d, J=8.5 Hz), MS (m/z): 403 (M+H)$^+$.

Step 3

N-{3-[4-(4-Chlorophenyl)-5-(2,2-difluoropropyl)-6-oxo-1,4,5,6-tetrahydropyrrolo[3,4-c]pyrazol-3-yl]phenyl}formamide To a solution of the compound obtained in the above step 2 (25 mg) in tetrahydrofuran (1 mL), N-formyl saccharin (16 mg) was added at room temperature, and the mixture was stirred at the same temperature for 3 days. The reaction mixture was concentrated under reduced pressure, the residue was purified by silica gel column chromatography (dichloromethane/methanol) to obtain the title compound (25 mg) as a solid.

$^1$H-NMR (CDCl$_3$) δ: 1.59-1.74 (3H, m), 2.82-2.97 (1H, m), 4.20-4.39 (1H, m), 5.81-5.83 (1H, m), 6.78-7.25 (4H, m), 7.30-7.42 (2H, m), 7.49-7.72 (1H, m), 7.99 (0.48H, s), 8.46 (0.52H, s), MS (m/z): 431 (M+H)$^+$.

Example 93

N-{3-[4-(4-Chlorophenyl)-5-(2,2-difluoropropyl)-6-oxo-1,4,5,6-tetrahydropyrrolo[3,4-c]pyrazol-3-yl]phenyl}urea

[Chemical Formula 187]

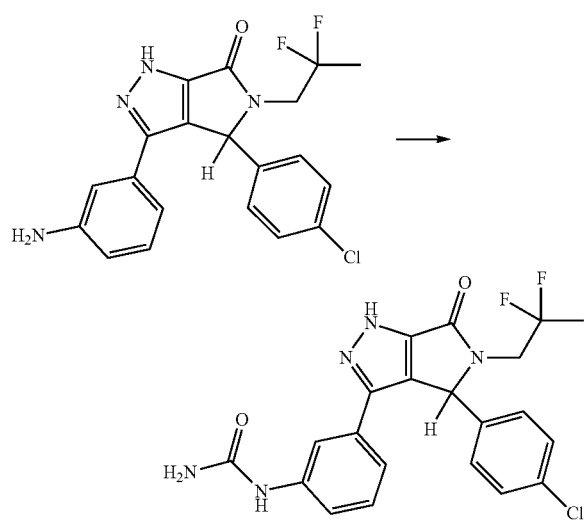

To a solution of the compound obtained in step 2 of Example 92 (26.0 mg) in dichloromethane (1 mL), pyridine (15.5 μL) and 4-nitrophenyl chloroformate (15.6 mg) were added, the mixture was stirred at room temperature for 40 minutes, and then, 28%-ammonia water (85 μL) was added, and the mixture was further stirred at the same temperature for 19 hours. To the reaction mixture, a saturated aqueous sodium hydrogen carbonate solution was added, the mixture was extracted with ethyl acetate, and the organic layer obtained was washed with brine, and then dried over anhydrous sodium sulfate. After filtration, the solvent was distilled off under reduced pressure, and the residue obtained was purified by silica gel column chromatography (dichloromethane/methanol) to obtain the title compound (20.4 mg) as a solid.

$^1$H-NMR (DMSO-D$_6$) δ: 1.63 (3H, t, J=19.1 Hz), 2.76-2.90 (1H, m), 4.10-4.27 (1H, m), 5.83-6.03 (3H, m), 6.96-7.43 (7H, m), 7.67-7.85 (1H, m), 8.54 (1H, s), 14.06-14.16 (1H, m), MS m/z: 446 (M+H)$^+$.

Example 94

4-{4-[4-(4-Chlorophenoxy)phenyl]-5-(2,2-difluoropropyl)-6-oxo-1,4,5,6-tetrahydro pyrrolo[3,4-c]pyrazol-3-yl}-1,3-dihydro-2H-benzimidazole-2-one

[Chemical Formula 188]

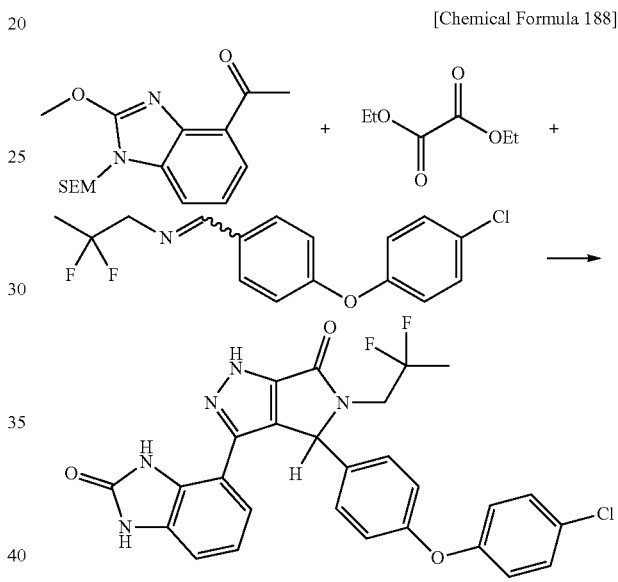

To a solution of the compound obtained in step 4 of Reference Example 6 (130 mg) in tetrahydrofuran (15 mL), potassium tert-butoxide (68.0 mg) was added at room temperature, the mixture was stirred at the same temperature for 30 minutes, and then diethyl oxalate (82.0 μL) was added, and the mixture was further stirred at the same temperature for 1 hour and a half. To the reaction mixture, 1 M-hydrochloric acid (0.7 mL) and water were added, the mixture was extracted with ethyl acetate, and the organic layer obtained was dried over anhydrous sodium sulfate. After filtration, the solvent was distilled off under reduced pressure, a mixture of the oil obtained (202 mg), the compound obtained in step 1 of Example 41 (125 mg), and acetic acid (2.0 mL) was stirred at room temperature for 4 days, and then hydrazine monohydrate (59.0 μL) was added, and the mixture was further stirred at 80° C. for 9 hours. The reaction mixture was cooled to room temperature, and then concentrated under reduced pressure, ethyl acetate was added to the residue, and the organic layer obtained was washed with a saturated aqueous sodium hydrogen carbonate solution, and then dried over anhydrous sodium sulfate. After filtration, the solvent was distilled off under reduced pressure, the residue obtained was dissolved in methanol (5.0 mL), potassium carbonate (168 mg) was added at room temperature, and the mixture was stirred at 70° C. for 2 hours. The reaction mixture was cooled to room temperature, ethyl acetate was added, and the organic layer obtained was washed with water, and then dried over anhydrous sodium sulfate. After filtration, the solvent was distilled off under reduced pressure, and a mixture of the residue obtained, 1,4-dioxane (5.0 mL), and 5 M-hydrochloric acid (2.0 mL) was stirred at 70° C. for 6 hours. The reaction mixture was cooled to room temperature, ethyl acetate was added, and the organic layer obtained was washed with water, and then dried over anhydrous sodium sulfate. After filtration, the solvent was distilled off under reduced pressure, the residue obtained was sequentially purified by silica gel column chromatography (chloroform/methanol) and reverse phase HPLC, and then solidified with an n-hexane-ethyl acetate mixed solution to obtain the title compound (41.0 mg).

$^1$H-NMR (DMSO-$D_6$) δ: 1.66 (3H, t, J=18.6 Hz), 2.81-2.95 (1H, m), 4.03-4.26 (1H, m), 5.98 (1H, s), 6.69-7.32 (9H, m), 7.41 (2H, d, J=8.5 Hz), 10.80 (1H, br s), MS (m/z): 536 (M+H)$^+$.

Example 95

7-[5-(2,2-Difluoropropyl)-6-oxo-4-{4-[4-(trifluoromethoxy)phenoxy]phenyl}-1,4,5,6-tetrahydropyrrolo[3,4-c]pyrazol-3-yl]-1,3-benzothiazol-2(3H)-one

[Chemical Formula 189]

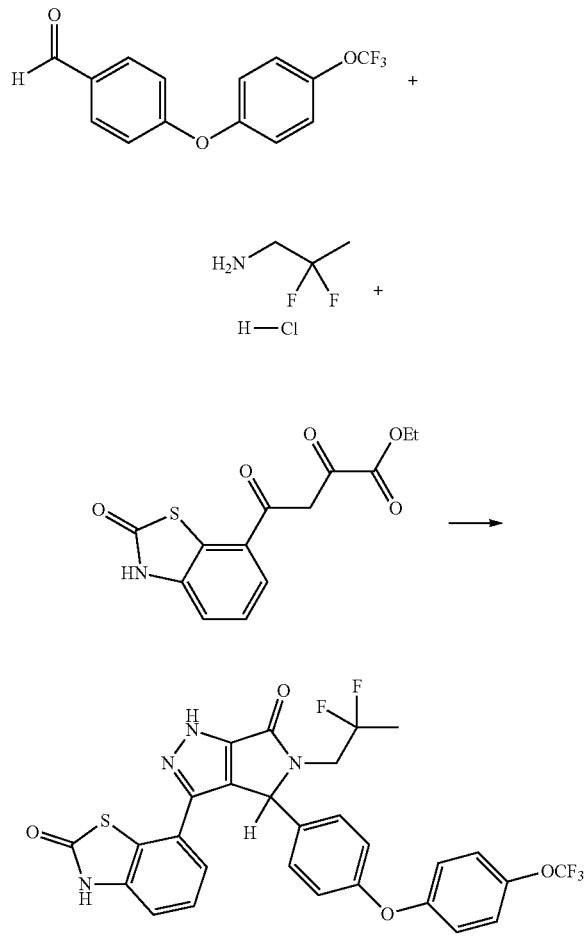

The compound obtained in Reference Example 25 (343 mg), 2,2-difluoropropylamine hydrochloride (160 mg, CAS number: 868241-48-9), and the compound obtained in step 2 of Reference Example 7 (297 mg) were used as manufacturing raw materials, and the same procedure as that in Example 26 was performed to obtain the title compound (85 mg) as a solid.

$^1$H-NMR (DMSO-$D_6$) δ: 1.65 (3H, t, J=19.2 Hz), 2.84-2.95 (1H, m), 4.06-4.22 (1H, m), 6.04 (1H, s), 6.98-7.41 (11H, m), 11.89 (1H, s), 14.40 (1H, s), MS (m/z): 603 (M+H)$^+$.

Example 96

7-[(4S)-4-{4-[3,5-Bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one 2-methylpropane-2-amine salt To (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (29.72 mg) synthesized in the same manner as Example 42, a 1.000 mol/L of aqueous 2-methylpropane-2-amine (CAS number: 75-64-9) solution (48.9 μL) and water (99.7 μL) was added at room temperature. The mixture was stirred at 40° C. overnight to obtain a solid. Then, the mixture was dried at room temperature overnight to obtain the title compound as a crystal.

$^1$H-NMR (DMSO-$D_6$) δ: 7.85 (1H, s), 7.60 (2H, s), 7.23 (2H, d, J=8.6 Hz), 7.02 (2H, d, J=8.6 Hz), 6.89 (1H, dd, J=8.0, 1.2 Hz), 6.81 (1H, dd, J=8.0, 7.3 Hz), 6.76 (1H, dd, J=7.3, 1.2 Hz), 6.03 (1H, s), 4.24-4.09 (1H, m), 2.97-2.84 (1H, m), 1.64 (3H, t, J=19.0 Hz), 1.18 (9H, s).

Elemental analysis found; C: 55.65%, H: 4.17%, N: 9.93%, F: 21.75%

FIG. 1 shows the powder X-ray diffraction of the crystal obtained.

Table 11 shows peaks having a relative intensity of 20 or more when the maximum peak intensity in FIG. 1 showing the diffraction pattern of the powder X-ray diffraction (CuKα, λ=1.54 angstrom, scanning rate=20°/min) is taken as 100.

TABLE 11

| Peak No. | 2θ | d value | Relative intensity | Peak No. | 2θ | d value | Relative intensity |
|---|---|---|---|---|---|---|---|
| 1 | 3.44 | 25.66 | 36 | 6 | 21.02 | 4.22 | 27 |
| 2 | 10.46 | 8.45 | 86 | 7 | 22.18 | 4.00 | 31 |
| 3 | 13.04 | 6.78 | 45 | 8 | 23.54 | 3.78 | 20 |
| 4 | 16.00 | 5.53 | 26 | 9 | 24.46 | 3.64 | 22 |
| 5 | 19.20 | 4.62 | 100 | 10 | 25.88 | 3.44 | 24 |

The compound obtained in a similar manner as Example 96 was subjected to single crystal X-ray crystallography, so that it was found that the compound of Example 96 is the 2-methylpropane-2-amine salt of the compound represented by formula (13B):

[Chemical Formula 190]

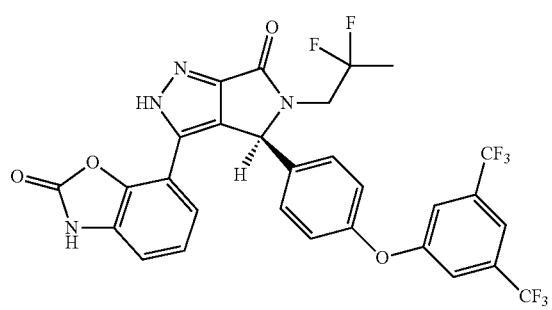

(13B)

in the single crystal. The name of the compound represented by formula (13B) is 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one.

The 2-methylpropane-2-amine salt of the compound represented by formula (13B):

[Chemical Formula 191]

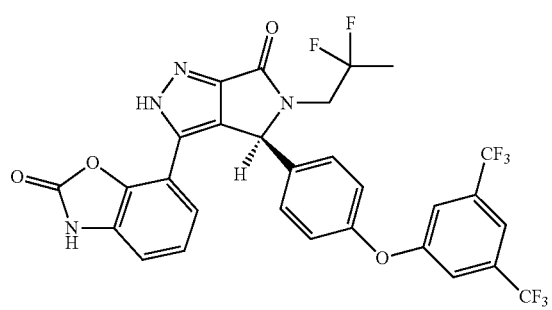

(13B)

and the 2-methylpropane-2-amine salt of the compound represented by formula (13A):

[Chemical Formula 192]

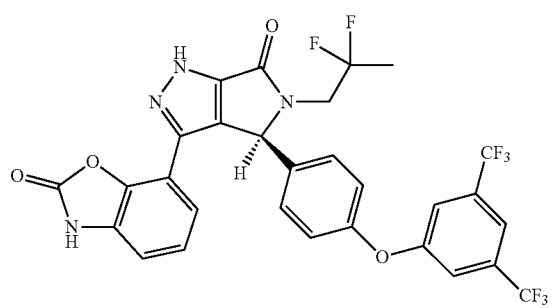

(13A)

are in a tautomeric relationship.

In general, tautomers may isomerize into each other depending on the temperature, pH, liquid phase/solid phase, and when the tautomers are solutions, depending on the type of the solvent, and therefore, it is considered that the 2-methylpropane-2-amine salt of the compound represented by formula (13B) may isomerize into the 2-methylpropane-2-amine salt of the compound represented by formula (13A) according to the changes in the above various physicochemical conditions.

Example 97

(−)-7-[4-{4-[3,5-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one isonicotinamide adduct To (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one (29.96 mg) synthesized in the same manner as Example 42, acetone (74.9 μL), isonicotinamide (6.13 mg, CAS number: 1453-82-3), and water (74.9 μL) were added at room temperature. The mixture was stirred at 40° C. overnight to obtain a solid. Then, the mixture was dried at room temperature overnight to obtain the title compound as a crystal.

$^1$H-NMR (DMSO-$D_6$) δ: 14.26 (1H, br s), 11.82 (1H, br s), 8.72 (1H, d, J=6.1 Hz), 8.25 (0.5H, br s), 7.84 (1H, s), 7.79-7.71 (1.5H, m), 7.53 (2H, s), 7.35-7.26 (1H, m), 7.25-6.98 (6H, m), 6.00 (1H, s), 4.29-4.06 (1H, m), 3.03-2.89 (1H, m), 1.64 (3H, t, J=19.0 Hz).

Elemental analysis found; C: 53.84%, H: 3.19%, N: 10.17%, F: 21.10%

Figure 2:
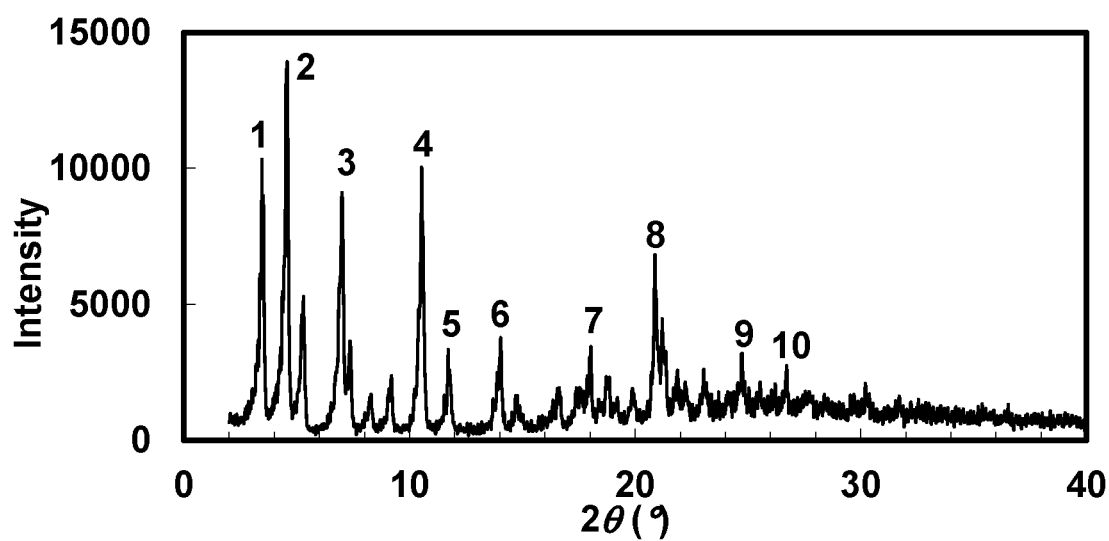
FIG. 2 is a powder X-ray diffraction diagram of the crystal obtained in Example 97. The ordinate indicates the diffraction intensity (Intensity) in units of counts/second (cps), and the abscissa indicates the value of diffraction angle 2θ.

FIG. 2 shows the powder X-ray diffraction of the crystal obtained.

Table 12 shows peaks having a relative intensity of 37 or more when the maximum peak intensity in FIG. 2 showing the diffraction pattern of the powder X-ray diffraction (CuKα, λ=1.54 angstrom, scanning rate=20°/min) is taken as 100.

TABLE 12

| Peak No. | 2θ | d value | Relative intensity | Peak No. | 2θ | d value | Relative intensity |
|---|---|---|---|---|---|---|---|
| 1 | 3.46 | 25.51 | 87 | 6 | 13.96 | 6.34 | 38 |
| 2 | 4.54 | 19.45 | 100 | 7 | 17.98 | 4.93 | 52 |
| 3 | 6.96 | 12.69 | 64 | 8 | 20.86 | 4.25 | 74 |
| 4 | 10.54 | 8.39 | 77 | 9 | 24.70 | 3.60 | 40 |
| 5 | 11.74 | 7.53 | 37 | 10 | 26.64 | 3.34 | 42 |

From the results of the single crystal X-ray crystallography obtained from the single crystal of the compound of Example 42 and the single crystal of the compound of Example 96, it is considered that the single crystal of the compound of Example 97 may show the structure of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one isonicotinamide adduct.

Example 98

(−)-7-[5-(2,2-Difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one 2-methylpropane-2-amine salt To (−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one (50.11 mg) synthesized in the same manner as Example 32, a 1.000 mol/L of aqueous 2-methylpropane-2-amine solution (87.6 µL) and water (163 µL) were added at room temperature. The mixture was stirred at 40° C. overnight to obtain a solid. Then, the mixture was dried at room temperature overnight to obtain the title compound as a crystal.

$^1$H-NMR (DMSO-D$_6$) δ: 7.29 (1H, dd, J=8.5, 1.2 Hz), 7.15 (2H, d, J=8.5 Hz), 7.02-6.94 (2H, m), 6.91-6.84 (4H, m), 6.81 (1H, dd, J=7.3, 1.2 Hz), 6.00 (1H, s), 4.24-4.09 (1H, m), 2.89-2.77 (1H, m), 2.21 (3H, s), 1.65 (3H, t, J=19.2 Hz), 1.21 (7H, s).

Elemental analysis found; C: 57.14%, H: 4.52%, N: 9.74%, F: 15.72%

Figure 3:
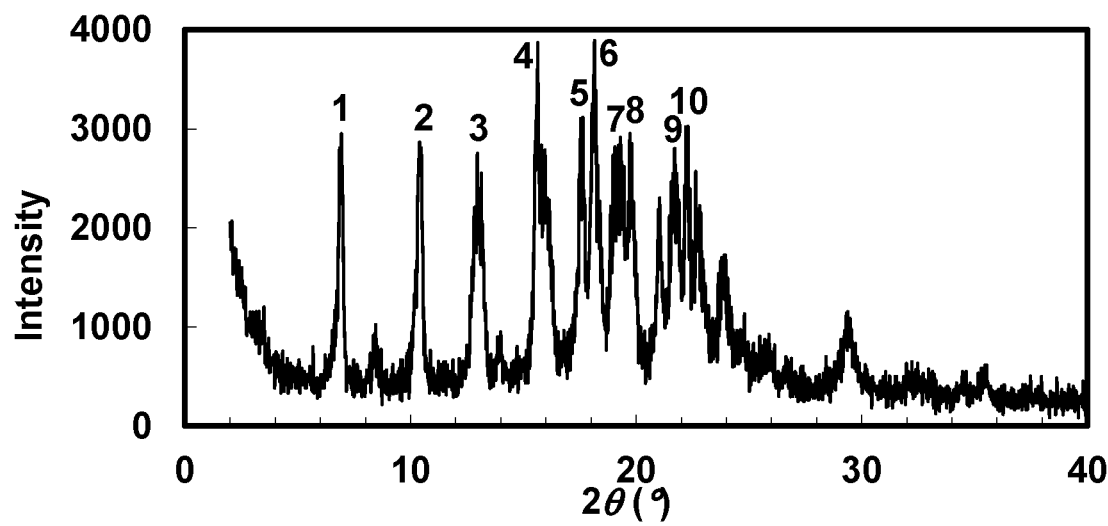
FIG. 3 is a powder X-ray diffraction diagram of the crystal obtained in Example 98. The ordinate indicates the diffraction intensity (Intensity) in units of counts/second (cps), and the abscissa indicates the value of diffraction angle 2θ.

FIG. 3 shows the powder X-ray diffraction of the crystal obtained.

Table 13 shows peaks having a relative intensity of 67 or more when the maximum peak intensity in FIG. 3 showing the diffraction pattern of the powder X-ray diffraction (CuKα, λ=1.54 angstrom, scanning rate=20°/min) is taken as 100.

TABLE 13

| Peak No. | 2θ | d value | Relative intensity | Peak No. | 2θ | d value | Relative intensity |
|---|---|---|---|---|---|---|---|
| 1 | 6.92 | 12.76 | 83 | 6 | 18.12 | 4.89 | 100 |
| 2 | 10.42 | 8.48 | 84 | 7 | 19.22 | 4.61 | 78 |
| 3 | 12.96 | 6.83 | 67 | 8 | 19.80 | 4.48 | 74 |
| 4 | 15.60 | 5.68 | 99 | 9 | 21.72 | 4.09 | 74 |
| 5 | 17.58 | 5.04 | 80 | 10 | 22.26 | 3.99 | 78 |

Example 99

(−)-7-[5-(2,2-Difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one isonicotinamide adduct To (−)-7-[5-(2,2-difluoropropyl)-4-{4-[3-methyl-4-(trifluoromethoxy)phenoxy]phenyl}-6-oxo-1,4,5,6-tetrahydropyrrolo[3,4-c]pyrazol-3-yl]-1,3-benzoxazol-2(3H)-one (69.53 mg) synthesized in the same manner as Example 32, 2-propanol (69.5 µL), isonicotinamide (15.11 mg), and water (278 µL) were added at room temperature. The mixture was stirred at 40° C. overnight to obtain a solid. Then, the mixture was dried at room temperature overnight to obtain the title compound as a crystal.

$^1$H-NMR (DMSO-D$_6$) δ: 14.25 (1H, br s), 11.84 (1H, br s), 8.72 (1.4H, d, J=6.1 Hz), 8.26 (0.7H, br s), 7.77 (1.4H, d, J=6.1 Hz), 7.74 (0.7H, br s), 7.38-7.25 (2H, m), 7.22-7.00 (4H, m), 6.98 (1H, d, J=3.1 Hz), 6.92 (2H, d, J=8.5 Hz), 6.85 (1H, dd, J=9.2, 3.1 Hz), 5.98 (1H, s), 4.27-4.06 (1H, m), 2.94-2.80 (1H, m), 2.21 (3H, s), 1.66 (3H, t, J=19.5 Hz).

Elemental analysis found; C: 57.55%, H: 3.87%, N: 11.23%, F: 13.72%

Figure 4:
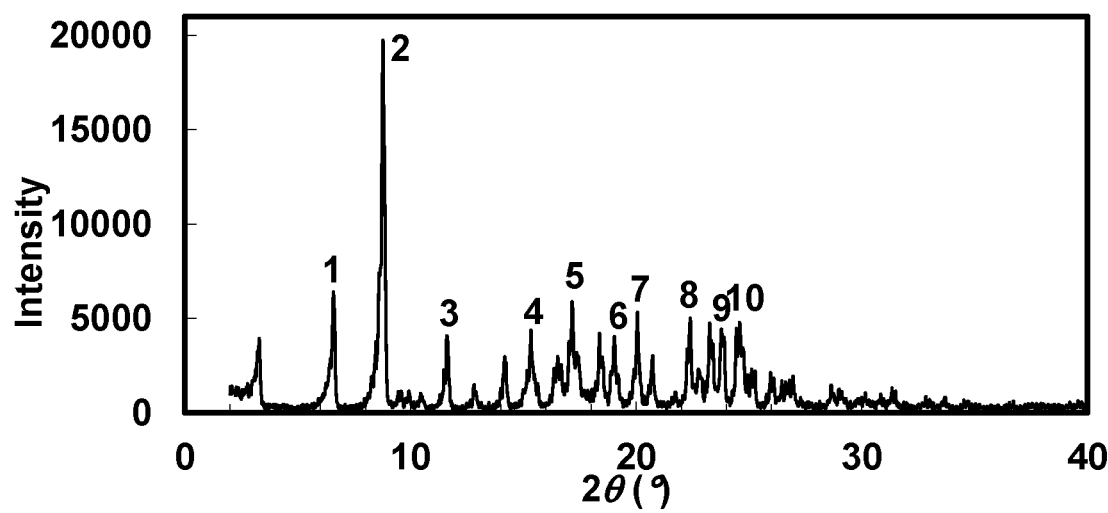
FIG. 4 is a powder X-ray diffraction diagram of the crystal obtained in Example 99. The ordinate indicates the diffraction intensity (Intensity) in units of counts/second (cps), and the abscissa indicates the value of diffraction angle 2θ.

FIG. 4 shows the powder X-ray diffraction of the crystal obtained.

Table 14 shows peaks having a relative intensity of 20 or more when the maximum peak intensity in FIG. 4 showing the diffraction pattern of the powder X-ray diffraction (CuKα, λ=1.54 angstrom, scanning rate=20°/min) is taken as 100.

TABLE 14

| Peak No. | 2θ | d value | Relative intensity | Peak No. | 2θ | d value | Relative intensity |
|---|---|---|---|---|---|---|---|
| 1 | 6.58 | 13.42 | 33 | 6 | 19.02 | 4.66 | 20 |
| 2 | 8.80 | 10.04 | 100 | 7 | 20.06 | 4.42 | 26 |

TABLE 14-continued

| Peak No. | 2θ | d value | Relative intensity | Peak No. | 2θ | d value | Relative intensity |
|---|---|---|---|---|---|---|---|
| 3 | 11.62 | 7.61 | 22 | 8 | 22.36 | 3.97 | 24 |
| 4 | 15.34 | 5.77 | 21 | 9 | 23.82 | 3.73 | 23 |
| 5 | 17.14 | 5.17 | 28 | 10 | 24.58 | 3.62 | 24 |

Example 100

(−)-7-[5-(2,2-Difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one 2-methylpropane-2-amine salt To (−)-7-[5-(2,2-difluoropropyl)-6-oxo-4-{4-[4-(trifluoromethoxy)-3-(trifluoromethyl)phenoxy]phenyl}-1,4,5,6-tetrahydropyrrolo[3,4-c]pyrazol-3-yl]-1,3-benzoxazol-2(3H)-one (14.55 mg) synthesized in the same manner as Example 33, a 1.000 mol/L of aqueous 2-methylpropane-2-amine solution (23.3 µL) and water (49.5 µL) were added at room temperature. The mixture was stirred at 40° C. overnight to obtain a solid. Then, the mixture was dried at room temperature overnight to obtain the title compound as a crystal.

$^1$H-NMR (DMSO-D$_6$) δ: 7.63 (1H, d, J=9.2 Hz), 7.44 (1H, d, J=3.1 Hz), 7.33 (1H, dd, J=9.2, 3.1 Hz), 7.20 (2H, d, J=8.5 Hz), 7.00 (2H, d, J=8.5 Hz), 6.97 (1H, d, J=7.9 Hz), 6.87 (1H, dd, J=7.9, 7.3 Hz), 6.81 (1H, d, J=7.3 Hz), 6.02 (1H, s), 4.26-4.07 (1H, m), 2.93-2.79 (1H, m), 1.65 (3H, t, J=19.5 Hz), 1.19 (7H, s).

Elemental analysis found; C: 53.01%, H: 3.75%, N: 9.25%, F: 23.46%

Figure 5:
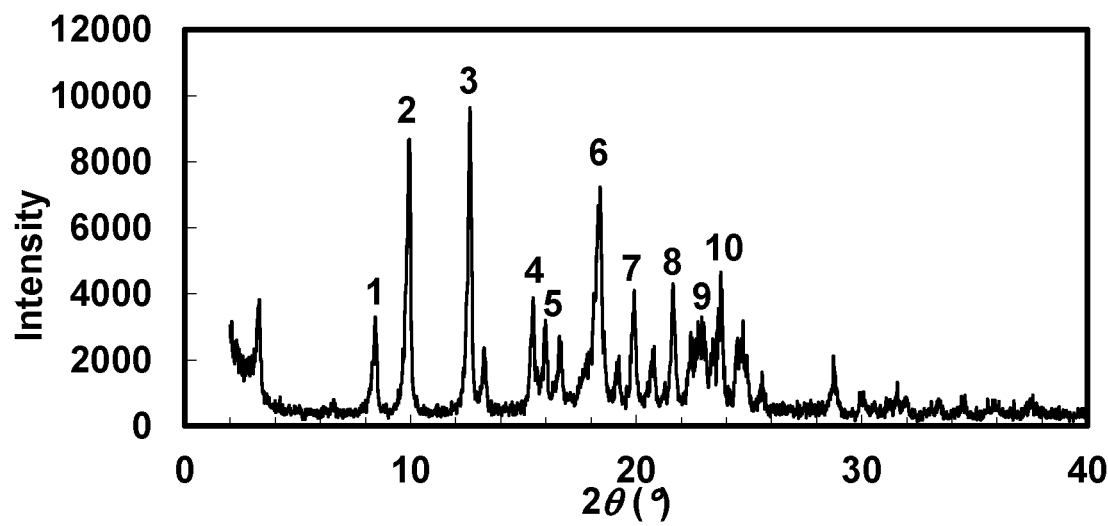
FIG. 5 is a powder X-ray diffraction diagram of the crystal obtained in Example 100. The ordinate indicates the diffraction intensity (Intensity) in units of counts/second (cps), and the abscissa indicates the value of diffraction angle 2θ.

FIG. 5 shows the powder X-ray diffraction of the crystal obtained.

Table 15 shows peaks having a relative intensity of 33 or more when the maximum peak intensity in FIG. 5 showing the diffraction pattern of the powder X-ray diffraction (CuKα, λ=1.54 angstrom, scanning rate=20°/min) is taken as 100.

TABLE 15

| Peak No. | 2θ | d value | Relative intensity | Peak No. | 2θ | d value | Relative intensity |
|---|---|---|---|---|---|---|---|
| 1 | 8.42 | 10.49 | 33 | 6 | 18.36 | 4.83 | 76 |
| 2 | 9.92 | 8.91 | 94 | 7 | 19.90 | 4.46 | 42 |
| 3 | 12.62 | 7.01 | 100 | 8 | 21.64 | 4.10 | 45 |
| 4 | 15.40 | 5.75 | 39 | 9 | 22.96 | 3.87 | 35 |
| 5 | 15.96 | 5.55 | 34 | 10 | 23.74 | 3.74 | 43 |

Example 101

(−)-7-[4-{4-[3-Chloro-4-(trifluoromethoxy)phenoxy]phenyl}-5-(2,2-difluoropropyl)-6-oxo-1,4,5,6,-tetrahydropyrrolo[3,4-c]pyrazol-3-yl]-1,3-benzoxazol-2-(3H)-one 2-methylpropane-2-amine salt To (−)-7-[4-{4-[3-chloro-4-(trifluoromethoxy)phenoxy]phenyl}-5-(2,2-difluoropropyl)-6-oxo-1,4,5,6,-tetrahydropyrrolo[3,4-c]pyrazol-3-yl]-1,3-benzoxazol-2-(3H)-one (50.33 mg) synthesized in the same manner as Example 31, a 1.000 mol/L of aqueous 2-methylpropane-2-amine solution (85.1 µL) and water (166.6 µL) were added at room temperature. The mixture was stirred at 40° C. overnight to obtain a solid. Then, the mixture was dried at room temperature overnight to obtain the title compound as a crystal.

$^1$H-NMR (DMSO-D$_6$) δ: 7.54 (1H, d, J=9.2 Hz), 7.30 (1H, d, J=3.1 Hz), 7.18 (2H, d, J=8.5 Hz), 7.01 (1H, dd, J=9.2, 3.1 Hz), 6.99-6.91 (2H, m), 6.86 (1H, t, J=7.9, 7.3 Hz), 6.80 (1H, d, J=7.3 Hz), 6.02 (1H, s), 4.25-4.09 (1H, m), 2.92-2.79 (1H, m), 1.65 (3H, t, J=19.5 Hz), 1.20 (7H, s).

Elemental analysis found; C: 54.29%, H: 4.14%, N: 9.65%, Cl: 5.31%, F: 13.69%

Figure 6:
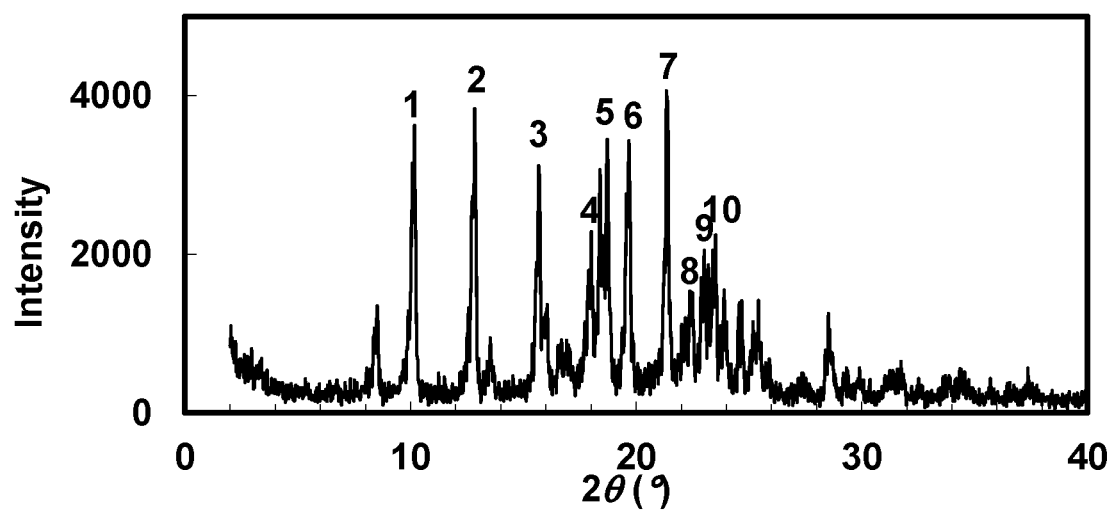
FIG. 6 is a powder X-ray diffraction diagram of the crystal obtained in Example 101. The ordinate indicates the diffraction intensity (Intensity) in units of counts/second (cps), and the abscissa indicates the value of diffraction angle 2θ.

FIG. 6 shows the powder X-ray diffraction of the crystal obtained.

Table 16 shows peaks having a relative intensity of 37 or more when the maximum peak intensity in FIG. 6 showing the diffraction pattern of the powder X-ray diffraction (CuKα, λ=1.54 angstrom, scanning rate=20°/min) is taken as 100.

TABLE 16

| Peak No. | 2θ | d value | Relative intensity | Peak No. | 2θ | d value | Relative intensity |
|---|---|---|---|---|---|---|---|
| 1 | 10.12 | 8.73 | 77 | 6 | 19.64 | 4.52 | 76 |
| 2 | 12.80 | 6.91 | 79 | 7 | 21.36 | 4.16 | 100 |
| 3 | 15.66 | 5.65 | 66 | 8 | 22.42 | 3.96 | 37 |
| 4 | 17.94 | 4.94 | 45 | 9 | 22.98 | 3.87 | 41 |
| 5 | 18.70 | 4.74 | 80 | 10 | 23.46 | 3.79 | 46 |

Example 102

(−)-7-[4-{4-[3-Chloro-4-(trifluoromethoxy)phenoxy]phenyl}-5-(2,2-difluoropropyl)-6-oxo-1,4,5,6,-tetrahydropyrrolo[3,4-c]pyrazol-3-yl]-1,3-benzoxazol-2-(3H)-one isonicotinamide adduct To (−)-7-[4-{4-[3-chloro-4-(trifluoromethoxy)phenoxy]phenyl}-5-(2,2-difluoropropyl)-6-oxo-1,4,5,6,-tetrahydropyrrolo[3,4-c]pyrazol-3-yl]-1,3-benzoxazol-2-(3H)-one (70.36 mg) synthesized in the same manner as Example 31, 2-propanol (70.4 μL), isonicotinamide (14.82 mg), and water (281 μL) were added at room temperature. The mixture was stirred at 40° C. overnight to obtain a solid. Then, the mixture was dried at room temperature overnight to obtain the title compound as a crystal.

$^1$H-NMR (DMSO-D$_6$) δ: 14.26 (1H, br s), 11.81 (1H, br s), 8.72 (1.8H, d, J=6.1 Hz), 8.25 (0.9H, br s), 7.77 (1.8H, d, J=6.1 Hz), 7.74 (1H, br s), 7.55 (1H, dd, J=9.2, 1.2 Hz), 7.34-7.26 (1H, m), 7.25 (1H, d, J=3.1 Hz), 7.20-7.10 (3H, m), 7.06-6.96 (4H, m), 5.99 (1H, s), 4.26-4.09 (1H, m), 2.97-2.84 (1H, m), 1.66 (3H, t, J=19.5 Hz).

Elemental analysis found; C: 53.96%, H: 3.34%, N: 10.82%, Cl: 4.85%, F: 14.13%

Figure 7:
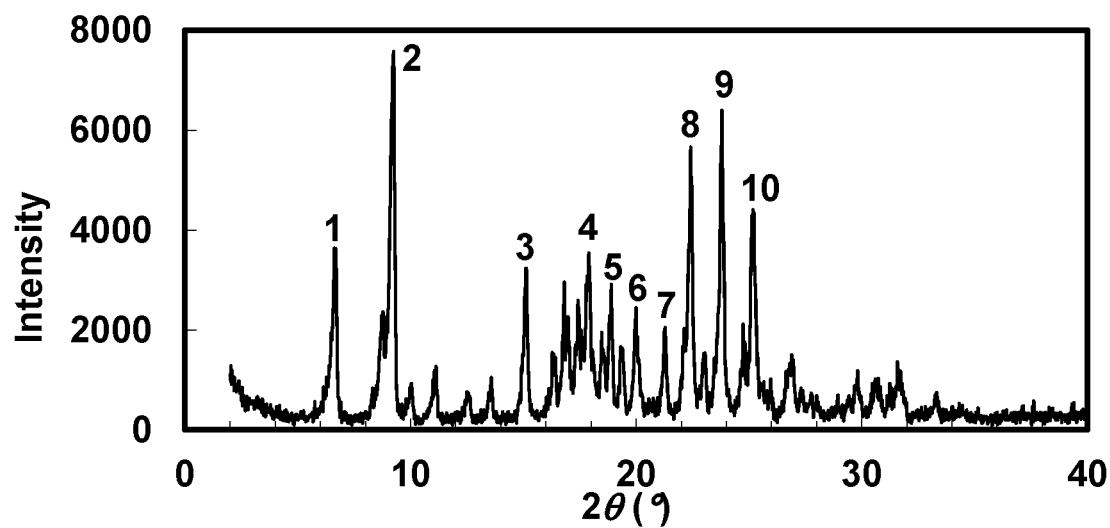
FIG. 7 is a powder X-ray diffraction diagram of the crystal obtained in Example 102. The ordinate indicates the diffraction intensity (Intensity) in units of counts/second (cps), and the abscissa indicates the value of diffraction angle 2θ.

FIG. 7 shows the powder X-ray diffraction of the crystal obtained.

Table 17 shows peaks having a relative intensity of 27 or more when the maximum peak intensity in FIG. 7 showing the diffraction pattern of the powder X-ray diffraction (CuKα, λ=1.54 angstrom, scanning rate=20°/min) is taken as 100.

TABLE 17

| Peak No. | 2θ | d value | Relative intensity | Peak No. | 2θ | d value | Relative intensity |
|---|---|---|---|---|---|---|---|
| 1 | 6.60 | 13.38 | 44 | 6 | 20.02 | 4.43 | 30 |
| 2 | 9.18 | 9.63 | 100 | 7 | 21.26 | 4.18 | 28 |
| 3 | 15.08 | 5.87 | 41 | 8 | 22.36 | 3.97 | 61 |

TABLE 17-continued

| Peak No. | 2θ | d value | Relative intensity | Peak No. | 2θ | d value | Relative intensity |
|---|---|---|---|---|---|---|---|
| 4 | 17.88 | 4.96 | 48 | 9 | 23.78 | 3.74 | 86 |
| 5 | 18.80 | 4.72 | 27 | 10 | 25.20 | 3.53 | 60 |

Example 103

(−)-7-[5-(2,2-Difluoropropyl)-6-oxo-4-{4-[4-(trifluoromethoxy)phenoxy]phenyl}-1,4,5,6,-tetrahydropyrrolo[3,4-c]pyrazol-3-yl]-1,3-benzoxazol-2-(3H)-one 2-methylpropane-2-amine salt To (−)-7-[5-(2,2-difluoropropyl)-6-oxo-4-{4-[4-(trifluoromethoxy)phenoxy]phenyl}-1,4,5,6,-tetrahydropyrrolo[3,4-c]pyrazol-3-yl]-1,3-benzoxazol-2-(3H)-one (49.70 mg) synthesized in the same manner as Example 30, a 1.000 mol/L of aqueous 2-methylpropane-2-amine solution (89.0 μL) and water (159.5 μL) were added at room temperature. The mixture was stirred at 40° C. overnight to obtain a solid. Then, the mixture was dried at room temperature overnight to obtain the title compound as a crystal.

$^1$H-NMR (DMSO-D$_6$) δ: 7.35 (2H, d, J=8.5 Hz), 7.15 (2H, d, J=8.5 Hz), 7.06 (2H, d, J=8.5 Hz), 6.99 (1H, dd, J=7.9, 1.2 Hz), 6.93-6.87 (3H, m), 6.83 (1H, dd, J=7.3, 1.2 Hz), 6.00 (1H, s), 4.24-4.10 (1H, m), 2.90-2.77 (1H, m), 1.65 (3H, t, J=19.5 Hz), 1.21 (6H, s).

Elemental analysis found; C: 56.23%, H: 4.26%, N: 9.94%, F: 15.84%

Figure 8:
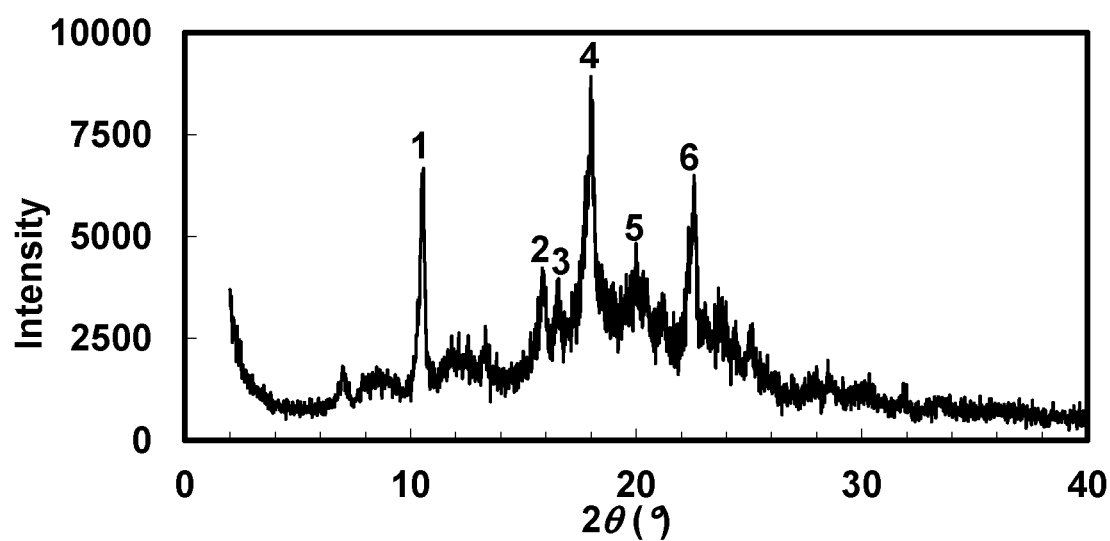
FIG. 8 is a powder X-ray diffraction diagram of the crystal obtained in Example 103. The ordinate indicates the diffraction intensity (Intensity) in units of counts/second (cps), and the abscissa indicates the value of diffraction angle 2θ.

FIG. 8 shows the powder X-ray diffraction of the crystal obtained.

Table 18 shows peaks having a relative intensity of 46 or more when the maximum peak intensity in FIG. 8 showing the diffraction pattern of the powder X-ray diffraction (CuKα, λ=1.54 angstrom, scanning rate=20°/min) is taken as 100.

TABLE 18

| Peak No. | 2θ | d value | Relative intensity | Peak No. | 2θ | d value | Relative intensity |
|---|---|---|---|---|---|---|---|
| 1 | 10.52 | 8.40 | 79 | 4 | 18.00 | 4.92 | 100 |
| 2 | 15.88 | 5.58 | 50 | 5 | 19.96 | 4.44 | 52 |
| 3 | 16.52 | 5.36 | 46 | 6 | 22.52 | 3.94 | 70 |

Test Examples

The pharmacological activity of the compound of the present invention was confirmed by the following test.

[Test Example 1] Evaluation on PSS1 Inhibitory Activity

100 μL of reaction solutions (50 mM Tris-HCl (pH 7.5), 5 mM CaCl$_2$, 1 μCi/ml L-[$^{14}$C(U)]-serine (PerkinElmer, NEC286E or Moravec, Inc., MC-265), 0.8 mg/ml PTDSS1-expressing Sf9 cell membrane fraction) containing different concentrations of compounds of Examples 1 to 95 were added to each well of 96-well plates, and allowed to stand at 37° C. for 20 minutes. After addition of 100 μL of 10 mM EDTA to stop the reaction, Sf9 cell membrane fractions were recovered using Unifilter-96 GF/C (PerkinElmer, #6005174)

and Unifilter Harvester (Packard, U.S.A., model 196), the filter was air-dried, and then 40 µL of Microscint™-20 (PerkinElmer, #6013621) was added dropwise to each well. Scintillation counts were measured on a TopCount-NXT-HTS (PerkinElmer, model C384V01). Based on the measured scintillation counts, the enzyme inhibitory rates of the compounds of Examples 1 to 95 at various concentrations were measured, and the data obtained were analyzed using a medical statistics analysis software, GraphPad Prism (GraphPad Software, Inc.) to calculate the $IC_{50}$ values. The PTDSS1-expressing Sf9 cell membrane fractions were produced and isolated by the following methods in DAIICHI SANKYO RD NOVARE CO., LTD. The PTDSS1 in which a Flag tag was attached to N-terminal and an HA tag was attached to C-terminal was amplificated according to the method described in the literature (Biomchem. J. 418. 421-429 (2009)) by PCR and cloned into pFastBacl vector (Invitrogen). The prepared vector was transformed into DH10bac (Invitrogen) to prepare a bacmid. A PTDSS1-expressing baculovirus was prepared using the prepared bacmid and infected into Sf9 cells. The Sf9 cells were recovered, suspended in buffer A (0.25 M sucrose, 10 mM HEPES (pH 7.5), 1 mM EDTA, 1 tablet/50 ml cOmplete EDTA-free (Roche, 4693132)), fractured by ultrasonication, and then centrifuged (1000×g, 10 minutes, 4° C.). The supernatant was recovered and treated by ultracentrifugation (100000×g, 1 hour, 4° C.), and then the pellet was suspended in buffer A again. This was treated by ultracentrifugation (100000×g, 1 hour, 4° C.) again, and then the pellet was suspended in a harvest buffer (10 mM HEPES (pH 7.5), 20% (v/v) glycerol, 1 tablet/50 ml cOmplete EDTA-free (Roche, 4693132)) to give a PTDSS1-expressing membrane fraction.

[Test Example 2] Evaluation on Phosphatidylserine De Novo Synthesis Inhibitory Activity in Cells HCT116 cells and PTDSS2 gene-disrupted (PTDSS2-KO) HCT116 cells which are derived from human bowel cancer were prepared in McCoy's 5A medium containing 10% bovine serum to 20,000 cells/50 µL/well, and then seeded into 96-well plates and cultured at 37° C. under 5% $CO_2$ overnight. HCT116 cells were purchased from American Type Culture Collection (ATCC). The medium was removed, and then 100 µL of MEM containing 10% bovine dialyzed serum containing compound solutions of Examples 1 to 95 (the final concentration of dimethyl sulfoxide is 0.2%) and L-[$^{14}$C(U)]-serine (PerkinElmer, NEC286E or Moravec, Inc., MC-265, the final concentration is 2.5 µCi/ml) was added, followed by culturing at 37° C. under 5% $CO_2$ for 24 hours. The medium was removed, cells were washed once with PBS, and then 100 µL of methanol was added to each well, followed by allowing to stand at room temperature for 30 minutes. Methanol was recovered in 96 well cluster tubes (Corning #4411), 50 µL of chloroform and 50 µL of 50 mM HEPES were added to each tube, which was stirred with a vortex mixer and then allowed to stand at room temperature for 10 minutes. Again, 50 µL of chloroform and 50 µL of 50 mM HEPES were added to each tube, which was stirred with a vortex mixer and then treated by ultracentrifugation (240×g, 4° C., 5 minutes). 90 µL was recovered from the organic layer of each tube and added to PicoPlate-96 (PerkinElmer, #6005162). After the plates were air-dried, 100 µL of Microscint™-20 (PerkinElmer, #6013621) was added to each well and scintillation counts were measured using TopCount-NXT-HTS. Based on the measured counts, phosphatidylserine de novo synthesis inhibitory rates in cells of the compounds of Examples 1 to 95 at various concentrations were measured, and the data obtained were analyzed using a medical statistics analysis software, GraphPad Prism (GraphPad Software, Inc.) to calculate the $IC_{50}$ values.

[Test Example 3] Evaluation on Cell Growth Suppression Activity 1

HCT116 cells and PTDSS2 gene-disrupted (PTDSS2-KO) HCT116 cells which are derived from human bowel cancer were used. McCoy's 5A medium containing 10% bovine serum was used as the culture medium for each cell. HCT116 cells were purchased from ATCC. The compounds of Examples 1 to 95 were diluted and prepared using a Freedom EVO 150 (Tecan Trading AG) (4 fold dilution, 10 steps, 25 mM-95 nM). They were added to each well of 384-well plates at 40 nL/well using an Echo555 (Labcyte Inc.). HCT116 cells or PTDSS2-KO HCT116 cells were seeded into the plates at 200 cells/40 µL/well (day 0) and cultured for 3 days. On the day of compound addition (day 0) and 3 days after compound addition (day 3), 10 µL/well of CellTiter-Glo® 2.0 Assay (Promega, #G9242), which is a reagent for ATP measurement, was added to each well, and the amount of luminescence in each well was measured with EnVision. From the amount of luminescence on the day of compound addition ($C_0$) and the amount of luminescence of the compound non-addition group ($C_3$) and compound addition group ($T_3$) after 3 days of culture, cell viability was calculated based on the following formula.

Cell viability (%)=$[(T_3-C_0)/(C_3-C_0)]\times 100$

The concentration which inhibits the cell growth of HCT116 cells or PTDSS2-KO HCT116 cells of each compound by 5000 ($GI_{50}$ value) was calculated by semi-logarithmically plotting the cell viability at each concentration against the compound concentration.

Table 19-1 to Table 19-5 show the results of Test Examples 1 to 3.

TABLE 19-1

| | | Test Example 2 | | Test Example 3 | |
|---|---|---|---|---|---|
| Example | Test Example 1 $IC_{50}$ (µM) | HCT116 $IC_{50}$ (µM) | PTDSS2-KO HCT116 $IC_{50}$ (µM) | HCT116 $GI_{50}$ (µM) | PTDSS2-KO HCT116 $GI_{50}$ (µM) |
| 1 | 0.050 | >20 | 0.0032 | 24 | 0.036 |
| 2 | 0.060 | >20 | 0.0071 | 10 | 0.12 |
| 3 | 0.31 | >20 | 0.14 | 13 | 0.77 |
| 4 | 0.77 | >20 | 0.59 | 17 | 3.2 |
| 5 | 0.24 | >20 | 0.088 | 12 | 0.91 |
| 6 | 0.37 | >5.0 | 0.039 | 24 | 0.71 |
| 7 | 1.3 | >20 | 0.065 | 15 | 0.75 |
| 8 | 0.92 | >20 | 0.082 | >25 | 1.1 |
| 9 | 5.7 | >20 | 0.16 | >25 | 0.70 |
| 10 | 0.18 | >20 | 0.0082 | 20 | 0.055 |
| 11 | 0.57 | >20 | 0.084 | >25 | 0.84 |
| 12 | 0.62 | >20 | 0.50 | >25 | 0.66 |
| 13 | 1.1 | >20 | 0.31 | >25 | 0.82 |
| 14 | 0.34 | >20 | 0.62 | 9.8 | 2.9 |
| 15 | 0.83 | >20 | 6.4 | >25 | 14 |
| 16 | 0.46 | >20 | 0.28 | >25 | 1.1 |
| 17 | 0.12 | >20 | 0.0045 | 13 | 0.047 |
| 18 | 0.10 | >4.0 | 0.0033 | 12 | 0.054 |
| 19 | 0.092 | >4.1 | 0.0054 | 11 | 0.062 |

TABLE 19-2

| 20 | 0.15 | >20 | 0.019 | 17 | 0.23 |
| 21 | 0.054 | >4.1 | 0.0034 | 8.4 | 0.028 |
| 22 | 0.34 | >20 | 0.055 | 21 | 0.86 |

TABLE 19-2-continued

| | | | | |
|---|---|---|---|---|
| 23 | 1.6 | >20 | 0.28 | >25 | 2.1 |
| 24 | 1.0 | >20 | 0.13 | >25 | 2.5 |
| 25 | 0.14 | >4.0 | 0.0016 | 8.9 | 0.025 |
| 26 | 2.1 | >20 | 0.056 | 22 | 0.48 |
| 27 | 0.14 | >4.1 | 0.0050 | 14 | 0.064 |
| 28 | 0.66 | >20 | 0.066 | 11 | 0.87 |
| 29 | 2.8 | >20 | 0.29 | 7.3 | 1.1 |
| 30 | 0.26 | >12 | 0.0038 | 6.3 | 0.041 |
| 31 | 0.34 | >4.0 | 0.0037 | 7.9 | 0.017 |
| 32 | 0.16 | >4.0 | 0.0025 | 8.3 | 0.019 |
| 33 | 0.43 | >4.4 | 0.0036 | 4.3 | 0.014 |
| 34 | 0.17 | >4.0 | 0.0031 | 7.9 | 0.020 |
| 35 | 0.19 | >4.0 | 0.0044 | 7.4 | 0.038 |
| 36 | 0.073 | >4.0 | 0.0026 | 8.0 | 0.014 |
| 37 | 0.20 | >4.0 | 0.0050 | 8.7 | 0.056 |
| 38 | 0.18 | >4.0 | 0.0095 | 9.2 | 0.073 |
| 39 | 0.24 | >4.4 | 0.0030 | 8.3 | 0.014 |
| 40 | 0.17 | >4.0 | 0.0054 | 3.3 | 0.020 |
| 41 | 0.24 | >20 | 0.0045 | 17 | 0.20 |

TABLE 19-3

| | | | | |
|---|---|---|---|---|
| 42 | 0.20 | >4.4 | 0.0030 | >25 | 0.014 |
| 43 | 0.15 | >4.0 | 0.0052 | 7.9 | 0.049 |
| 44 | 0.11 | >4.0 | 0.0042 | 3.9 | 0.019 |
| 45 | 0.20 | >4.0 | 0.0032 | 8.4 | 0.016 |
| 46 | 0.12 | >4.4 | 0.0034 | 8.0 | 0.040 |
| 47 | 0.18 | >4.2 | 0.0068 | 7.5 | 0.040 |
| 48 | 0.36 | >4.4 | 0.0043 | 7.8 | 0.017 |
| 49 | 0.14 | >4.0 | 0.0030 | 7.8 | 0.016 |
| 50 | 0.25 | >4.0 | 0.0051 | 6.5 | 0.018 |
| 51 | 0.36 | >4.0 | 0.017 | 5.4 | 0.14 |
| 52 | 0.12 | >4.0 | 0.0065 | 5.9 | 0.063 |
| 53 | 0.098 | >4.1 | 0.0025 | 13 | 0.017 |
| 54 | 0.19 | >4.0 | 0.0030 | 11 | 0.014 |
| 55 | 0.16 | >4.0 | 0.0034 | 8.9 | 0.027 |
| 56 | 0.10 | >4.1 | 0.0069 | 21 | 0.052 |
| 57 | 0.13 | >4.1 | 0.0025 | 8.4 | 0.055 |
| 58 | 0.13 | >4.0 | 0.0018 | 8.8 | 0.050 |
| 59 | 0.14 | >4.1 | 0.0015 | 8.2 | 0.026 |
| 60 | 0.17 | >4.0 | 0.0067 | 3.5 | 0.059 |
| 61 | 0.39 | >4.0 | 0.014 | 7.1 | 0.076 |
| 62 | 0.60 | >4.0 | 0.0025 | 11 | 0.014 |
| 63 | 0.21 | >4.0 | 0.0024 | 7.7 | 0.020 |

TABLE 19-4

| | | | | |
|---|---|---|---|---|
| 64 | 0.15 | >4.2 | 0.0029 | 8.3 | 0.015 |
| 65 | 0.18 | >4.0 | 0.0028 | 7.9 | 0.016 |
| 66 | 0.29 | >4.0 | 0.0018 | >25 | 0.016 |
| 67 | 0.23 | >4.0 | 0.0035 | 8.3 | 0.032 |
| 68 | 0.33 | >4.0 | 0.0099 | 5.1 | 0.070 |
| 69 | 0.13 | >4.0 | 0.0037 | 8.1 | 0.066 |
| 70 | 0.18 | >4.0 | 0.0046 | 7.8 | 0.031 |
| 71 | 0.28 | >4.0 | 0.0047 | 3.6 | 0.019 |
| 72 | 1.1 | >20 | 0.11 | >25 | 0.28 |
| 73 | 4.4 | >20 | 0.24 | 19 | 0.89 |
| 74 | 2.0 | >20 | 0.099 | 7.7 | 0.89 |
| 75 | 4.3 | >20 | 0.49 | 18 | 3.4 |
| 76 | 0.43 | >20 | 0.017 | 7.8 | 0.20 |
| 77 | 0.51 | >20 | 0.11 | >25 | 1.0 |
| 78 | 1.6 | >20 | 0.11 | >25 | 0.61 |
| 79 | 0.54 | >4.0 | 0.025 | 13 | 0.22 |
| 80 | 0.50 | >4.0 | 0.017 | 8.3 | 0.17 |
| 81 | 0.53 | >4.4 | 0.0072 | 3.0 | 0.015 |
| 82 | 0.34 | >4.0 | 0.0070 | 12 | 0.022 |
| 83 | 0.65 | >4.0 | 0.031 | >25 | 0.26 |
| 84 | 0.14 | >4.0 | 0.0040 | 10 | 0.035 |
| 85 | 0.25 | >4.4 | 0.0061 | 11 | 0.050 |

TABLE 19-5

| | | | | |
|---|---|---|---|---|
| 86 | 0.12 | >4.0 | 0.016 | 12 | 0.055 |
| 87 | 0.17 | >4.0 | 0.0028 | 3.1 | 0.054 |
| 88 | 0.78 | >20. | 0.020 | 7.9 | 0.12 |
| 89 | 0.76 | >4.1 | 0.053 | 17 | 0.10 |
| 90 | 0.25 | >4.0 | 0.069 | 16 | 0.80 |
| 91 | 0.18 | >4.2 | 0.019 | 15 | 0.24 |
| 92 | 0.42 | >20.00 | 1.3 | 11 | 7.9 |
| 93 | 1.2 | >20 | 3.5 | >25 | 7.2 |
| 94 | 0.30 | >4.0 | 0.92 | 7.4 | 3.6 |
| 95 | 0.25 | >4.0 | 1.1 | 7.3 | 6.4 |

[Test Example 4] Evaluation on Antitumor Activity on PTDSS2-KO

HCT116 cell-subcutaneous transplanted model PTDSS2-KO HCT116 cells were transplanted to a right subcutaneous axillary portion of female BALB/c-nu/nu mice at a proportion of $1 \times 10^7$ cells/head, and when the tumor volume reached 100 to 300 mm$^3$ (estimated tumor volume (major axis×minor axis×minor axis/2)), mice were divided into groups of 6 or 5 mice each such that there was no difference between groups. The female BALB/c-nu/nu mice were purchased from CHARLES RIVER LABORATORIES JAPAN, INC. The compounds of Examples 58, 57, 53, 30, 42, 32, 34, 33, and 31 were orally administered from the day of grouping in the dosing schedule shown in Table 12 (twice daily, 11 successive days (BID×11), or once daily, 13 successive days (QD×13)). The tumor volume was measured until the next day of completion of the administration (test end date). 0.5% methylcellulose (MC) was administered to the vehicle control group as the vehicle.

The antitumor activity on PTDSS2-KO HCT116 cell-subcutaneous transplanted model of Test Example 4 was calculated by the following formula on each test end date.

$$TGI \% = (1 - TVt/TVc) \times 100$$

TGI: Tumor growth suppression rate
TVt: Group mean tumor volume of compound administration group on test end date
TVc: Group mean tumor volume of vehicle control group on test end date Table 20 shows the results of Test Example 4.

TABLE 20

| PTDSS2-KO HCT116 cell | | | |
|---|---|---|---|
| Example No. | Dose (mg/kg) | Dosing schedule | TGI (%) |
| 58 | 200 | BID × 11 | 87 |
| 57 | 50 | BID × 11 | 89 |
|  | 100 | BID × 11 | 97 |
| 53 | 50 | BID × 11 | 41 |
|  | 100 | BID × 11 | 83 |
| 30 | 10 | QD × 13 | 26 |
|  | 20 | QD × 13 | 50 |
|  | 40 | QD × 13 | 83 |
| 42 | 10 | QD × 13 | 97 |
|  | 20 | QD × 13 | 98 |
|  | 40 | QD × 13 | 99 |
| 32 | 10 | QD × 13 | 95 |
|  | 20 | QD × 13 | 98 |
|  | 40 | QD × 13 | 98 |
| 34 | 10 | QD × 13 | 63 |
|  | 20 | QD × 13 | 87 |
|  | 40 | QD × 13 | 96 |
| 33 | 10 | QD × 13 | 97 |
|  | 20 | QD × 13 | 98 |
|  | 40 | QD × 13 | 98 |
| 31 | 40 | QD × 13 | 88 |

[Test Example 5] Evaluation on Cell Growth Suppression Activity 2

NCI-N87 derived from human stomach cancer was used. RPMI medium containing 10% bovine serum was used as the culture medium. NCI-N87 cells were purchased from ATCC. NCI-N87 cells were seeded into 96 well plates at 5,000 cells/50 μL/well (day −1). The compound of Example 42 was serially diluted and prepared (10 steps, 20 μM-6 nM) and added to each well of 96 well plates at 50 μL/well. On the day of compound addition (day 0) and 7 days after compound addition (day 7), 50 μL/well of CellTiter-Glo® 2.0 Assay (Promega, #G9242), which is a reagent for ATP measurement, was added to each well, and the amount of luminescence in each well was measured with EnVision. From the amount of luminescence on the day of compound addition ($C_0$) and the amount of luminescence of the compound non-addition group ($C_7$) and compound addition group ($T_7$) after 7 days of culture, cell viability was calculated based on the following formula.

Cell viability (%)=[$(T_7-C_0)/(C_7-C_0)$]×100

The concentration which inhibits the cell growth of NCI-N87 cells of the compound by 50% ($GI_{50}$ value) was calculated by semi-logarithmically plotting the cell viability at each concentration against the compound concentration. The $GI_{50}$ of the compound of Example 42 in the present test was 7.4 nM.

[Test Example 6] Evaluation on Cell Growth Suppression Activity 3

ZR-75-1 cells derived from human breast cancer were used. RPMI medium containing 10% bovine serum was used as the culture medium. ZR-75-1 cells were purchased from ATCC. ZR-75-1 cells were seeded into 96 well plates at 5,000 cells/50 μL/well (day −1). The compound of Example 42 was serially diluted and prepared (10 steps, 20 μM-6 nM) and added to each well of 96 well plates at 50 μL/well. On the day of compound addition (day 0) and 6 days after compound addition (day 6), 50 μL/well of CellTiter-Glo® 2.0 Assay (Promega, #G9242), which is a reagent for ATP measurement, was added to each well, and the amount of luminescence in each well was measured with EnVision. From the amount of luminescence on the day of compound addition ($C_0$) and the amount of luminescence of compound non-addition group ($C_6$) and compound addition group ($T_6$) after 6 days of culture, cell viability was calculated based on the following formula.

Cell viability (%)=[$(T_6-C_0)/(C_6-C_0)$]×100

The concentration which inhibits the cell growth of ZR-75-1 cells of the compound by 50% ($GI_{50}$ value) was calculated by semi-logarithmically plotting the cell viability at each concentration against the compound concentration. The $GI_{50}$ of the compound of Example 42 in the present test was 2.9 μM.

[Test Example 7] Evaluation on Cell Growth Suppression Activity 4

Jeko-1 cells derived from human mantle cell lymphoma were used. RPMI medium containing 10% bovine serum was used as the culture medium. Jeko-1 cells were purchased from ATCC. Jeko-1 cells were seeded into 96 well plates at 50,000 cells/50 μL/well (day 0). The compound of Example 42 was serially diluted and prepared (10 steps, 30 μM-3 nM) and added to each well of 96 well plates at 50 μL/well. On the day of compound addition (day 0) and 3 days after compound addition (day 3), 30 μL/well of CellTiter-Glo® 2.0 Assay (Promega, #G9242), which is a reagent for ATP measurement, was added to each well, and the amount of luminescence in each well was measured with EnVision. The amount of luminescence on the day of compound addition ($C_0$) and the amount of luminescence of the compound non-addition group ($C_3$) and compound addition group ($T_3$) after 3 days of culture, cell viability was calculated based on the following formula.

Cell viability (%)=[$(T_3-C_0)/(C_3-C_0)$]×100

The concentration which inhibits the cell growth of Jeko-1 cells of the compound by 50% ($GI_{50}$ value) was calculated by semi-logarithmically plotting the cell viability at each concentration against the compound concentration. The $GI_{50}$ of the compound of Example 42 in the present test was 417.1 nM.

[Test Example 8] Evaluation on Antitumor Activity on PTDSS2-KO

A375 Cell-Subcutaneous Transplanted Model

PTDSS2-KO A375 cells were transplanted to a right subcutaneous axillary portion of female BALB/c-nu/nu mice at a proportion of 1×10$^6$ cells/head, and when the tumor volume reached 100 to 300 mm$^3$ (estimated tumor volume (major axis×minor axis×minor axis/2)), mice were divided into groups of 6 each such that there was no difference between groups. The female BALB/c-nu/nu mice were purchased from CHARLES RIVER LABORATORIES JAPAN, INC. The compound of Example 42 was orally administered from the day of grouping, once daily for 10 successive days (QD×10). The tumor volume was measured until the next day of completion of the administration (test end date). 0.5% methylcellulose (MC) was administered to the vehicle control group as the vehicle.

The antitumor activity on PTDSS2-KO A375 cell-subcutaneous transplanted model of Test Example 8 was calculated by the following formula on each test end date.

TGI %=(1−$TVt/TVc$)×100

TGI: Tumor growth suppression rate
TVt: Group mean tumor volume of compound administration group on test end date
TVc: Group mean tumor volume of vehicle control group on test end date
Table 21 shows the results of Test Example 8.

TABLE 21

| Dose (mg/kg) | TGI (%) |
|---|---|
| 100 | 100 |
| 30 | 100 |
| 10 | 100 |
| 3 | 47 |

INDUSTRIAL APPLICABILITY

Since the compound represented by general formula (1) of the present invention or a pharmaceutically acceptable salt thereof exhibits an inhibitory effect on phosphatidylserine synthase (PSS1), it can be used in the treatment of a cancer having a suppressed phosphatidylserine synthase 2 (PSS2) function. Specifically, the compound represented by general formula (1) of the present invention or a pharmaceutically acceptable salt thereof is preferably useful as a therapeutic drug for testicular germ cell tumor, ovarian cancer, bladder cancer, lung cancer, breast cancer, esophageal cancer, colon cancer, prostate cancer, stomach cancer, cervical cancer, endometrial cancer, uterine cancer, kidney cancer, thyroid cancer, squamous cell cancer, osteosarcoma, melanoma, glioblastoma, neuroblastoma, head and neck cancer, testicular tumor, bowel cancer, blood cancer, retinoblastoma, or pancreatic cancer, and more preferably, testicular germ cell tumor, ovarian cancer, bladder cancer, lung cancer, breast cancer, or esophageal cancer.

The invention claimed is:

1. A compound represented by general formula (1) or a pharmaceutically acceptable salt thereof:

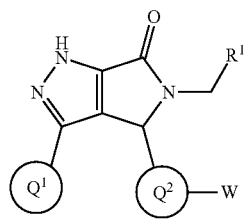

(1)

wherein
$R^1$ represents a halogeno $C_{1-6}$ alkyl group, a $C_{3-8}$ cycloalkyl group, or a 5- or 6-membered aromatic heterocyclic group,
ring $Q^1$ represents any one of formulas (2A) to (2C):

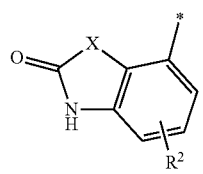

(2A)

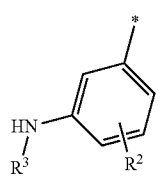

(2B)

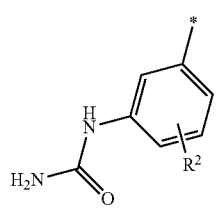

(2C)

wherein
* represents a bond,
X represents an oxygen atom, a sulfur atom, or —NH—,
$R^2$ represents a hydrogen atom, a halogen atom, or a phenoxy group, and
$R^3$ represents a $C_{1-6}$ alkanoyl group,
ring $Q^2$ represents a phenylene group which may have 1 or 2 substituents independently selected from substituent group 1, a 6-membered aromatic heterocyclic group which may have 1 or 2 substituents independently selected from substituent group 1, a 5-membered aromatic heterocyclic group which may have a substituent selected from substituent group 1, or a 9-membered bicyclic aromatic heterocyclic group which may have a substituent selected from substituent group 1,
W is any one substituent selected from substituent group 1, or represents formula (3A):

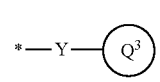

(3A)

wherein
* represents a bond,
Y represents an oxygen atom, a single bond, a sulfur atom, —NH—, *—O—$R^4$—**: (wherein * is bonded to ring $Q^2$ and ** is bonded to ring $Q^3$), a $C_{1-6}$ alkylene group, a $C_{1-6}$ alkoxy $C_{1-6}$ alkylene group, or a halogeno $C_{1-6}$ alkylene group,
$R^4$ represents a $C_{1-6}$ alkylene group, and
ring $Q^3$ represents a phenyl group which may have 1 to 3 substituents independently selected from substituent group 2, a 6-membered aromatic heterocyclic group which may have 1 or 2 substituents independently selected from substituent group 2, a 5-membered aromatic heterocyclic group which may have 1 or 2 substituents independently selected from substituent group 2, a 3- to 8-membered saturated hydrocarbon ring group which may have 1 or 2 substituents independently selected from substituent group 2, a 6-membered saturated heterocyclic group which may have 1 or 2 substituents independently selected from substituent group 2, a 9-membered bicyclic aromatic heterocyclic group which may have a substituent selected from substituent group 2, or a 10-membered bicyclic partially unsaturated heterocyclic group which may have 1 to 4 substituents independently selected from substituent group 2;

substituent group 1 represents a group consisting of a halogen atom, a $C_{1-6}$ alkyl group, a halogeno $C_{1-6}$ alkyl group, a halogeno $C_{1-6}$ alkoxy group, and a $C_{3-8}$ cycloalkyl group; and substituent group 2 represents a group consisting of a halogen atom, a $C_{1-6}$ alkyl group, a halogeno $C_{1-6}$ alkyl group, a halogeno $C_{1-6}$ alkoxy group, a halogeno $C_{1-6}$ alkylsulfanyl group, and a halogeno $C_{1-6}$ alkylsulfonyl group;

wherein the compound represented by formula (1):

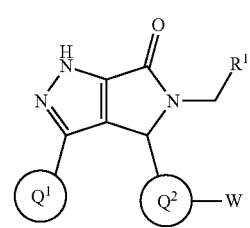

(1)

wherein $R^1$, $Q^1$, $Q^2$, and W are as defined above, may include its tautomer, a compound represented by formula (1'):

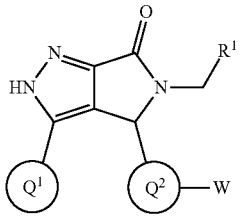

(1')

wherein $R^1$, $Q^1$, $Q^2$, and W are as defined above, in any ratio, and the ratio of the compound represented by formula (1) may be 100%, or the ratio of the compound represented by formula (1') may be 100%.

2. The compound according to claim 1 or a pharmaceutically acceptable salt thereof, wherein $R^1$ is a 1,1-difluoroethyl group.

3. The compound according to claim 1 or a pharmaceutically acceptable salt thereof, wherein ring $Q^1$ represents either formula (5A) or (5B):

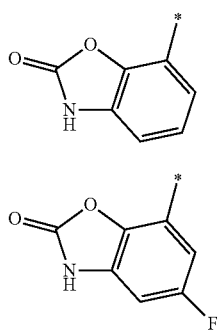

(5A)

(5B)

wherein * represents a bond.

4. The compound according to claim 1 or a pharmaceutically acceptable salt thereof, wherein ring $Q^2$ represents any one of formulas (8A) to (8E):

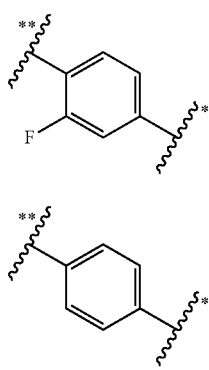

(8A)

(8B)

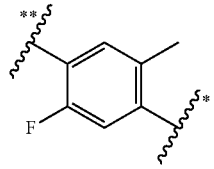

(8C)

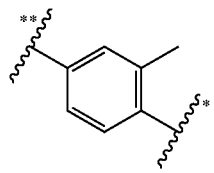

(8D)

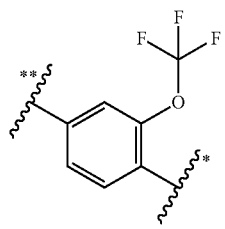

(8E)

wherein
* is bonded to W, and
in formula (1), ** is bonded to a carbon atom represented by a in a moiety represented by formula (1A) (hereinafter, referred to as "the carbon atom represented by a"):

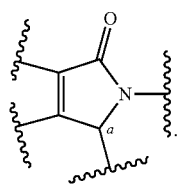

(1A)

5. The compound according to claim 1 or a pharmaceutically acceptable salt thereof, wherein
W represents formula (3A);
in formula (3A), Y is as defined above; and
ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group.

6. The compound according to claim 1 or a pharmaceutically acceptable salt thereof, wherein Y is an oxygen atom.

7. The compound according to claim 1 or a pharmaceutically acceptable salt thereof, wherein
$R^1$ is a trifluoromethyl group, a 1,1-difluoroethyl group, a 1,1-difluoropropyl group, a cyclopropyl group, a 2-pyridyl group, or an oxazol-2-yl group;

ring Q¹ represents either formula (4A) or (4B):

(4A)

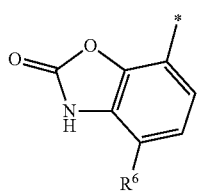
(4B)

wherein
* represents a bond,
R⁵ represents a hydrogen atom or a halogen atom, and
R⁶ represents a halogen atom;
ring Q² represents any one of formulas (7A) to (7C):

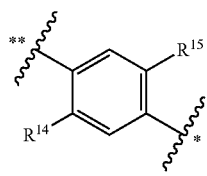
(7A)

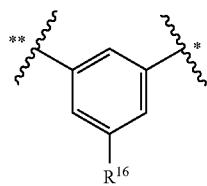
(7B)

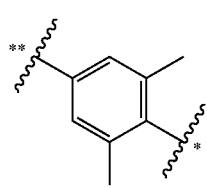
(7C)

wherein
* is bonded to W,
** is bonded to the carbon atom represented by a,
R¹⁴ represents a hydrogen atom, a fluorine atom, a chlorine atom, or a methyl group,
R¹⁵ represents a hydrogen atom, a chlorine atom, a methyl group, an ethyl group, a trifluoromethyl group, a trifluoromethoxy group, a 4,4,4-trifluorobutoxy group, or a cyclopropyl group, and
R¹⁶ represents a hydrogen atom or a trifluoromethyl group;

W is a fluorine atom, a chlorine atom, an n-butyl group, an n-hexyl group, a trifluoromethyl group, a trifluoromethoxy group, or a 4,4,4-trifluorobutoxy group, or
W represents formula (3A);
ring Q³ represents any one of formulas (10A) to (10C):

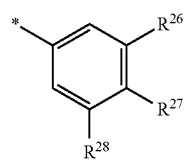
(10A)

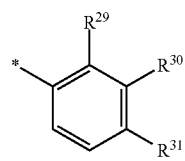
(10B)

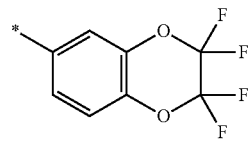
(10C)

wherein
* represents a bond,
R²⁶ and R²⁸ each independently represent a hydrogen atom, a chlorine atom, a methyl group, a trifluoromethyl group, or a trifluoromethoxy group,
R²⁷ represents a hydrogen atom, a fluorine atom, a chlorine atom, a trifluoromethyl group, a trifluoromethoxy group, a trifluoromethylsulfanyl group, or a trifluoromethylsulfonyl group,
R²⁹ represents a fluorine atom, a chlorine atom, a methyl group, a trifluoromethyl group, or a trifluoromethoxy group,
R³⁰ represents a hydrogen atom or a chlorine atom, and
R³¹ represents a hydrogen atom, a trifluoromethyl group, or a trifluoromethoxy group; and
Y represents an oxygen atom, a single bond, a sulfur atom, —NH—, a methylene group, or any one of formulas (11A) to (11C):

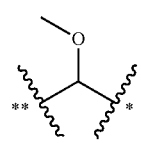
(11A)

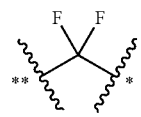
(11B)

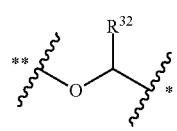
(11C)

wherein

* is bonded to ring $Q^3$,

** is bonded to ring $Q^2$, and $R^{32}$ represents a hydrogen atom or a methyl group.

8. The compound according to claim 1 or a pharmaceutically acceptable salt thereof, wherein $R^1$ is a 1,1-difluoroethyl group;

ring $Q^1$ represents formula (5A) or (5B):

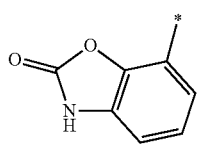
(5A)

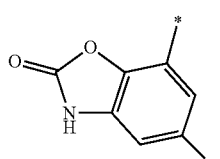
(5B)

wherein * represents a bond;

ring $Q^2$ represents any one of formulas (8A) to (8E):

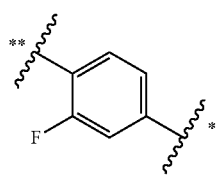
(8A)

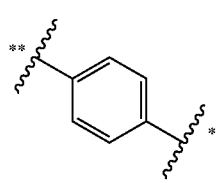
(8B)

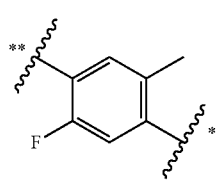
(8C)

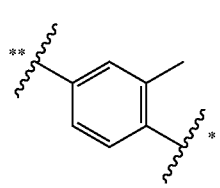
(8D)

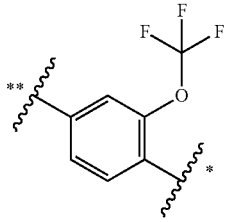
(8E)

wherein

* is bonded to W, and

** is bonded to the carbon atom represented by a;

W represents formula (3A);

ring $Q^3$ is a 4-chlorophenyl group, a 4-(trifluoromethoxy)phenyl group, a 3,4-dichlorophenyl group, a 4-(trifluoromethyl)phenyl group, a 4-(trifluoromethylsulfanyl)phenyl group, a 3-chloro-4-(trifluoromethoxy)phenyl group, a 3,5-bis(trifluoromethyl)phenyl group, a 3-methyl-4-(trifluoromethoxy)phenyl group, a 3-chloro-5-(trifluoromethoxy)phenyl group, a 3,5-dichloro-4-(trifluoromethoxy)phenyl group, a 3-chloro-5-(trifluoromethyl)phenyl group, a 4-(trifluoromethoxy)-3-(trifluoromethyl)phenyl group, a 3,4-bis(trifluoromethyl)phenyl group, a 3-chloro-2-(trifluoromethoxy)phenyl group, or a 2,2,3,3-tetrafluoro-1,4-benzodioxin-6-yl group; and Y is an oxygen atom.

9. (−)-7-[4-{4-[3,5-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to claim 1 or a pharmaceutically acceptable salt thereof, wherein (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

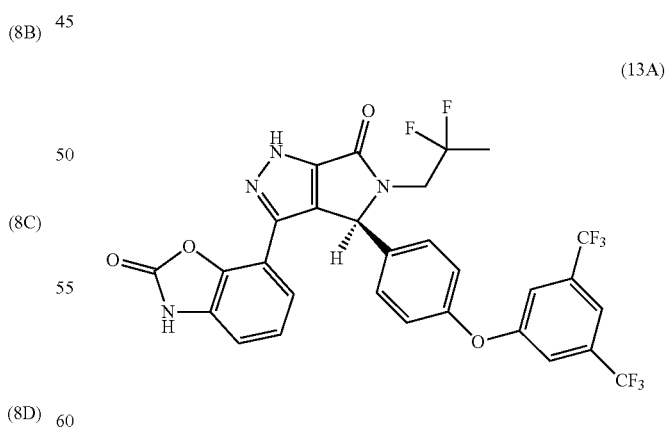
(13A)

may include its tautomer, 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

in any ratio, and
the ratio of the compound represented by formula (13A) may be 100%, or the ratio of the compound represented by formula (13B) may be 100%.

10. (−)-7-[4-{4-[3,5-Bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to claim 1 or a pharmaceutically acceptable salt thereof,
wherein (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

does not include its tautomer, 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

11. 7-[(4S)-4-{4-[3,5-Bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1 or a pharmaceutically acceptable salt thereof,
wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

may include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

in any ratio, and
the ratio of the compound represented by formula (13A) may be 100%, or the ratio of the compound represented by formula (13B) may be 100%.

12. 7-[(4S)-4-{4-[3,5-Bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1 or a pharmaceutically acceptable salt thereof,
wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

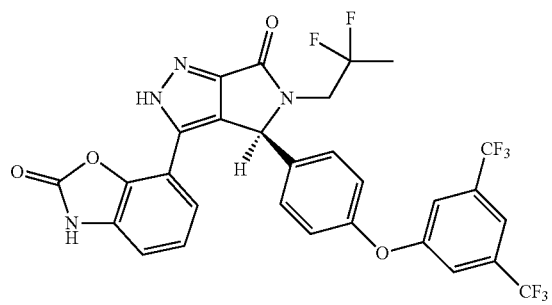

does not include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

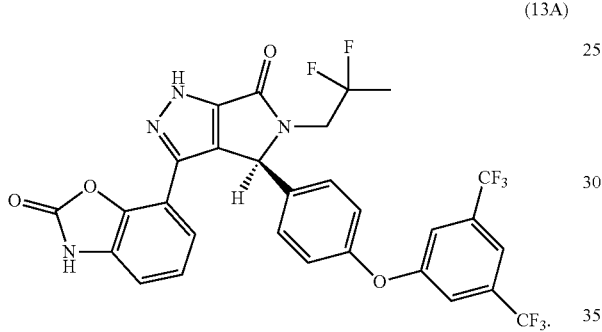

13. A 2-methylpropane-2-amine salt of (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to claim 1, wherein (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

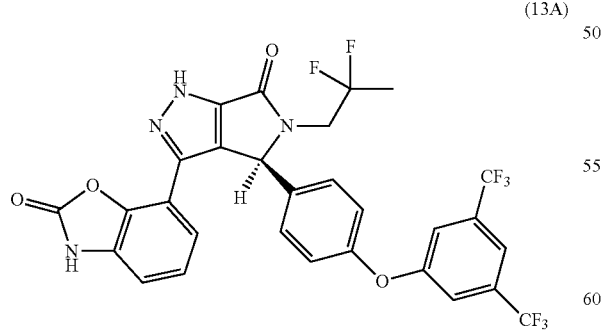

may include its tautomer, 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

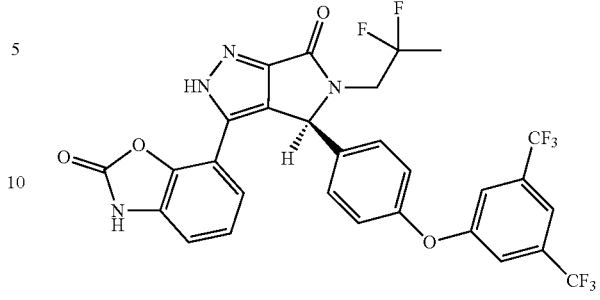

in any ratio, and
the ratio of the compound represented by formula (13A) may be 100%, or the ratio of the compound represented by formula (13B) may be 100%.

14. A 2-methylpropane-2-amine salt of (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one according to claim 1, wherein (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

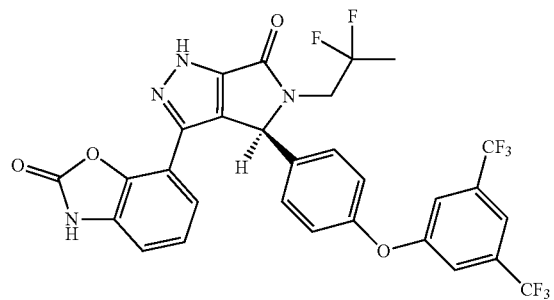

does not include its tautomer, 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

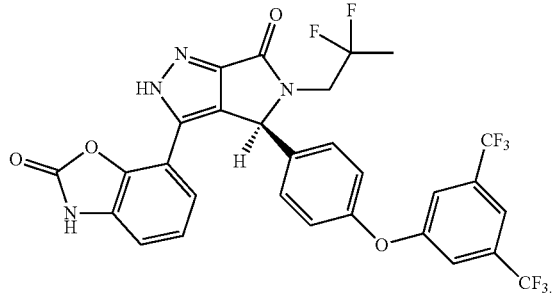

15. A 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1,
wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

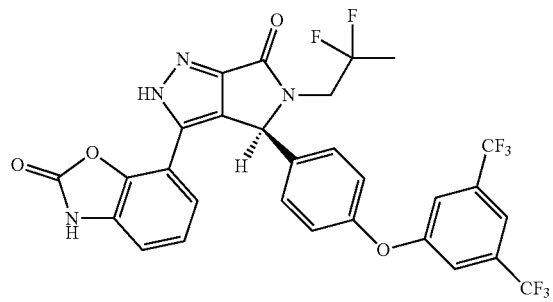

may include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

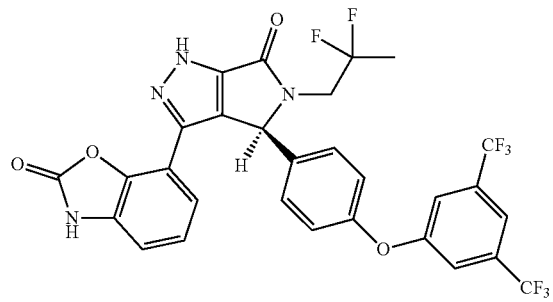

in any ratio, and
the ratio of the compound represented by formula (13A) may be 100%, or the ratio of the compound represented by formula (13B) may be 100%.

16. A 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1,
wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

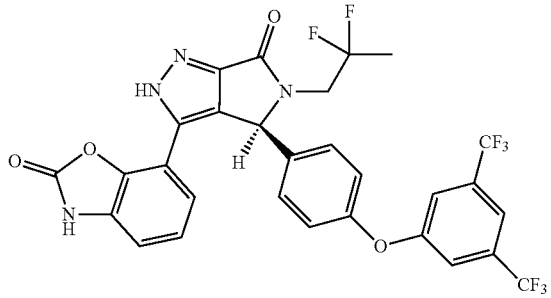

does not include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

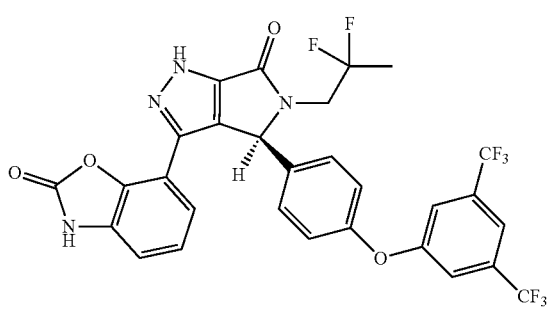

17. A crystal of a 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1, wherein the crystal has at least five peaks at diffraction angles (2θ) selected from 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2 in a powder X-ray diffraction diagram obtained by irradiation with copper Kα radiation (λ=1.54 angstrom),
wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

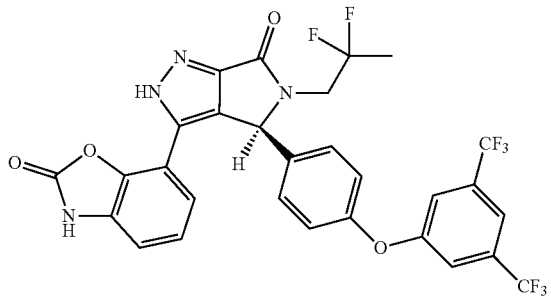

does not include its tautomer, (−)-7-[4-{4-[3,5-bis(trifluoromethyl)phenoxy]phenyl}-5-(2,2-difluoropropyl)-6- oxo-1,4,5,6-tetrahydropyrrolo[3,4-c]pyrazol-3-yl]-1,3-benzoxazol-2(3H)-one represented by formula (13A):

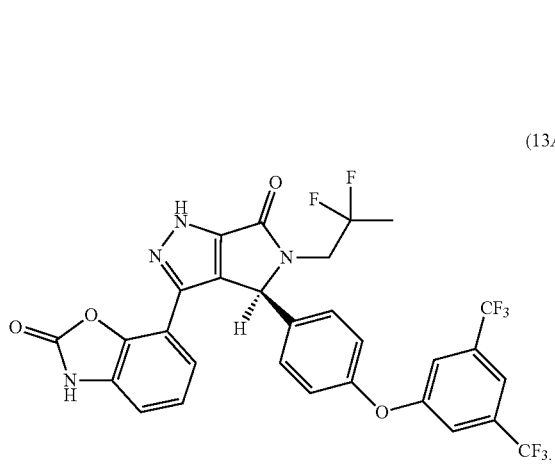
(13A)

18. An inhibitor of phosphatidylserine synthase 1 comprising the compound according to claim 1 or a pharmaceutically acceptable salt thereof or the crystal of a 2-methyl-propane-2-amine salt of 7-[(4S)-4-{4-[3,5-bis(trifluoromethyl)phenoxyphenyl}-5-(2,2-difluoropropyl)-6-oxo-2,4,5,6-tetrahydropyrrolo[3,4-c]pyrazol-3-yl]-1,3-benzoxazol-2(3H)-one according to claim 1, wherein the crystal has at least five peaks at diffraction angles (2θ) selected from 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2 in a powder X-ray diffraction diagram obtained by irradiation with copper Kα radiation (λ=1.54 angstrom), wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

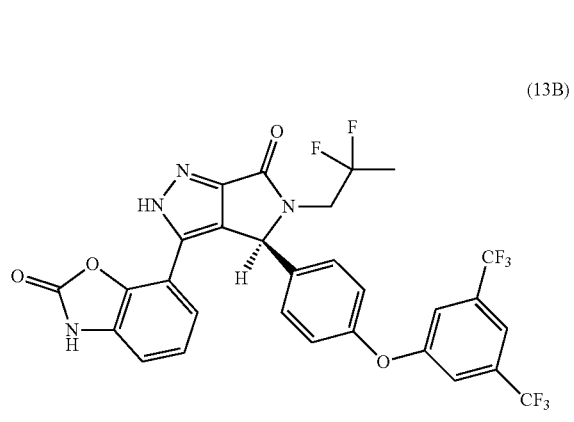
(13B)

does not include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

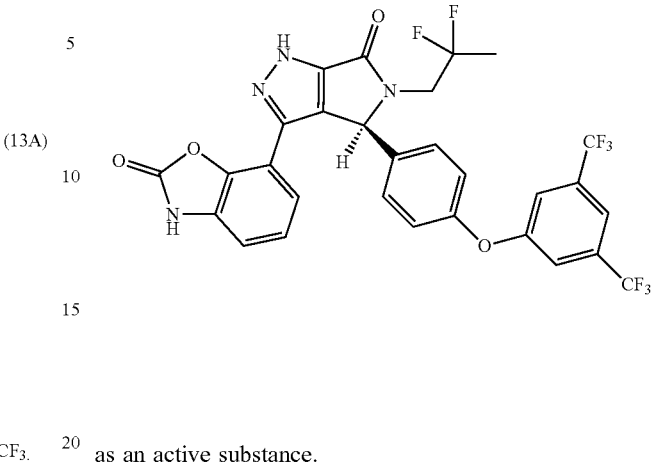
(13A)

as an active substance.

19. A pharmaceutical composition comprising the compound according to claim 1 or a pharmaceutically acceptable salt thereof or the crystal of a 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1, wherein the crystal has at least five peaks at diffraction angles (2θ) selected from 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2 in a powder X-ray diffraction diagram obtained by irradiation with copper Kα radiation (λ=1.54 angstrom), wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

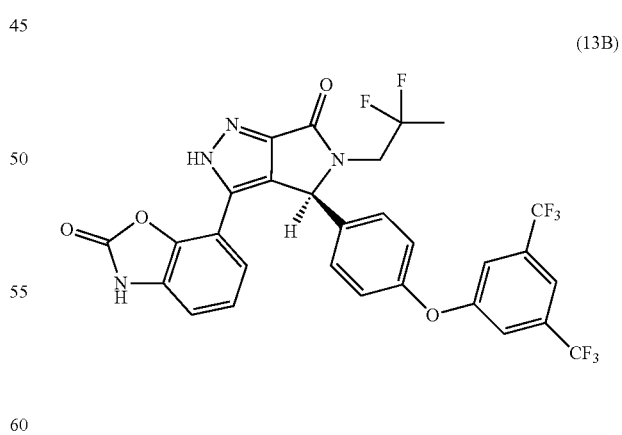
(13B)

does not include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13A):

(13A)

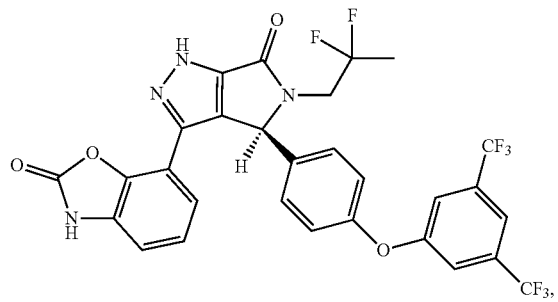

and a pharmaceutically acceptable carrier.

20. A method for treating cancer, comprising administering the compound according to claim 1 or a pharmaceutically acceptable salt thereof or the crystal of a 2-methylpropane-2-amine salt of 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one according to claim 1, wherein the crystal has at least five peaks at diffraction angles (2θ) selected from 3.44±0.2, 10.46±0.2, 13.04±0.2, 16.00±0.2, 19.20±0.2, 21.02±0.2, 22.18±0.2, 23.54±0.2, 24.46±0.2, and 25.88±0.2 in a powder X-ray diffraction diagram obtained by irradiation with copper Kα radiation (λ=1.54 angstrom), wherein 7-[(4S)-4-{4-[3,5-bis(trifluoromethyl)phenoxy]phenyl}-5-(2,2-difluoropropyl)-6-oxo-2,4,5,6-tetrahydropyrrolo[3,4-c]pyrazol-3-yl]-1,3-benzoxazol-2(3H)-one represented by formula (13B):

(13B)

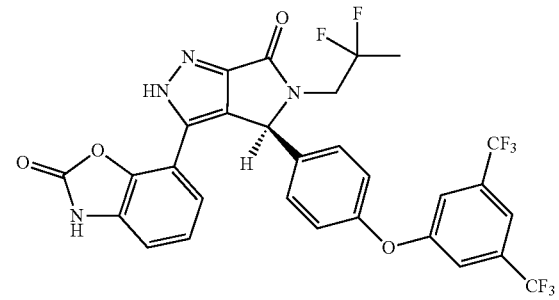

does not include its tautomer, (−)-7-[4-{4-[3,5-bis(trifluoromethyl)phenoxy]phenyl}-5-(2,2-difluoropropyl)-6-oxo-1,4,5,6-tetrahydropyrrolo[3,4-c]pyrazol-3-yl]-1,3-benzoxazol-2(3H)-one represented by formula (13AB):

(13A)

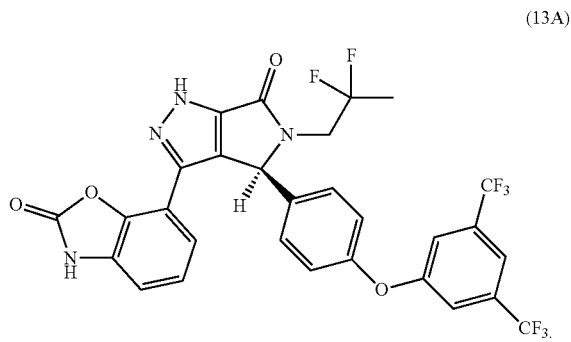 [SMILES: CC(F)(F)CN1C(=O)c2[nH]nc(-c3cccc4[nH]c(=O)oc34)c2[C@@H]1c1ccc(Oc2cc(C(F)(F)F)cc(C(F)(F)F)c2)cc1]

\* \* \* \* \*